(12) United States Patent
Nowick et al.

(10) Patent No.: US 11,319,348 B2
(45) Date of Patent: *May 3, 2022

(54) SYNTHETIC BETA-AMYLOID PEPTIDES CAPABLE OF FORMING STABLE ANTIGENIC OLIGOMERS

(71) Applicant: The Regents of the University of California, Oakland, CA (US)

(72) Inventors: James S. Nowick, Irvine, CA (US); Adam G. Kreutzer, Irvine, CA (US); Ryan K. Spencer, Ripon, CA (US); Patrick J. Salveson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 11 days.

This patent is subject to a terminal disclaimer.

(21) Appl. No.: 16/847,500

(22) Filed: Apr. 13, 2020

(65) Prior Publication Data

US 2020/0347099 A1    Nov. 5, 2020

Related U.S. Application Data

(63) Continuation of application No. 15/794,776, filed on Oct. 26, 2017, now Pat. No. 10,662,226.

(60) Provisional application No. 62/414,326, filed on Oct. 28, 2016.

(51) Int. Cl.
| | | |
|---|---|---|
| *C07K 14/00* | (2006.01) | |
| *C07K 1/22* | (2006.01) | |
| *C07K 16/18* | (2006.01) | |
| *C07K 14/47* | (2006.01) | |

(52) U.S. Cl.
CPC .............. *C07K 14/001* (2013.01); *C07K 1/22* (2013.01); *C07K 14/4711* (2013.01); *C07K 16/18* (2013.01); *C07K 2317/34* (2013.01)

(58) Field of Classification Search
CPC .. C07K 16/18; C07K 2317/34; C07K 14/001; C07K 1/22; C07K 14/4711
See application file for complete search history.

(56) References Cited

U.S. PATENT DOCUMENTS

| | | |
|---|---|---|
| 3,791,932 A | 2/1974 | Schuurs et al. |
| 3,949,064 A | 4/1976 | Bornstein et al. |
| 4,174,384 A | 11/1979 | Ullman et al. |
| 4,596,792 A | 6/1986 | Vyas et al. |
| 4,599,230 A | 7/1986 | Milich et al. |
| 4,599,231 A | 7/1986 | Milich et al. |
| 4,601,903 A | 7/1986 | Frasch et al. |
| 4,608,251 A | 8/1986 | Mia et al. |
| 5,084,269 A | 1/1992 | Kullenberg et al. |
| 6,656,462 B2 | 12/2003 | Dondero et al. |
| 6,733,754 B2 | 5/2004 | Roberts et al. |
| 6,793,923 B2 | 9/2004 | Kimmins et al. |
| 6,814,971 B2 | 11/2004 | Roberts et al. |
| 8,106,015 B2 | 1/2012 | Matsuda et al. |
| 8,906,367 B2 | 12/2014 | Hock et al. |
| 10,662,226 B2 | 5/2020 | Nowick et al. |
| 2006/0018918 A1 | 1/2006 | Chang |
| 2018/0118790 A1 | 5/2018 | Nowick et al. |

FOREIGN PATENT DOCUMENTS

| | | |
|---|---|---|
| WO | 2010004434 A2 | 1/2010 |
| WO | 2014089500 A1 | 6/2014 |
| WO | 2016087944 A2 | 6/2016 |

OTHER PUBLICATIONS

Arndt et al., "Structural Basis of Unique Selectivity of Aducanumab for Oligomeric Forms of Amyloid-β", Alzheimer's & Dementia: The Journal of the Alzheimer's Association, Jul. 2016, vol. 12, Issue 7, Supplement, pp. P466-P467. http://dx.doi.org/10.1016/j.jalz.2016.06.915.
Benilova et al., "The toxic Aβ oligomer and Alzheimer's disease: an emperor in need of clothes", Nature Neuroscience, vol. 15, No. 3, Mar. 2012. pp. 349-357, doi:10.1038/nn.3028, Published online: Jan. 29, 2012.
Chothia et al., "Canonical structures for the hypervariable regions of immunoglobulins", Journal of Molecular Biology, vol. 196, Issue 4, Aug. 20, 1987, pp. 901-917, https://doi.org/10.1016/0022-2836(87)90412-8.
Dauter et al., "Novel approach to phasing proteins: derivatization by short cryo-soaking with halides", Acta Crystallographica, Section D Biological Crystallography, vol. 56, Part 2, 2000, pp. 232-237, https://doi.org/10.1107/S0907444999016352.
DOI et al., "Solid-state NMR analysis of the β-strand orientation of the protofibrils of amyloid β-protein", Biochemical and Biophysical Research Communications, vol. 428, Issue 4, Nov. 30, 2012, pp. 458-462, https://doi.org/10.1016/j.bbrc.2012.10.096.
Fezoui et al., "An improved method of preparing the amyloid β-protein for fibrillogenesis and neurotoxicity experiments", Amyloid, The Journal of Protein Folding Disorders, vol. 7, Issue 3, 2000, pp. 166-178, https://doi.org/10.3109/13506120009146531, Published online: Jul. 6, 2009.
Kohler et al, "Continuous cultures of fused cells secreting antibody of predefined specificity", Nature, Aug. 7, 1975, vol. 256, pp. 495-497.
Kreutzer et al., "A Hexamer of a Peptide Derived from Aβ16-36", Biochemistry, 2017, vol. 56, No. 45, pp. 6061-6071, DOI: 10.1021/acs.biochem.7b00831, Online Publication Date Oct. 13, 2017.
Kreutzer et al., "X-ray Crystallographic Structures of a Trimer, Dodecamer, and Annular Pore Formed by an Aβ17-36 β-Hairpin". Journal of the American Chemical Society, vol. 138, No. 13, 2016, pp. 4634-4642, DOI: 10.1021/jacs.6b01332, Online Publication Date: Mar. 11, 2016.
Larson et al., "Soluble Aβ oligomer production and toxicity", Journal of Neurochemistry, vol. 120, Issue s1, Jan. 2012, pp. 125-139, DOI: 10.1111/j.1471-4159.2011.07478.x, First Published Nov. 28, 2011.

(Continued)

Primary Examiner — Gregory S Emch
(74) Attorney, Agent, or Firm — KPPB LLP

(57) ABSTRACT

Synthetic Aβ peptides, oligomers, their methods of synthesis, and their applications are provided. The Aβ peptides can form stable, soluble oligomers important for the advancement of knowledge, detection, and treatment of Alzheimer's disease. Antibodies specific to oligomeric Aβ and their methods of synthesis are also described.

14 Claims, 70 Drawing Sheets
(60 of 70 Drawing Sheet(s) Filed in Color)
Specification includes a Sequence Listing.

(56) References Cited

OTHER PUBLICATIONS

Lesne et al., "A specific amyloid-β protein assembly in the brain impairs memory", Nature, vol. 440, Mar. 16, 2006, pp. 352-357, doi:10.1038/nature04533.

Liu et al., "Structures from Anomalous Diffraction of Native Biological Macromolecules" Science, vol. 336, Issue 6084, May 25, 2012, pp. 1033-1037, DOI: 10.1126/science. 1218753.

Phillips et al., "Scalable molecular dynamics with NAMD", Journal of Computational Chemistry, vol. 26, Issue 16, Dec. 2005, pp. 1781-1802, DOI: 10.1002/jcc.20289.

Rambaran et al., "Amyloid fibrils", Prion, vol. 2, Issue 3, 2008, pp. 112-117, https://doi.org/10.4161/pri.2.3.7488. Published online: Nov. 25, 2008.

Salveson et al., "X-ray Crystallographic Structure of a Compact Dodecamer from a Peptide Derived from Aβ16-36", Org. Lett., 2017, vol. 19, No. 13, pp. 3462-3465, DOI: 10.1021/acs.orglett. 7b1445, Online Publication Date Jun. 15, 2017

Salveson et al., "X-ray Crystallographic Structure of Oligomers Formed by a Toxic β-Hairpin Derived from α-Synuclein: Trimers and Higher-Order Oligomers", Journal of the American Chemical Society. vol. 138, No. 13, 2016, pp. 4458-4467, DOI: 10.1021/jacs. 5b13261, Online Publication Date: Feb. 29, 2016.

Sarma et al., "In-house sulfur SAD phasing: a case study of the effects of date quality and resolution cutoffs", Acta Crystallographica. Section D Biological Crystallography, vol. 62, Part 7, 2006, pp. 707-716, https://doi.org/10.1107/S0907444906014946.

Scheidt et al., "Solid-state NMR Reveals a Close Structural Relationship between Amyloid-β Protofibrils and Oligomers", The Journal of Biological Chemistry, vol. 287, No. 27, Jun. 29, 2012, pp. 22822-22826, doi: 10.1074/jbc.M112.367474, first published May 15, 2012.

Sevigny et al., "The antibody aducanumab reduces Aβ plaques in Alzheimer's disease", Nature, vol. 537, Sep. 1, 2016, pp. 50-56, doi:10.1038/nature19323, Published online: Aug. 31, 2016

Spencer et al., "A Newcomer's Guide to Peptide Crystallography", Israel Journal of Chemistry, vol. 55, Issue 6-7, Jun. 2015, pp. 698-710, DOI: 10.1002/ijch.201400179, First published: Mar. 31, 2015.

Spencer et al., "X-ray Crystallographic Structures of Oligomers of Peptides Derived from β2-Microglobulin", Journal of the American Chemical Society, vol. 137, No. 19, 2015, pp. 6304-6311, DOI: 10.1021/jacs.5b01673, Online Publication Date: Apr. 27, 2015.

Spencer et al., "X-ray Crystallagraphic Structures of Trimers and Higher-Order Oligomeric Assemblies of a Peptide Derived from Aβ17-36", Journal of the American Chemical Society, vol. 136, No. 15, 2014, pp. 5595-5598, DOI: 10.1021/ja5017409, Online Publication Date: Mar. 26, 2014.

Sugita et al., "Replica-exchange molecular dynamics method for protein folding", Chemical Physics Letters, vol. 314, Issues 1-2, Nov. 26, 1999, pp. 141-151, https://doi.org/10.1016/S0009-2614(99)01123-9.

Tay et al., "The Alzheimer's Amyloid-β(1-42) Peptide Forms Off-Pathway Oligomers and Fibrils That Are Distinguished Structurally by Intermolecular Organization", Journal of Molecular Biology, vol. 425, Issue 14, Jul. 24, 2013, pp. 2494-2508, https://doi.org/10. 1016/j.jmb.2013.04.003.

Teplow, "Preparation of Amyloid β-Protein for Structural and Functional Studies", Methods in Enzymology, vol. 413, 2006, pp. 20-33. https://doi.org/10.1016/S0076-6879(06)13002-5.

Townsend et al., "Effects of secreted oligomers of amyloid β-protein on hippocampal synaptic plasticity: a potent role for trimers", The Journal of Physiology, vol. 572, Issue 2, Apr. 2006, pp. 477-492, DOI:10.1113/jphysiol.2005.103754, Apr. 5, 2006.

Van Der Kant et al., "Cellular Functions of the Amyloid Precursor Protein from Development to Dementia", Developmental Cell, vol. 32, Issue 4, Feb. 23, 2015, pp. 502-515.

Winner et al., "In vivo demonstration that α-synuclein oligomers are toxic", PNAS, vol. 108, No. 10, Mar. 8, 2011, pp. 4194-4199, https://doi.org/10.1073/pnas. 1100976108.

Yu et al., "Structural Characterization of a Soluble Amyloid β-Peptide Oligomer", Biochemistry, vol. 48, No. 2009, pp. 1870-1877, DOI:10. 1021/biB02046n, Online Publication Date: Feb. 13, 2009.

Zhao et al., "The Toxicity of Amyloid β Oligomers", International Journal of Molecular Sciences, vol. 13, Issue6, Jun. 13, 2012, pp. 7303-7327; doi:10.3390/ijms13067303.

Kreutzer et al., "Stabilization, Assembly, and Toxicity of Trimers Derived from Aβ", J Am Chem Soc. Jan. 18, 2017; 139(2):966-975. Published Dec. 21, 2016.

FIG. 1

Aβ1-40 (Seq. ID No. 1)
D-A-E-F-R-H-D-S-G-Y-E-V-H-H-Q-K-L-V-F-F-A-E-D-V-G-S-N-K-G-A-I-I-G-L-M-V-G-G-V-V

Aβ1-42 (Seq. ID No. 2)
D-A-E-F-R-H-D-S-G-Y-E-V-H-H-Q-K-L-V-F-F-A-E-D-V-G-S-N-K-G-A-I-I-G-L-M-V-G-G-V-V-I-A

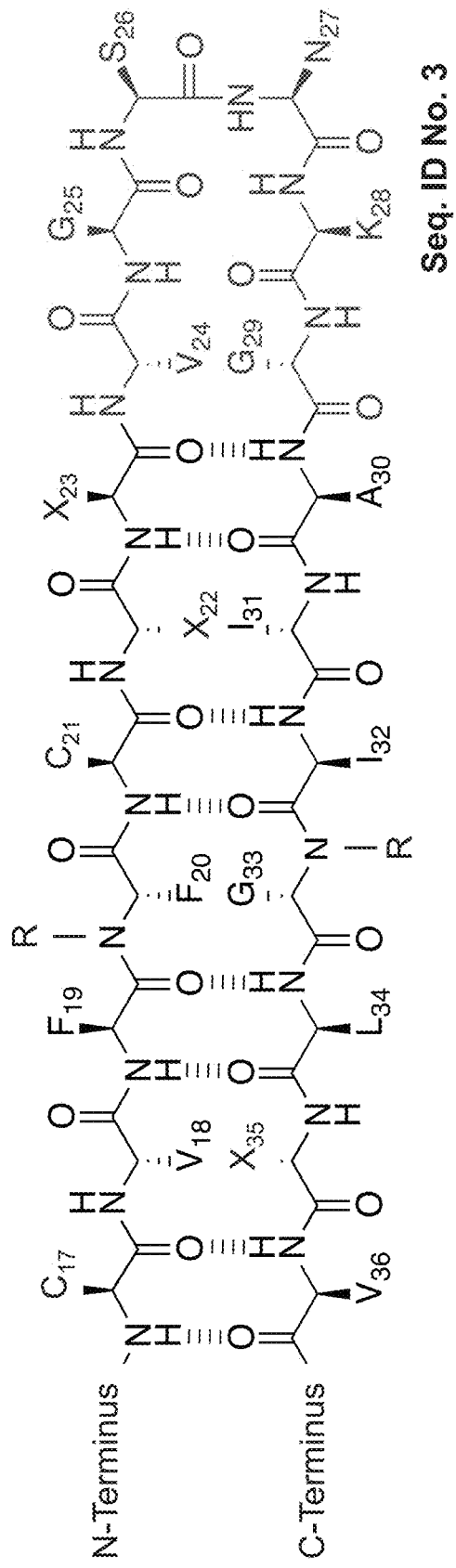

N-Terminus = Aβ$_{1-16}$ (Seq. ID No. 9), Orn$_{16}$, Del

C-Terminus = Aβ$_{37-40}$ (Seq. ID No. 10), Aβ$_{37-42}$ (Seq. ID No. 11), Del

X$_{22}$ = E$_{22}$, Q$_{22}$, K$_{22}$, Del

X$_{23}$ = D$_{23}$, N$_{23}$

X$_{35}$ = M$_{35}$, Orn$_{35}$, MetO$_{35}$

R = H, Me, alkyl, aryl $X_{22}$ = $E_{22}$, $Q_{22}$, $K_{22}$, Del
$X_{23}$ = $D_{23}$, $N_{23}$
$X_{35}$ = $M_{35}$, $Orn_{35}$, $MetO_{35}$
R = H, Me, alkyl, aryl Top Strand: Seq. ID No. 5
Bottom Strand: Seq. ID No. 6

Seq. ID No. 3

N-Terminus = Aβ$_{1-16}$ (Seq. ID No. 9), Orn$_{16}$, Del

C-Terminus = Aβ$_{37-40}$ (Seq. ID No. 10), Aβ$_{37-42}$ (Seq. ID No. 11), Del $X_{22}$ = E$_{22}$, Q$_{22}$, K$_{22}$, Del $X_{23}$ = D$_{23}$, N$_{23}$ $X_{35}$ = M$_{35}$, Orn$_{35}$, MetO$_{35}$ R = H, Me, alkyl, aryl Top Strand: Seq. ID No. 5
Bottom Strand: Seq. ID No. 6

$X_{22}$ = $E_{22}$, $Q_{22}$, $K_{22}$, Del $X_{23}$ = $D_{23}$, $N_{23}$ $X_{35}$ = $M_{35}$, $Orn_{35}$, $MetO_{35}$

R = H, Me, alkyl, aryl

N-Terminus = Aβ$_{1-16}$ (Seq. ID No. 9), Orn$_{16}$, Del

C-Terminus = Aβ$_{37-40}$ (Seq. ID No. 10), Aβ$_{37-42}$ (Seq. ID No. 11), Del

X$_{22}$ = E$_{22}$, Q$_{22}$, K$_{22}$, Del

X$_{23}$ = D$_{23}$, N$_{23}$

X$_{35}$ = M$_{35}$, Orn$_{35}$, MetO$_{35}$

R = H, Me, alkyl, aryl

N-Terminus = Aβ₁₋₁₆ (Seq. ID No. 9), Orn₁₆, Del

C-Terminus = Aβ₃₇₋₄₀ (Seq. ID No. 10), Aβ₃₇₋₄₂ (Seq. ID No. 11), Del $X_{22}$ = $E_{22}$, $Q_{22}$, $K_{22}$, Del $X_{23}$ = $D_{23}$, $N_{23}$ $X_{35}$ = $M_{35}$, $Orn_{35}$, $MetO_{35}$ R = H, Me, alkyl, aryl Peptide 1

Top Strand: Seq. ID No. 18
Bottom Strand: Seq. ID No. 19

Peptide 2

Top Strand: Seq. ID No. 20
Bottom Strand: Seq. ID No. 21

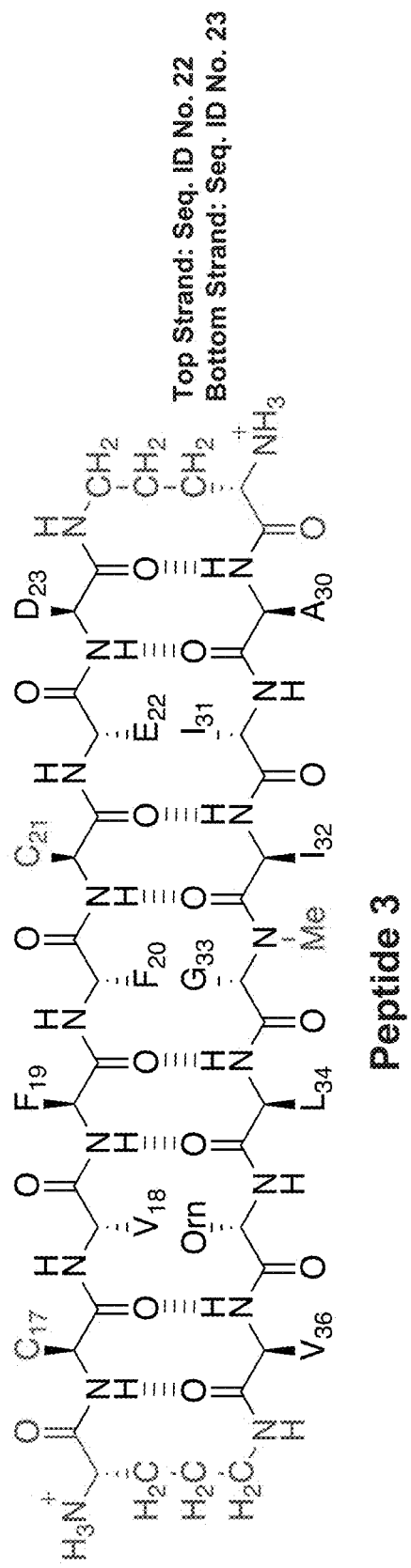
FIG. 17A Peptide 3
Top Strand: Seq. ID No. 22
Bottom Strand: Seq. ID No. 23
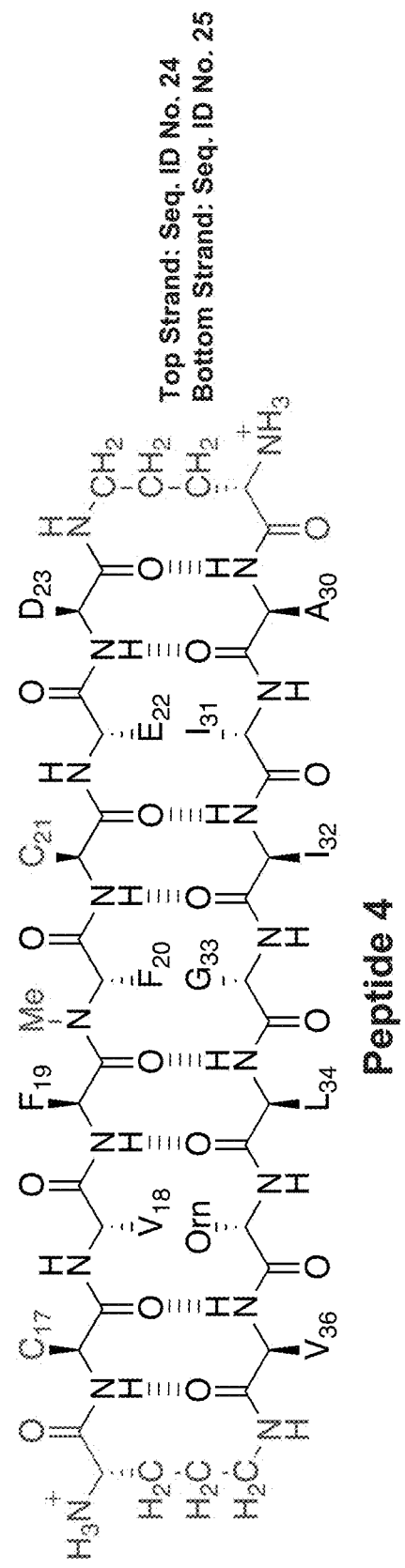
FIG. 17B Peptide 4
Top Strand: Seq. ID No. 24
Bottom Strand: Seq. ID No. 25

Top Strand: Seq. ID No. 22
Bottom Strand: Seq. ID No. 23

Trimer 3

Top Strand: Seq. ID No. 24
Bottom Strand: Seq. ID No. 25

Trimer 4

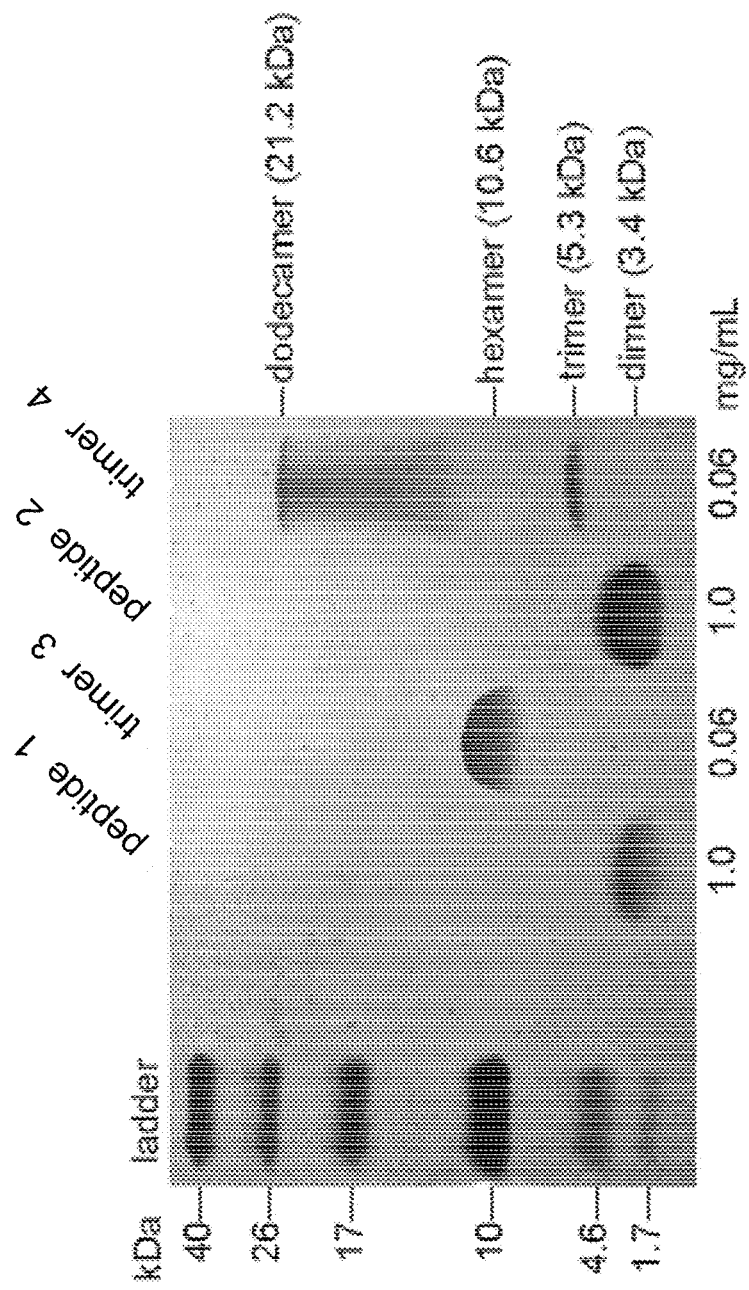

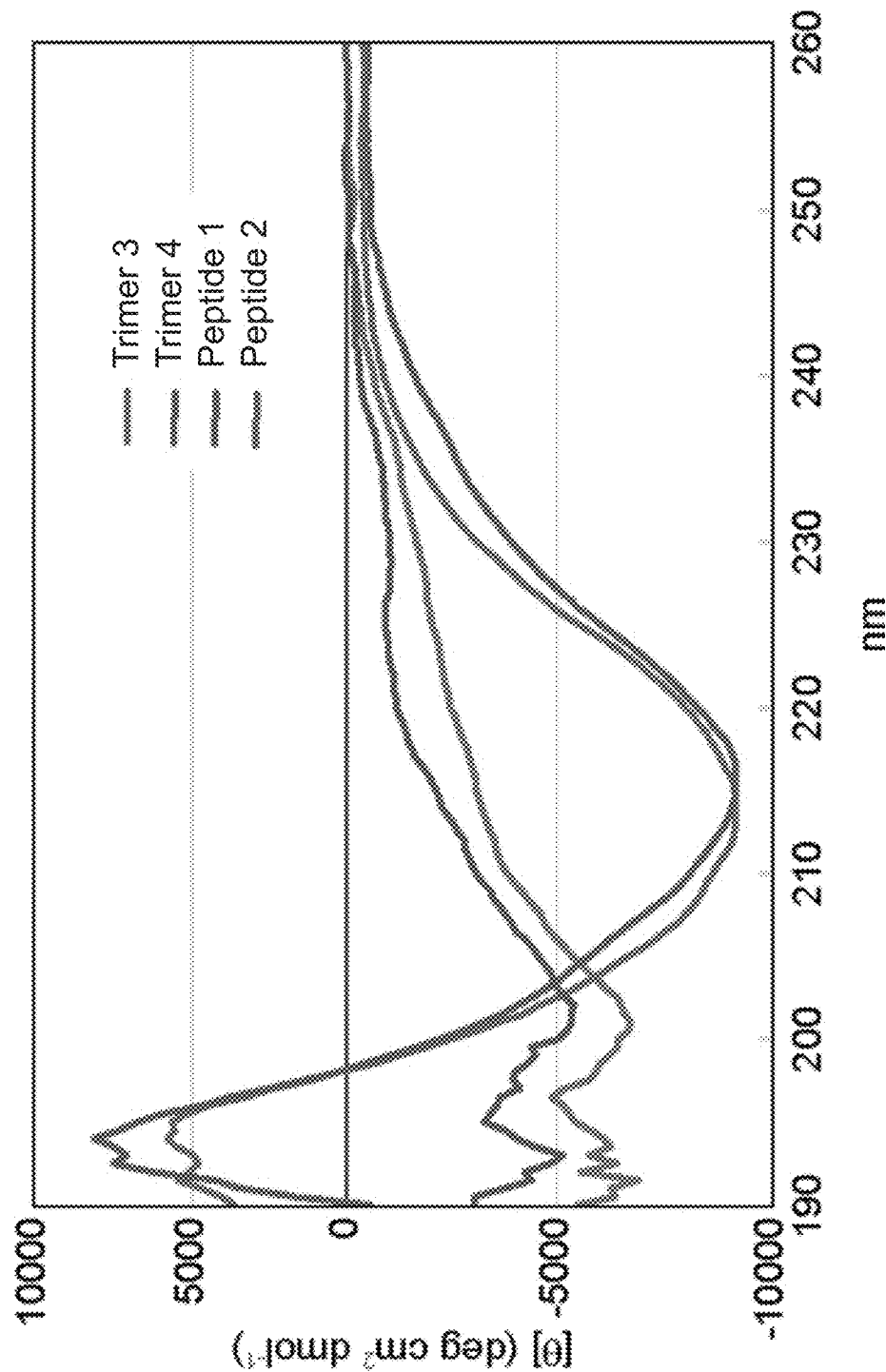

Aβ$_{17-36}$ β-hairpin    Aβ$_{16-36}$ β-hairpin    Aβ$_{15-36}$ β-hairpin peptide 5 (from Aβ$_{17-36}$) — Top Strand: Seq. ID No. 26; Bottom Strand: Seq. ID No. 27 peptide 6 (from Aβ$_{16-36}$) — Top Strand: Seq. ID No. 28; Bottom Strand: Seq. ID No. 29 peptide 7 (from Aβ$_{15-36}$) — Top Strand: Seq. ID No. 30; Bottom Strand: Seq. ID No. 31

FIG. 35
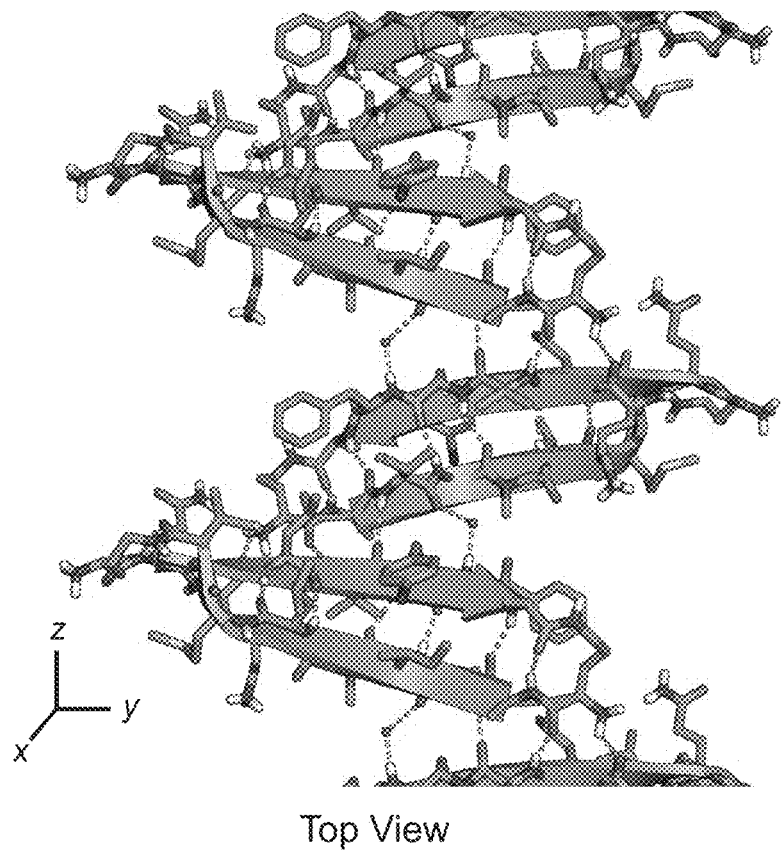
Top View
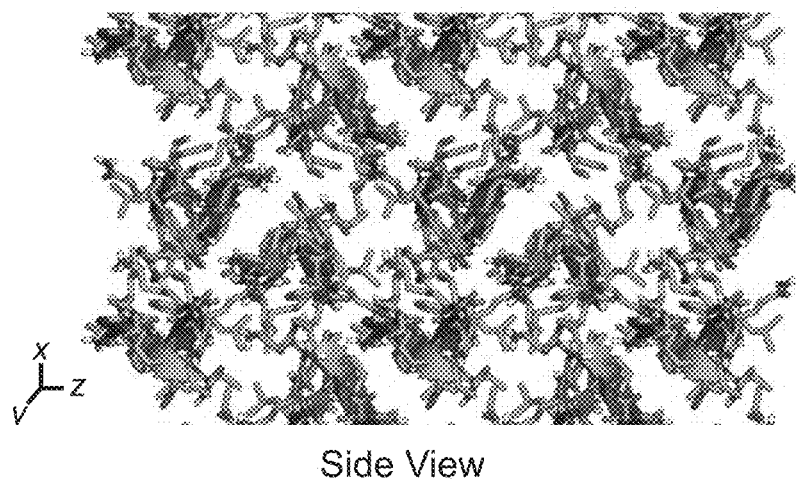
Side View front view            side view

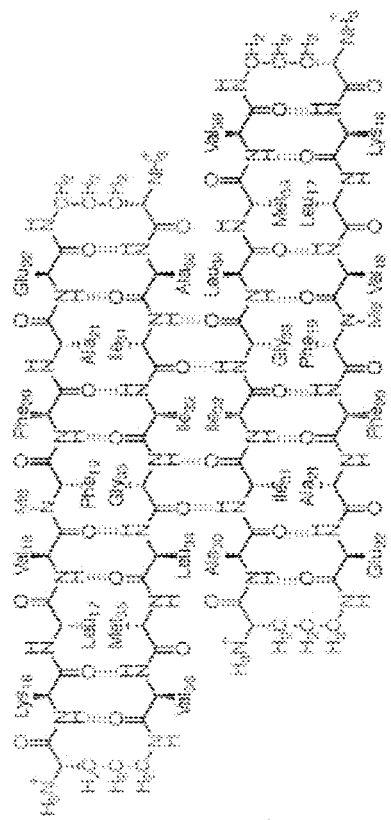
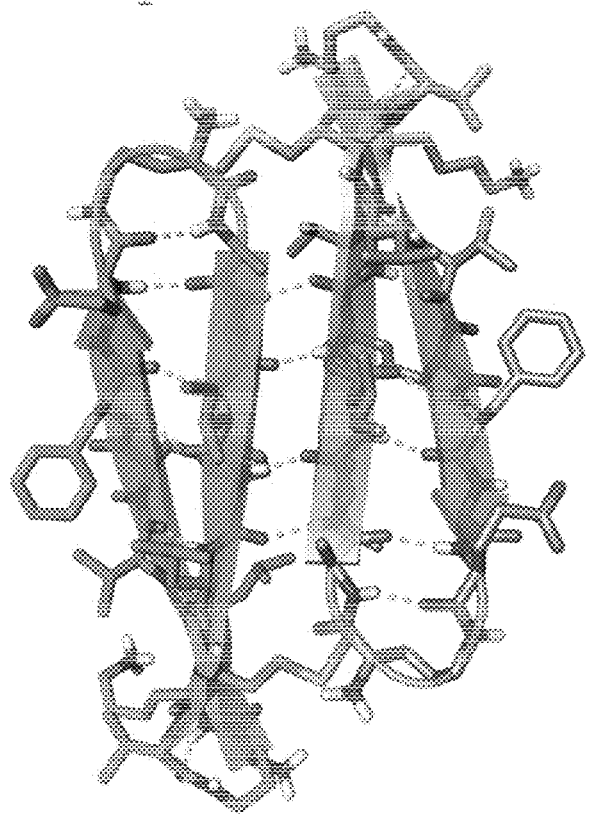
FIG. 46B
FIG. 46A
Top Strand: Seq. ID No. 33
Bottom Strand: Seq. ID No. 34

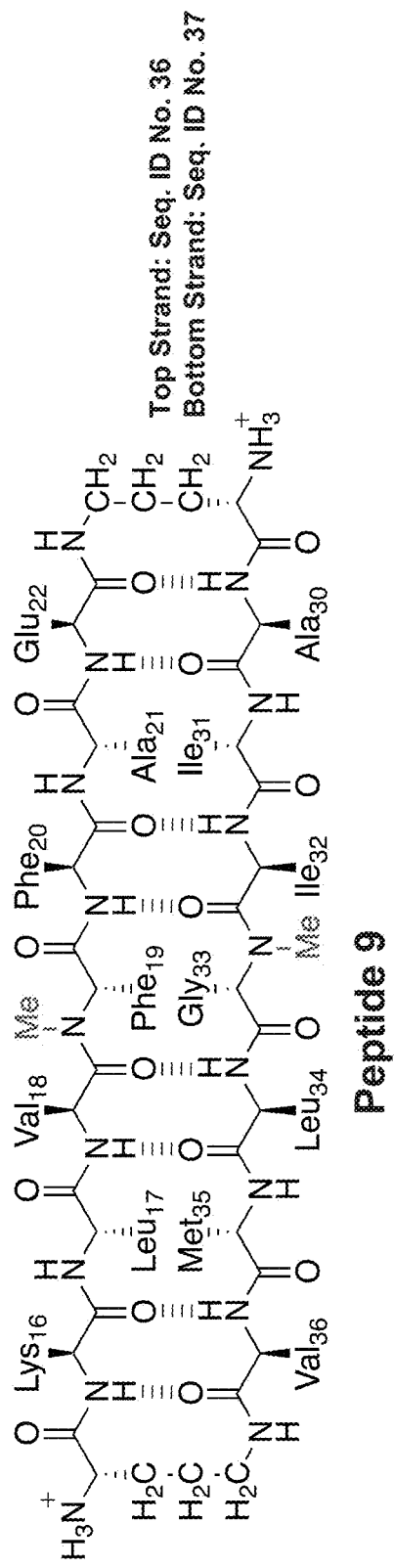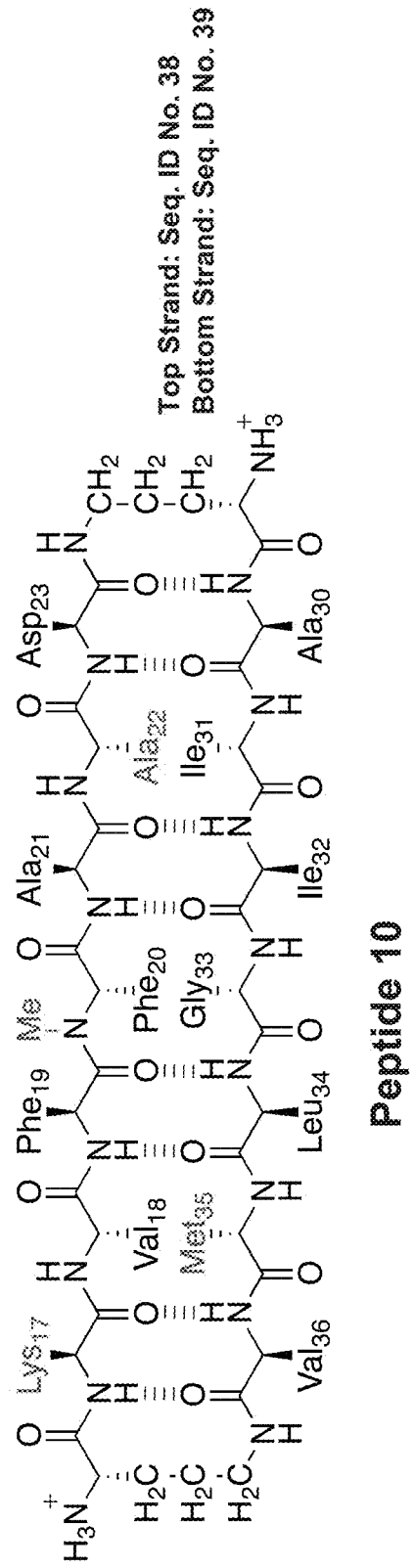

peptide 2 peptide 8 peptide 10

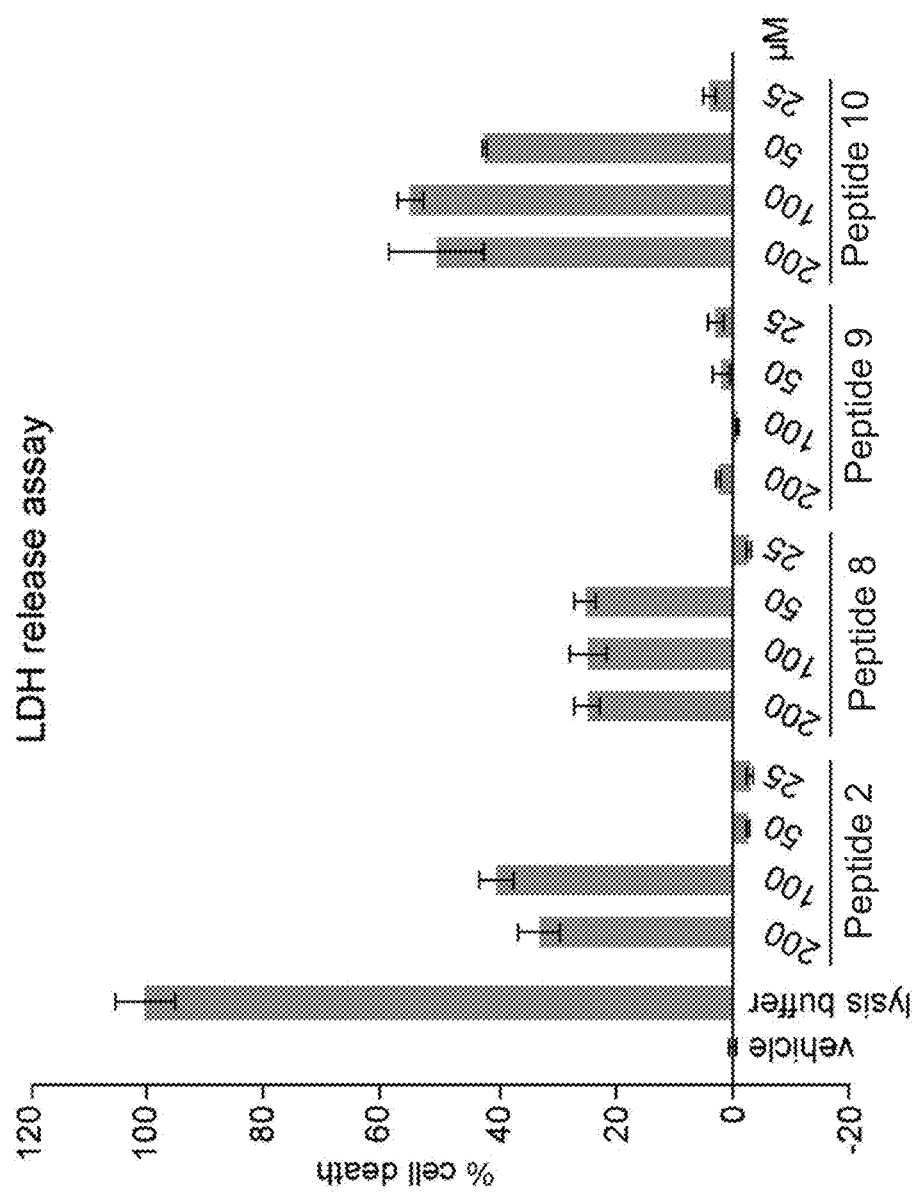

FIG. 59
AD brain slice
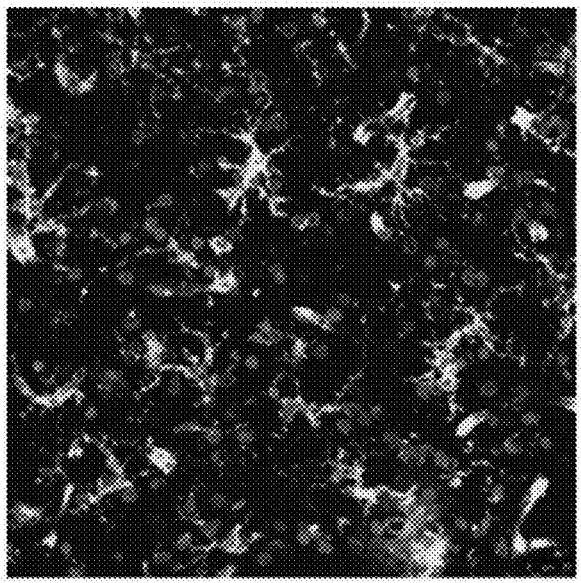
normal brain slice
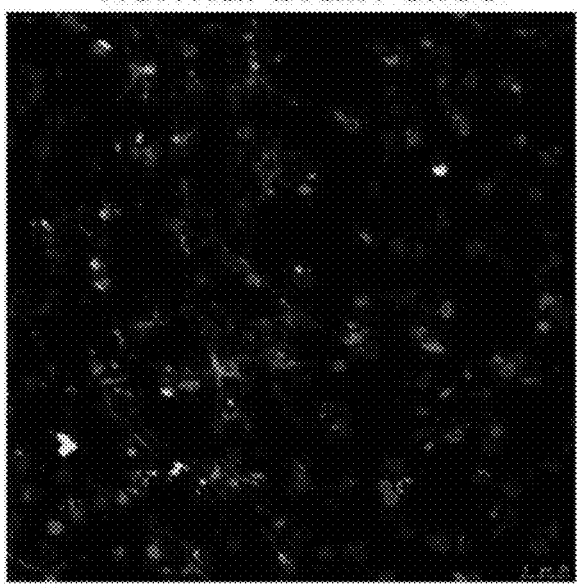
yellow: polyclonal antibodies against crosslinked trimer
blue: DAPI (nuclei)
red: glial fibrillary acidic protein (GFAP), an astrocyte specific marker
brain slices from superior temporal gyrus

FIG. 61
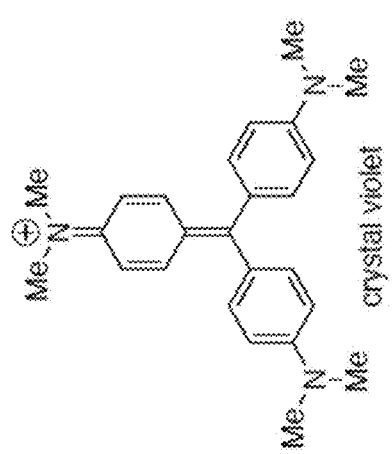
crystal violet
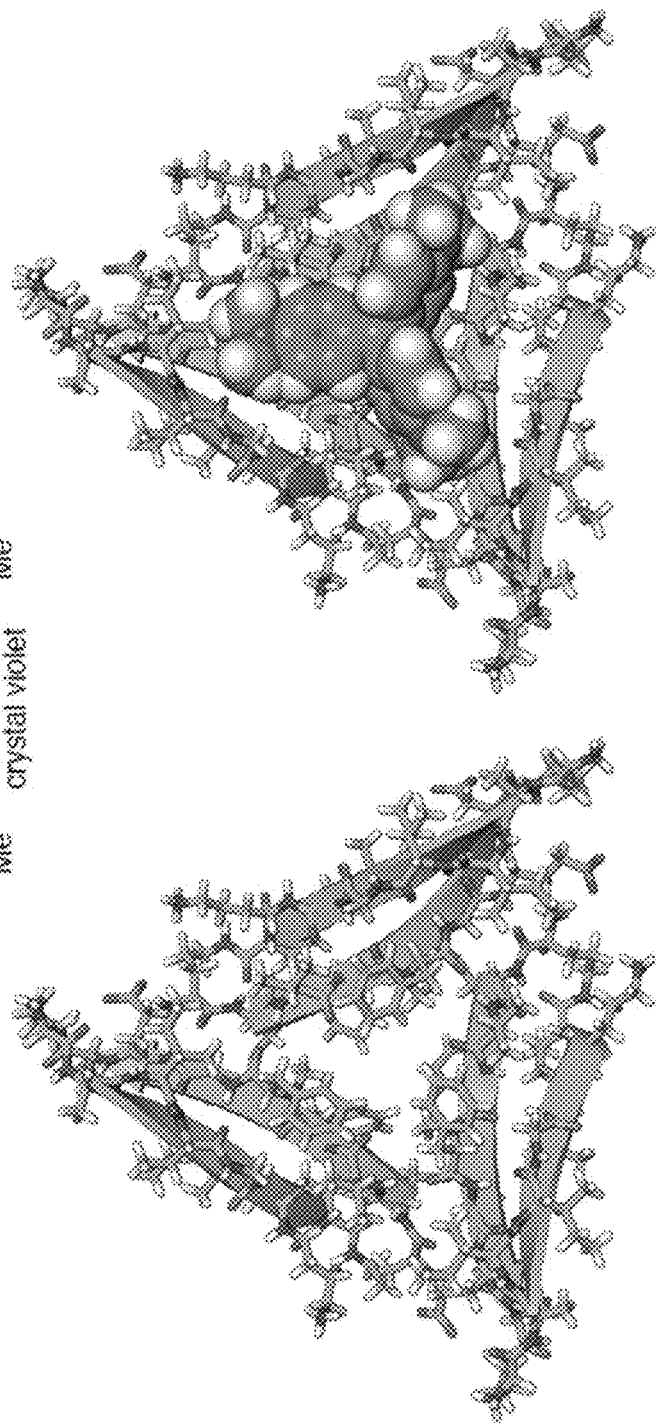

fluorescence spectra

SYNTHETIC BETA-AMYLOID PEPTIDES CAPABLE OF FORMING STABLE ANTIGENIC OLIGOMERS

CROSS REFERENCE TO RELATED APPLICATIONS

This application is a continuation of U.S. patent application Ser. No. 15/794,776, entitled "Synthetic Beta-Amyloid Peptides Capable of Forming Stable Antigenic Oligomers" to Nowick et al., filed Oct. 26, 2017, which claims priority to U.S. Provisional Application Ser. No. 62/414,326, entitled "Synthetic Beta-Amyloid Peptides Capable of Stabilized, Cross-Linked Oligomerization" to Nowick et al., filed Oct. 28, 2016, which is incorporated herein by reference in its entirety.

STATEMENT REGARDING FEDERALLY SPONSORED RESEARCH OR DEVELOPMENT

This invention was made with Governmental support under Grant No. GM09762 awarded by the National Institutes of Health. The government has certain rights in the invention.

REFERENCE TO A SEQUENCE LISTING SUBMITTED ELECTRONICALLY VIA EFS-WEB

The instant application contains a Sequence Listing which has been filed electronically in ASCII format and is herein incorporated by reference in its entirety. Said ASCII copy, created on Jul. 28, 2020, is named "04843conSeqList_ST25" and is 16,684 bytes in size.

FIELD OF THE INVENTION

The present invention is directed to synthetic peptides and oligomers, and methods of synthesis and applications thereof; and more particularly to synthetic peptides and stabilized antigenic oligomers that mimic amyloid-beta and higher-order conformations thereof. The present invention is also directed to antigen binding molecules that specifically and preferentially target soluble amyloid-beta oligomers.

BACKGROUND OF THE INVENTION

Amyloid precursor protein (APP) is an integral membrane protein expressed in mammalian neurons. The protein concentrates around synapses and likely is involved in neural development and synaptogenesis (Rik van der Kant and Lawrence S. B. Goldstein, *Dev Cell* 2015; 32(4):502-15, the disclosure of which is incorporated herein by reference). Although expression is highest during development, APP remains expressed throughout life, possibly regulating lipid reorganization during synaptic activity.

APP undergoes extensive and complex proteolytic processing to create several peptide fragments. These fragments include μ-amyloid (Aβ), soluble APPα (sAPPα), soluble APPβ (sAPPβ), APP intracellular domain (AICD), c-terminal fragment 99 (C99), c-terminal fragment (C83), and P3. Of particular interest are the Aβ fragments, which are peptides typically between 30 and 51 amino acids derived from the extracellular portion of APP. The most common Aβ peptides are $A\beta_{1-40}$ and $A\beta_{1-42}$ (FIG. 1 and Seq. ID Nos. 1 and 2).

Common features in the neurodegenerative Alzheimer's disease (AD) are oligomerization and fibril aggregation of Aβ in the extracellular space around neuronal junctions. Some experts have suggested that soluble oligomeric forms of the peptide are causal in development of the disease (see, I. Benilova, et al. *Nat. Neurosci.* 2012 15, 349-357; and L. N. Zhao, et al., *Int J Mol Sci.* 2012 13, 7303-7327; the disclosures of which are incorporated herein by reference). Despite great efforts to research and comprehend the relationship between Aβ oligomers and AD, there are still many unanswered and challenging questions regarding this relationship.

SUMMARY OF THE INVENTION

Many embodiments are directed a synthetic beta-amyloid peptide that comprises a peptide selected from a group consisting of: (1) a peptide having a substantially similar sequence to Seq. ID. No. 3; (2) a peptide having a substantially similar sequence to Seq. ID. No. 4; (3) a peptide consisting of a first and a second strand, wherein the first strand has a sequence substantially similar to Seq. ID No. 5 and the second strand has a sequence substantially similar to Seq. ID No. 6, wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand; and (4) a peptide consisting of a first and a second strand, wherein the first strand has a sequence substantially similar to Seq. ID No. 7 and the second strand has a sequence substantially similar to Seq. ID No. 8, wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand. It should be understood that these embodiments can be restated visually, such that a synthetic beta-amyloid peptide comprising a peptide having a molecular formula selected from a group consisting of:

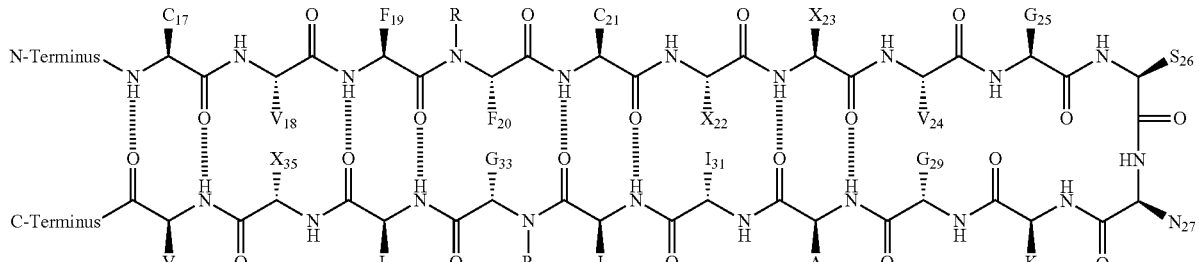

and

-continued

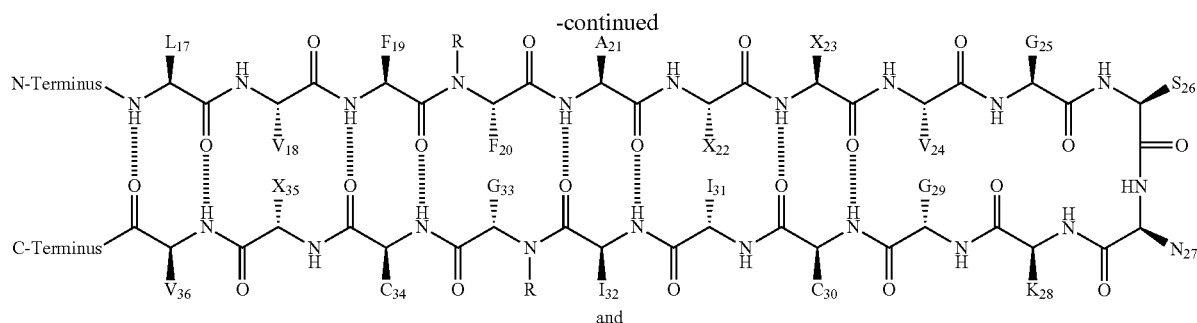

and

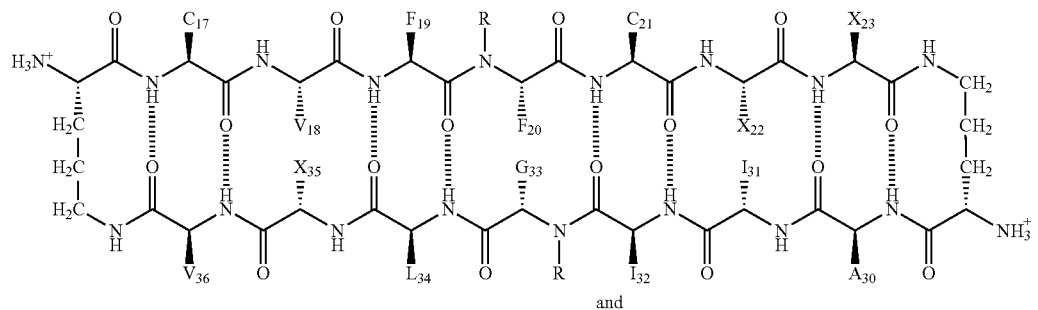

and

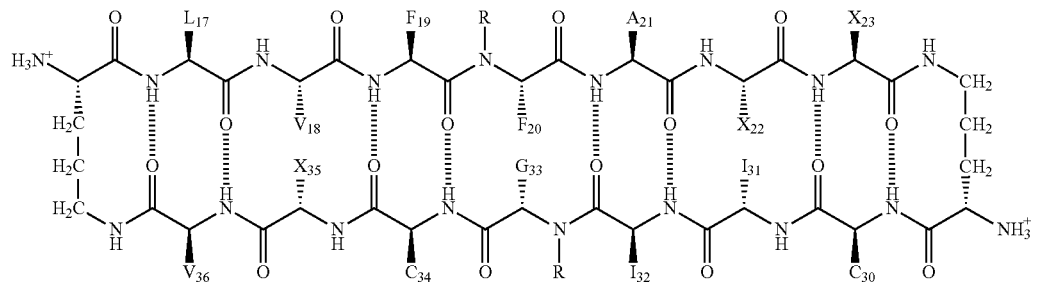

wherein N-terminus is an optional peptide having a sequence selected from a group consisting of Seq. ID No. 9 and $Orn_{16}$; wherein C-terminus is an optional peptide having a sequence selected from a group consisting of Seq. ID No. 10 and Seq. ID No. 11; wherein $X_{22}$ is an amino acid selected from a group consisting of $E_{22}$, $Q_{22}$, and $K_{22}$; wherein $X_{23}$ is an amino acid selected from a group consisting of $D_{23}$ and $N_{23}$; wherein $X_{35}$ is an amino acid selected from a group consisting of $M_{35}$, $Orn_{35}$, and $MetO_{35}$; and wherein R is a substituent selected from a group consisting of H, Me, alkyl, and aryl.

In more embodiments, a synthetic beta-amyloid peptide further comprises at least two more synthetic beta-amyloid peptides, wherein three synthetic beta-amyloid peptides are covalently linked by cysteine disulfide bridges to form a trimer.

In even more embodiments, the trimer consists of a first, a second, and a third synthetic beta-amyloid peptide; wherein each peptide consists of a first and a second strand; wherein the first strand has a sequence substantially similar to Seq. ID No. 5 and the second strand has a sequence substantially similar to Seq. ID No. 6; wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand; and (4) a peptide consisting of a first and a second strand, wherein the first strand has a sequence substantially similar to Seq. ID No. 7 and the second strand has a sequence substantially similar to Seq. ID No. 8, wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand. It should be understood that these embodiments can be restated visually, such that a synthetic beta-amyloid peptide comprising a peptide having a molecular formula selected from a group consisting of:

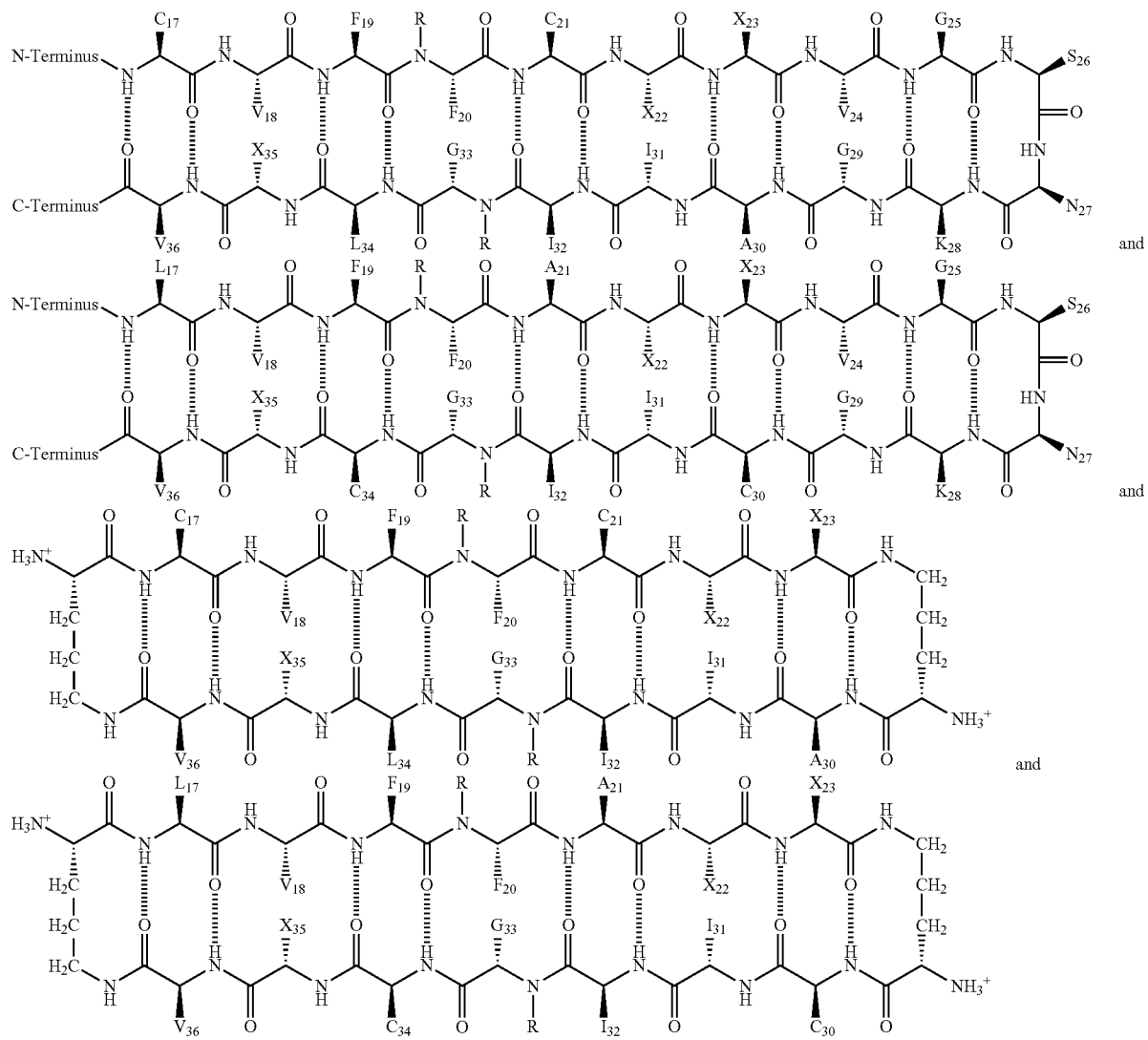

wherein N-terminus is an optional peptide having a sequence selected from a group consisting of Seq. ID No. 9 and $Orn_{16}$; wherein C-terminus is an optional peptide having a sequence selected from a group consisting of Seq. ID No. 10 and Seq. ID No. 11; wherein $X_{22}$ is an amino acid selected from a group consisting of $E_{22}$, $Q_{22}$, and $K_{22}$; wherein $X_{23}$ is an amino acid selected from a group consisting of $D_{23}$ and $N_{23}$; wherein $X_{35}$ is an amino acid selected from a group consisting of $M_{35}$, $Orn_{35}$, and $MetO_{35}$; and wherein R is a substituent selected from a group consisting of H, Me, alkyl, and aryl.

In more embodiments, a synthetic beta-amyloid peptide further comprises at least two more synthetic beta-amyloid peptides, wherein three synthetic beta-amyloid peptides are covalently linked by cysteine disulfide bridges to form a trimer.

In even more embodiments, the trimer consists of a first, a second, and a third synthetic beta-amyloid peptide; wherein each peptide consists of a first and a second strand; wherein the first strand has a sequence substantially similar to Seq. ID No. 5 and the second strand has a sequence substantially similar to Seq. ID No. 6; wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand. Furthermore, the cysteine in amino acid position two of the first strand of the first peptide forms a disulfide linkage with the cysteine in amino acid position six of the first strand of the second peptide; and the cysteine in amino acid position two of the first strand of the second peptide forms a disulfide linkage with the cysteine in amino acid position six of the first strand of the third peptide; and the cysteine in amino acid position two of the first strand of the third peptide forms a disulfide linkage with the cysteine in amino acid position six of the first strand of the first peptide. It should be understood that these embodiments can be restated visually, such that the trimer has the molecular formula:

N-terminal ornithine of the first strand to the C-terminus of the second strand, and wherein the first and second strand are also covalently linked by the delta-amino group of the side chain of the N-terminal ornithine of the second strand to the C-terminus of the first strand. Furthermore, the cysteine in amino acid position two of the first strand of the first peptide forms a disulfide linkage with the cysteine in amino acid position six of the first strand of the second peptide; and the cysteine in amino acid position two of the first strand of the second peptide forms a disulfide linkage with the cysteine in amino acid position six of the first strand of the third peptide; and the cysteine in amino acid position two of the first strand of the third peptide forms a disulfide linkage with the cysteine in amino acid position six of the first strand of the first peptide. It should be understood that these embodiments can be restated visually, such that the trimer has the molecular formula:

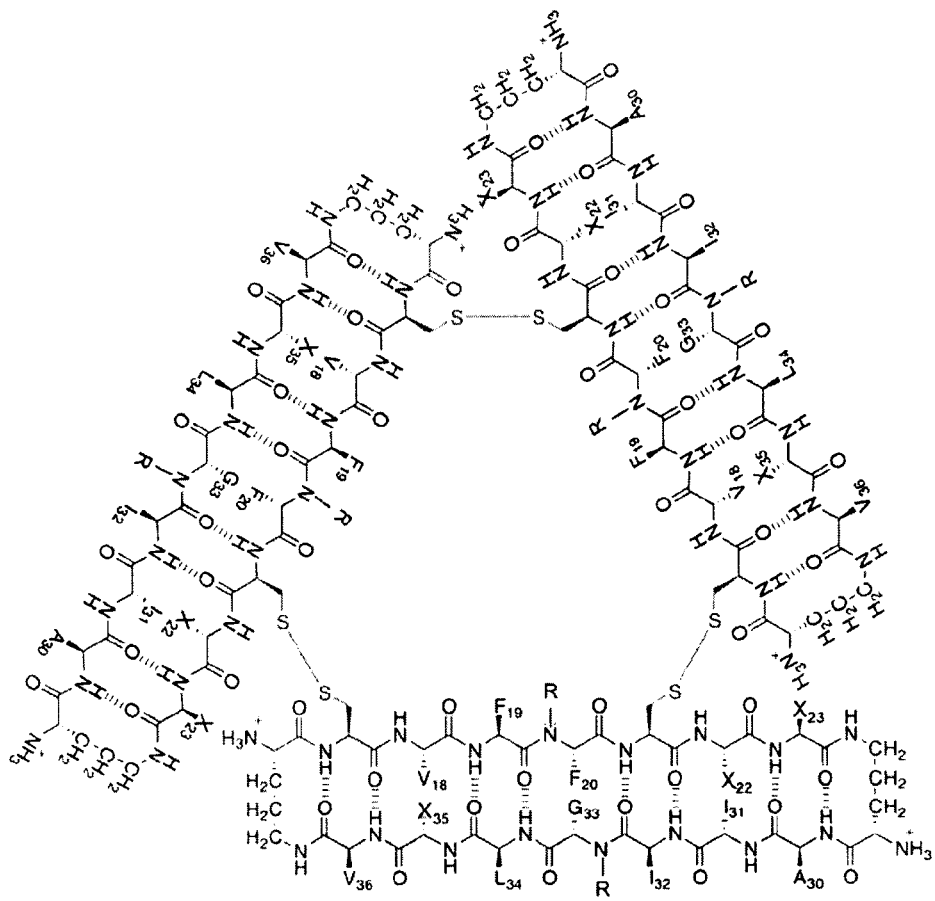

wherein $X_{22}$ is an amino acid selected from a group consisting of $E_{22}$, $Q_{22}$, and $K_{22}$; wherein $X_{23}$ is an amino acid selected from a group consisting of $D_{23}$ and $N_{23}$; wherein wherein $X_{22}$ is an amino acid selected from a group consisting of $E_{22}$, $Q_{22}$, and $K_{22}$;
wherein $X_{23}$ is an amino acid selected from a group consisting of $D_{23}$ and $N_{23}$; wherein
$X_{35}$ is an amino acid selected from a group consisting of $M_{35}$, $Orn_{35}$, and $MetO_{35}$; and
wherein R is a substituent selected from a group consisting of H, Me, alkyl, and aryl.

In further more embodiments, the trimer consists of a first, a second, and a third synthetic beta-amyloid peptide; wherein each consists of a first and a second strand; wherein the first strand has a sequence substantially similar to Seq. ID No. 7 and the second strand has a sequence substantially similar to Seq. ID No. 8; wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand. Furthermore, the cysteine in amino acid position two of the second strand of the first peptide forms a disulfide linkage with the cysteine in amino acid position six of the second strand of the second peptide; and the cysteine in amino acid position two of the second strand of the second peptide forms a disulfide linkage with the cysteine in amino acid position six of the second strand of the third peptide; and the cysteine in amino acid position two of the second strand of the third peptide forms a disulfide linkage with the cysteine in amino acid position six of the second strand of the first peptide.

In even further more embodiments, at least one synthetic beta-amyloid peptide incorporates an ornithine in the amino acid position that corresponds to methionine35 of a naturally occurring beta-amyloid peptide.

In even further more embodiments, at least one central amino acid is N-methylated.

In even further more embodiments, the synthetic beta-amyloid peptide has at least one amino acid mutation that corresponds to familial Alzheimer's disease.

Many embodiments are directed to a method of producing antibodies having affinity for soluble beta-amyloid oligomers that comprises administering an immunocompetent animal with an immunogenic cocktail comprising synthetic crosslinked beta-amyloid trimers, wherein at least one trimer consists of three beta-amyloid peptides; wherein each peptide of the at least one trimer has the same sequence: and wherein each peptide of the at least one trimer is selected from the group consisting of: (1) a peptide having a substantially similar sequence to Seq. ID. No. 3; (2) a peptide having a substantially similar sequence to Seq. ID. No. 4; (3) a peptide consisting of a first and a second strand, wherein the first strand has a sequence substantially similar to Seq. ID No. 5 and the second strand has a sequence substantially similar to Seq. ID No. 6, wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand; and (4) a peptide consisting of a first and a second strand, wherein the first strand has a sequence substantially similar to Seq. ID No. 7 and the second strand has a sequence substantially similar to Seq. ID No. 8, wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand. It should be understood that these embodiments can be restated visually, such that a method of producing antibodies having affinity for soluble beta-amyloid oligomers comprises administering an immunocompetent animal with an immunogenic cocktail comprising synthetic crosslinked beta-amyloid trimers, wherein at least one trimer consists of three beta-amyloid peptides having a molecular formula selected from a group consisting of:

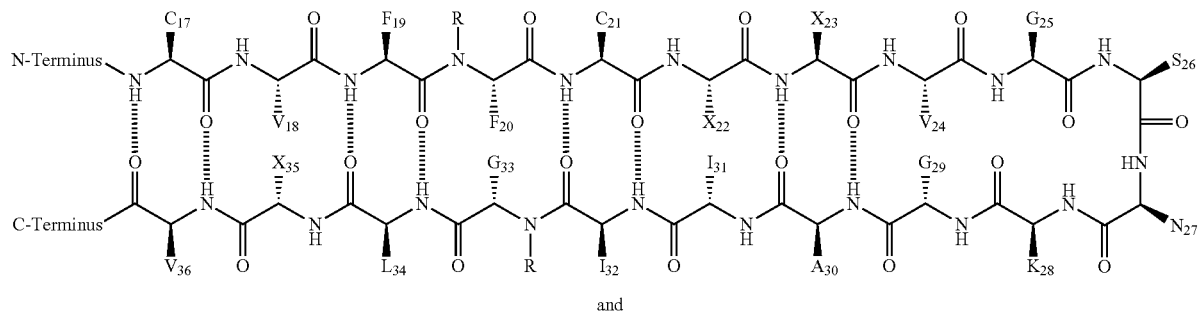

and

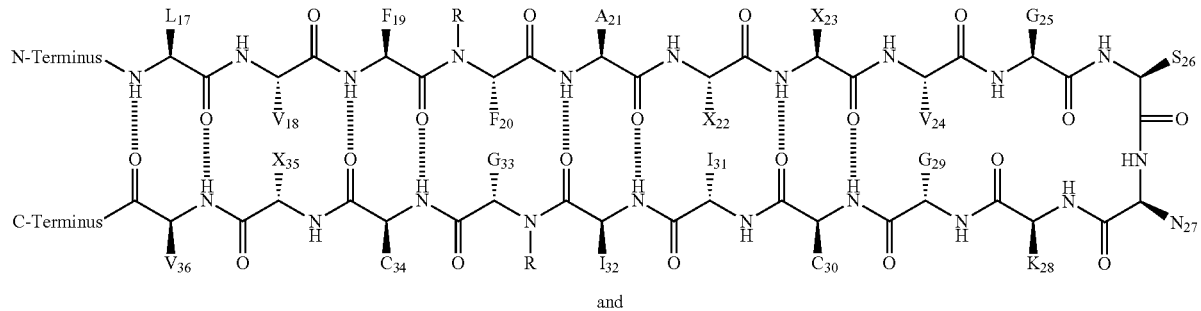

and

-continued

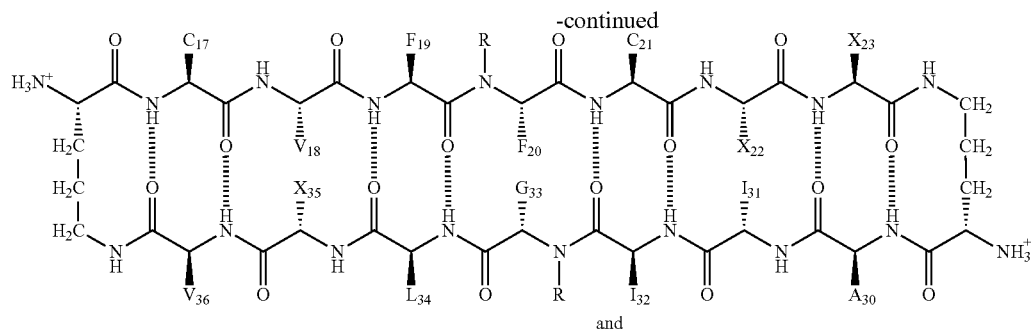

and

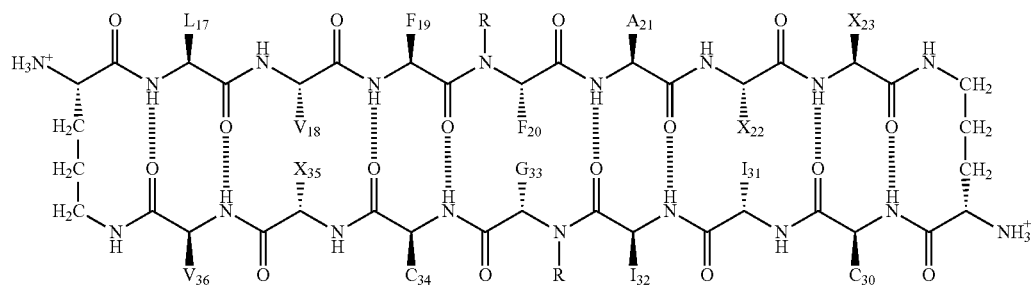

wherein N-terminus is an optional peptide having a sequence selected from a group consisting of Seq. ID No. 9 and Orn$_{16}$; wherein C-terminus is an optional peptide having a sequence selected from a group consisting of Seq. ID No. 10 and Seq. ID No. 11; wherein $X_{22}$ is an amino acid selected from a group consisting of $E_{22}$, $Q_{22}$, and $K_{22}$; wherein $X_{23}$ is an amino acid selected from a group consisting of $D_{23}$ and $N_{23}$; wherein $X_{35}$ is an amino acid selected from a group consisting of $M_{35}$, Orn$_{35}$, and MetO$_{35}$; and wherein R is a substituent selected from a group consisting of H, Me, alkyl, and aryl.

In more embodiments, a method of producing antibodies further comprises harvesting antibodies from the immunocompetent animal.

In even more embodiments, a method of producing antibodies further comprises repeating administration of beta-amyloid trimers to the immunocompetent animal.

In further more embodiments, the immunocompetent animal is selected from the group consisting of human, rabbit, goat, mouse, rat, chicken, and guinea pig.

In even further more embodiments, the immunogenic cocktail further comprises an adjuvant.

In even further more embodiments, the adjuvant is Freund's adjuvant.

In even further more embodiments, the at least one beta-amyloid trimer is conjugated with hemocyanin.

In even further more embodiments, the immunocompetent animal is a human individual for the purpose of vaccination.

Many embodiments are direct to a method to purify antibodies that comprises having antigen binding molecules in solution. Passing the antigen binding molecules through an affinity chromatography solid phase; wherein the solid phase comprises synthetic crosslinked beta-amyloid trimers able to capture the antigen binding molecules, wherein at least one beta-amyloid trimer consists of three beta-amyloid peptides; wherein each beta-amyloid peptide of the at least one trimer has the same peptide sequence; wherein each peptide of the at least one trimer is selected from the group consisting of (1) a peptide having a substantially similar sequence to Seq. ID. No. 3; (2) a peptide having a substantially similar sequence to Seq. ID. No. 4; (3) a peptide consisting of a first and a second strand, wherein the first strand has a sequence substantially similar to Seq. ID No. 5 and the second strand has a sequence substantially similar to Seq. ID No. 6, wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand; and (4) a peptide consisting of a first and a second strand, wherein the first strand has a sequence substantially similar to Seq. ID No. 7 and the second strand has a sequence substantially similar to Seq. ID No. 8, wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand. Eluting the captured antibodies from the solid phase using a buffer capable of dissociating the captured antibodies from the synthetic crosslinked beta-amyloid trimers. It should be understood that these embodiments can be restated visually, such that a method to purify antibodies comprises having antigen binding molecules in solution. Passing the antigen binding molecules through an affinity chromatography solid phase, wherein the solid phase comprises synthetic crosslinked beta-amyloid trimers able to capture the antigen binding molecules, wherein the beta-amyloid trimers comprise at least three beta-amyloid peptides having a molecular formula selected from a group consisting of:

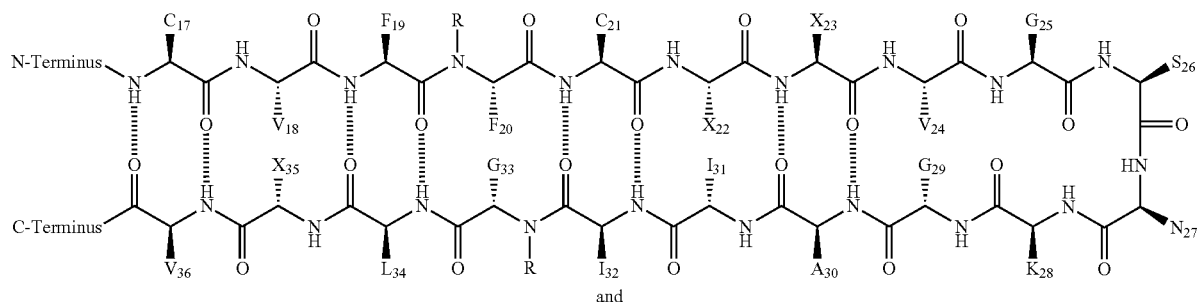
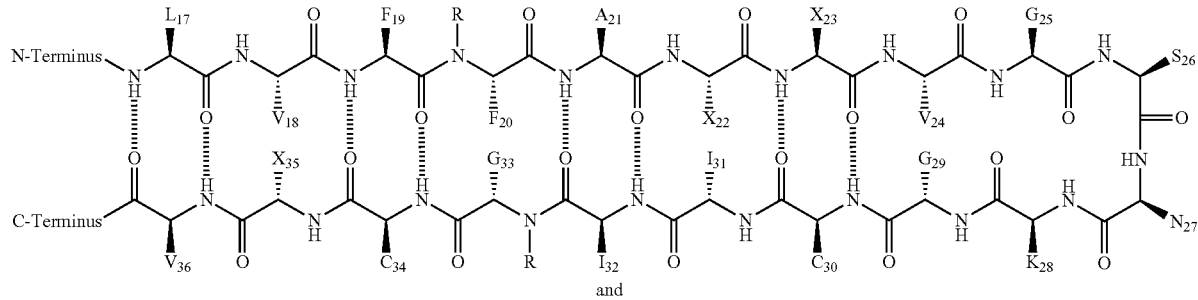
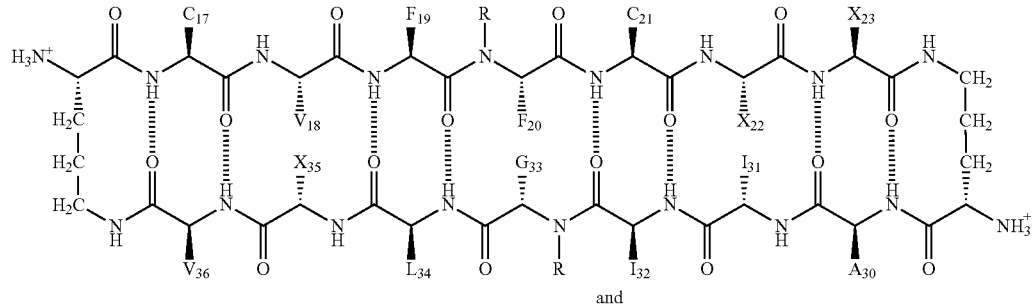
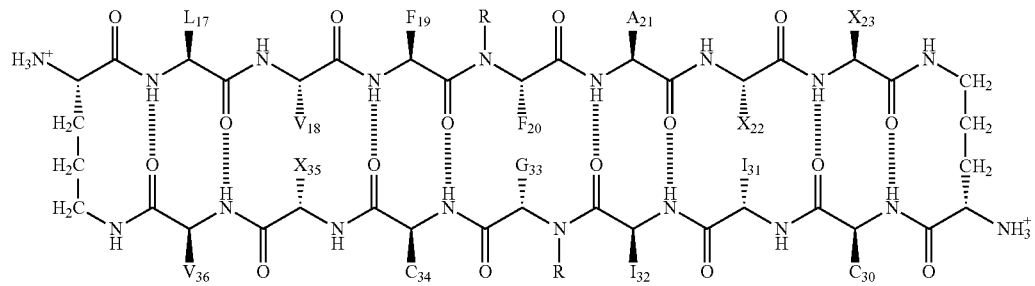

wherein N-terminus is an optional peptide having a sequence selected from a group consisting of Seq. ID No. 9 and $Orn_{16}$; wherein C-terminus is an optional peptide having a sequence selected from a group consisting of Seq. ID No. 10 and Seq. ID No. 11; wherein $X_{22}$ is an amino acid selected from a group consisting of $E_{22}$, $Q_{22}$, and $K_{22}$; wherein $X_{23}$ is an amino acid selected from a group consisting of $D_{23}$ and $N_{23}$; wherein $X_{35}$ is an amino acid selected from a group consisting of $M_{35}$, $Orn_{35}$, and $MetO_{35}$; and wherein R is a substituent selected from a group consisting of H, Me, alkyl, and aryl.

In more embodiments, the antigen binding molecules are a type of molecules selected from the group consisting of polyclonal antibodies, monoclonal antibodies, multispecific antibodies, human antibodies, humanized antibodies, primatized antibodies, chimeric antibodies, single chain antibodies, and epitope-binding fragments of antibodies.

In even more embodiments, the antigen binding molecules are antibodies generated in an immunocompetent animal.

In further more embodiments, the antibodies are generated by administering the immunocompetent animal with an immunogenic cocktail comprising synthetic crosslinked beta-amyloid trimers; wherein at least one beta-amyloid trimer consists of three beta-amyloid peptides; wherein each peptide of the at least one trimer has the same sequence: and wherein each peptide of the at least one trimer is selected from the group consisting of (1) a peptide having a substantially similar sequence to Seq. ID. No. 3; (2) a peptide having a substantially similar sequence to Seq. ID. No. 4; (3) a peptide consisting of a first and a second strand, wherein the first strand has a sequence substantially similar to Seq. ID No. 5 and the second strand has a sequence substantially similar to Seq. ID No. 6, wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand; and (4) a peptide consisting of a first and a second strand, wherein the first strand has a sequence substantially similar to Seq. ID No. 7 and the second strand has a sequence substantially similar to Seq. ID No. 8, wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand. It should be understood that these embodiments can be restated visually, such that the antibodies are generated by administering the immunocompetent animal with an immunogenic cocktail comprising synthetic crosslinked beta-amyloid trimers; wherein at least one trimer consists of three beta-amyloid peptides having a molecular formula selected from a group consisting of:

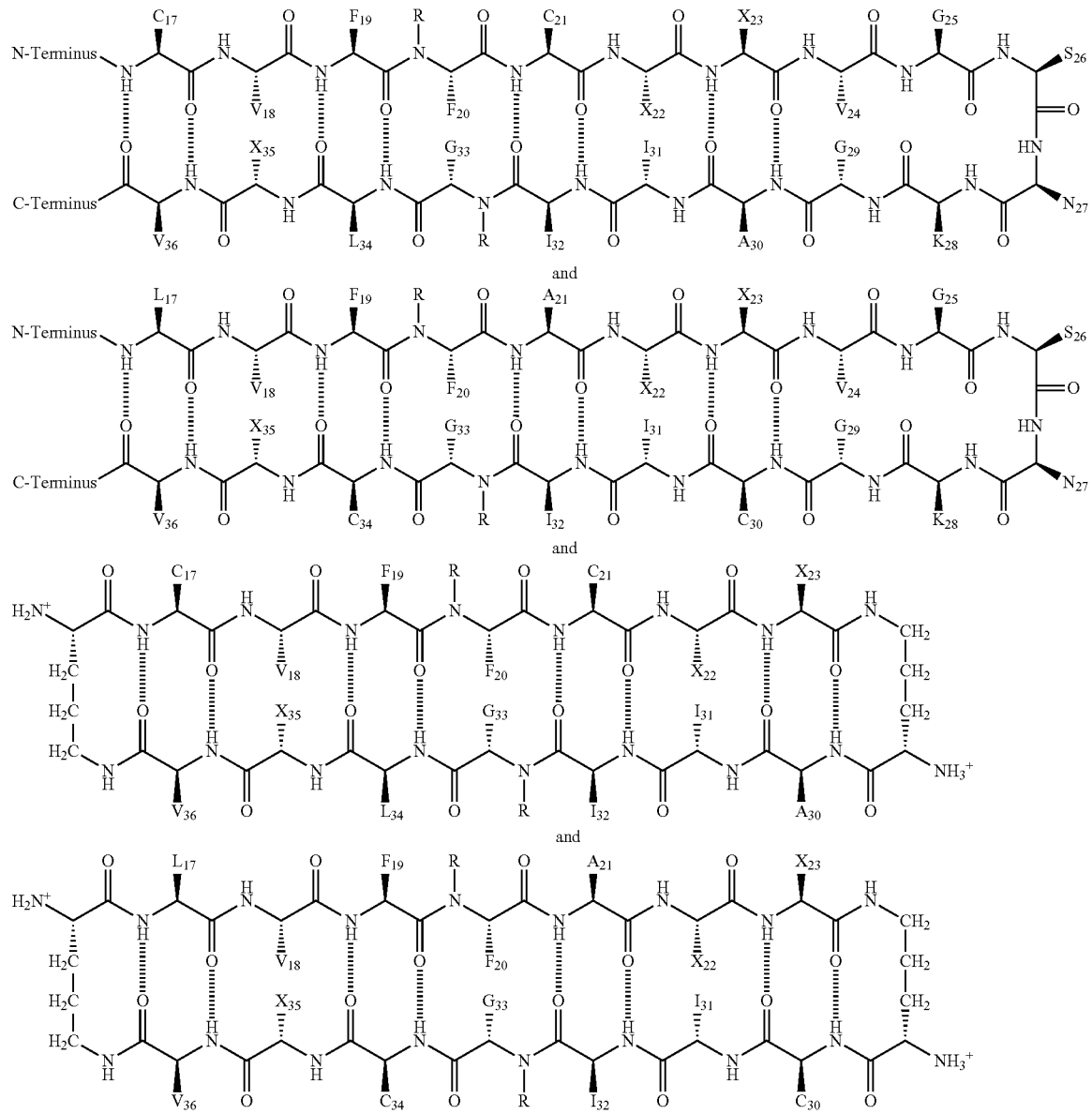

wherein N-terminus is an optional peptide having a sequence selected from a group consisting of Seq. ID No. 9 and $Orn_{16}$; wherein C-terminus is an optional peptide having a sequence selected from a group consisting of Seq. ID No. 10 and Seq. ID No. 11; wherein $X_{22}$ is an amino acid selected from a group consisting of $E_{22}$, $Q_{22}$, and $K_{22}$; wherein $X_{23}$ is an amino acid selected from a group consisting of $D_{23}$ and $N_{23}$; wherein $X_{35}$ is an amino acid selected from a group consisting of $M_{35}$, $Orn_{35}$, and $MetO_{35}$; and wherein R is a substituent selected from a group consisting of H, Me, alkyl, and aryl.

In even further more embodiments, the eluted antigen binding molecules have higher affinity for a soluble oligomer of naturally occurring beta-amyloid than both a monomer of naturally occurring beta-amyloid and an insoluble fibril of naturally occurring beta-amyloid.

In even further more embodiments, the oligomer of naturally occurring beta-amyloid is an oligomer selected from a group consisting of trimers, hexamers, and dodecamers.

In even further more embodiments, the antibodies are derived from an antibody producing cell sourced from a human subject.

In even further more embodiments, the human subject is of at least 65 years of age, having full cognitive capacity, good health, and no clinical signs of dementia.

In even further more embodiments, wherein the antibody producing cell is selected from a group consisting of B cells, B memory cells, hybridomas, and recombinant host cells expressing at least one antibody.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and other features and advantages of the present invention will be better understood by reference to the following detailed description when considered in conjunction with the accompanying drawings where:

FIG. 1 provides a schematic detailing the amino acid sequence of beta-amyloid (Aβ).

FIGS. 3A and 3B provide molecular structure diagrams detailing the chemical structure and peptide sequence of synthetic Aβ peptides with cysteine substitutions in accordance with various embodiments of the invention.

FIG. 17A provides a molecular structure diagram detailing the chemical structure and peptide sequence of peptide 3 in accordance with various embodiments of the invention.

FIG. 17B provides a molecular structure diagram detailing the chemical structure and peptide sequence of peptide 4 in accordance with various embodiments of the invention.

FIG. 31B provides a silver stain of an SDS-PAGE gel of peptides 1 and 2 and trimers 3 and 4 that were ran through an electrophoresis apparatus, generated in accordance with various embodiments of the invention.

FIG. 31C provides a data graph of circular dichroism spectra of peptides 1 and 2 and trimers 3 and 4, generated in accordance with various embodiments of the invention.

FIGS. 35 and 36 provide X-ray crystallographic schematics detailing the chemical structure of fibril-like assemblies formed by peptide 7, generated in accordance with various embodiments of the invention.

FIG. 46A provides an X-ray crystallographic schematic detailing the chemical structures of dimers formed by peptide 8, generated in accordance with various embodiments of the invention.

FIG. 46B provides a molecular structure diagram detailing the chemical structure and peptide sequence of a dimer formed by peptide 8, generated in accordance with various embodiments of the invention.

FIG. 50A provides a molecular structure diagram detailing the chemical structure and peptide sequence of peptide 9 in accordance with various embodiments of the invention.

FIG. 50B provides a molecular structure diagram detailing the chemical structure and peptide sequence of peptide 10 in accordance with various embodiments of the invention.

FIG. 53 provides a data graph detailing the toxicity of peptides 2 and 9-10 to SH-SY5Y cells, generated in accordance with various embodiments of the invention.

FIG. 59 provides fluorescent microscopic images of Alzheimer's disease and healthy brain tissue slices using affinity purified antibodies, generated in accordance with embodiments of the invention.

FIG. 61 provides X-ray crystallographic schematic detailing the ability of crystal violet dye molecules to integrate into a crosslinked trimer 4, generated in accordance with various embodiments of the invention.

DETAILED DISCLOSURE OF THE INVENTION

Figure 2:
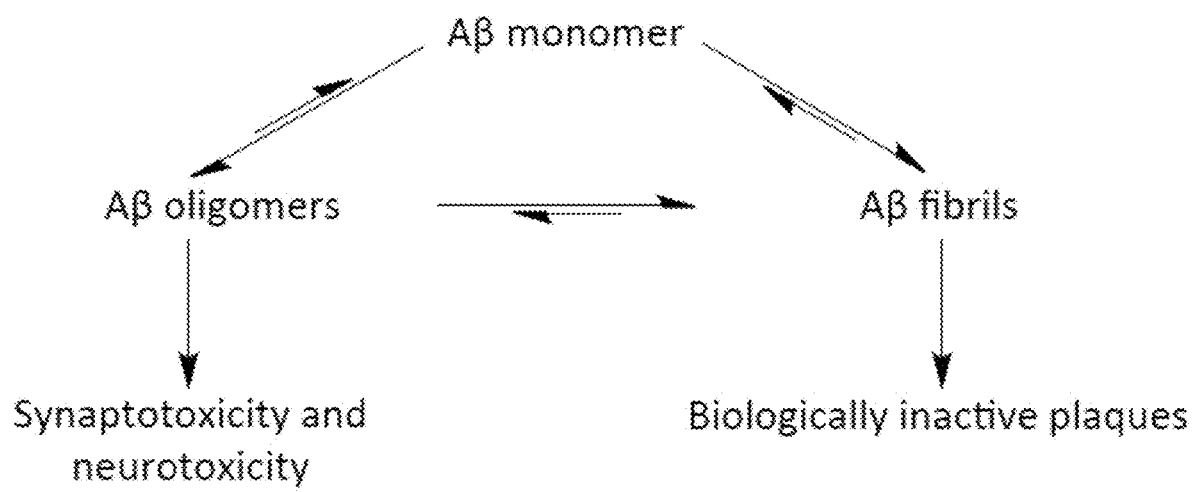
FIG. 2 provides a schematic explaining the higher-order structure of Aβ peptides.

Turning now to the diagrams and figures, synthetic beta-amyloid (Aβ) peptides capable of forming stable oligomers, and synthesis thereof, are described. Embodiments of the invention are directed to synthetic Aβ peptides that are modified from the naturally occurring Aβ found in nature. Some of these embodiments include peptides having a substituted cysteine amino acid in place of a naturally occurring amino acid. Particular Aβ peptide embodiments incorporate the cysteine into amino acid position 17 or 21.

Many other embodiments of the invention are directed to other Aβ peptide modifications; these may include truncation and removal of amino acids, N-methylation of amino acids, covalent linkage of peptides by δ-linked ornithine ($^\delta$Orn) turn mimics, substitution of hydrophobic amino acids with a hydrophilic isostere, or incorporation of amino acid substitutions that correspond with familial version of Alzheimer's disease (AD). In some particular embodiments, the N-terminal region or C-terminal region of the Aβ peptide can be removed. For example, embodiments of the invention include a truncated $A\beta_{17\text{-}36}$ peptide and thus amino acids 1-16 and 37-42 have been removed. In other particular embodiments, amino acids 24-29 are removed to yield distinct N-terminal and C-terminal Aβ peptides. In other embodiments, other truncated Aβ peptides are possible, such as those to mimic $A\beta_{16\text{-}36}$ and $A\beta_{15\text{-}36}$. The various truncations may be combined or in solitude. In addition, a number of embodiments will have a $^\delta$Orn turn mimic to replace the truncated portion of the Aβ peptide. For example, embodiments may have a turn mimic link the N-terminus of Alanine at position 30 ($A_{30}$) with the C-terminus of another amino acid of the peptide (e.g., Aspartate at position 23 ($D_{23}$)). A similar embodiment may have a $^\delta$Orn linkage between the N-terminus of Leucine at position 17 ($L_{17}$) and the C-terminus of another amino acid (e.g., Valine at position 36 ($V_{36}$)). Other embodiments are directed to methylation of the amide of certain amino acids of the Aβ peptide. The methylation can help prevent improper aggregation and fibril formation of the peptides. In particular embodiments, central and outer amides of the Aβ β-hairpin are methylated. In some embodiments, Phenylalanine at position 20 ($F_{20}$), Phenylalanine at position 19 ($F_{19}$) or Glycine at position 33 ($G_{33}$) of Aβ are N-methylated. Other embodiments are directed to increasing the solubility of the peptide by exchanging a hydrophobic amino acid with a hydrophilic isostere. For example, embodiments are direct to Aβ peptides that have substituted the hydrophilic Ornithine at position 35 ($Orn_{35}$) in place of the naturally occurring hydrophobic Methionine ($M_{35}$) that corresponds to naturally occurring Aβ peptides. More embodiments are directed to synthetic Aβ peptides that incorporate amino acid substitutions corresponding with familial AD. In particular, embodiments are directed to Aβ peptides that incorporate known AD mutations, including the Dutch (E22Q), the Iowa (D23N), the Dutch Iowa (E22Q, D23N), the Italian (E22K), and the Osaka (E22del) mutations.

Various embodiments of the invention are also directed to the ability of synthetic Aβ peptides to form secondary structures and tertiary conformations. In several embodiments, the synthetic Aβ peptides form a complementary β-hairpin secondary structure. In accordance with other embodiments, tertiary structures are produced by the Aβ peptides that are higher-order oligomers composed of Aβ monomers. Disulfide crosslinking between modified Aβ peptides with cysteine substitutions assist in the formation, stability, or homogeneity of oligomers of many embodiments. Likewise, embodiments are directed to oligomers that are trimers, hexamers, dodecamers, or annular-pore complexes.

Many other embodiments of the invention are directed to properties or applications of use of synthetic Aβ peptides and oligomers. Many embodiments are directed to Aβ peptides having advantageous properties, including, but not limited to, solubility, cytotoxicity, neurotoxicity, synaptotoxicity, antigenicity, or ability to be targeted by small molecules. As such, embodiments are directed to Aβ peptides and oligomers that remain soluble and do not aggregate to form fibrils. Other embodiments are directed to Aβ peptides and oligomers that are toxic to neuronal cells and disrupt synapse connections. Even other embodiments are directed to the ability to design and produce polyclonal or monoclonal antibodies that bind to synthetic or natural Aβ peptides and oligomers. And even other embodiments are directed to the ability to design small molecule probes or drugs that have an effect on Aβ peptides and oligomers.

More embodiments are direct to antigen binding molecules that have high specificity, preference, and affinity towards soluble oligomers of Aβ. In many of these embodiments, the antigen binding molecules have low affinity for Aβ monomers and insoluble fibrils. Various embodiments include monoclonal or polyclonal antibodies that may be derived from a number of methodologies. In some embodiments, stable crosslinked trimers may be injected into an animal to stimulate an immune response to produce antibodies. In additional embodiments, antigen binding molecules may be selected and/or purified based on their affinity to crosslinked trimers.

Synthetic Aβ Peptides Capable of Crosslinking

In its naturally derived form, Aβ can form peptides of 40 (Aβ$_{40}$) and 42 (Aβ$_{42}$) amino acids (FIG. 1 and Seq. ID Nos. 1 and 2). These naturally occurring peptide monomers are known to form tertiary conformations, including soluble oligomers and insoluble fibrils (FIG. 2). While the insoluble Aβ fibrils form biologically inactive plaques, the Aβ oligomers have been shown to cause neurotoxicity and synaptotoxicity that may be responsible for neurodegeneration in AD. Although it is difficult to control the tertiary conformation of Aβ peptides, it would be beneficial to prevent the formation of fibrils and promote the formation of oligomers for further application. As such, embodiments of the invention are directed to synthetic Aβ peptides modified from the naturally occurring Aβ peptide capable of solubility and oligomer formation. Furthermore, embodiments of the peptide also have the capability of preventing fibril formation and uncontrolled aggregation.

Some embodiments are directed to a synthetic Aβ peptide with cysteine substitutions, replacing some of the naturally occurring amino acids. In many of these embodiments, a cysteine in one synthetic Aβ peptide is capable of forming disulfide bond with a cysteine of another synthetic Aβ peptide. The disulfide bond formation, in many embodiments, can help formulate and stabilize a crosslinked trimer conformation, such that three synthetic Aβ peptides conform into a triangular shape, each monomer linked to another by a disulfide bridge.

Figure 5:
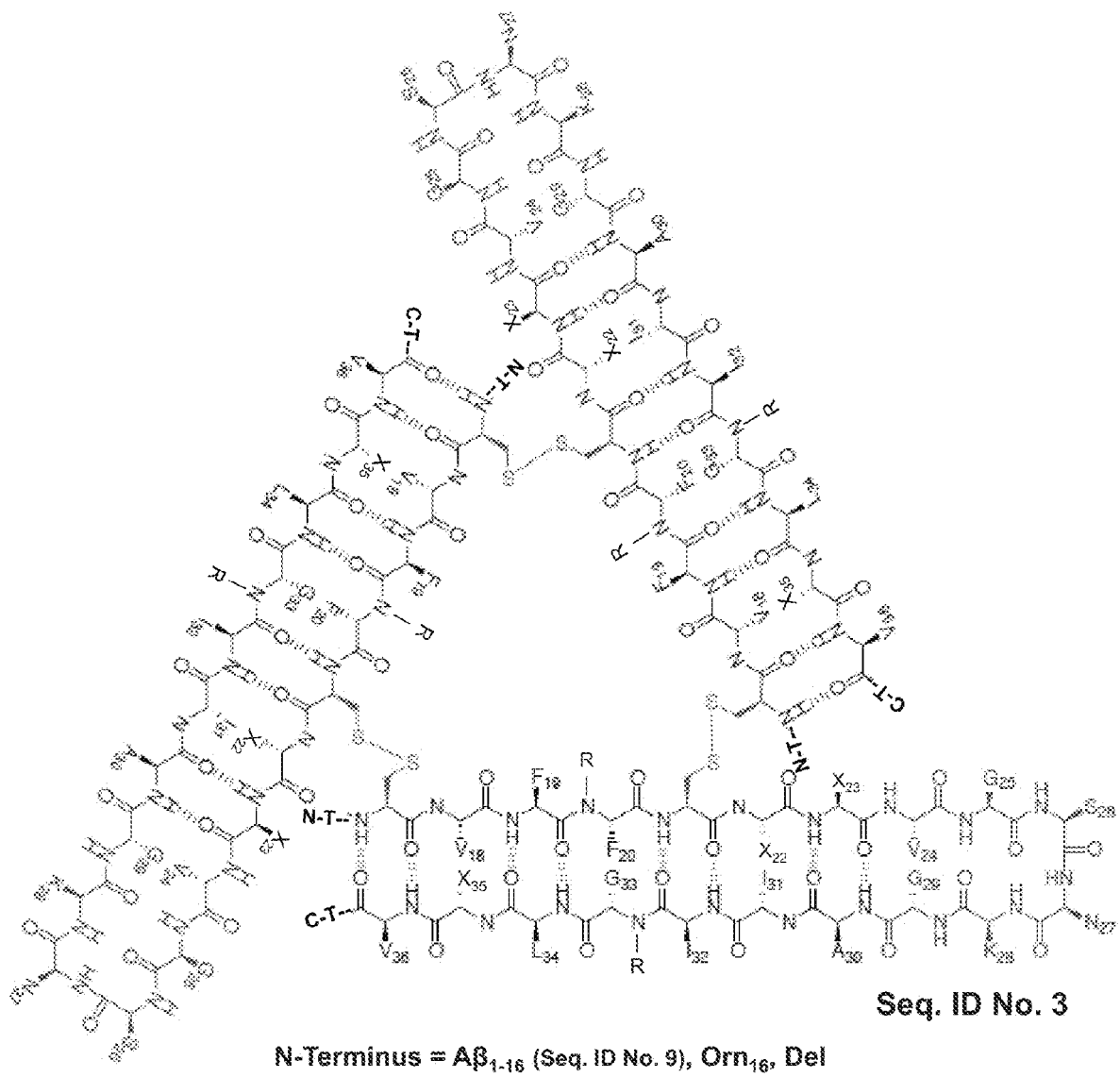
FIGS. 5 and 6 provide molecular structure diagrams detailing the chemical structure and peptide sequence of synthetic crosslinked Aβ trimers with cysteine substitutions in accordance with various embodiments of the invention.
Figure 6:
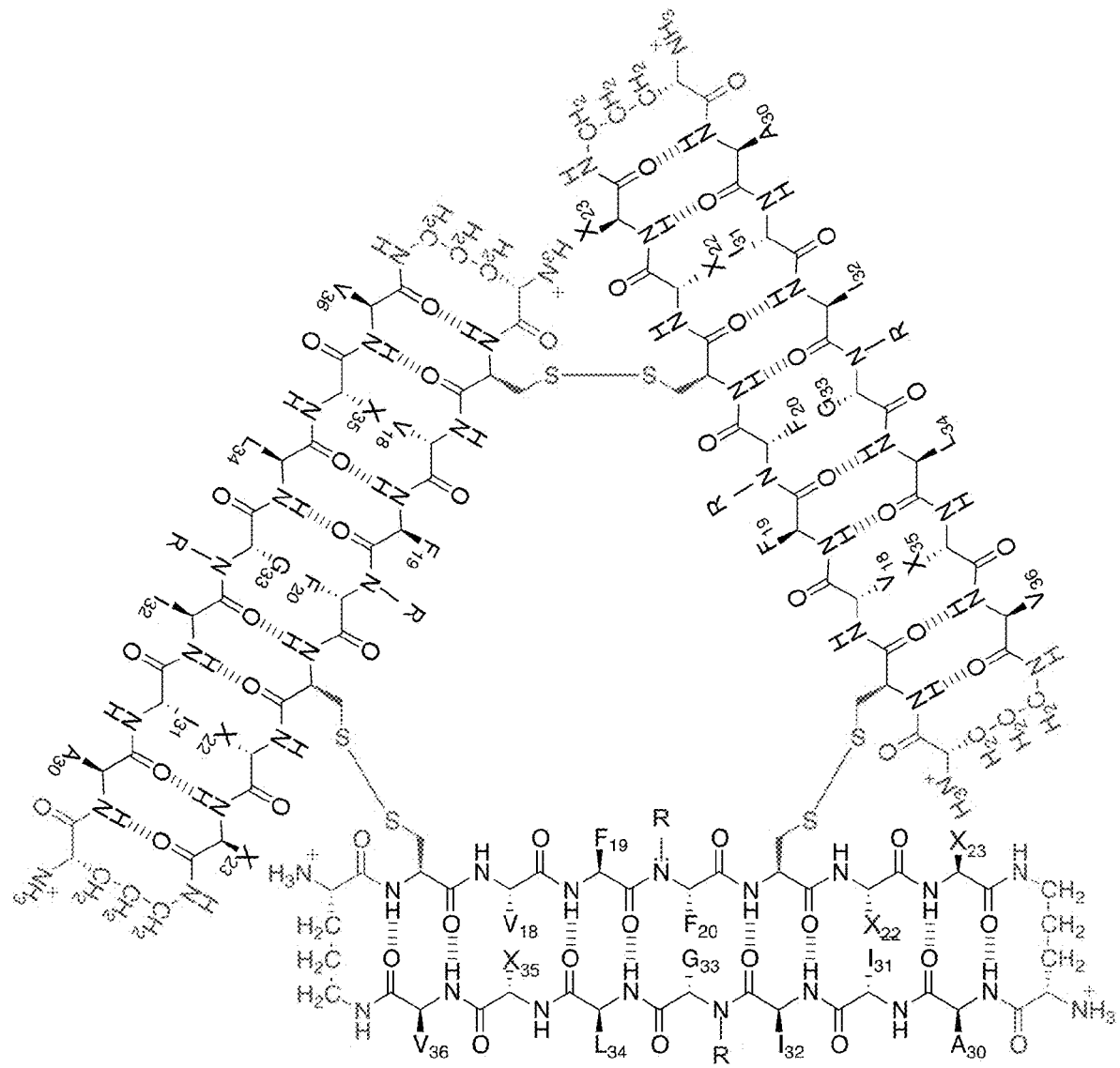

FIGS. 3A to 4B depict some particular embodiments of synthetic Aβ peptides with cysteine substitutions (Seq. ID Nos. 3-8). As shown in FIGS. 3A and 4A, cysteines have been incorporated into amino acid positions 17 and 21, replacing the naturally occurring amino acids $L_{17}$ and $A_{21}$ (Seq. ID Nos. 3 and 5). These cysteines assist formulation and stabilization of a trimer conformation between three monomeric synthetic Aβ peptides (FIGS. 5 and 6). Specifically, the formation of a trimer occurs when a disulfide bond is formed between $C_{17}$ of a first monomer and the $C_{21}$ of a second monomer. The same bond is repeated between the second monomer and a third, and again with the third monomer and the first. This trimer formation helps to form a stable triangular-like shape that is resistant to fibril formation and uncontrolled aggregation.

Figure 3B:
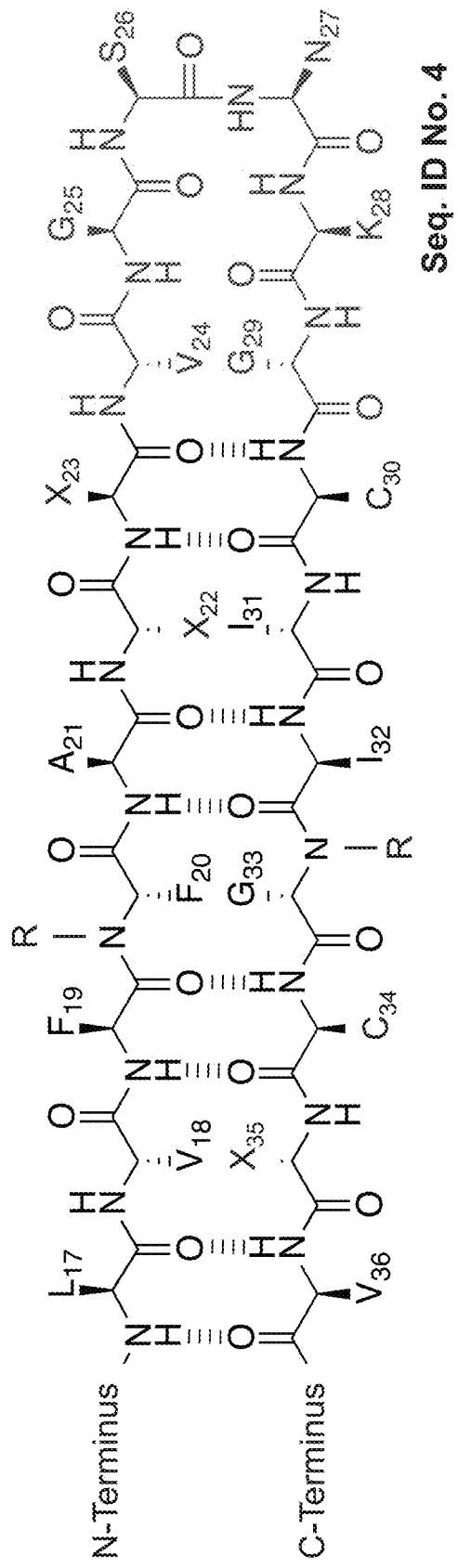
Figure 4A:
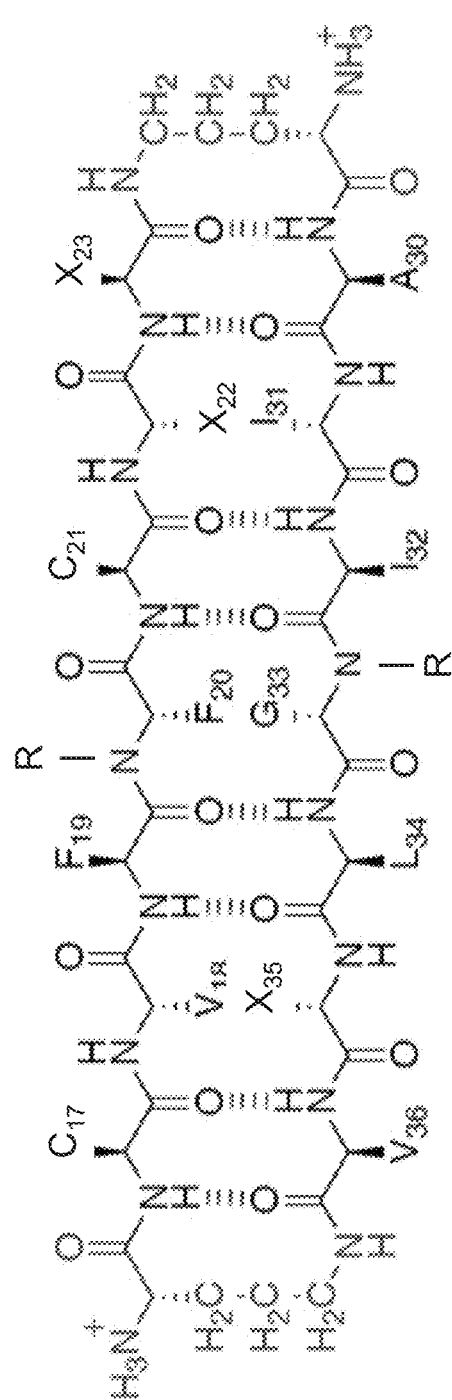
FIGS. 4A and 4B provide molecular structure diagrams detailing the chemical structure and peptide sequence of synthetic crosslinked Aβ peptides with cysteine substitutions in accordance with various embodiments of the invention.
Figure 4B:
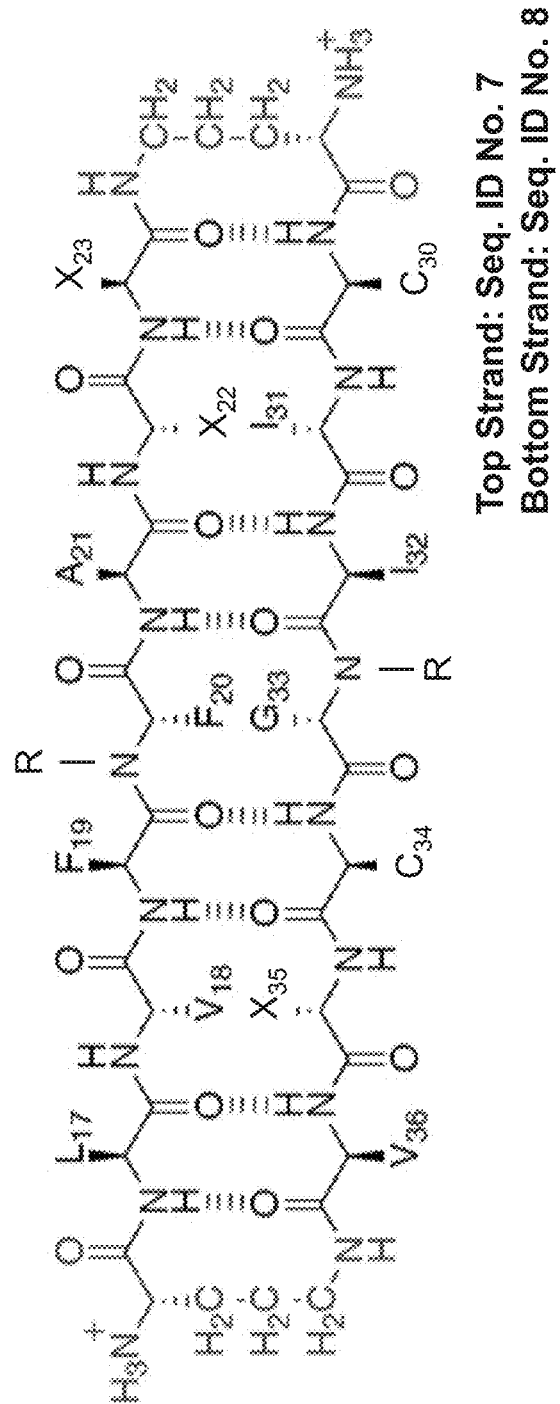

Although FIGS. 3A and 4A depict cysteine substitutions in amino acid position 17 and 21, other substitutions are possible. For example, replacing $A_{30}$ and $L_{34}$ with cysteines will also result in a peptide capable of forming a triangular trimer that is stable and resistant to fibril formation (FIGS. 3B and 4B; Seq. ID Nos. 4 and 8). It is possible that other amino acids could be substituted with cysteines as well, however proper location of the cysteines is necessary to ensure proper distance between the bridged cysteines for quality bond formation and stable conformation.

Several more embodiments are directed to further modification of synthetic Aβ peptides. Modifications include truncation and removal of amino acids, N-methylation of amino acids, covalent linkage of peptides by $^δ$Orn turn mimics, and substitution of hydrophobic amino acids with a hydrophilic isostere. The modifications may assist with solubility, stable oligomer formation, prevention of uncontrolled aggregation, or ease of synthesis.

Figure 7A:
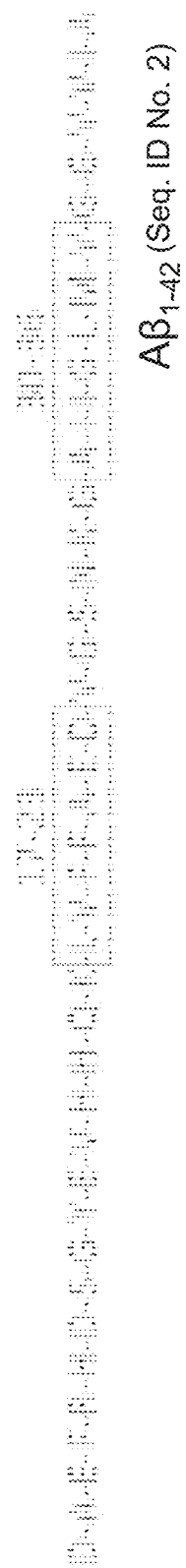
FIGS. 7A and 7B provide schematics detailing the important amino acids for β-hairpin formation in Aβ peptides.
Figure 7B:
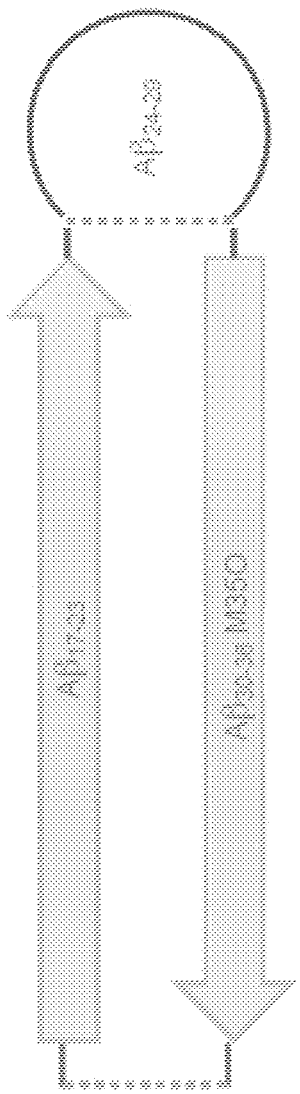

Many embodiments are directed to synthetic Aβ peptides that are truncated with portions of naturally occurring amino acids removed. Truncation of the peptides has several benefits, including, but not limited to, facilitating synthesis of the peptide, removing unnecessary amino acids for oligomer formation, and increasing solubility. Truncation of the peptide can vary and still obtain equivalent or similar results. Some important peptides for Aβ β-hairpin formation are amino acids 17-23 and 30-36, respectively (See FIGS. 7A and 7B). Thus, the Aβ peptide can be truncated at the N-terminal end from amino acid position 1 to approximately amino acid position 16 (Seq. ID No. 9), at the C-terminal end from approximately amino acid position 37 to amino acid position 40/42 (Seq. ID Nos. 10 and 11), and within the peptide between approximately amino acid 24 to approximately amino acid 29 (See FIGS. 3A-4B and 7B; Seq. ID Nos. 3-8). In accordance with these principles, embodiments are directed to Aβ peptide truncations that remove amino acids that are unnecessary for β-hairpin formation, including any N-terminal amino acids, C-terminal amino acids, or internal amino acids.

More embodiments of synthetic Aβ peptides are directed to stabilization of β-hairpin formation. As described in the preceding paragraph, important amino acids for β-hairpin formation include 17-23 or 30-36 and unnecessary amino acids can be removed. In various formulations of these embodiments, the β-hairpins can be covalently linked by an N-terminal $^δ$Orn on one β-strand peptide to the opposing, anti-parallel β-strand peptide such that the β-amino group of the ornithine side chain is covalently bonded to the C-terminus of the opposing, anti-parallel β-strand peptide (see FIGS. 4A and 4B; Seq. ID Nos. 5-8). The $^δ$Orn turn mimic stabilizes the interactions (e.g., hydrogen bonds) between the β-strand peptides, ensuring a stable conformation. $^δ$Orn also provides an alternative to replace the naturally occurring Aβ amino acids when the peptide is truncated. Specifically, various embodiments have a $^δ$Orn inserted into amino acid position 16 to covalently link amino acid 16 with the C-terminus of amino acid 36, effectively eliminating the native C and N-termini (FIGS. 3A-4B; Seq. ID Nos. 3-5 and 7). In addition, other embodiments have a $^\delta$Orn inserted into amino acid position 29 to covalently link amino acid 29 with the C-terminus of amino acid 23, effectively eliminating the amino acids 24 to 29 (FIGS. 4A and 4B; Seq. ID Nos. 6 and 8). Accordingly, many embodiments are directed to $^\delta$Orn turn mimics that covalently link opposing, anti-parallel β-strand peptides, and more specifically to an N-terminal $^\delta$Orn covalent linkage of a peptide strand to the C-terminus of the anti-parallel peptide strand.

Further embodiments of synthetic Aβ peptides inhibit fibril formation and uncontrolled aggregation by modifying the peptides with functional groups that promote steric hindrance. Fibril formation and uncontrolled aggregation of Aβ peptides occur when the β-strands of peptides align in a parallel, stacked formation, much like a ladder (R. N. Rambaran and L. C. Serpell, *Prion* 2008, 2, 112-117, the disclosure of which is incorporated herein by reference). This stacking promotes aggregation of Aβ peptides in an uncontrolled and infinitive manner. One way to prevent this aggregation is to substitute alkyl (e.g., methyl), aryl (e.g., benzyl, nitrobenzyl) or other similarly bulky groups with an H on one of the amides of a central amino acid having an outward-facing amide that is not involved in β-hairpin hydrogen bonding (see FIGS. 3A-4B; Seq. ID Nos. 3-8). The bulky group can be substituted on either β-strand, but should not interfere with trimer formation. As shown in FIGS. 3A to 4B, amino acids $F_{20}$ and $G_{33}$ are good candidates for N-methylation in accordance with a number of embodiments. The addition of bulky groups to the peptide backbone sterically hinders the interaction and stacking of β-strands and thus prevents uncontrolled aggregation of Aβ peptides into fibrils. As such, various embodiments are directed to synthetic Aβ peptides with bulky functional groups attached to the peptide backbone that promote steric hindrance, and more specifically to synthetic Aβ peptides with N-methylated amino acids.

Various embodiments also incorporate methods to improve solubility, which is a factor to improve oligomerization and prevent fibril aggregation. To increase solubility, hydrophobic amino acids can be substituted with hydrophilic amino acids. Ideally, in order to keep similar secondary and tertiary structure, isosteric hydrophilic amino acid replacements are preferred, but any suitable hydrophilic amino acid will suffice. Another method to increase solubility is to incorporate oxidized variations of amino acids. For example, a methionine can be oxidized to or substituted with ornithine, methionine sulfoxide or methionine sulfone (e.g., $Met_{35} \rightarrow Orn_{35}$, $Met_{35} \rightarrow MetO_{35}$). Accordingly, embodiments are directed to replacement of hydrophobic amino acids with hydrophilic amino acids, and more specifically to isosteric hydrophilic amino acid replacements. More embodiments are directed to oxidation of various amino acids or replacement of amino acids with an oxidized equivalent (see FIGS. 3A-4B; Seq. ID Nos. 3, 4, 6, and 8). And more specifically, a number of embodiments are directed to incorporating an ornithine in the amino acid position that corresponds to $M_{35}$ of naturally occurring beta-amyloid peptides.

Many other embodiments are directed to modifications that mimic aspects of AD. Mutations can occur in the Aβ region of the APP gene that result in altered amino acid composition (I. Benilova, et al., *Nat. Neurosci.* 2012, 15, 349-357, the disclosure of which is incorporated herein by reference). Many of these mutations are highly correlated with familial forms of AD. Thus, Aβ peptides and oligomers that incorporate these mutations are beneficial to study and develop tools that target AD-related peptides. Accordingly, embodiments are directed to synthetic Aβ peptides that reflect familial AD peptides. In particular, synthetic Aβ peptide embodiments incorporate familial mutations that occur within the β-hairpin region of the peptide. Many mutations are known to occur within this region, including the Dutch (E22Q), the Iowa (D23N), the Dutch Iowa (E22Q, D23N), the Italian (E22K), and the Osaka (E22del) mutations and various embodiments are directed to synthetic Aβ peptides with these amino acid substitutions that correspond to familial AD (see FIGS. 3A-4B; Seq. ID Nos. 3-5, and 7) (I. Benilova, et al., 2012, cited supra).

Although FIGS. 3A to 7B describe a number of modifications, it should be understood that various other modifications are possible that can reach the same desired properties of solubility, stability of formed oligomers, prevention of uncontrolled aggregation, and ease of synthesis and fall with various embodiments of the invention. In addition, it should be understood that a number embodiments of the synthetic Aβ peptides within the scope of the invention can incorporate different sets of modifications. Some embodiments may only incorporate one modification. Other embodiments may incorporate many, if not all, possible modifications. Thus, FIGS. 3A to 7B are merely representative of the available modifications to achieve the desired properties.

Furthermore, synthetic Aβ peptides having substantially similar sequences are also to be covered. A substantially similar sequence is a sequence having characteristics very similar to the original sequence such that the properties of β-sheet formation, trimer formation, higher order oligomer formation, solubility, prevention of fibril-like formation, and stability via cysteine disulfide bridges (if applicable), as those found in the original sequence are maintained. It is to be anticipated that synthetic cysteine-substituted Aβ peptides described herein would be able to tolerate various alterations (e.g., an amino acid substitution) and still maintain the properties of said Aβ peptides. In some embodiments, synthetic Aβ peptides may be altered by adding, removing, or substituting one amino acid. In more embodiments, peptides may be altered by adding, removing, or substituting two amino acids. And in even more embodiments, peptides may be altered by adding, removing, or substituting three or more amino acids, assuming at least some of the properties of the original sequence are maintained. As it is well known in the art, substitution of amino acids with similar qualities (e.g., hydrophobic for hydrophobic, hydrophilic for hydrophilic, acidic for acidic, basic for basic, etc.) are well tolerated and often have little effect on peptide properties. Accordingly, synthetic Aβ peptides may have substantial alterations and still fall within the scope of peptides described herein.

In various embodiments, synthetic cysteine-substituted Aβ peptides with further modification can form covalently linked trimers. Various embodiments are shown in FIGS. 5 and 6. In these embodiments, three monomers of synthetic Aβ peptides can form trimers. Specifically, in this embodiment, the formation of the trimers occurs when a disulfide bond is formed between $C_{17}$ of a first monomer and the $C_{21}$ of a second monomer. The same bond is repeated between the second monomer and a third, and again with the third monomer and the first. This trimer formation ensures a stable triangular-like shape that is resistant to fibril formation and uncontrolled aggregation. The further modifications can also assist with trimer formation, dependent on various embodiments. For example, the N-methylation on various amino acids prevents monomer stacking and aggregation, thus promoting the monomers to form a trimer conformation. In addition, isosteric hydrophilic amino acid replacement increases solubility monomers, which also promotes the formation of oligomers and prevents insoluble fibril formation. The truncations can remove amino acids that are unnecessary for oligomer formation and the $^\delta$Orn turn mimics ensure β-hairpin formation that promote stability and proper conformation of the oligomers. It should be noted, however, that the trimers in FIGS. 5 and 6 are not exhaustive of trimers, and that specific modifications may be changed, removed, or duplicated and still achieve the desired soluble oligomer formation. For example, cross-linked trimers can be formed using synthetic Aβ peptides having $C_{30}$ and $C_{34}$ modifications.

Oligomers of the Synthetic Aβ Peptides

Figure 8:
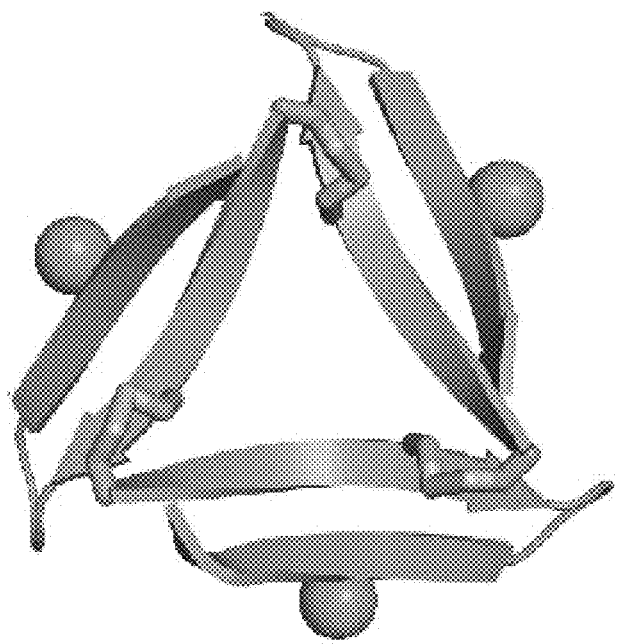
FIG. 8 provides a schematic detailing the structure of a synthetic crosslinked Aβ trimer in accordance with various embodiments of the invention.

In several embodiments, the synthetic monomeric Aβ peptides can oligomerize to form higher-order tertiary conformations. Embodiments of these higher-order conformations include trimers, hexamers, dodecamers, and annular pores. Trimer embodiments are formulated from three monomeric Aβ peptides and conforming into a triangular structure (FIG. 8). Disulfide bridges that extend between cysteines of the monomeric peptides covalently link some embodiments of the trimer. Other embodiments of the trimer may include further modifications of the monomeric peptides, which may help formulate and stabilize the trimers.

Trimers may be assembled using various Aβ peptides, in accordance with a number embodiments. Crosslinked trimers require paired cysteine modifications, such as $C_{17}$ and $C_{21}$ or $C_{30}$ and $C_{34}$, for example. The characteristics of the trimer to be built depends on peptides and modifications selected. Accordingly, peptides having various modifications can result in trimers having increased solubility, stability of formed oligomers, prevention of uncontrolled aggregation, and ease of synthesis.

Figure 9:
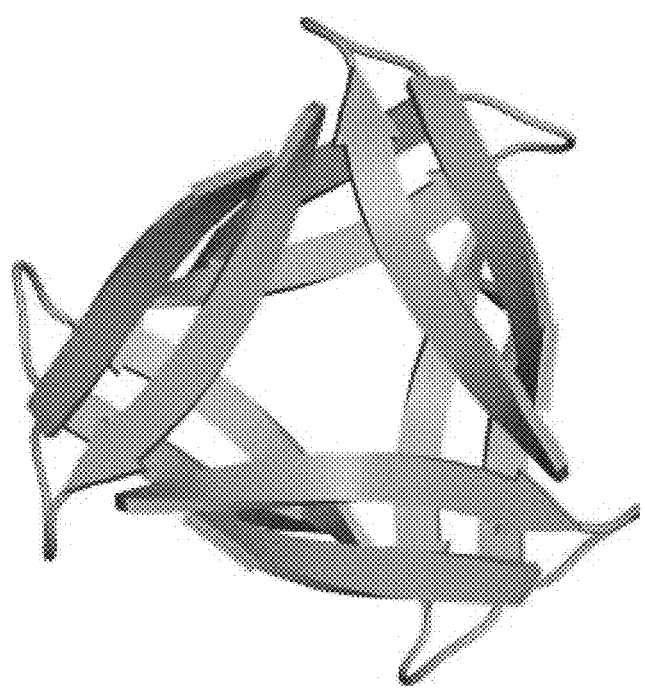
FIG. 9 provides a schematic detailing the structure of a hexamer formed from two synthetic crosslinked Aβ trimers in accordance with various embodiments of the invention.

More embodiments are directed to Aβ trimers that can further conform into hexamers, dodecamers, and annular pores. Hexamer embodiments are formed from Aβ trimers that sandwich on top of one another (FIG. 9). Hydrophobic amino acids (e.g., $F_{19}$, $I_{32}$, $L_{34}$, and $V_{36}$) can form hydrophobic surfaces on a trimer, which can interact with other hydrophobic surfaces of another trimer to conform into a stacked hexamer. The hexamers can further stack upon one another to form a higher-order column. This mode of assembly is characteristic of certain Aβ trimer embodiments.

Figure 10:
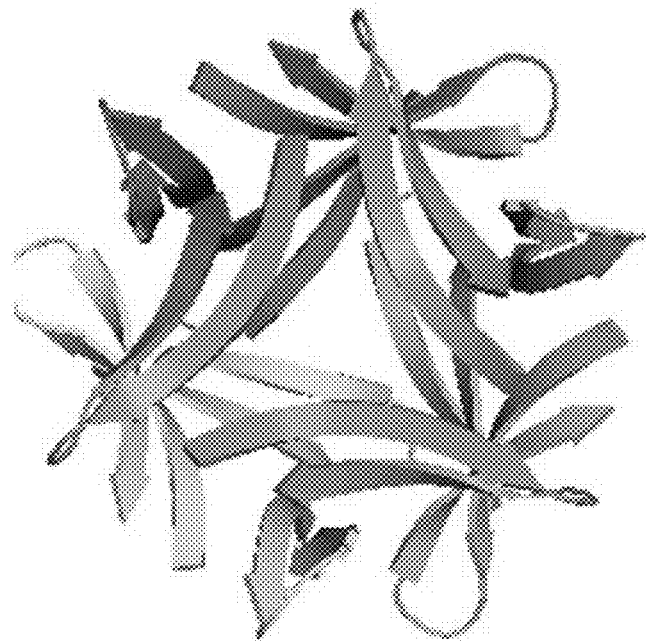
FIG. 10 provides a schematic detailing the structure of a dodecamer formed from four synthetic crosslinked Aβ trimers in accordance with various embodiments of the invention.

Particular dodecamer embodiments are also formed by a hydrophobic stacking mechanism. Hydrophobic surfaces on four trimers can assemble in a tetrahedral fashion to conform into ball-shaped dodecamer (FIG. 10). Hydrogen bonds among the outer edges of the four trimers can stabilize the dodecamer conformation. Furthermore, the hydrophobic surfaces of the four trimers can line the inside of the dodecamer, creating a large hydrophobic cavity.

Figure 11:
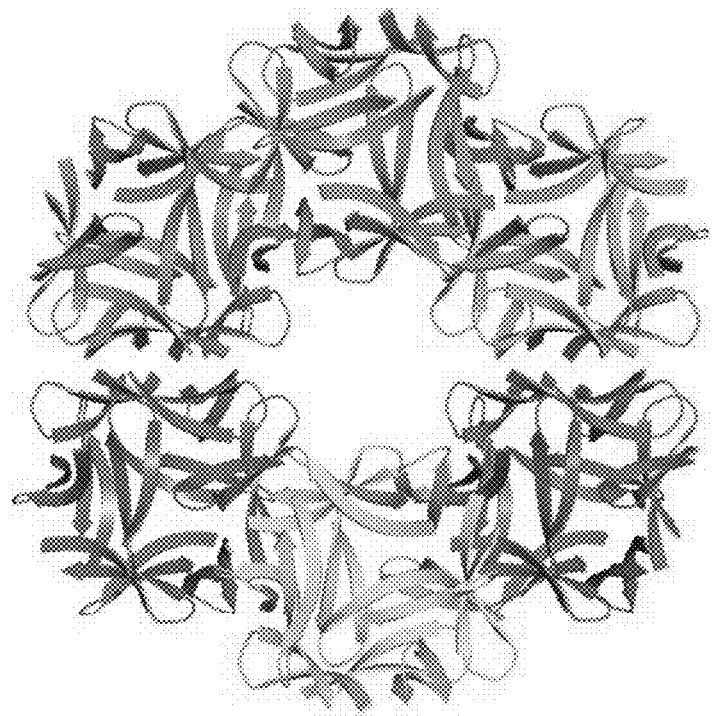
FIG. 11 provides a schematic detailing the structure of an annular pore like structure formed from twenty-four synthetic crosslinked Aβ trimers in accordance with various embodiments of the invention.

Further embodiments are direct to ball-shaped dodecamers capable of packing to form a crystal lattice. Within the crystal lattice, six dodecamers can assemble to form annular pore like structures (FIG. 11). Hydrophobic surfaces displayed on the exterior of each dodecamer can stabilize these annular pore-like structures. At the interfaces between the dodecamers in the annular pore, two trimers can pack to form a sandwich-like hexamer. Each interface can be stabilized by hydrophobic packing between the side chains of hydrophobic surfaces on each trimer.

Offset Synthetic Aβ Peptides

Figure 12:
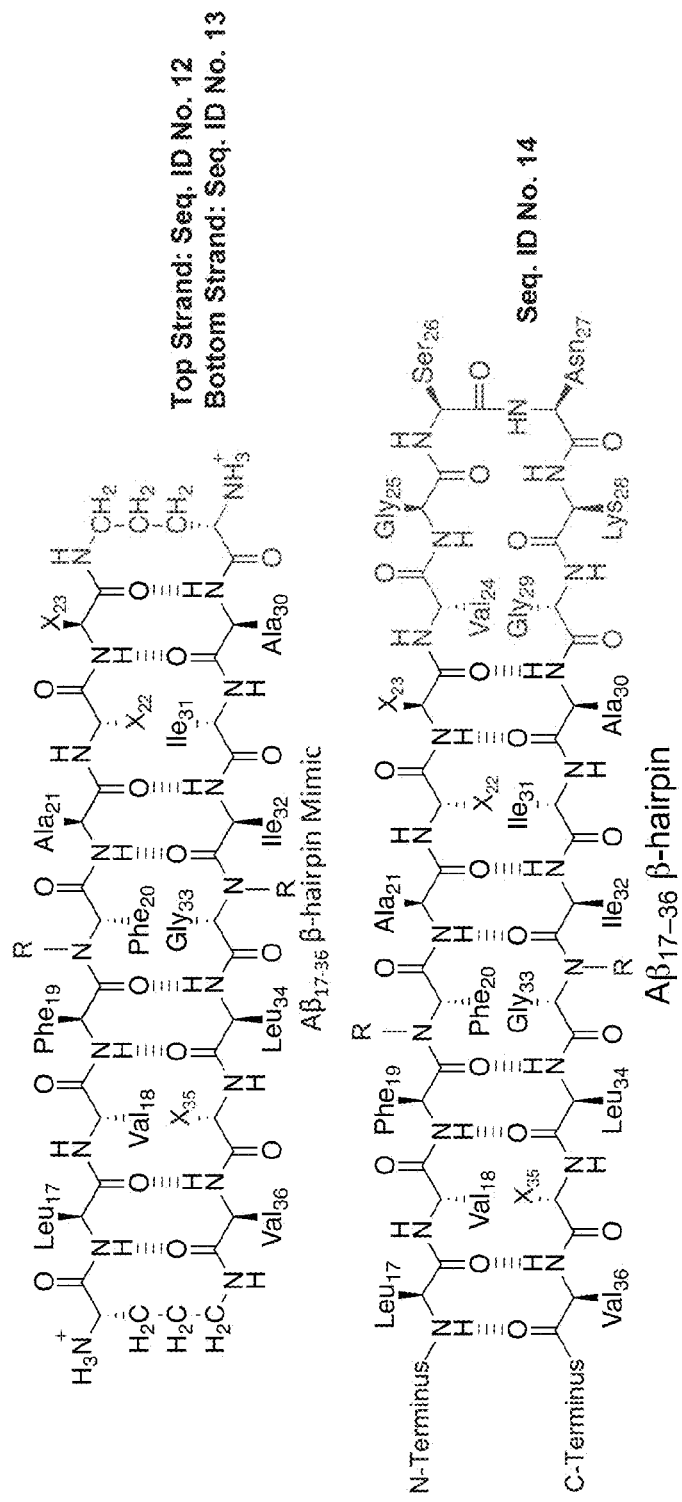
FIG. 12 provides molecular structure diagrams detailing the chemical structure and peptide sequence of synthetic Aβ peptides in accordance with various embodiments of the invention.
Figure 13:
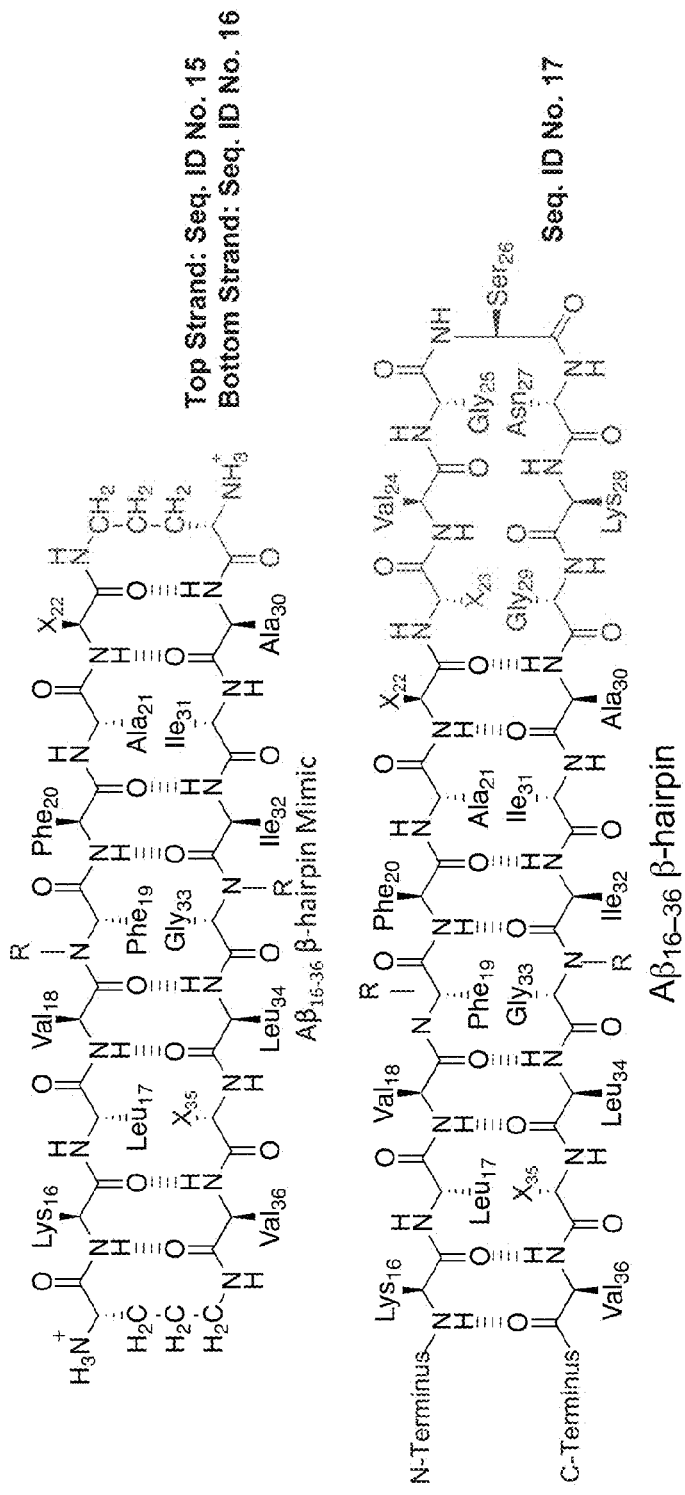
FIG. 13 provides molecular structure diagrams detailing the chemical structure and peptide sequence of synthetic Aβ peptides with offset β-hairpin hydrogen binding in accordance with various embodiments of the invention.

A number of embodiments are also directed to synthetic Aβ peptides with offset β-strands. FIG. 12 provides a representation of an $Aβ_{17-36}$ β-hairpin and a truncated mimic having canonical β-hairpin (Seq. ID Nos. 12-14). In this peptide, the β-strands lineup such that the amides and carboxyl groups form hydrogen between the following pairs of amino acids: $L_{17}$ with $V_{36}$, $F_{19}$ with $L_{34}$, $A_{21}$ with $I_{32}$, and $D_{23}$ with $A_{30}$. This canonical β-hairpin pairing, however, can be altered, as depicted in FIG. 13. In this noncanonical pairing, the β-strands lineup such that the amides and carboxyl groups form hydrogen between the following pairs of amino acids: $K_{16}$ with $V_{36}$, $V_{18}$ with $L_{34}$, $F_{20}$ with $I_{32}$, and $E_{22}$ with $A_{30}$.

In several embodiments, offset Aβ β-hairpins are truncated and a $^\delta$Orn is inserted into amino acid position 15 to covalently link amino acid 15 with the C-terminus of amino acid 36, effectively eliminating the native C and N-termini (FIG. 13; Seq. ID Nos. 15-17). In addition, other embodiments have a $^\delta$Orn inserted into amino acid position 29 to covalently link amino acid 29 with the C-terminus of amino acid 22, effectively eliminating the amino acids 23 to 29 (FIG. 13).

Embodiments are also directed to substitution of alkyl (e.g., methyl), aryl (e.g., benzyl, nitrobenzyl) or other similarly bulky groups with an H on one of the amides of a central amino acid having an outward-facing amide that is not involved in β-hairpin hydrogen bonding (see FIGS. 12 and 13). The bulky group can be substituted on either β-strand, but should not interfere with trimer formation. As shown in FIG. 12, amino acids $F_{20}$ and $G_{33}$ are ideal candidates for N-methylation in accordance with a number of embodiments for the $Aβ_{17-36}$ β-hairpin. Likewise, amino acids $F_{19}$ and $G_{33}$ are ideal candidates for N-methylation in accordance with a number of embodiments for the offset Aβ β-hairpin (FIG. 13). The addition of bulky groups to the peptide backbone sterically hinders the interaction and stacking of β-strands and thus prevents uncontrolled aggregation of Aβ peptides into fibrils.

More embodiments are directed to replacement of hydrophobic amino acids with hydrophilic amino acids, and more specifically to isosteric hydrophilic amino acid replacements. For example, a methionine can be oxidized to or substituted with ornithine, methionine sulfoxide or methionine sulfone (e.g., $Met_{35} \rightarrow Orn_{35}$, $Met_{35} \rightarrow MetO_{35}$) (see FIGS. 12 and 13).

Many embodiments are directed to synthetic Aβ peptides that reflect familial AD peptides. In particular, synthetic Aβ peptide embodiments incorporate familial mutations that occur within the β-hairpin region of the peptide. Many mutations are known to occur within this region, including the Dutch (E22Q), the Iowa (D23N), the Dutch Iowa (E22Q, D23N), the Italian (E22K), and the Osaka (E22del) mutations and various embodiments are directed to synthetic Aβ peptides with these amino acid substitutions that mimic familial AD (see FIGS. 12 and 13).

Although FIGS. 12 and 13 describe a number of modifications, it should be understood that various other modifications are possible that can reach the same desired characteristics of solubility, stability of formed oligomers, prevention of uncontrolled aggregation, and ease of synthesis and fall with various embodiments of the invention. In addition, it should be understood that a number embodiments of the synthetic Aβ peptides within the scope of the invention can incorporate different sets of modifications. Some embodiments may only incorporate one modification. Other embodiments may incorporate many, if not all, possible modifications. Thus, FIGS. 12 and 13 are merely representative of the available modifications to achieve the desired properties.

Furthermore, synthetic Aβ peptides having substantially similar sequences are also to be covered. A substantially similar sequence is a sequence having characteristics very similar to the original sequence such that the properties of β-sheet formation, trimer formation, higher order oligomer formation, solubility, prevention of fibril-like formation, and stability, as those found in the original sequence are maintained. It is to be anticipated that synthetic offset Aβ peptides described herein would be able to tolerate various alterations (e.g., an amino acid substitution) and still maintain the properties of said Aβ peptides. In some embodiments, synthetic Aβ peptides may be altered by adding, removing, or substituting one amino acid. In more embodiments, peptides may be altered by adding, removing, or substituting two amino acids. And in even more embodiments, peptides may be altered by adding, removing, or substituting three or more amino acids, assuming at least some of the properties of the original sequence are maintained. As it is well known in the art, substitution of amino acids with similar qualities (e.g., hydrophobic for hydrophobic, hydrophilic for hydrophilic, acidic for acidic, basic for basic, etc.) are well tolerated and often have little effect on peptide properties. Accordingly, synthetic Aβ peptides may have substantial alterations and still fall within the scope of peptides described herein.

Applications of Synthetic Aβ Peptides

Several embodiments are directed to applications and uses of synthetic Aβ peptides and oligomers, including various embodiments directed to toxicological administration, antigen binding molecule development, and small molecule development. In several embodiments, synthetic Aβ peptides and oligomers are cytotoxic and can cause cell death, apoptosis, necrosis, autophagy, or any combination thereof. In more specific embodiments, the peptides and oligomers are especially toxic to neurons and other neuronal cells. Other embodiments are directed to the ability of peptides and oligomers to stimulate cellular lactate dehydrogenase (LDH) release or caspase-3 induction.

A number of embodiments are also directed to antigen binding molecule development using immunogenic cocktails having synthetic Aβ peptides and oligomers. Several of these embodiments utilize Aβ peptides and oligomers as antigens, with or without adjuvant, to produce antibodies in an immunocompetent animal, such as human, rabbit, goat, mouse, rat, chicken, guinea pig, or any other suitable species. Further embodiments include development of monoclonal antibodies that recognize synthetic Aβ peptides and oligomers. Other embodiments are directed to developed antigen binding molecules that specifically recognize Aβ oligomers but not Aβ monomers.

Various embodiments are also directed to the development of small molecules (e.g., dyes) capable of interacting with synthetic Aβ peptides and oligomers. In many embodiments, the small molecules are able to elicit a response when in contact, or in the vicinity, of Aβ peptides or oligomers. Some embodiments are small molecule probes that are able to detect Aβ peptides and oligomers by a suitable method (e.g. fluorescence microscopy, positron emission tomography (PET)). More particular embodiments the small molecule probes detect Aβ oligomers but not monomers. Other embodiments are small molecule drugs capable of reducing the toxic effects of Aβ peptides and oligomers.

Antigen Binding Molecule Development & Purification

In accordance with a number of embodiments, antigen binding molecules (e.g., antibodies) can be developed with high specificity, preference and affinity for soluble oligomeric Aβ, but not monomer or insoluble fibrils. In many of these embodiments, the high affinity oligomer antigen binding molecules are developed using synthetic Aβ trimers, such as those described herein. Embodiments are also directed to the use of synthetic Aβ trimers to select and/or purify antigen binding molecules, as determined by their specificity, preference, and affinity to Aβ oligomers.

Antigen binding molecules are to be any antibodies, fragments of antibodies, variants, and derivatives thereof capable of specifically binding an antigen. These include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, and fragments produced by a Fab expression library.

By "specifically binds," or "specifically recognizes," used interchangeably herein, it is generally meant that an antigen binding molecule (e.g., an antibody binds to an epitope via its antigen binding domain) and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope.

By "preferentially binds," it is meant that an antigen binding molecule (e.g., antibody) specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

As used herein, the term "affinity" refers to a measure of the strength of the binding of an individual epitope by the antigen binding molecule.

Antibodies are composed of a light chain and heavy chain. In general, the light and heavy chains are covalently bonded to each other, and the "tail" portions of the two heavy chains are typically bonded to each other by covalent disulfide linkages. Non-covalent linkages between two heavy chains can be used, however, as is typical when the antibodies are generated in culture.

Both the light and heavy chains are divided into regions of structural and functional homology, such as the constant and variable domains. The variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fe receptor binding, complement binding, etc.

The antigen recognition of the VL and VH domains is determined by the complementarity determining regions (CDRs). In naturally occurring antibodies, there are six CDRs, which are short, non-contiguous sequences that are specifically positioned to form the antigen binding domain. The antigen binding domain formed by the positioned CDRs defines a surface complementary to the epitope on the innmunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, Chothia and Lesk, *J. Mol. Biol.* 1987 196, 901-917, which is incorporated herein by reference).

Antibody Acquisition by Immunization

Figure 14:
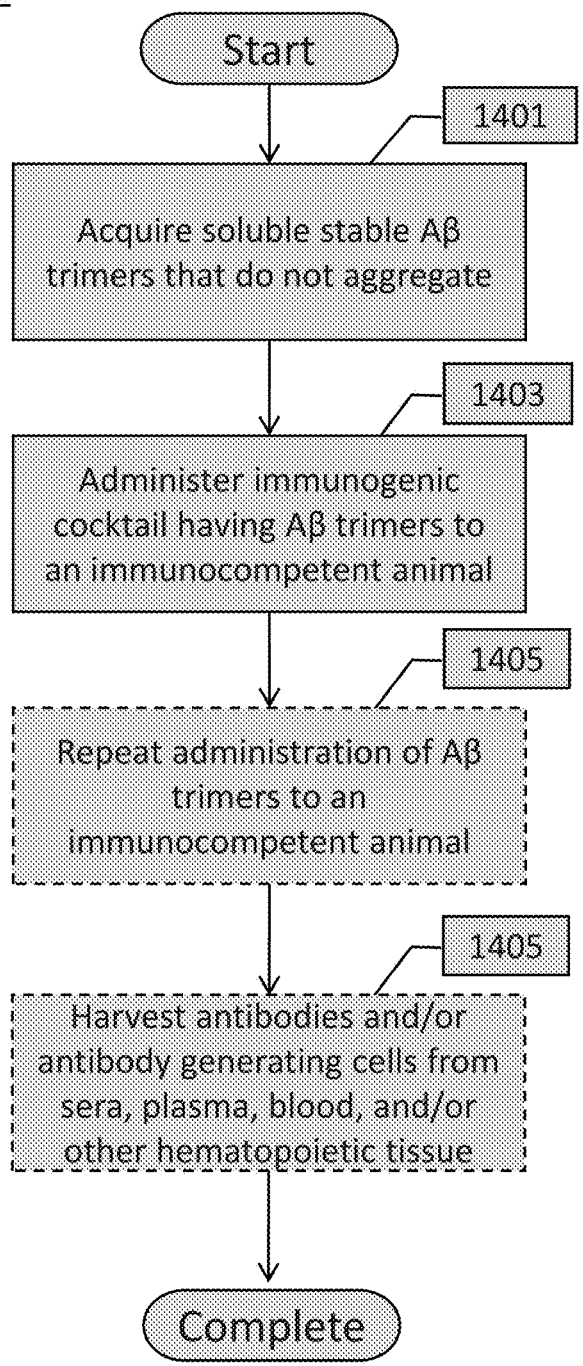
FIG. 14 provides a process to generate antibodies using Aβ trimers in accordance with various embodiments of the invention.

An embodiment for the production of antibodies with high affinity for soluble Aβ oligomers is depicted in FIG. 14. Process 1400 begins with an acquisition of soluble Aβ trimers (1401). Ideally, Aβ trimers would form stable oligomers and not aggregate and form fibrils, such as the synthetic Aβ trimers described herein. The specific Aβ trimer to be used would likely depend on the result desired. For example, antibodies could be generated with high affinity for Aβ oligomers having specific familial AD mutations.

Process 1400 continues with administering immunocompetent animals with an immunogenic cocktail having soluble Aβ trimers (1403). Any immunocompetent animal can be used, such as, for example, human, rabbit, goat, mouse, rat, chicken, or guinea pig. Immunocompetent animals can be administered with a stimulating amount of with soluble Aβ trimer, with or without conjugate and with or without adjuvant. A stimulating amount of soluble Aβ trimer is the amount required to stimulate an immune response that results in production of a collectable amount of antibodies that have affinity for soluble Aβ oligomers. The stimulating amount may also depend on the use of conjugate and/or adjuvant. Any appropriate conjugate can be used, such as, for example, hemocyanin. Likewise, any appropriate adjuvant can be used, such as, for example, complete Freund's adjuvant.

Injection of soluble Aβ trimers into an immunocompetent animal can be optionally repeated multiple (1405). Often, repeat administrations can improve antibody production. The appropriate amount of administrations depends on the application, however, typically one, two, three, or four administrations are performed.

Sera, plasma, blood, and/or other hematopoietic tissue having high affinity antibodies and/or antibody generating cells are harvested from immunocompetent animals an appropriate amount of time after the final administration of soluble Aβ trimer (1407). The appropriate amount of time is the time required for the immunocompetent animal to have an immune response and generate antibodies, which is dependent in part on the immunocompetent animal used. For example, an appropriate time to harvest antibodies from rabbits is typically around 30 days after last immunization. Harvesting of sera, plasma and/or blood can be performed by any of the many methods known in the art.

Once sera, plasma, blood and/or hematopoietic tissue having high affinity antibodies cells are harvested, antibodies may be used in their natural buffer or further purified by a number of methods in accordance of a number of embodiments. Likewise, antibody generating cells may be cultured and/or stored in accordance with several embodiments.

Oligomer Aβ Vaccination

A number of embodiments utilize methods for preventing or ameliorating Alzheimer's disease. Accordingly, various embodiments contemplate administering to individuals immunogenic compositions, proposed to be suitable for use as a vaccine, prepared using soluble Aβ peptides, trimers and higher order oligomers, as described herein. In other embodiments Aβ compositions can be used in combination with other secreted virulence proteins, surface proteins or immunogenic fragments thereof. In certain aspects, antigenic material is extensively dialyzed to remove undesired small molecular weight molecules and/or lyophilized for more ready formulation into a desired vehicle.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; and 4,596,792; each of which is incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, each of which is incorporated herein by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Vaccine compositions would normally be administered as pharmaceutically acceptable compositions that include physiologically acceptable carriers, buffers or other excipients. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

Upon formulation, solutions will be administered in a manner compatible with the dosage formulation and in such amount as is therapeutically or prophylactically effective. The formulations are easily administered in a variety of dosage forms, such as the type of injectable solutions described within.

The manner of application may be varied widely. Any of the conventional methods for administration of a vaccine are applicable. These are believed to include oral application within a solid physiologically acceptable base or in a physiologically acceptable dispersion, parenterally, by injection and the like. The dosage of the vaccine will depend on the route of administration and will vary according to the size and health of the subject.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies. The course of the immunization may be followed by assays for antibodies against the antigens, as described in U.S. Pat. Nos. 3,791,932; 4,174,384 and 3,949,064, each of which is incorporated herein by reference.

A given composition may vary in its immunogenicity. It is often necessary therefore to boost the host immune system, as may be achieved by coupling a peptide or polypeptide to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

The immunogenicity of polypeptide or peptide compositions can be enhanced by the use of non-specific stimulators of the immune response, known as adjuvants. Suitable adjuvants include all acceptable immunostimulatory compounds, such as cytokines, toxins, or synthetic compositions. A number of adjuvants can be used to enhance an antibody response against Aβ peptides, trimers and higher order oligomers. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference.

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (Fluosol-DA®) used as a block substitute may also be employed to produce an adjuvant effect.

Examples of adjuvants include complete Freund's adjuvant (a non-specific stimulator of the immune response containing killed *Mycobacterium tuberculosis*), incomplete Freund's adjuvants, and aluminum hydroxide.

Administration of the immunogenic compositions, in accordance with numerous embodiments, to a patient/subject will follow general protocols for the administration of such compounds, taking into account the toxicity, if any, of the synthetic Aβ peptide/oligomer composition, or other compositions described herein. It is expected that the treatment cycles would be repeated as necessary. It also is contemplated that various standard therapies, such as hydration, may be applied in combination with the described therapy.

Soluble synthetic Aβ peptides and oligomers can be formulated for parenteral administration (e.g., formulated for injection via the intravenous, intramuscular, subcutaneous, or even intraperitoneal routes). The preparation of an aqueous composition that contains a compound or compounds that increase the expression of an MHC class I molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of soluble synthetic Aβ peptides and oligomers can be prepared in water suitably and can be mixed with a surfactant, if necessary. Dispersions can also be prepared in glycerol, liquid polyethylene glycols, and mixtures thereof and in oils. Under ordinary conditions of storage and use, these preparations contain a preservative to prevent the growth of microorganisms.

Sterile injectable solutions can be prepared by incorporating the soluble synthetic Aβ peptides and oligomers in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

Antibody Acquisition from Human Patients

Antibodies and antibody generating cells can also be identified acquired from other sources in addition to immunized animals. For example, antibodies and antibody generating cells can be acquired from an unimmunized human subject. It is possible to identify an antibody or antibody-producing cell from specific collectives or healthy subjects, preselected by clinical criteria (e.g., age, cognitive ability, propensity for AD), without prerecognition of a target structure epitope (e.g., soluble Aβ oligomers). Once a subject is identified, B cells and B memory cells can be collected and tested for their production of antibodies having high specificity, preference, and affinity.

In one particular embodiment, it may be ideal to source antibody producing cells of an aging individual not having cognitive defects or clinical signs of dementia. In this embodiment, the sample is obtained from subject having the following criteria: a) being 65, preferably 70 and more preferably 75 years of age or older; b) having full cognitive capacity and good health; and c) having no clinical signs of dementia or having unusually slow rates of progression of disease despite the presence of an established clinical diagnosis of probable Alzheimer's disease or having unusually low conversion rates from Mild Cognitive Impairment (MCI) to full blown Alzheimer's disease.

In another embodiment, samples may be obtained from the selected individuals by a) purifying B cells or B memory cells from a sample which has been identified to contain antibodies which preferentially bind to soluble Aβ trimers but not or with significantly lower affinity to monomers and/or insoluble fibrils; b) obtaining the immunoglobulin gene repertoire encoding said antibodies from said B cells or B memory cells; and c) using said repertoire to express at least one of said antibodies in a recombinant system. In various embodiments, the immunoglobulin gene repertoire may be determined by sequencing the mRNA or DNA by a number of known methods practiced in the field.

There are a number of known methods to produce clones of immortalized human B cell and B memory lymphocyte colonies, such as, for example using Epstein Barr Virus in the presence of a polyclonal B cell activator or construction of human hybridomas. Antibodies may be continually produced using an immortalized human B cell line and harvested and purified by methods known in the art.

Antigen binding molecules may also be continually produced by recombinant expression in a production cell line. Genetic material can be created using the appropriate immunoglobulin cDNA representing the antibody to be expressed. The coding sequences, at a minimum, should include the variable regions that provide the antigen binding ability. The genetic information can be inserted into a vector, which can be transfected in to standard recombinant host cells. A number of recombinant host cells are known in the art, including, but not limited to CHO cells, HEK 293 cells, and HeLa cells. Antigen binding molecules may be harvested and purified from the production cells by methods known in the art.

Monoclonal Antibody Development

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. 1988, the disclosure of which is incorporated herein by reference. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells that have been immortalized via transformation.

In the well-known hybridoma process (Kohler et al., Nature 1975 256, 495; the disclosure of which is incorporated herein by reference) the relatively short-lived, or mortal, lymphocytes from a mammal (e.g., B cells derived from a human subject as described herein) are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. Each single strain produces antibodies, which are homogeneous against a desired antigen.

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen (e.g., soluble Aβ oligomers). The binding specificity of the monoclonal antibodies produced by hybridoma cells is determined by in vitro assays such as immunoprecipitation, radioimmunoassay (RIA), or enzyme-linked immunosorbent assay (ELISA). After hybridoma cells are identified that produce antibodies of the desired specificity, affinity and/or activity, the clones may be subcloned by limiting dilution procedures and grown by standard methods (Goding, Monoclonal Antibodies: Principles and Practice, Academic Press, 1986 pp 59-103)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Selection and Purification of Soluble Aβ Oligomer Binding Molecule

Embodiments are also directed to the selection of antigen binding molecules having high specificity, preference, and affinity for soluble Aβ oligomers. In this embodiment, soluble Aβ trimers, such as those described herein, are used to identify and select such antigen binding molecules. Soluble Aβ binding molecules can be used for a variety downstream applications, including, but not limited to, diagnosis and treatment of Aβ related diseases (e.g., AD).

Embodiments can begin with acquisition of antigen binding molecules. Antigen binding molecules can be obtained in a variety of methods, including those described herein. Once antigen binding molecules are obtained, they can be screened for their specificity, preference, and affinity for soluble Aβ oligomers using soluble Aβ trimers). Preferably, highly stable, crosslinked trimers that do not form fibrils are used, such as those described herein.

Many assays are known in the art to screen the specificity of antibodies for a particular antigen. These assays include, but are not limited to, Western blot, immunoprecipitation, RIA, and ELISA. Accordingly, highly stable, crosslinked trimers that do not form fibrils can be used as antigens in these assays to determine their specificity to soluble Aβ oligomers.

A number of assays are also known to determine antibody preference for a particular antigen over a similar antigen. Particularly, in this application, antigen binding molecules that preferentially bind soluble Aβ oligomers with low cross-reactivity with monomers and insoluble fibrils is desired. Accordingly, specificity assays, such as those described above, can be used to directly compare antigen binding molecules' ability to bind soluble Aβ oligomers, monomers, and insoluble fibrils. In addition to comparison assays, direct competition assays can be performed, wherein antigen binding molecules are in contact with soluble Aβ oligomers, monomers, and insoluble fibrils and their preference for each antigen is determined.

Binding affinities of antigen binding molecules can be measured by a number of assays. In many of these assays, the dissociation constant (Kd) can be measured directly. Alternatively, affinity can be determined qualitatively by a number assays, including, but not limited to Western blot, immunoprecipitation, RIA, and ELISA.

Soluble Aβ trimers can also be used to purify solutions of antigen binding molecules, such as those derived from the methods described herein. Accordingly, antibodies may be derived from animal hematopoietic tissue (e.g., sera, plasma, blood) or from tissue culture (e.g., hybridoma, immortalized B-cell lines). These antigen binding cells may be a purified from a variety of known purification procedures such as, for example, protein-A, hydroxylapatite chromatography, gel electrophoresis, dialysis or affinity chromatography. In particular, soluble Aβ oligomer binding molecules can be specifically purified using soluble Aβ trimers via affinity chromatography.

Affinity chromatography is a method of separating biochemical mixtures based on highly specific interaction between antigen and antibody. Accordingly, soluble Aβ trimers, such as those described herein, can be fixed to matrix (e.g., agarose) to create a solid support. Often, the solid support is packed into a column, but alternative methods are also acceptable (e.g., slurry centrifugation techniques). Antibody containing solutions can be optionally mixed with binding solutions (e.g., phosphate buffered saline (PBS)) before being passed through the solid phase, wherein the highly specific antibodies are captured by the fixed soluble Aβ trimers. Once the antibody containing solution passes through, the solid support can be washed with an appropriate buffer (e.g. PBS) multiple times to clear all non-binding molecules. Once washed, the antibodies can be eluted using a suitable buffer (e.g., 0.1 M glycine-HCl, pH 2.5-30) that will dissociate the antibody from the soluble Aβ trimers. Once pure, the elution buffer can be neutralized, if necessary, and/or exchanged with an appropriate storage or application buffer.

Affinity chromatography can also be used to remove cross-reactive antibodies that have are reactive to undesired antigens, such as Aβ monomers and insoluble fibrils. Accordingly, Aβ monomers and insoluble fibrils can be fixed to a matrix to create a solid support. Antibody solutions can be passed through the solid support, wherein antibodies specific to these antigens will bind. The unbound antibodies can be passed through in a neutral buffer (e.g., PBS). The elute containing soluble Aβ oligomer antibodies can either be stored, or then processed through the previously described affinity chromatography method with soluble Aβ trimers fixed to a solid support to further purify the antibody solution.

EXEMPLARY EMBODIMENTS

Biological and chemical data support the aforementioned synthetic Aβ peptides and oligomers in variety embodiments as described. The data demonstrate that Aβ peptides can be synthesized with various modifications that are capable of supramolecular assembly. X-ray crystallography confirms the peptide conformations, intramolecular interaction, and higher-order oligomerization. Analytical reverse-phase high performance liquid chromatography (RP-HPLC) establishes that the described methods yield high levels of Aβ oligomers that are capable of even higher ordered structures. Biochemical assays reveal that synthetic Aβ peptides and oligomers are cytotoxic and capable of antibody production and detection.

Aβ Peptides Capable of Crosslinked Trimerization

Figure 15A:
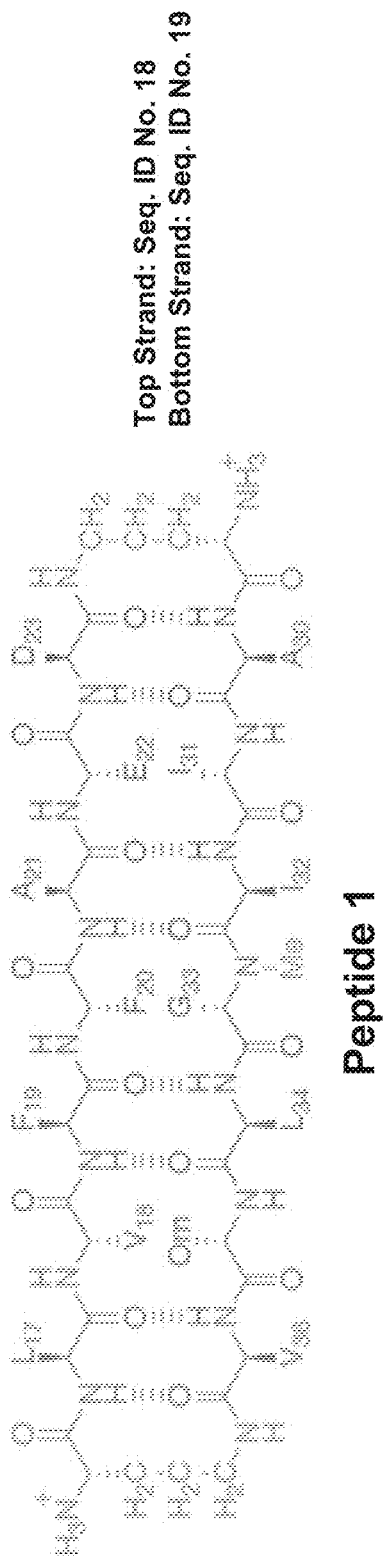
FIG. 15A provides a molecular structure diagram detailing the chemical structure and peptide sequence of peptide 1 in accordance with various embodiments of the invention.
Figure 15B:
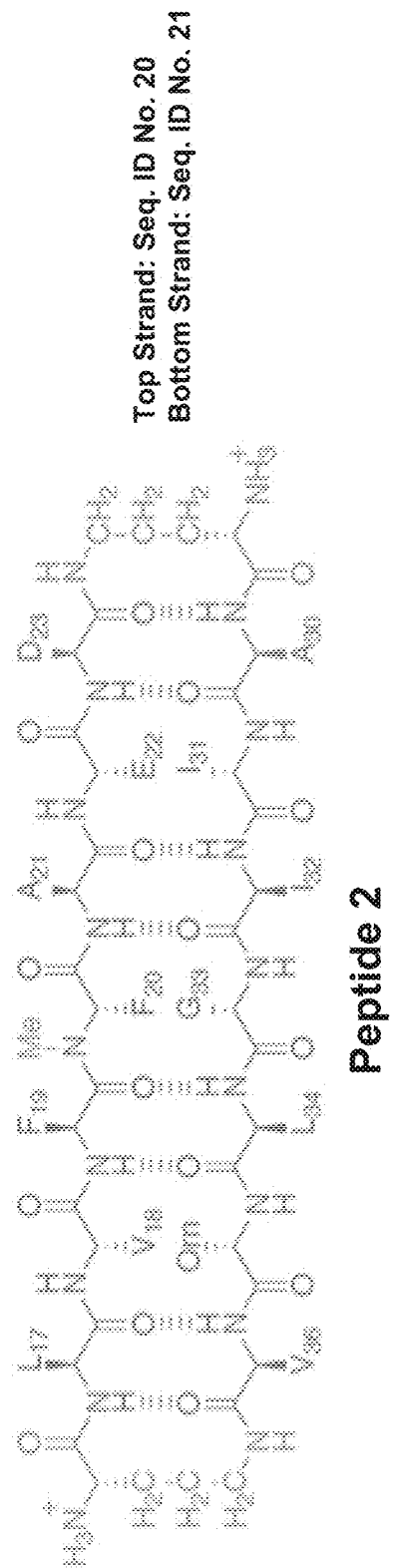
FIG. 15B provides a molecular structure diagram detailing the chemical structure and peptide sequence of peptide 2 in accordance with various embodiments of the invention.

Previous studies have identified and elucidated hitherto undiscovered modes of supramolecular assembly of macrocyclic β-sheet peptides derived from amyloidogenic peptides and proteins (R. K. Spencer, et al., *J. Am. Chem. Soc.* 2014 136, 5595-5598; R. K. Spencer, et al., *J. Am. Chem. Soc.* 2015 137, 6304-6311; P. J. Salveson, et al., *J. Am. Chem. Soc.* 2016 138, 4458-4467; the disclosures of which are incorporated herein by reference). These studies reported X-ray crystallographic structures of two homologous trimers formed by two macrocyclic β-sheet peptides derived from $Aβ_{17-36}$. These peptides—peptides 1 and 2—contain $Aβ_{17-23}$ and $Aβ_{30-36}$ β-strands covalently linked by two δ-linked ornithine ($^δ$Orn) turn mimics (FIGS. 15A and 15B; Seq. ID Nos. 18-21). The δOrn that connects residues $D_{23}$ and $A_{30}$ replaces the $Aβ_{24-29}$ loop; the δOrn that connects residues $L_{17}$ and $V_{36}$ reinforces β-sheet structure. Ornithine (α-linked) was included as a hydrophilic isostere of methionine at position 35 to improve the solubility of the peptides. Peptides 1 and 2 both contain an N-methyl group to block uncontrolled aggregation: peptide contains an N-methyl group on $G_{33}$; peptide 2 contains an N-methyl group on $F_{20}$.

Figure 16A:
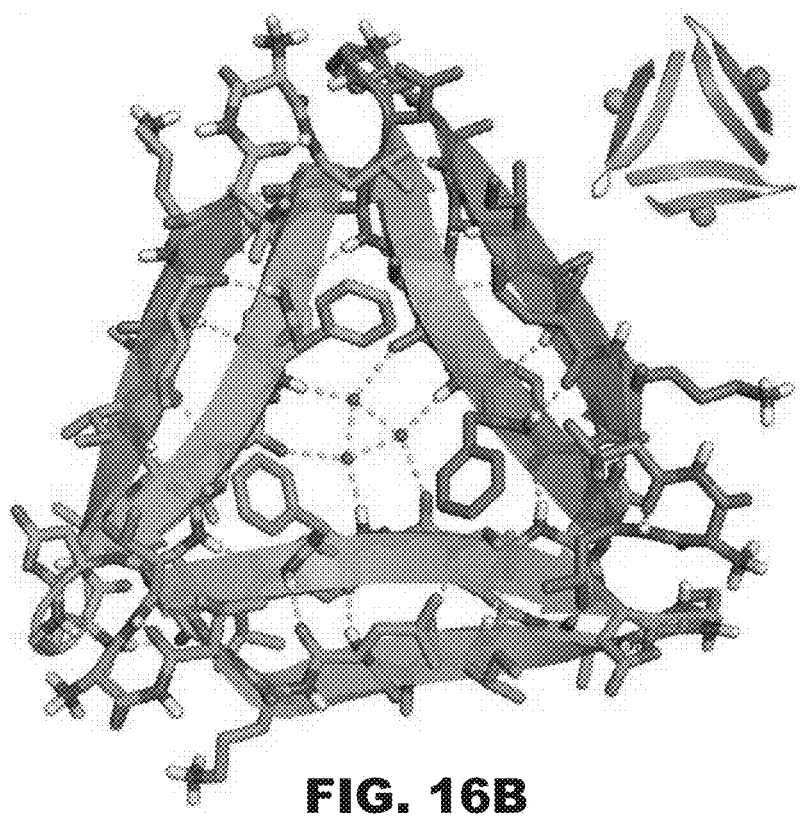
FIG. 16A provides an X-ray crystallographic schematic detailing the structure of a synthetic crosslinked Aβ trimer generated using peptide 1 in accordance with various embodiments of the invention.
Figure 16B:
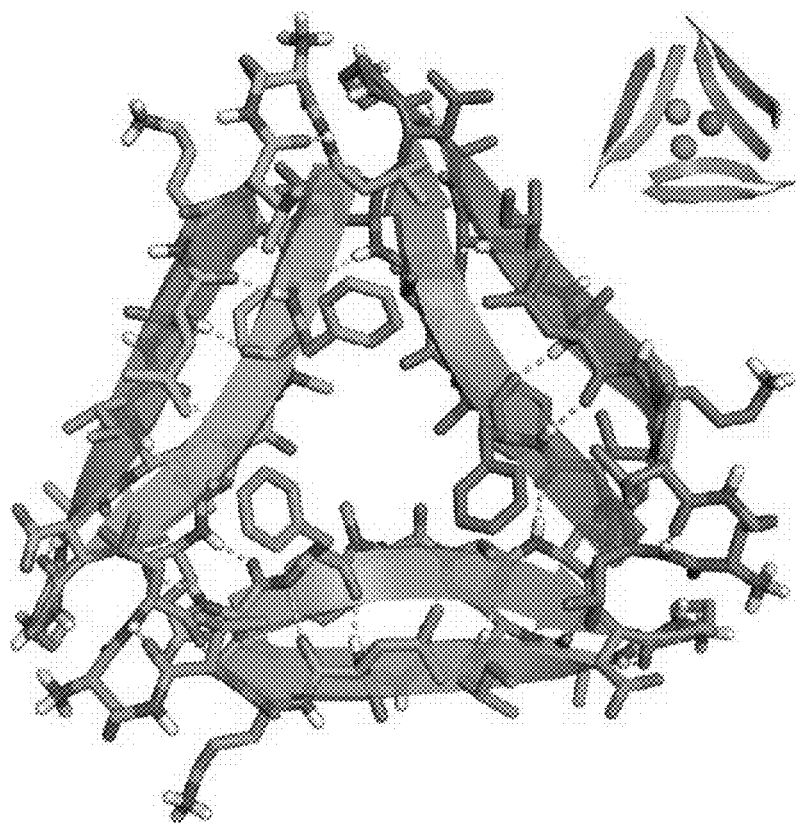
FIG. 16B provides an X-ray crystallographic schematic detailing the structure of a synthetic crosslinked Aβ trimer generated using peptide 2 in accordance with various embodiments of the invention.

X-ray crystallography revealed that peptides 1 and 2 fold to form β-hairpins that assemble to form oligomers. In the X-ray crystallographic structures of peptides 1 and 2, three β-hairpins assemble in a triangular fashion to form trimers, which are stabilized by hydrogen bonding and hydrophobic interactions between monomers (FIGS. 16A and 16B). At the three corners of each trimer, the main chain of residue $V_{18}$ on one macrocyclic β-sheet hydrogen bonds with the main chain of residue $E_{22}$ on the adjacent macrocyclic β-sheet. Clustering between hydrophobic residues at the corners of each trimer provides additional stability. In the crystal lattice, the trimers further assemble to form hexamers and dodecamers. The trimers, hexamers, and dodecamers formed by peptide 1 are morphologically identical to the trimers, hexamers, and dodecamers formed by peptide 2. The oligomers formed by peptides 1 and 2, however, are labile and dynamic in aqueous solution, making it difficult to correlate their biological and biophysical properties with their structures. Stabilization of Aβ oligomers would help overcome these complications.

Aβ Peptides Capable of Stable Trimerization with Covalent Disulfide Linkage

Design and Synthesis of Peptides 3 and 4 and Trimers 3 and 4.

The structures of the trimers formed by peptides 1 and 2 could be improved if the trimers could be further stabilized.

To try to stabilize the trimers, amino acid residues $L_{17}$ and $A_{21}$ were replaced with cysteine residues that possibly could allow crosslinking the peptides to form covalent trimers containing three disulfide linkages (see FIGS. 17A and 17B; Seq. ID Nos. 22-25). It was predicted that the cysteine substitutions would be tolerated because the resulting $C_{17}$-$C_{21}$ crosslinks would be near isosteric with $L_{17}$ and $A_{21}$, maintaining a similar level of hydrophobicity and would not alter the charge of the trimer.

Peptides 3 and 4 were synthesized by similar procedures to those developed for other macrocyclic peptides: synthesis of the corresponding linear peptide on 2-chlorotrityl resin, followed by cleavage of the protected linear peptide from the resin, solution-phase macrolactamization, and global deprotection of the resulting macrocyclic peptide (See, R. K. Spencer, et al., *J. Am. Chem. Soc.* 2014 136, 5595-5598; R. K Spencer, et al., *J. Am. Chem. Soc.* 2015 137, 6304-6311; P. J. Salveson, et al., *J. Am. Chem. Soc.* 2016 138, 4458-4467; cited supra). Peptides 3 and 4 were purified by reverse-phase HPLC (RP-HPLC) followed by lyophilization of pure fractions. Typical syntheses on a 0.1 mmol scale afforded ~55 mg of peptides 3 and 4 in ≥95% purity. High purity of peptides 3 and 4 minimized off-target products in the subsequent oxidation reactions.

Figure 18:
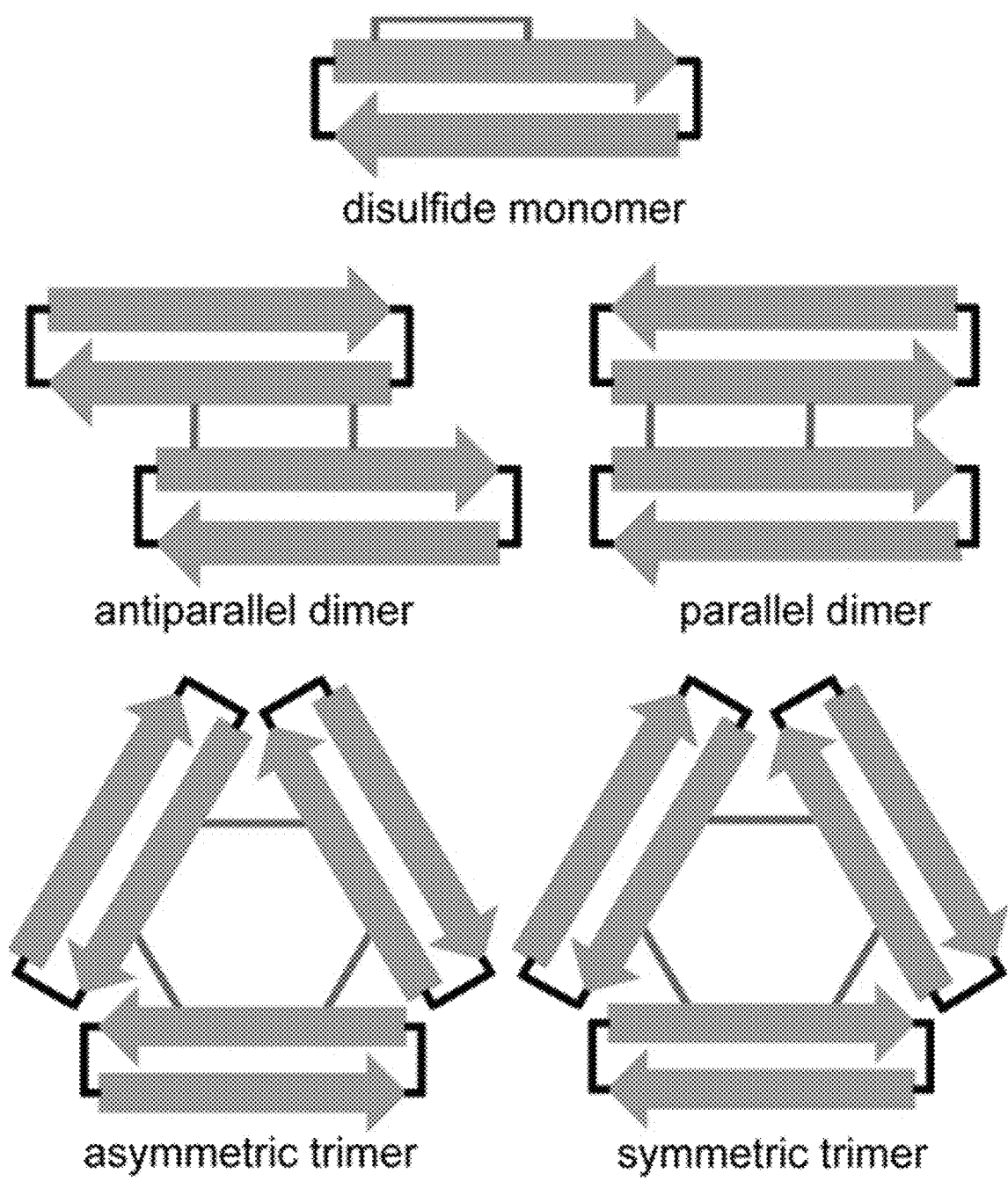
FIG. 18 provides schematics of various structures that can hypothetically be generated by crosslinking Aβ peptides having cysteines.
Figure 19A:
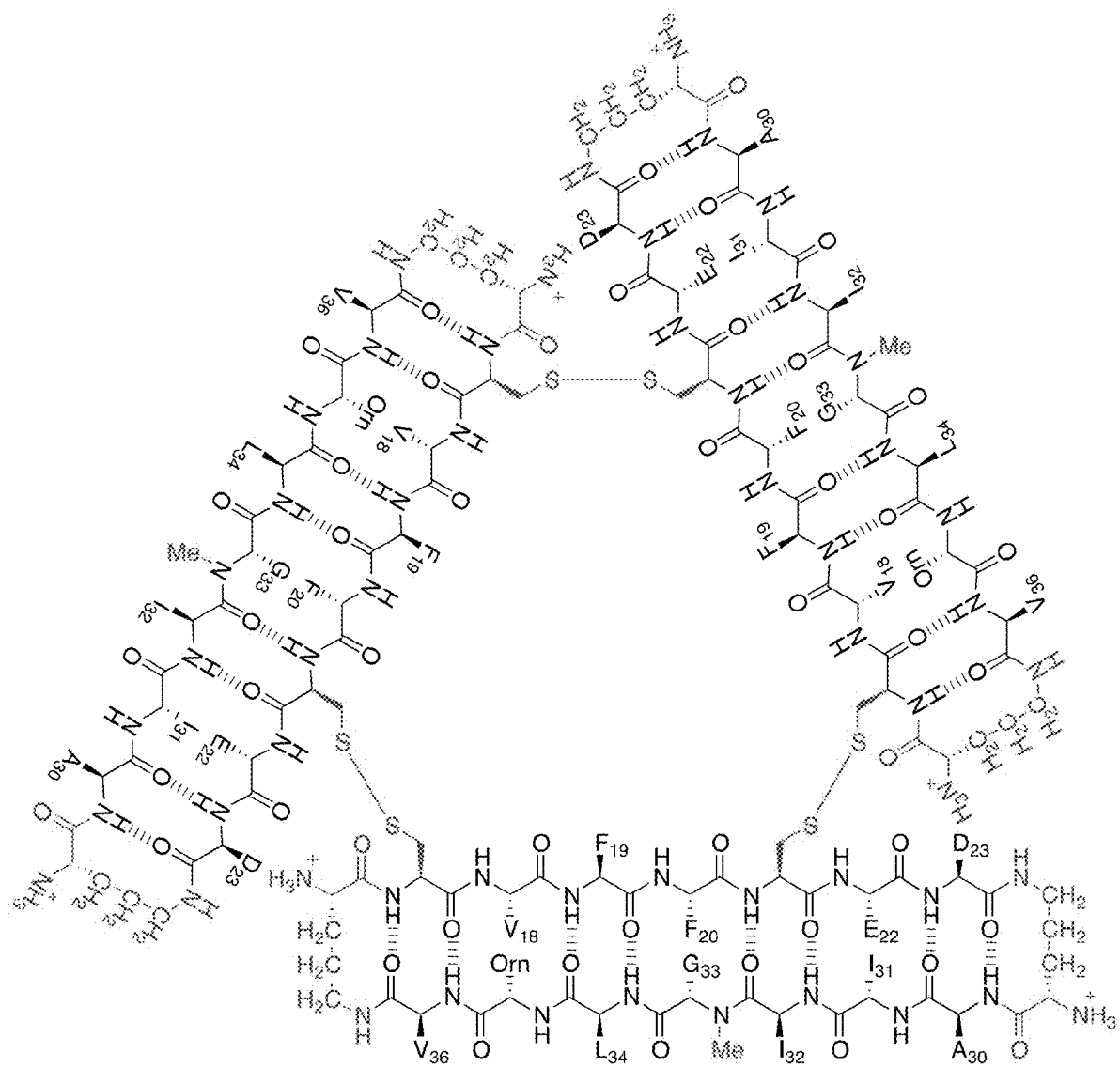
FIG. 19A provides a molecular structure diagram detailing the chemical structure and peptide sequence of trimer 3 generated from peptide 3 in accordance with various embodiments of the invention.
Figure 19B:
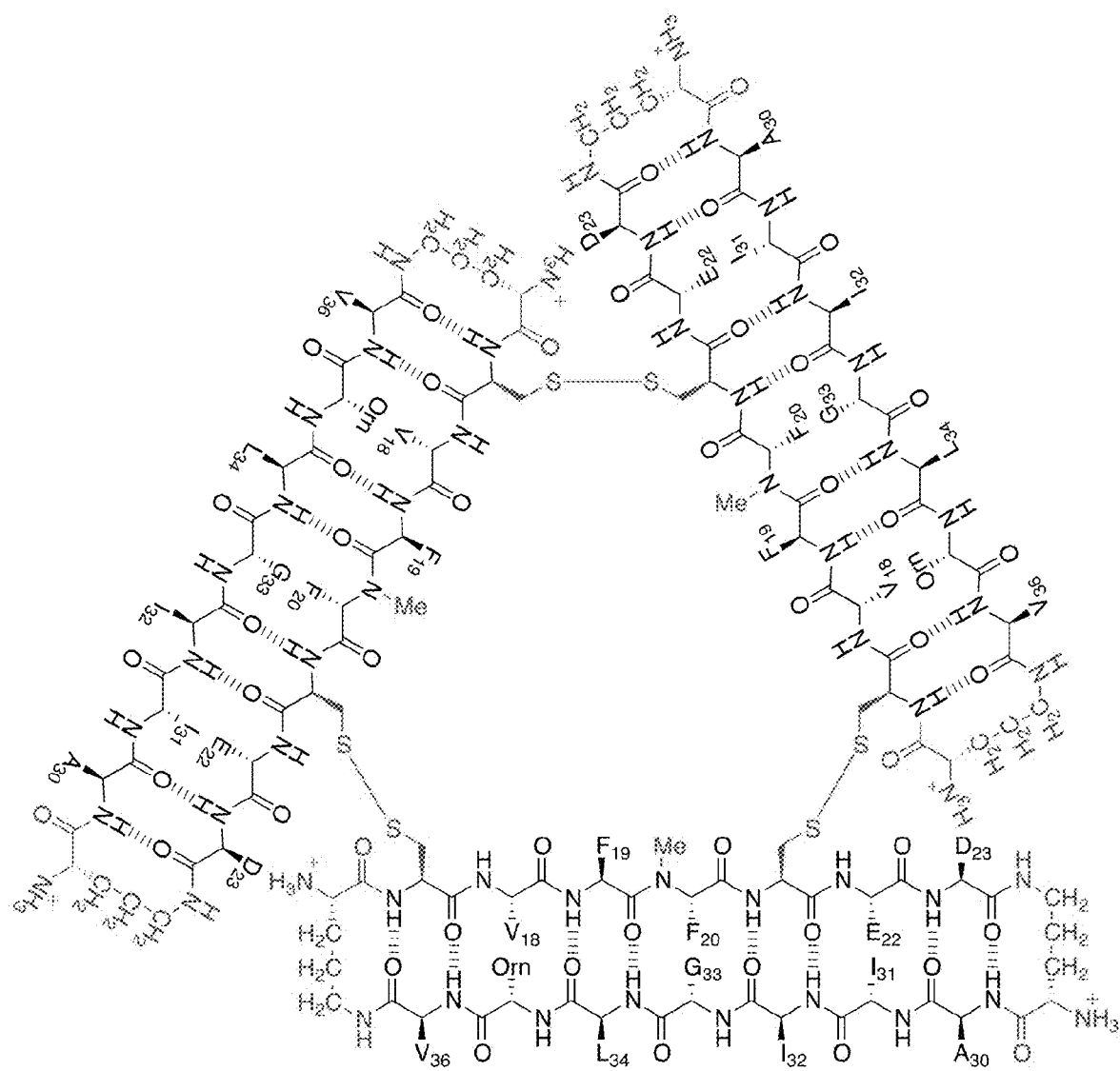
FIG. 19B provides a molecular structure diagram detailing the chemical structure and peptide sequence of trimer 4 generated from peptide 4 in accordance with various embodiments of the invention.

It was anticipated that oxidation of peptides 3 and 4 to form trimers would be challenging. The peptides have the potential to form complex mixtures of monomeric, dimeric, trimeric, and higher oligomeric oxidation products. Five different oxidation products of trimer size or smaller are possible in the oxidation reactions of peptides 3 and 4: (1) a monomer that contains an intramolecular disulfide bond between $C_{17}$ and $C_{21}$, (2) an antiparallel bis-disulfide crosslinked dimer, (3) a parallel bis-disulfide crosslinked dimer, (4) an asymmetric tris-disulfide crosslinked trimer, and (5) a symmetric tris-disulfide crosslinked trimer (FIG. 18). The desired trimers 3 and 4 are symmetric tris-disulfide crosslinked trimers (FIGS. 19A and 19B).

Figure 20A:
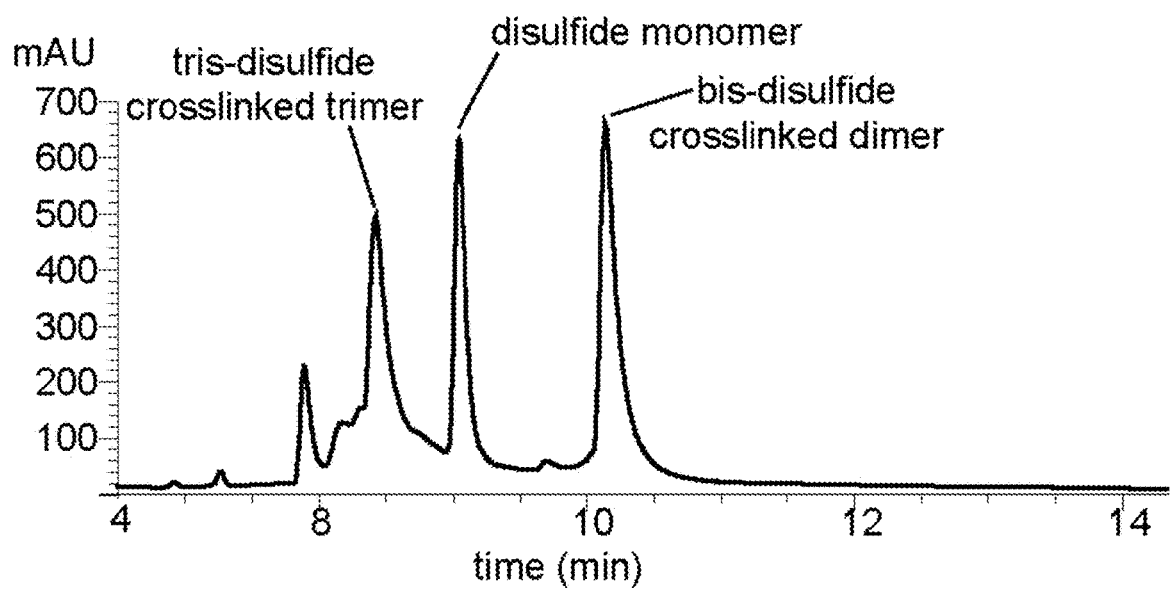
FIG. 20A provides a graphical representation of reverse-phase HPLC elutes produced by crosslinking peptide 3 in accordance with various embodiments of the invention.
Figure 20B:
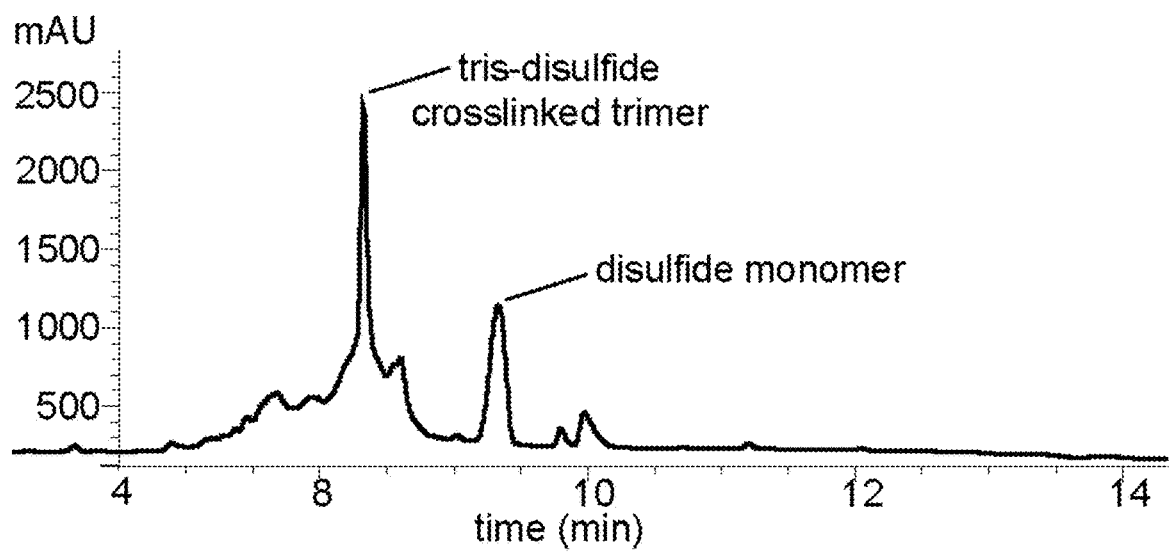
FIG. 20B provides a graphical representation of reverse-phase HPLC elutes produced by crosslinking peptide 4 in accordance with various embodiments of the invention.

A two-step procedure was developed for preparing trimers 3 and 4 from peptides 3 and 4. In the first step, peptides 3 and 4 were allowed to oxidize at relatively high concentration of peptide (6 mM) in 20% (v/v) aqueous DMSO for 48 h. In the second step, the reaction mixture was diluted with water to a low concentration (~250 µM) and the oxidized peptides were allowed to equilibrate over 48 h. Through this procedure, peptides 3 and 4 crosslink to form substantial amounts of the desired symmetric crosslinked trimers 3 and 4. In the oxidation reaction of peptide 3 three major products were observed—timer 3, a crosslinked dimer, and the disulfide monomer (FIG. 20A). In the oxidation reaction of peptides 4, two major products were observed—timer 4 and the disulfide monomer, but not appreciable amounts of either possible crosslinked dimer (FIG. 20B). Trimers 3 and 4 were purified by RP-HPLC followed by lyophilization of pure fractions to yield ~15 mg of trimer 3 and ~25 mg of trimer 4—each with ≥95% purity—from a 0.1 mmol scale synthesis of peptides 3 and 4.

X-Ray Crystallographic Structure Determination of Trimers 3 and 4.

The structures of trimers 3 and 4 were elucidated by X-ray crystallography. One of the challenges in X-ray crystallography is determining the X-ray crystallographic phases. Doing so often requires incorporation of a heavy atom—such as selenium, bromine or iodine—through covalent modification. In previously solving the X-ray crystallographic structures of peptides 1 and 2, homologues were prepared containing p-iodophenylalanine. In solving the X-ray crystallographic structures of trimers 3 and 4, two techniques for X-ray crystallographic phase determination that have not been widely used for peptides were employed: sulfur single-wavelength anomalous diffraction (S-SAD) and post-crystallization incorporation of iodide ions into the crystal lattice.

S-SAD was used to determine the X-ray crystallographic structure of trimer 4. The intrinsic anomalous scattering of the sulfur atoms in the asymmetric unit provided sufficient data to determine the X-ray crystallographic phases. Five data sets were collected from a single crystal of trimer 4 using an in-house X-ray diffractometer equipped with a rotating copper anode, and the data sets were merged to increase the strength of the anomalous signal from sulfur. The X-ray crystallographic structure generated by S-SAD (PDB 5SUS) was used as a search model for molecular replacement to solve the X-ray crystallographic phases of a higher resolution data set for trimer 4 collected using a synchrotron radiation source (PDB 5SUR).

Iodide ion incorporation and conventional SAD phasing was used to determine the X-ray crystallographic structure of trimer 3. To incorporate the iodide ions into the crystal lattice a crystal of trimer 3 was soaked in a mixture of crystallization buffer and aqueous potassium iodide (KI). The X-ray crystallographic structure of the KI-soaked trimer 3 (PDB 5SUU) was used as a search model for molecular replacement to determine the X-ray crystallographic phases of a higher resolution data set of unsoaked trimer 3 collected using a synchrotron radiation source (PDB 5SUT).

X-Ray Crystallographic Structure and Supramolecular Assembly of Trimer 3.

Figure 21:
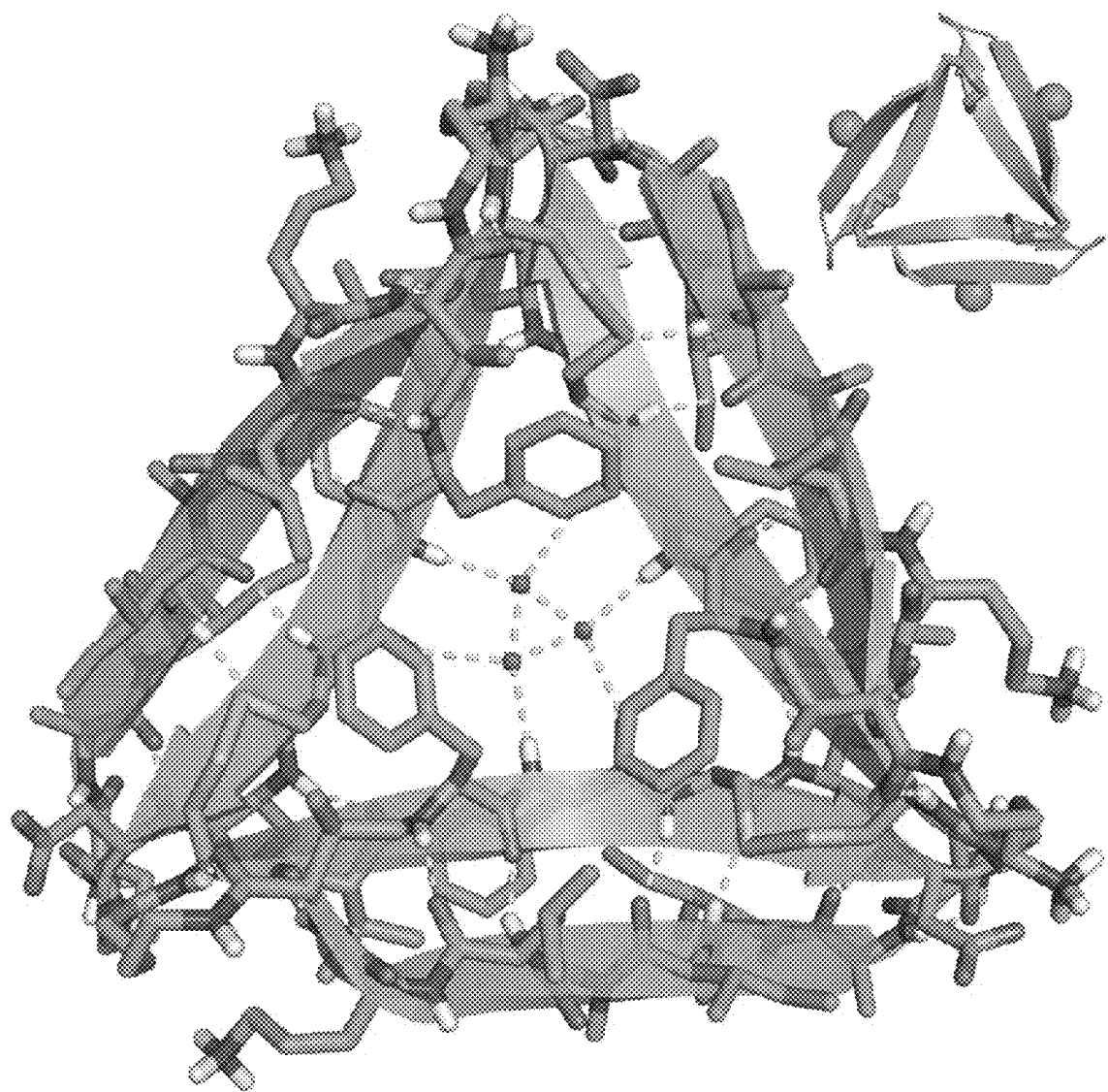
FIG. 21 provides an X-ray crystallographic schematic detailing the chemical structure of trimer 3 in accordance with various embodiments of the invention.
Figure 22:
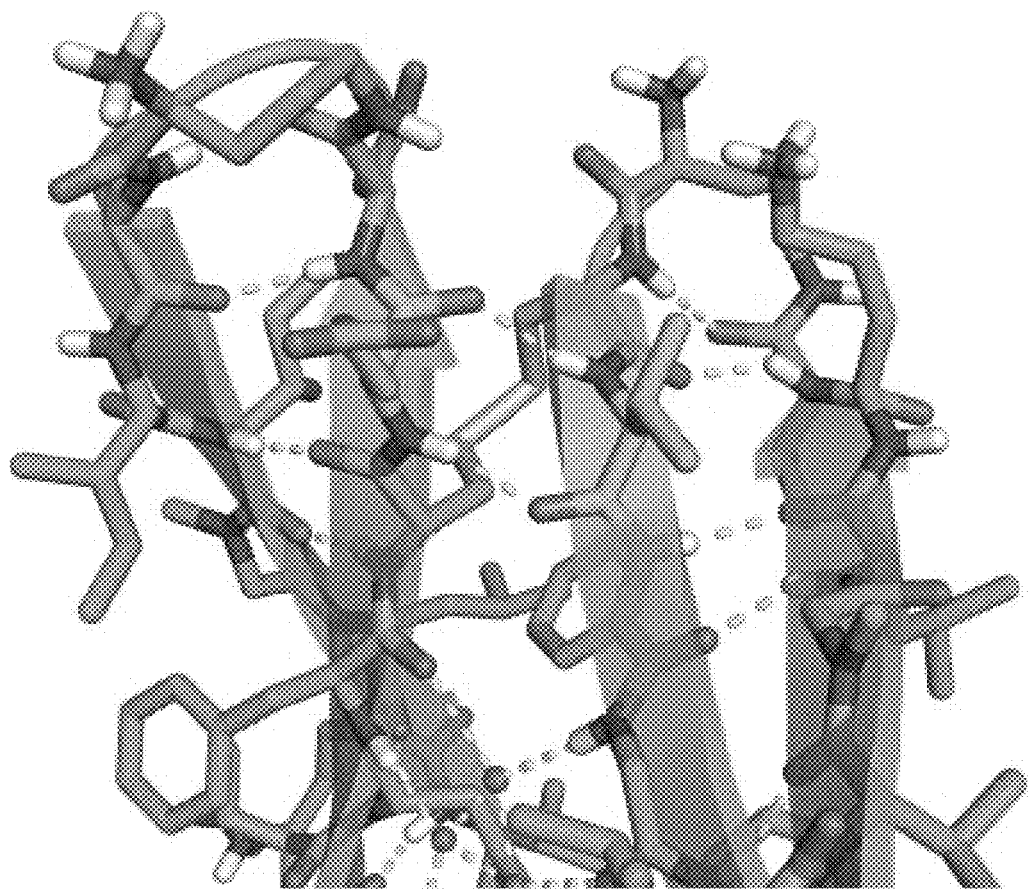
FIG. 22 provides an X-ray crystallographic schematic detailing the chemical structure of trimer 3, zoomed in on the trimer-trimer contact point, in accordance with various embodiments of the invention.

The X-ray crystallographic structure of trimer 3 reveals a symmetric trimer with three disulfide linkages between the monomeric subunits (FIG. 21). Replacement of $L_{17}$ and $A_{21}$ with cysteine was found not to perturb the triangular trimer structure. Trimer 3 is composed of three folded macrocyclic β-sheets and is virtually identical to the trimers formed by peptides 1 and 2. Trimer 3 maintains the intersheet hydrogen bonds and hydrophobic clustering of amino acid side chains. At each corner of trimer 3, the main chain of residue $V_{18}$ on one monomeric subunit hydrogen bonds with the main chain of residue $E_{22}$ on the adjacent monomeric subunit (FIG. 22).

The N-methyl groups in trimer 3 are located on the outer hydrogen bonding edges of the trimer. These N-methyl groups block the outer hydrogen-bonding edges of trimer 3 from hydrogen bonding with other trimers in the crystal lattice. Three ordered water molecules fill the hole in the center of trimer 3, hydrogen bonding with each other and with the main chain of residue $F_{20}$.

Clusters of hydrophobic residues in trimer 3 create two surfaces. The front surface displays the side chains of residues $F_{19}$, $I_{32}$, $L_{34}$, and $V_{36}$ as well as the $C_{17}$-$C_{21}$ disulfide linkage. This surface is termed the "$F_{19}$ face". The back surface displays the side chains of residues $V_{18}$, $F_{20}$, and $I_{31}$. This surface is termed the "$F_{20}$ face". Trimer 3 packs on both the $F_{19}$ face and the $F_{20}$ face to form higher-order assemblies in the crystal lattice.

Figure 23A:
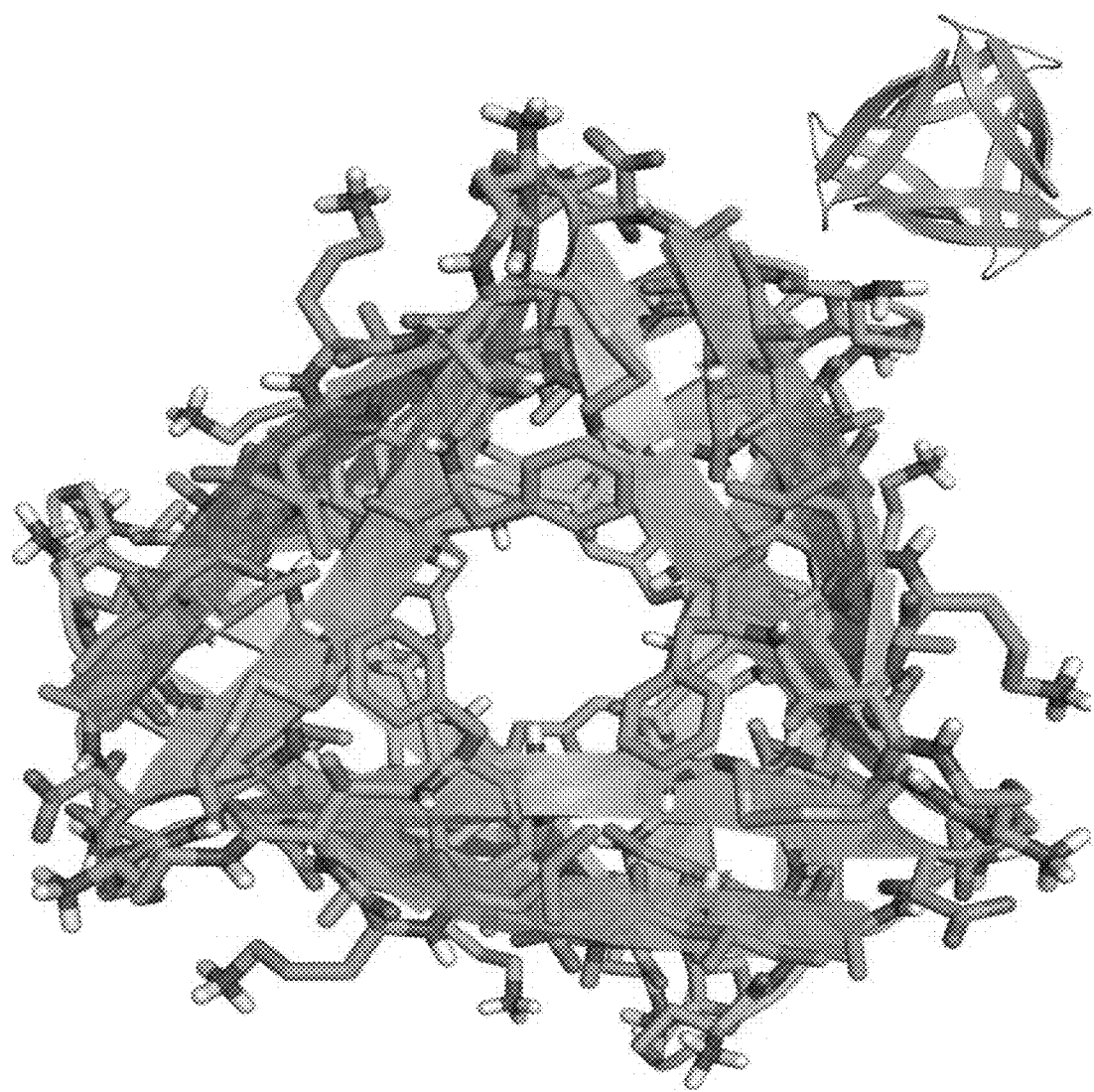
FIGS. 23A, 23B and 23C provide X-ray crystallographic schematics detailing the chemical structure of hexamers and columns formed by trimer 3, generated in accordance with various embodiments of the invention.
Figure 23C:
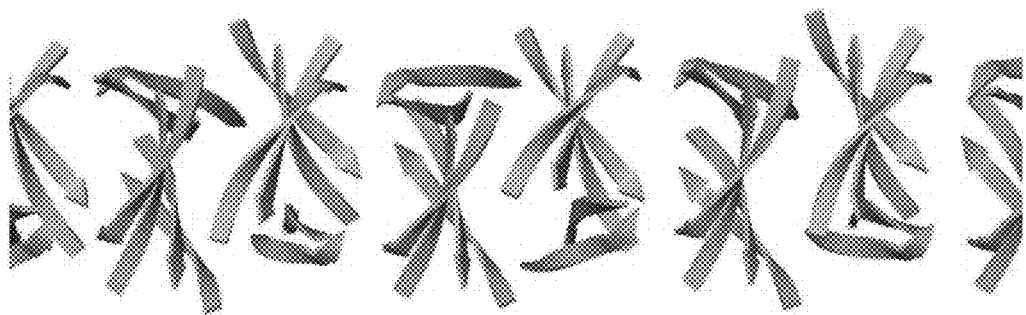
Figure 23B:
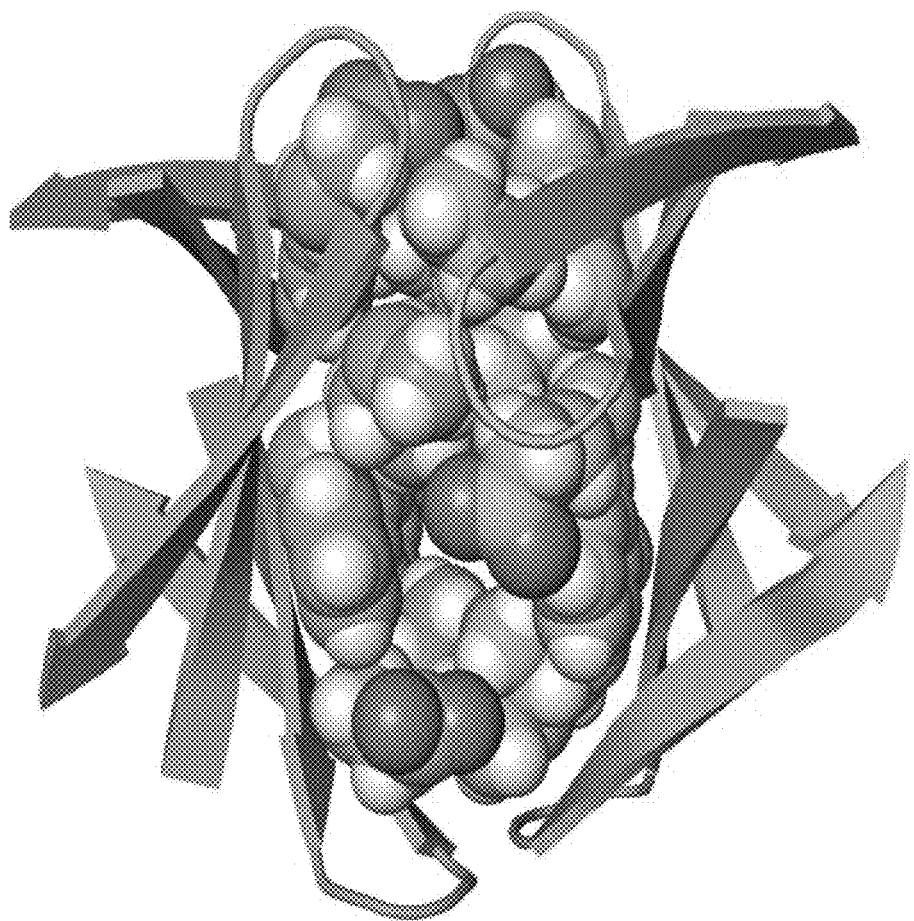

In the X-ray crystallographic structure of trimer 3, two trimers pack to form a sandwich-like hexamer (FIGS. 23A-23C). In the hexamer, the $F_{20}$ face of one trimer packs against the $F_{20}$ face of another trimer (FIG. 23B). The hexamers further assemble to form columns by stacking on their $F_{19}$ faces (FIG. 23C). The columns are arranged in a hexagonal fashion in the crystal lattice. The hexamer formed by trimer 3 is morphologically identical to the hexamers formed by peptides 1 and 2.

This mode of assembly, in which the hydrophobic faces displayed on triangular trimers pack together to form hexamers, appears to be characteristic of triangular trimers formed by amyloid-derived macrocyclic β-sheets and β-hairpins. It has also been observed that this mode of assembly occurs with a larger peptide derived from Aβ$_{17-36}$; and by a macrocyclic β-sheet peptide derived from β$_2$-microglobulin.

X-Ray Crystallographic Structure and Supramolecular Assembly of Trimer 4.

Figure 24:
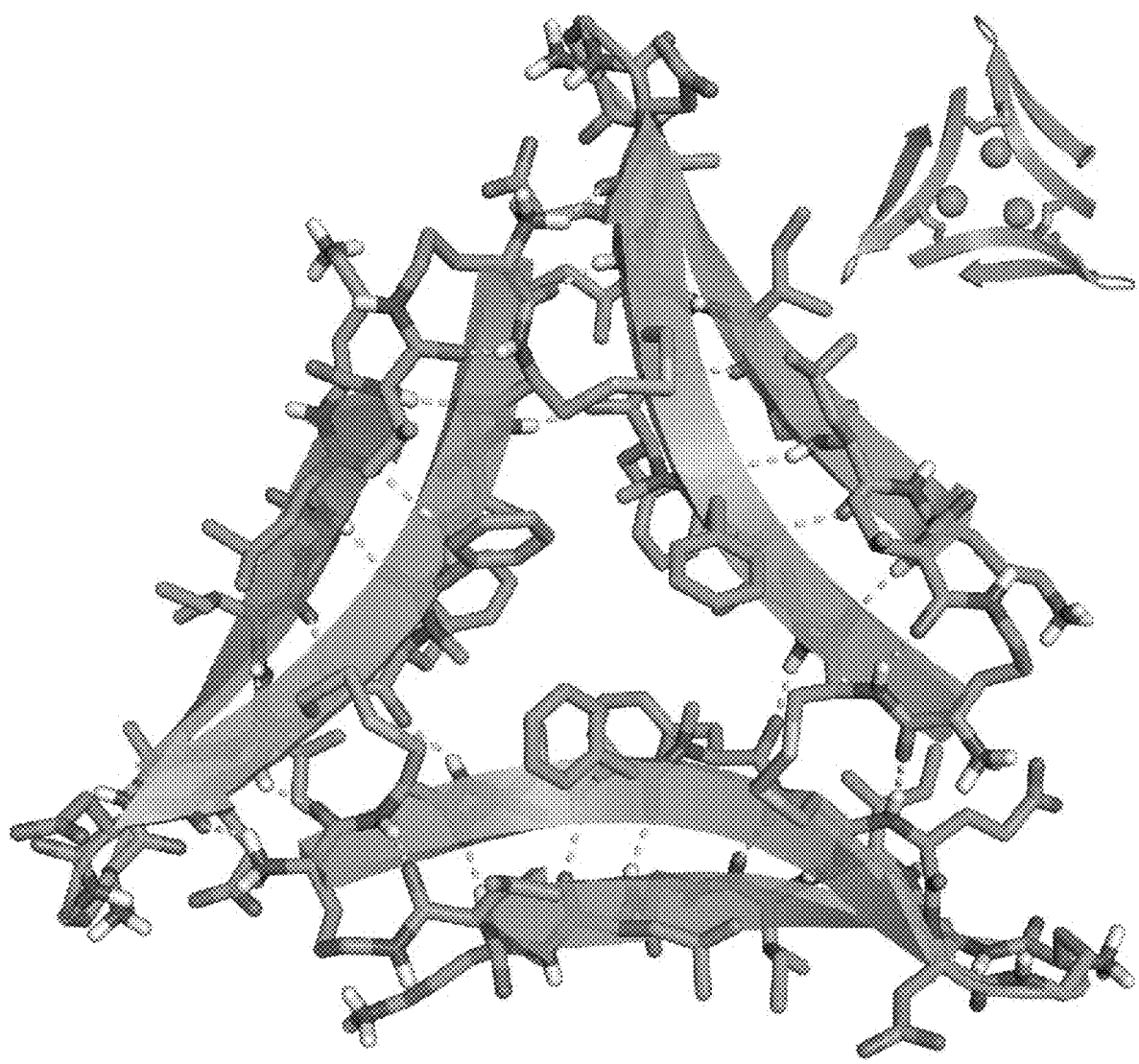
FIG. 24 provides an X-ray crystallographic schematic detailing the chemical structure of trimer 4 in accordance with various embodiments of the invention.
Figure 25:
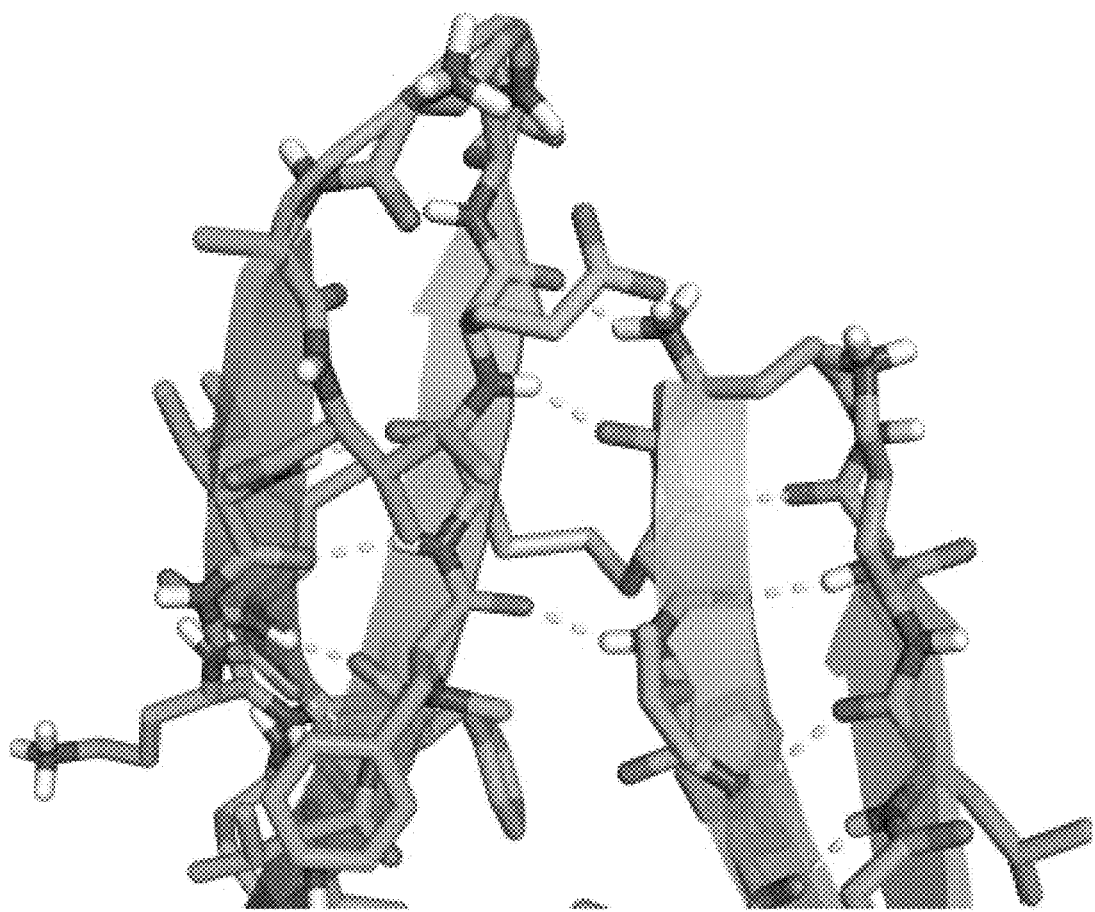
FIG. 25 provides an X-ray crystallographic schematic detailing the chemical structure of trimer 4, zoomed in on the trimer-trimer contact point, in accordance with various embodiments of the invention.

The X-ray crystallographic structure of trimer 4 reveals a symmetric trimer that is crosslinked through disulfide linkages between C$_{17}$ of one monomeric subunit and C$_{21}$ of the adjacent monomeric subunit (FIG. 24). Although trimer 4 is composed of three folded macrocyclic β-sheets, it differs in conformation from the trimers formed by peptides 1 and 2, and also differs in conformation from trimer 3. In the three other trimers, the main chains of residues V$_{18}$ and E$_{22}$ are hydrogen bonded at the corners of the trimer. In trimer 4 residues V$_{18}$ and E$_{22}$ shift out of alignment by two residues, such that residue V$_{18}$ is across from residue F$_{20}$ and residue E$_{22}$ is across from $^δ$Orn (FIG. 25). In further contrast to trimer 3, the N-methyl groups in trimer 4 are sequestered in the center hole of the trimer, exposing the outer hydrogen-bonding edges and allowing trimer 4 to hydrogen bond with other trimers in the crystal lattice.

Clusters of hydrophobic residues in trimer 4 create two surfaces, termed the "F$_{19}$ face" and the "F$_{20}$ face," respectively. The F$_{19}$ face displays the hydrophobic side chains of residues F$_{19}$, I$_{32}$, L$_{34}$, and V$_{36}$, as well as the C$_{17}$-C$_{21}$ disulfide linkage. The F$_{20}$ face displays the hydrophobic side chains of residues V$_{18}$, F$_{20}$, and 131.

Figure 26:
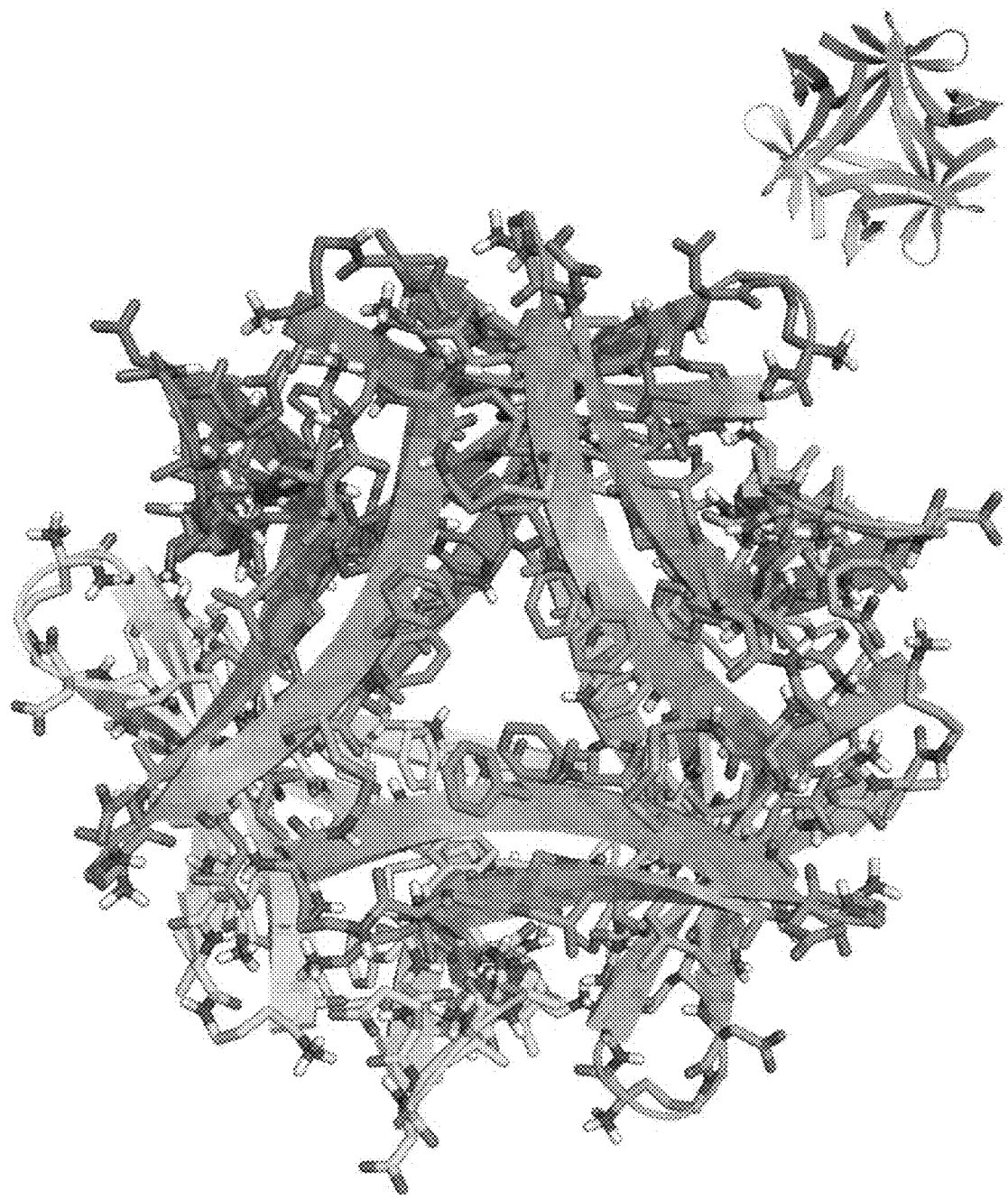
FIG. 26 provides an X-ray crystallographic schematic detailing a dodecamer formed by trimer 4, generated in accordance with various embodiments of the invention.

In the X-ray crystallographic structure of trimer 4, four trimers assemble in a tetrahedral fashion to form a ball-shaped dodecamer (FIG. 26). The dodecamer is stabilized by a network of hydrogen bonds among the outer edges of the four trimers: the main chains of residues G$_{33}$ and Orn$_{35}$ on one trimer hydrogen bond with the main chains of residues I$_{31}$ and $^δ$Orn on an adjacent trimer. The hydrophobic residues on the F$_{20}$ faces of the four trimers line the inside of the dodecamer, creating a large hydrophobic cavity approximately 20 nm in diameter.

Figure 27A:
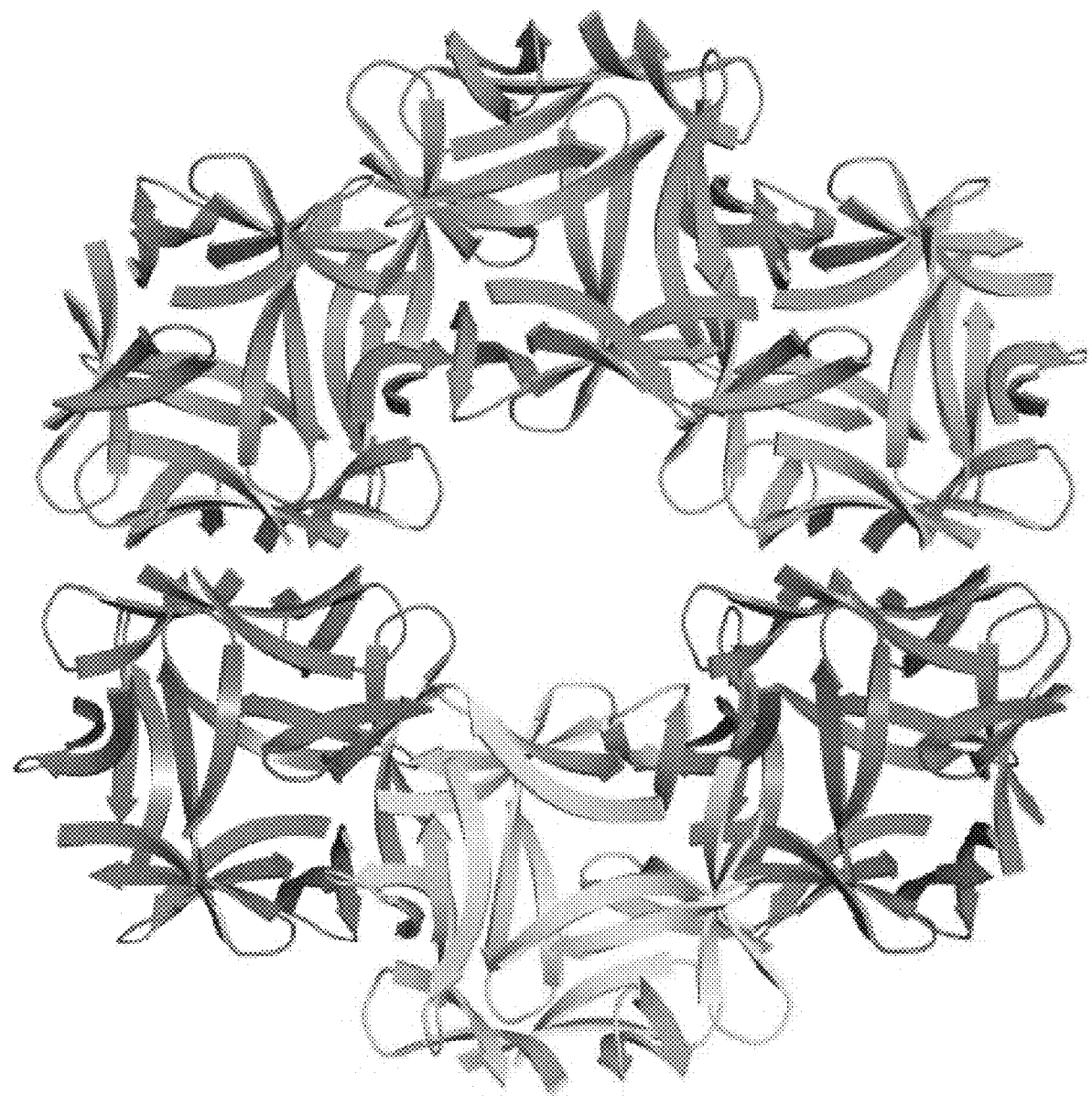
FIGS. 27A, 27B and 27C provide X-ray crystallographic schematics detailing an annular pore formed by trimer 4, generated in accordance with various embodiments of the invention.
Figure 27C:
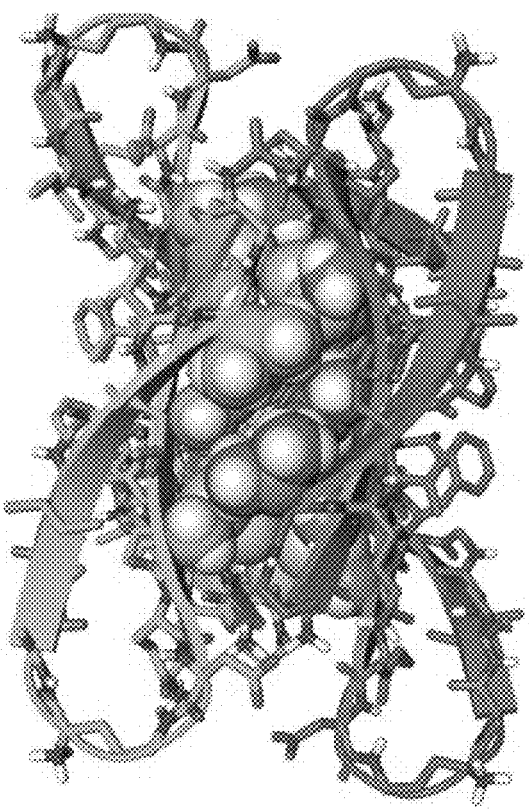
Figure 27B:
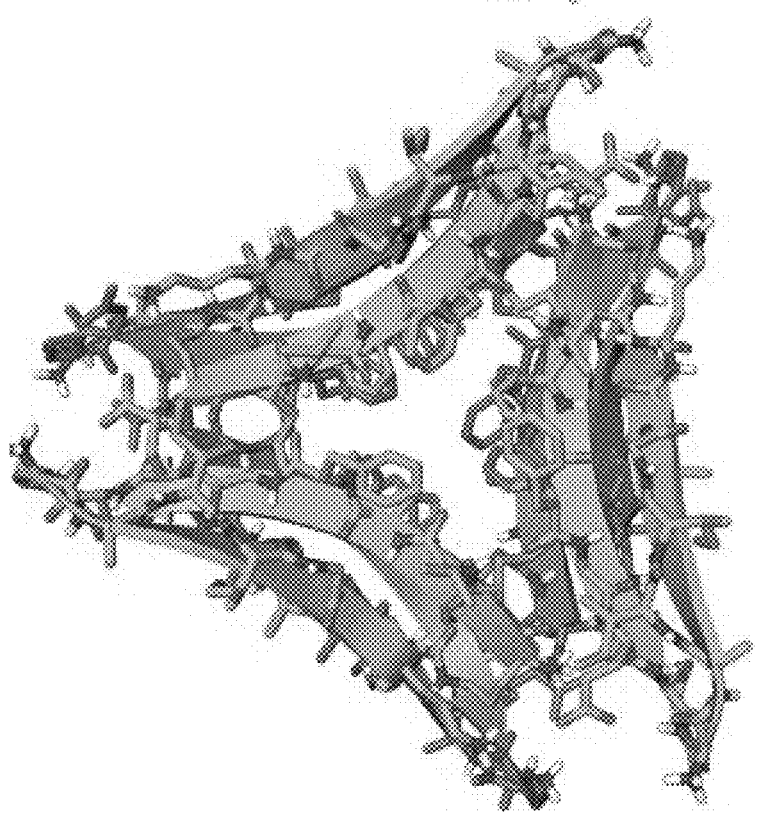

The ball-shaped dodecamers pack to form a crystal lattice. Within the crystal lattice, six dodecamers assemble to form annular porelike structures (FIG. 27A). Hydrophobic packing between the F$_{19}$ faces displayed on the exterior of each dodecamer stabilizes these annular porelike structures. At the interfaces between the dodecamers in the annular pore, two trimers pack to form a sandwich-like hexamer (FIGS. 27B and 27C). Each interface is stabilized by hydrophobic packing between the side chains of residues on the F$_{19}$ face and pi stacking between the F$_{19}$ residues on each trimer.

As explained in the preceding paragraphs, trimer 3 and trimer 4 assemble to form different higher-order assemblies within the crystal lattice. Trimer 3 packs to form sandwich-like hexamers, whereas trimer 4 assembles to form ball-shaped dodecamers that further assemble to form annular pores. The difference in the position of the N-methyl group on the two trimers may explain the differences in the assemblies that form. In trimer 4, the N-methyl group on residue F$_{20}$ is sequestered in the center hole of the trimer, exposing the outer hydrogen-bonding edges and allowing trimer 4 to hydrogen bond with the three other trimer 4 subunits that comprise the ball-shaped dodecamer. In trimer 3, the N-methyl group on residue G$_{33}$ prevents dodecamer formation by blocking hydrogen bonds with other trimers. Instead, trimer 3 forms a sandwich-like hexamer that is primarily stabilized by packing between the hydrophobic surfaces of the two trimers.

The ball-shaped dodecamers formed by trimer 4 may better represent the types of oligomers that full-length Aβ can form. In trimer 4 the N-methyl group is hidden and does not block further assembly. A β-hairpin formed by full-length Aβ could assemble in the same fashion to form trimers and dodecamers. This scenario appears likely, since β-hairpins are thought to be the building blocks of some Aβ oligomers and since trimers and dodecamers are known to be important Aβ oligomers (L. Yu, et al., Biochemistry 2009 48, 1870-1877; H. A. Scheidt, et al., *J. Biol. Chem.* 2012 287, 22822-22826; T. Doi, et al., *Biochem. Biophys. Res. Commun.* 2012 428, 458-462; and W. M. Tay, et al., *J. Mol. Biol.* 2013 425, 2494-2508; the disclosures of which are incorporated herein by reference).

Biological Studies and Solution-Phase Biophysical Studies of Trimers 3 and 4.

Trimers 3 and 4 constitute the first covalently stabilized oligomers derived from Aβ with well-defined structures and thus provide tools to investigate the biological significance of the triangular assembly. Trimers 3 and 4, as well as peptides 1 and 2, were compared in a series of biological and biophysical experiments to evaluate the effect of covalent stabilization of the trimers, and also to correlate the differences in structure and supramolecular assembly observed in the X-ray crystallographic studies with biological and solution-phase behavior.

Figure 28B:
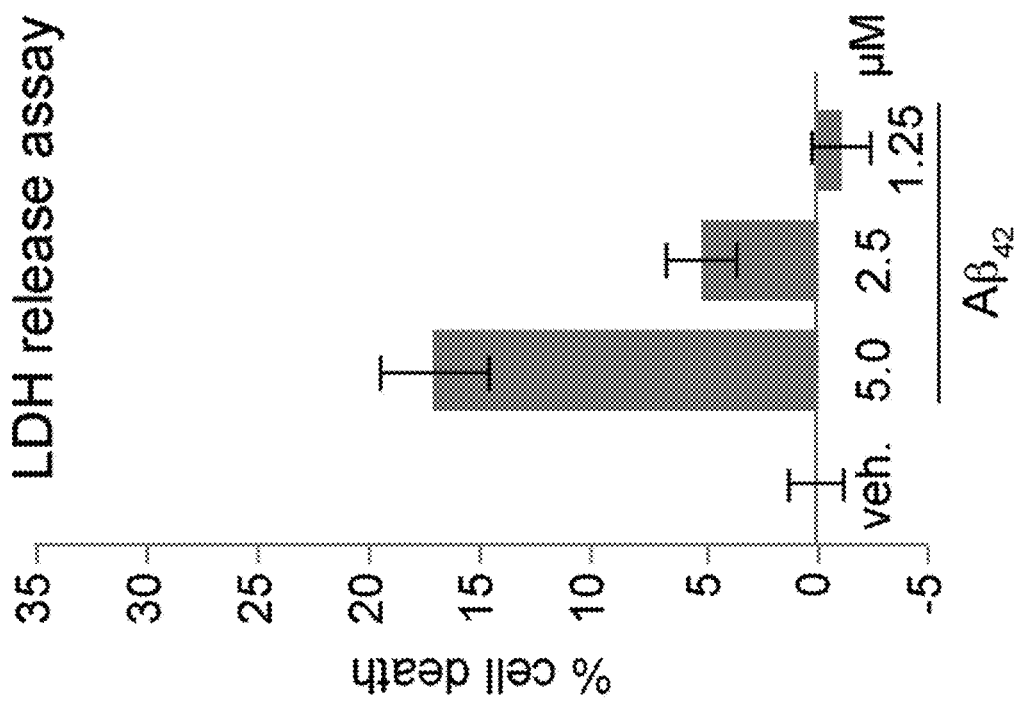
FIG. 28B provides a data graph demonstrating that $A\beta_{1-42}$ is toxic to SH-SY5Y cells.
Figure 28A:
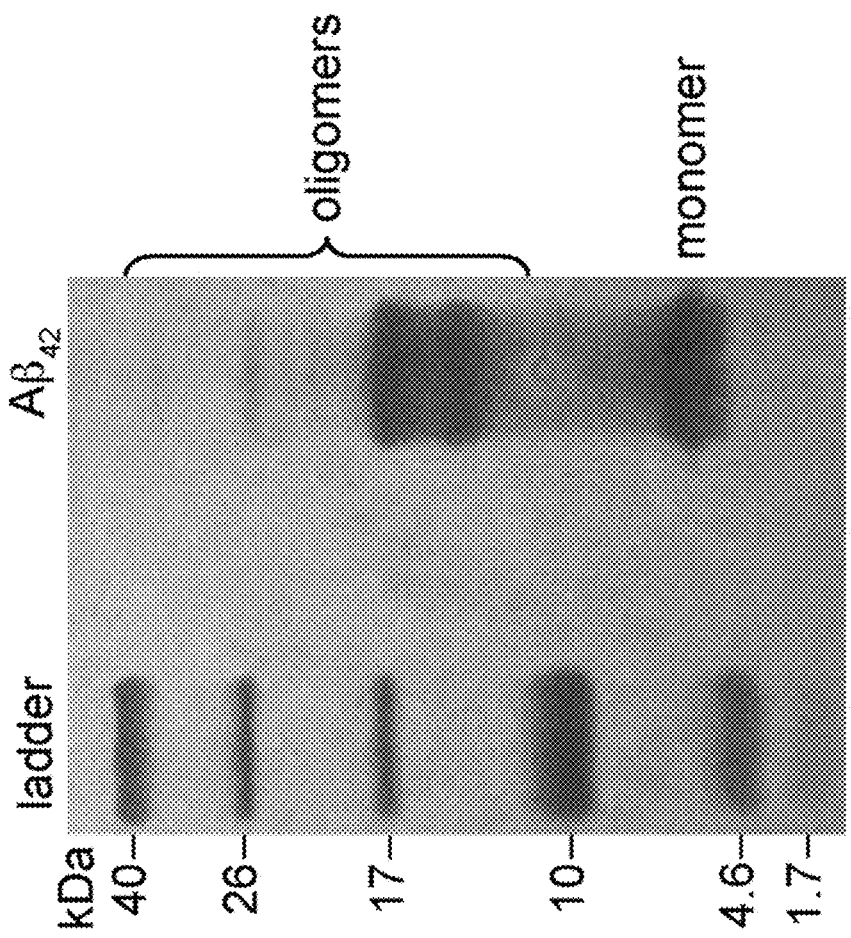
FIG. 28A provides an image of a silver stain demonstrating that $A\beta_{1-42}$ forms oligomers.

Aβ is known to be toxic toward neurons and neuronally derived cells (I. Benilova, et al., 2012, cited supra). To corroborate the toxicity of Aβ, we prepared oligomers of Aβ$_{42}$ and studied their toxicity toward a human neuroblastoma cell line, SH-SY5Y. Aβ oligomers were prepared according to the procedure developed by Teplow and coworkers using recombinantly expressed Aβ$_{42}$ pretreated with NH$_4$OH (purchased from rPeptide) (D. B. Teplow, *Methods Enzymol.* 2006 413, 20-33; and Y. Fezoui, et al., *Amyloid.* 2000 7, 166-178; the disclosures of which are incorporated herein by reference). Under the conditions of the oligomer preparation, Aβ$_{42}$ forms predominantly monomer, trimer, and tetramer as assessed by SDS-PAGE (FIG. 28A). It was also observed that bands migrated with molecular weights consistent with a pentamer and hexamer. SH-SY5Y cells were treated with varying concentrations of Aβ$_{42}$, and toxicity was evaluated using a lactate dehydrogenase (LDH) release assay. Aβ$_{42}$ increased LDH release in a dose-dependent manner at concentrations as low as 2.5 µM, corroborating the toxicity of Aβ$_{42}$ (FIG. 28B).

Figure 29A:
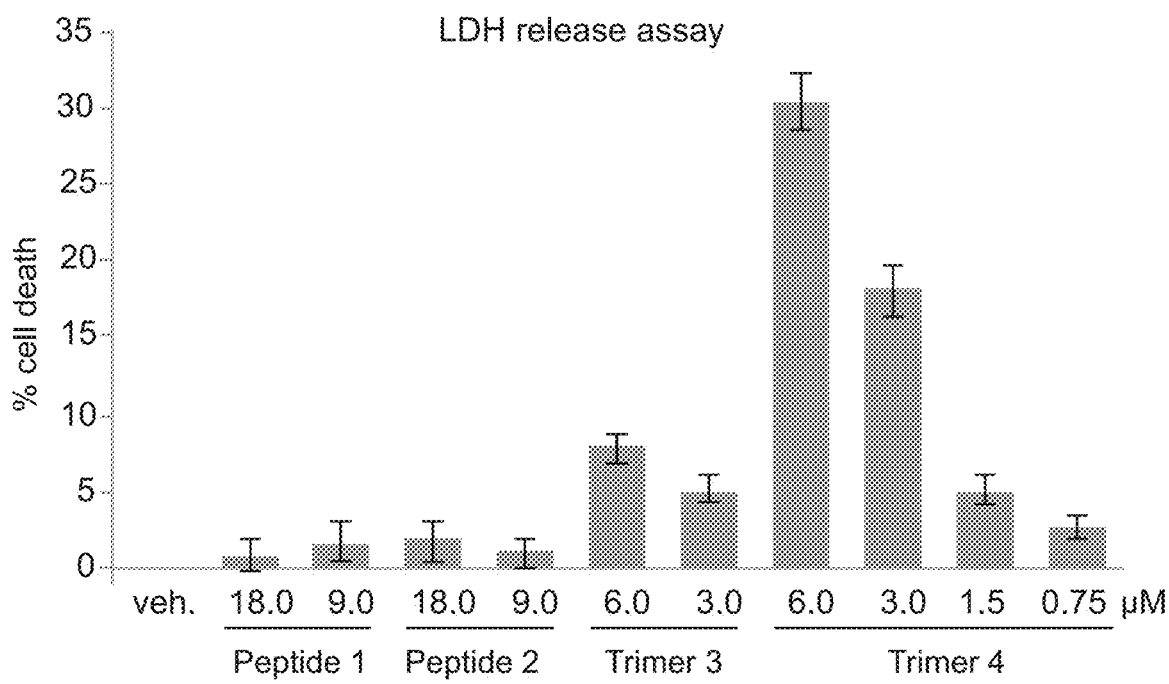
FIG. 29A provides a data graph detailing the toxicity of peptides 1 and 2 and trimers 3 and 4 to SH-SY5Y cells, generated in accordance with various embodiments of the invention.
Figure 29B:
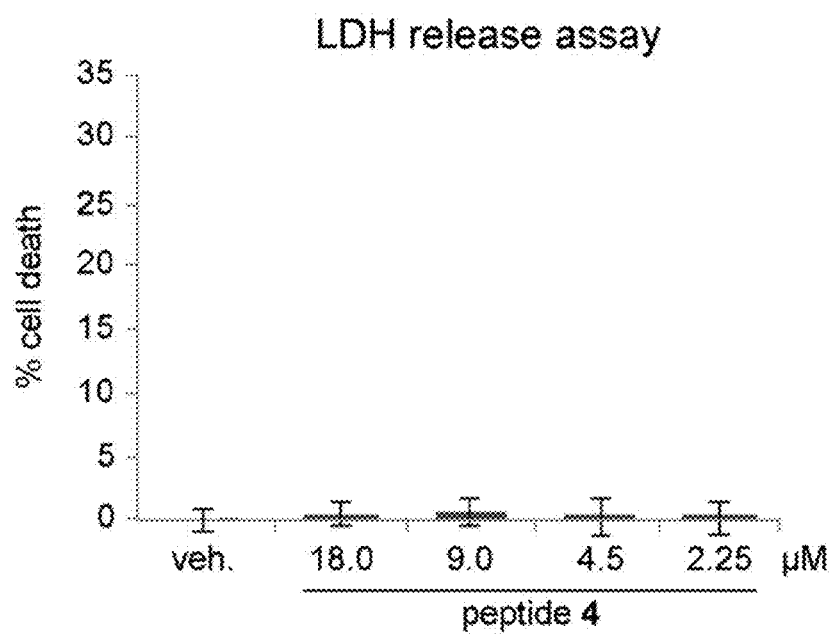
FIG. 29B provides a data graph demonstrating that peptide 4 is not toxic to SH-SY5Y cells.

It was hypothesized that trimers 3 and 4 may elicit toxicity similarly to Aβ$_{42}$. The toxicities of trimers 3 and 4 towards SH-SY5Y cells were evaluated using an LDH assay, using deionized water (vehicle) and peptides 1 and 2 as controls. Trimer 4 increased LDH release in a dose-dependent manner at concentrations as low as 1.5 µM, indicating toxicity toward SH-SY5Y cells (FIG. 29A). LDH release was observed as early as 48 h after addition to the cells and reached a maximum after 72 h. The toxicity of timer 4 does not arise from in situ reduction to peptide 4, as peptides 4 shows little or no toxicity in LDH release assays (FIG. 293). Trimer 3 showed far less LDH release than trimer 4. Peptides 1 and 2 showed little or no LDH release.

Figure 30A:
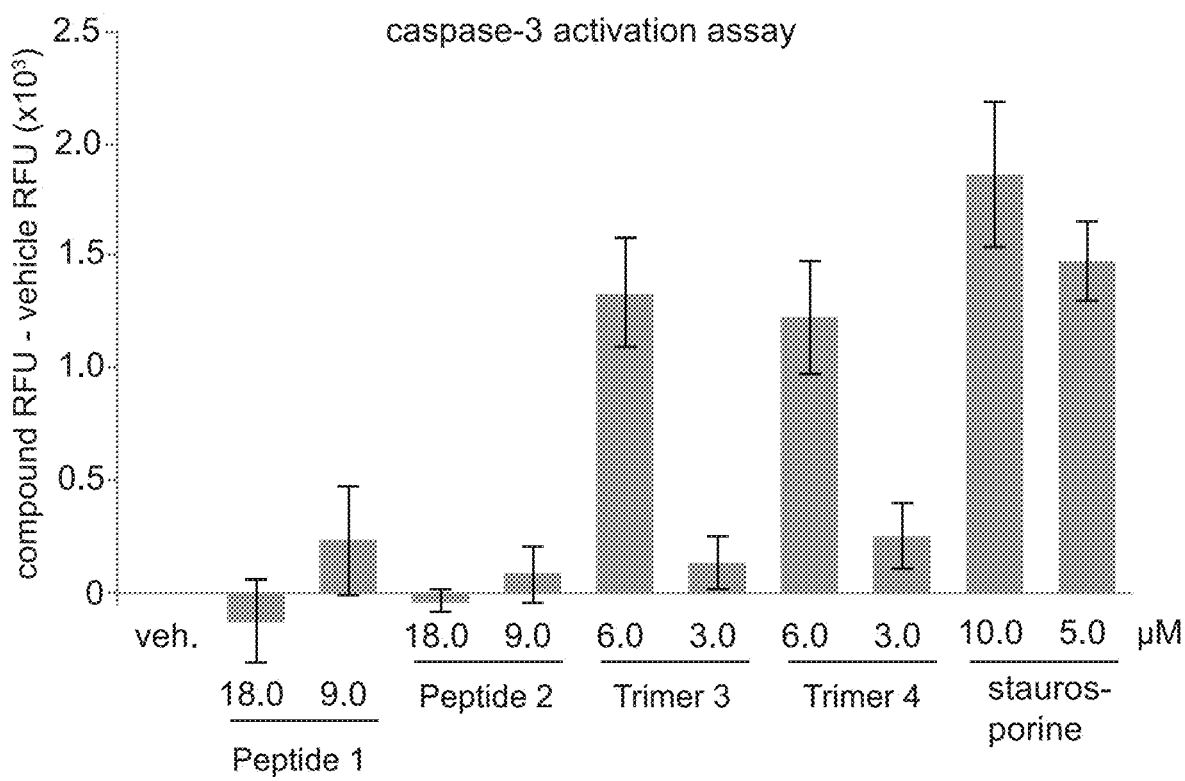
FIG. 30A provides a data graph detailing the toxicity of peptides 1 and 2 and trimers 3 and 4 to SH-SY5Y cells, generated in accordance with various embodiments of the invention.

One of the ways in which A oligomers elicit toxicity is through induction of caspase-3 mediated apoptosis. Trimers 3 and 4 were evaluated for their ability to induce caspase-3 mediated apoptosis using a rhodamine-based caspase-3 activity assay. At 6 µM, both trimers 3 and 4 induced apoptosis within 72 h after addition to the cells, whereas peptides 1 and 2 show little or no effect (FIG. 30A).

Caspase-3 activity levels after treatment with trimers 3 and 4 is comparable, to that of the known caspase-3 activator, staurosporine.

Figure 30B:
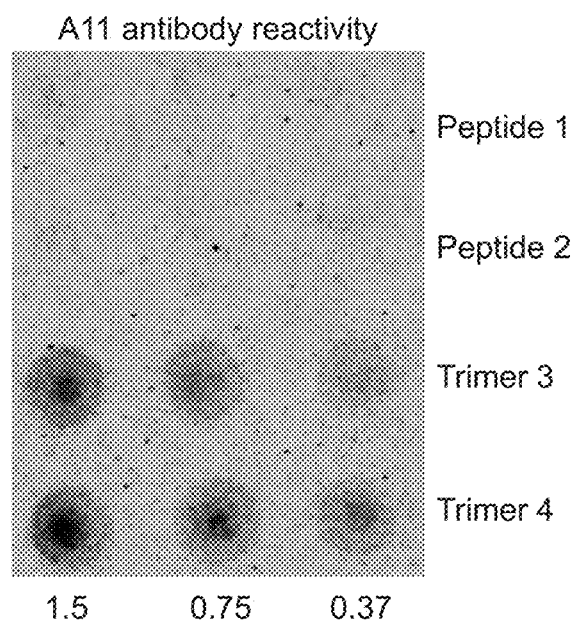
FIG. 30B provides a dot blot detailing trimers 3 and 4, but not peptides 1 and 2, are recognizable by the A11 antibody, generated in accordance with embodiments of the invention.

The LDH release and caspase-3 activation studies indicate that trimers 3 and 4 behave similarly to oligomers of full-length Aβ, providing evidence for the biological significance of the triangular assembly. To further evaluate how the biological properties of trimers 3 and 4 compare to those of full-length Aβ, the reactivity of trimers 3 and 4 with the conformation specific antibody A11 was examined. The A11 antibody specifically recognizes oligomeric assemblies of Aβ, but does not recognize Aβ, monomers or Aβ fibrils. The structures of the A oligomers recognized by the A11 antibody are not known. We investigated whether the A11 antibody recognizes trimers 3 and 4 by dot blot analysis. Trimers 3 and 4 react with the A11 antibody, but peptides 1 and 2 do not (FIG. 30B). These results demonstrate that the A11 antibody recognizes trimers 3 and 4, suggesting that oligomers of full-length Aβ may also contain triangular trimers.

31B). Trimer 3 migrates as a single band at a molecular weight consistent with a hexamer. Trimer 4, in contrast, migrates as two distinct bands: a band consistent with the molecular weight of a dodecamer, and a band consistent with the molecular weight of a trimer. The dodecamer band shows pronounced streaking, suggesting equilibrium with lower molecular weight oligomers, such as nonamers and hexamers. Peptides and 2 migrate at molecular weights consistent with either a monomer or dimer.

Circular dichroism spectra reflect the cooperative folding and assembly of macrocyclic β-sheet peptides. Trimers 3 and 4 exhibit canonical 3-sheet character as evidenced by a negative band at ~217 nm and positive band at ~195 nm (FIG. 31C). The spectra of peptides 1 and 2, in contrast, show no well-defined structure. These results indicate that covalent stabilization not only locks in conformation, but also promotes folding of the monomeric subunits into β-hairpins. Table 1 summarizes the results of the structural and biological studies described above.

TABLE 1

Structures, stoichiometries, and biological activities of trimer 4 and trimer 4, and peptides 1 and 2.

| compound | PDB ID | oligomer size by | | | A11 reactivity | LDH release | caspase-3 activation |
| --- | --- | --- | --- | --- | --- | --- | --- |
| | | crystallography | SEC | SDS-PAGE | | | |
| trimer 3 | 5SUT | 6 | 6 | 6 | yes | some | yes |
| trimer 4 | 5SUR | 6 and 12* | 6 | 3 and 12 | yes | yes | yes |
| peptide 1 | 4NTR | 3, 6, and 12 | 1-2 | 1-2 | no | no | no |
| peptide 2 | 4NW9 | 3, 6, and 12 | 1-2 | 1-2 | no | no | no |

*In the X-ray crystallographic structure of trimer 4, the dodecamers further assemble to form annular porelike structures.

The differences in LDH release, caspase-3 activation, and A11 antibody reactivity between the covalently attached trimers and the peptides suggest that covalent stabilization of the triangular trimer is necessary for these small peptides to mimic the oligomers of full-length Aβ at micromolar concentrations. Furthermore, the difference in LDH release between trimer 3 and trimer 4 may reflect differences in the solution-phase behavior. To understand more about the solution-phase behavior, size exclusion chromatography (SEC), SDS-PAGE, and circular dichroism (CD) were performed.

Figure 31A:
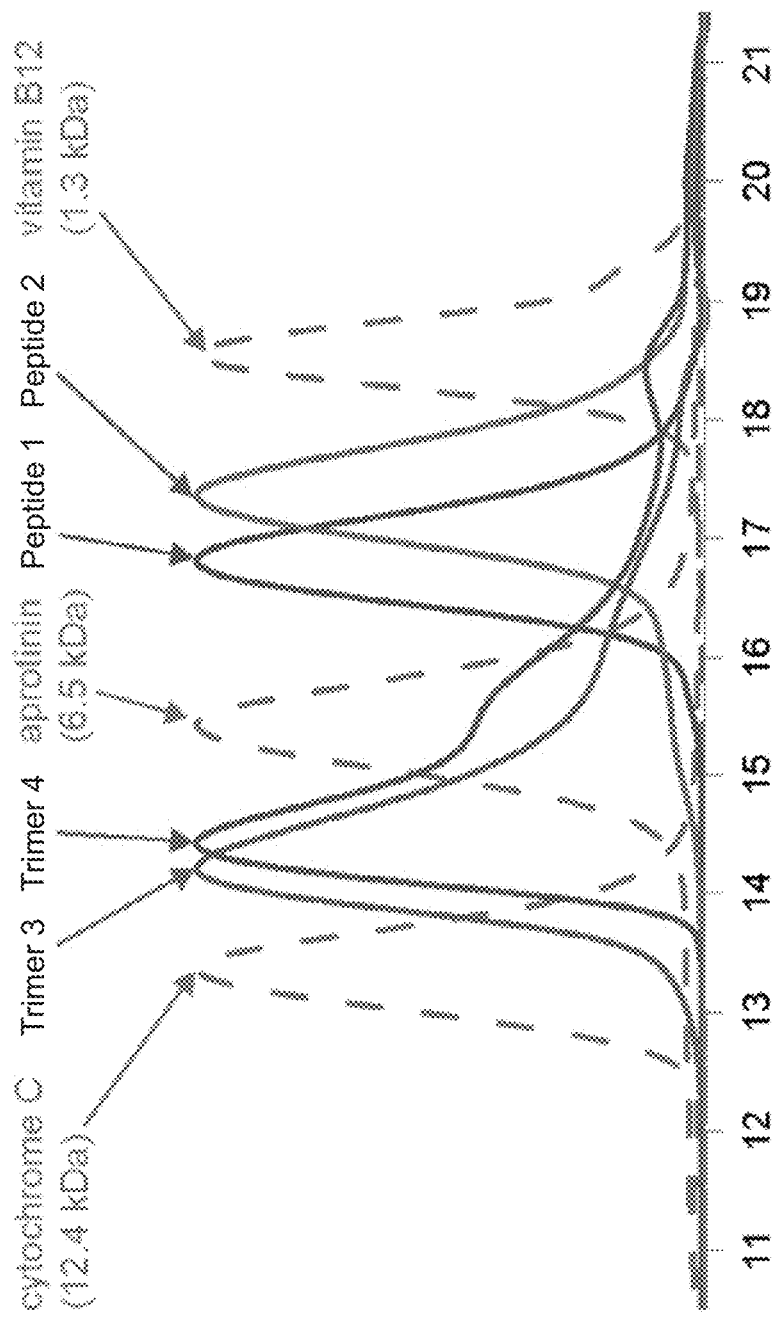
FIG. 31A provides a data graph of size exclusion chromatography of peptides 1 and 2, trimers 3 and 4, and other reference proteins, generated in accordance with embodiments of the invention.

SEC studies revealed that trimers 3 and 4 assemble to form higher-order oligomers in solution. The elution profiles in acetate buffer of trimers were compared to peptides 1 and 2. Size standards vitamin B12 (1.3 kDa), aprotinin (6.5 kDa), and cytochrome c oxidase (12.4 kDa) eluted at 18.6 mL, 15.4 mL, and 13.4 mL, respectively (FIG. 31A). Trimer 3 and 5 eluted at 14.3 mL and at 14.5 mL, respectively. These elution volumes are consistent with the molecular weight of a hexamer (10.6 kDa). The peaks for trimers 3 and 4 tail slightly and may reflect a trimer-hexamer equilibrium in which the hexamer predominates. The tail of trimer 4 demonstrates a distinct hump at 15.6 mL, suggesting a slow equilibrium between the trimer and hexamer.

Under the conditions of the SEC experiments, peptides 1 and 2 do not assemble to form trimers. Peptides 1 and 2 elute at 16.8 mL and 17.3 mL, respectively. These volumes are lower than would be expected for a 1.7 kDa monomer and higher than would be expected for a 5.3 kDa trimer, suggesting that peptides 1 and 2 may form dimers in solution.

SDS-PAGE followed by silver staining reveals that trimers 3 and 4 assemble to form SDS-stable oligomers (FIG.

Offset Aβ Hairpin Peptides

In the current example, it was set out to explore how altering the residue pairing of the β-hairpin associated with peptide 1 alters the resulting supramolecular assembly. It was envisioned that a scenario in which $A\beta_{15\text{-}23}$ is free to adopt three pairings with $A\beta_{0\text{-}36}$: one in which $A\beta_{17\text{-}23}$ pairs with $A\beta_{30\text{-}36}$, one in which $A\beta_{16\text{-}22}$ pairs with $A\beta_{30\text{-}36}$, and one in which $A\beta_{15\_21}$ pairs with $A\beta_{30\_36}$. FIG. 32 illustrates this concept. These shifts in pairing sequentially pull $Lys_{16}$ and $Gln_{15}$ into the upper β-strand while pushing $Asp_{23}$ and $Glu_{22}$ out of the β-strand and into the loop.

Figure 32A:
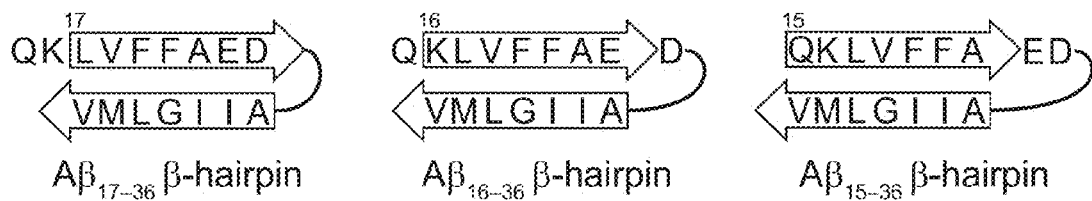
FIG. 32A provides schematics of three different β-hairpins formed by $A\beta_{15-36}$, with different residue pairings.
Figure 32B:
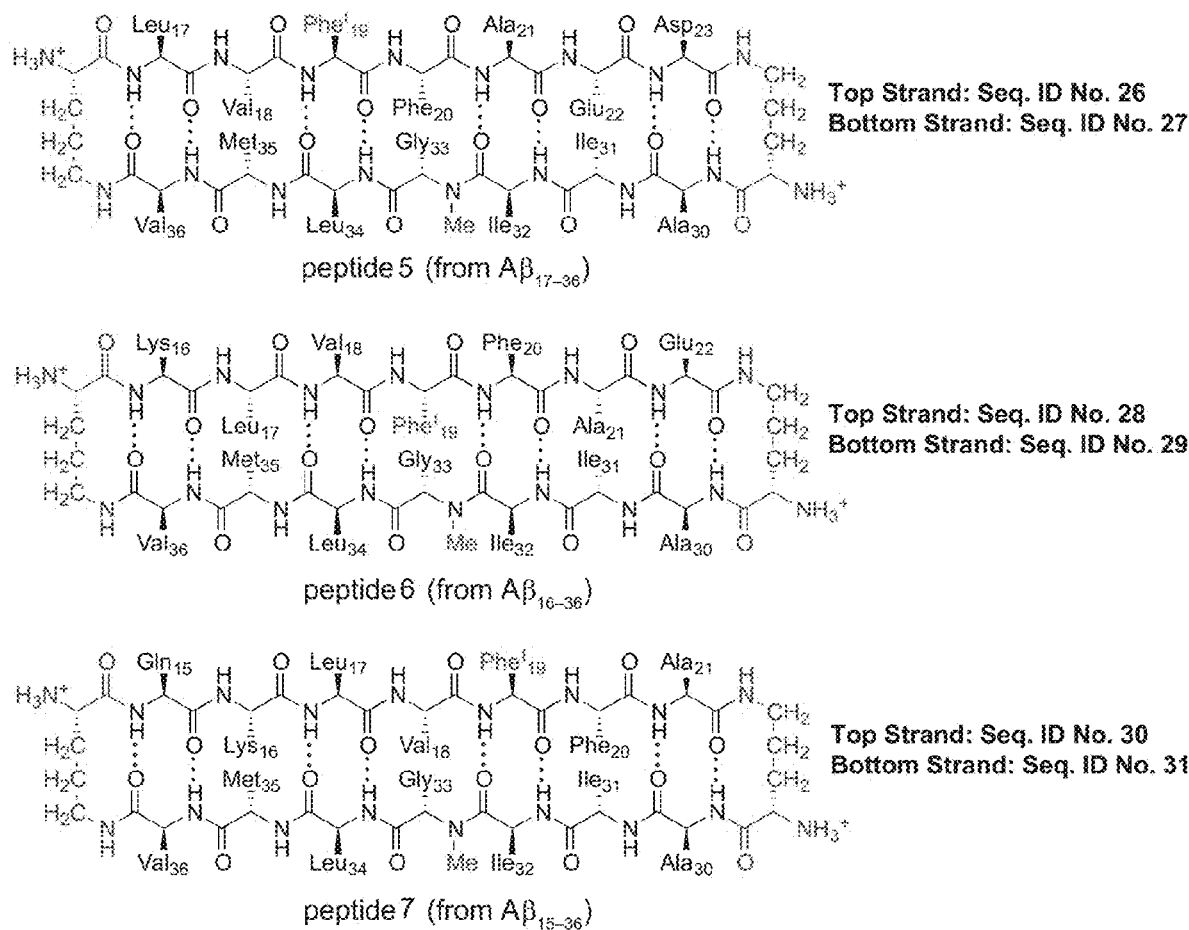
FIG. 32B provides molecular structure diagrams detailing the chemical structure and peptide sequence of peptides 5-7 in accordance with various embodiments of the invention.

Macrocyclic β-hairpin peptides 5, 6, and 7 were designed to explore the concept embodied in FIG. 32A and characterized the resulting assemblies by X-ray crystallography. The native $Met_{35}$ was incorporated into each of these peptides, rather than the α-linked ornithine isostere, to better mimic the native β-hairpins. $Phe_{19}$ was replaced with para-iodophenylalanine ($Phe^I$) to facilitate crystallographic phase determination by single wavelength anomalous diffraction phasing (R. K. Spencer and J. S. Nowick, Israel J. Chem. 2015, 55, 689-710, the disclosure of which is incorporated herein by reference). Peptides 5 to 7 were synthesized and crystalized, and their crystallographic structures were determined using procedures that we have previously reported (FIG. 32B; Seq. ID Nos. 26-31). It is noted, however, that sonication permits the dissolution of $Met_{35}$-containing peptides, which is substantially less soluble then $Orn_{35}$-containing peptide 1.

Figure 33B:
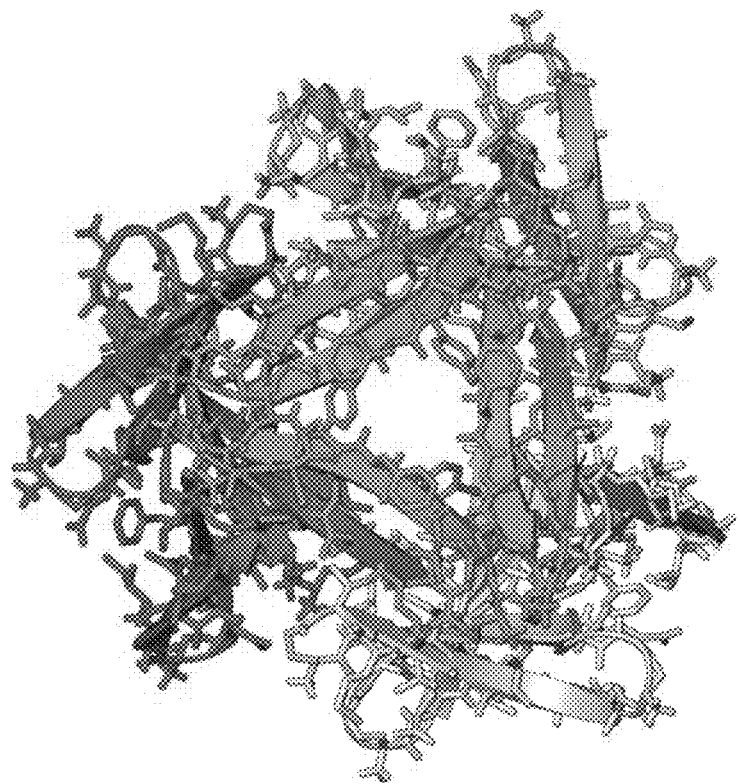
FIG. 33B provides an X-ray crystallographic schematic detailing the chemical structure of a dodecamer formed by peptide 5, generated in accordance with various embodiments of the invention.
Figure 33A:
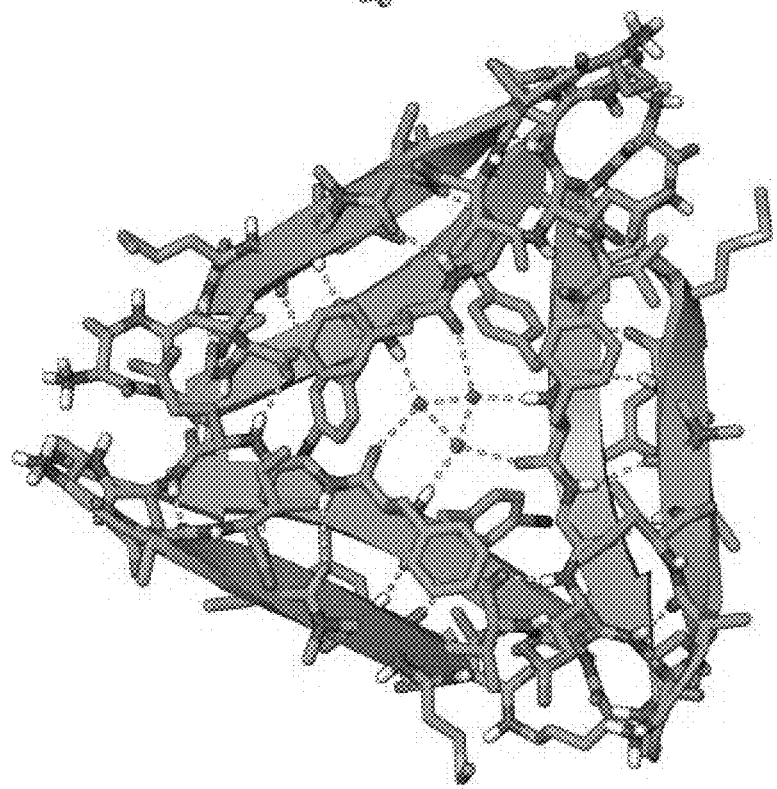
FIG. 33A provides an X-ray crystallographic schematic detailing the chemical structure of a trimer formed by peptide 5, generated in accordance with various embodiments of the invention.

Peptide 5 assembles in an identical fashion to peptide 1, forming triangular trimers that further assemble into spherical dodecamers (FIG. 33A-F). In each trimer, three monomers occupy the edges of an equilateral triangle (FIG. 33A).

The Aβ$_{17-23}$ β-strands of the monomers come together, hydrogen bonding to each other and to three water molecules that sit in the center of each trimer. The Aβ$_{30-36}$ β-strands of the monomers form the outer edges of the trimer. The side chains of Leu$_{17}$, Phe$^{I}_{19}$, and Val$_{36}$ of one monomer pack against the side chains of Ala$_{21}$, Asp$_{23}$, Ile$_{32}$, and Leu$_{34}$ from an adjacent monomer at the three vertices of the trimer. Four trimers further assemble in a tetrahedral arrangement into a loosely packed hollow dodecamer (FIG. 33B). The asymmetric unit of the crystal lattice formed by peptide 5 contains 16 peptide molecules, which assemble into four crystallographically unique dodecamers, each containing four unique peptide molecules. The four dodecamers, however, are very similar in structure. The diameter of the dodecamer spans 4-6 nm, depending on the points of measure, while its central cavity spans ca. 1.4 nm. The side chains of Phe$^{I}_{19}$, Leu$_{34}$, and Val$_{36}$ line the cavity. The dodecamers further pack to form the lattice, with each interface between two dodecamers constituting a sandwich-like hexamer (FIG. 33C). The side chains of Phe$_{20}$, Glu$_{22}$, and Ile$_{31}$ pack against one another in the interior of the hexamer.

Figure 33D:
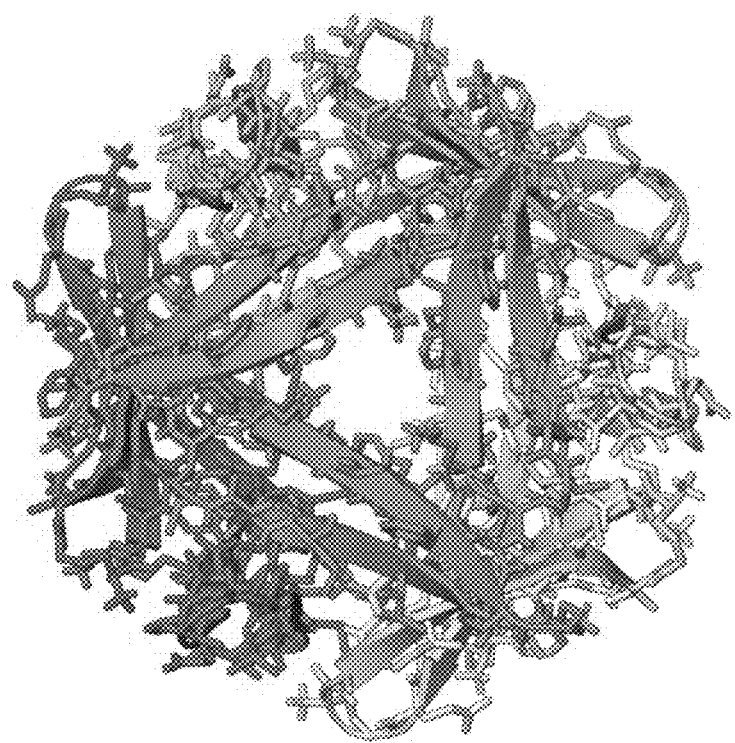
FIG. 33D provides an X-ray crystallographic schematic detailing the chemical structure of a ball-shaped dodecamer formed by peptide 6, generated in accordance with various embodiments of the invention.
Figure 33C:
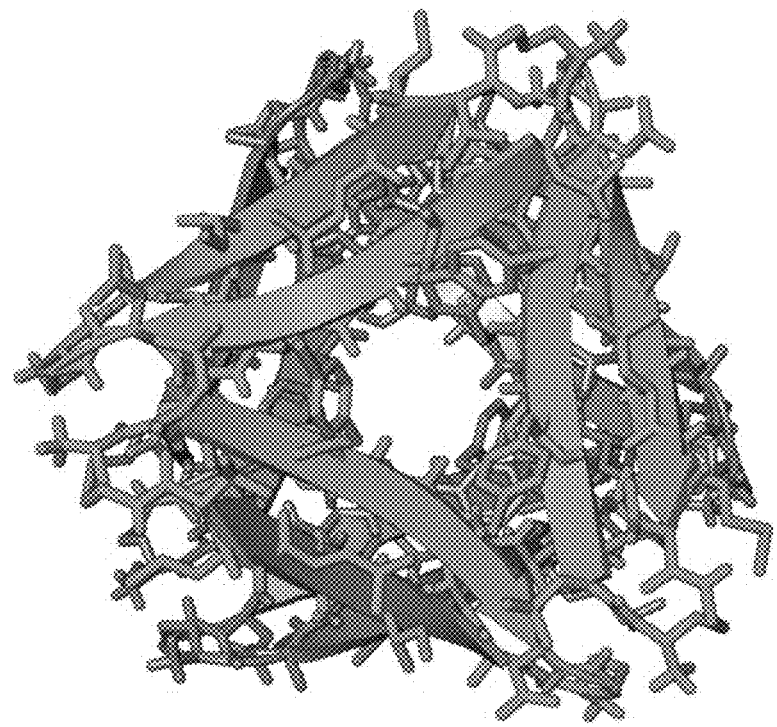
FIG. 33C provides an X-ray crystallographic schematic detailing the chemical structure of a sandwich-like hexamer formed by peptide 5, generated in accordance with various embodiments of the invention.

Peptide 6 assembles into compact ball-shaped dodecamers that differ from those formed by peptide 5 (FIG. 33D). The dodecamer formed by peptide 5 comprises discrete triangular trimers, while the dodecamer formed by peptide 6 comprises fused triangular trimers. Each trimer in the dodecamer formed by peptide 6 shares three edges with the three adjacent trimers. As a result, the trimers are not discrete entities within the ball-shaped dodecamer, but instead are fused like the benzene rings of naphthalene or graphite.

Figure 33E:
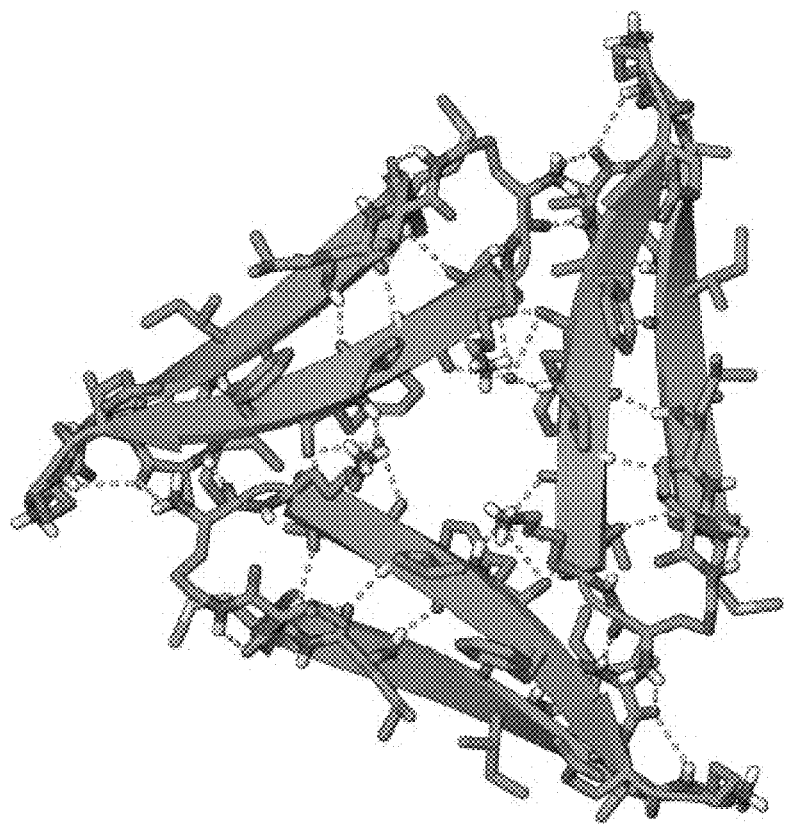
FIGS. 33E and 33F provide X-ray crystallographic schematics detailing the chemical structure of two types of trimers within the dodecamer formed by peptide 6, generated in accordance with various embodiments of the invention.
Figure 33F:
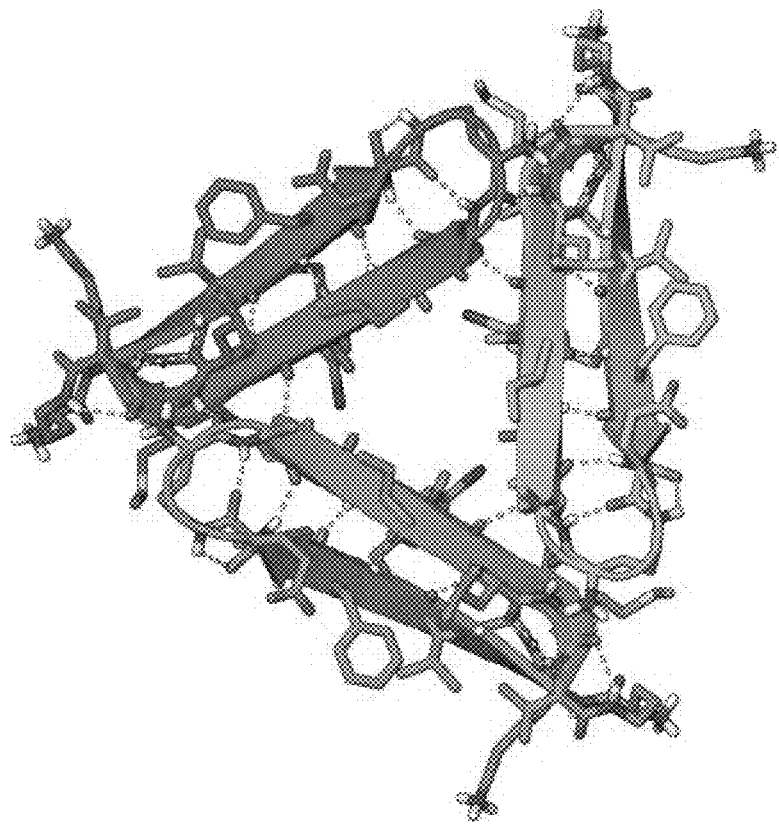

Two types of trimers make up the ball-shaped dodecamer formed by peptide 6 (FIGS. 33E and 33F). The two types of trimers differ in the placement of the Aβ$_{16-22}$ and Aβ$_{30-36}$ β-strands. The Aβ$_{16-22}$ β-strands of the monomers hydrogen bond to each other within the trimer depicted in FIG. 33E, while the Aβ$_{30-36}$ β-strands hydrogen bond to each other within the trimer depicted in FIG. 33F. The outer edges of the trimer depicted in FIG. 33E lie within three different trimers, like the one depicted in FIG. 33F. Conversely, the outer edges of the trimer depicted in FIG. 33F lie within three different trimers, like the one depicted in FIG. 33E. Three water molecules occupy the center of the trimer depicted in FIG. 33E. The three N-methyl groups occupy the center of the trimer depicted in FIG. 33F, in lieu of three water molecules.

The ball-shaped dodecamer formed by peptide 6 is hollow, like the dodecamer formed by peptide 5. The diameter of the ball-shaped dodecamer spans 3-4 nm depending on the points of measure, while its central cavity spans ca. 1.0 nm. The side chains of Phe$^{I}_{19}$ line the cavity, while the exterior surface of the dodecamer displays the side chains of Lys$_{16}$, Val$_{18}$, Phe$_{20}$, Glu$_{22}$, Alan, Ile$_{32}$, Leu$_{34}$, and Val$_{36}$. Unlike the dodecamers formed by peptide 5, the dodecamers formed by peptide 6 do not form sandwich-like hexamers. Instead these dodecamers pack hexagonally and stack like cannonballs.

Figure 34:
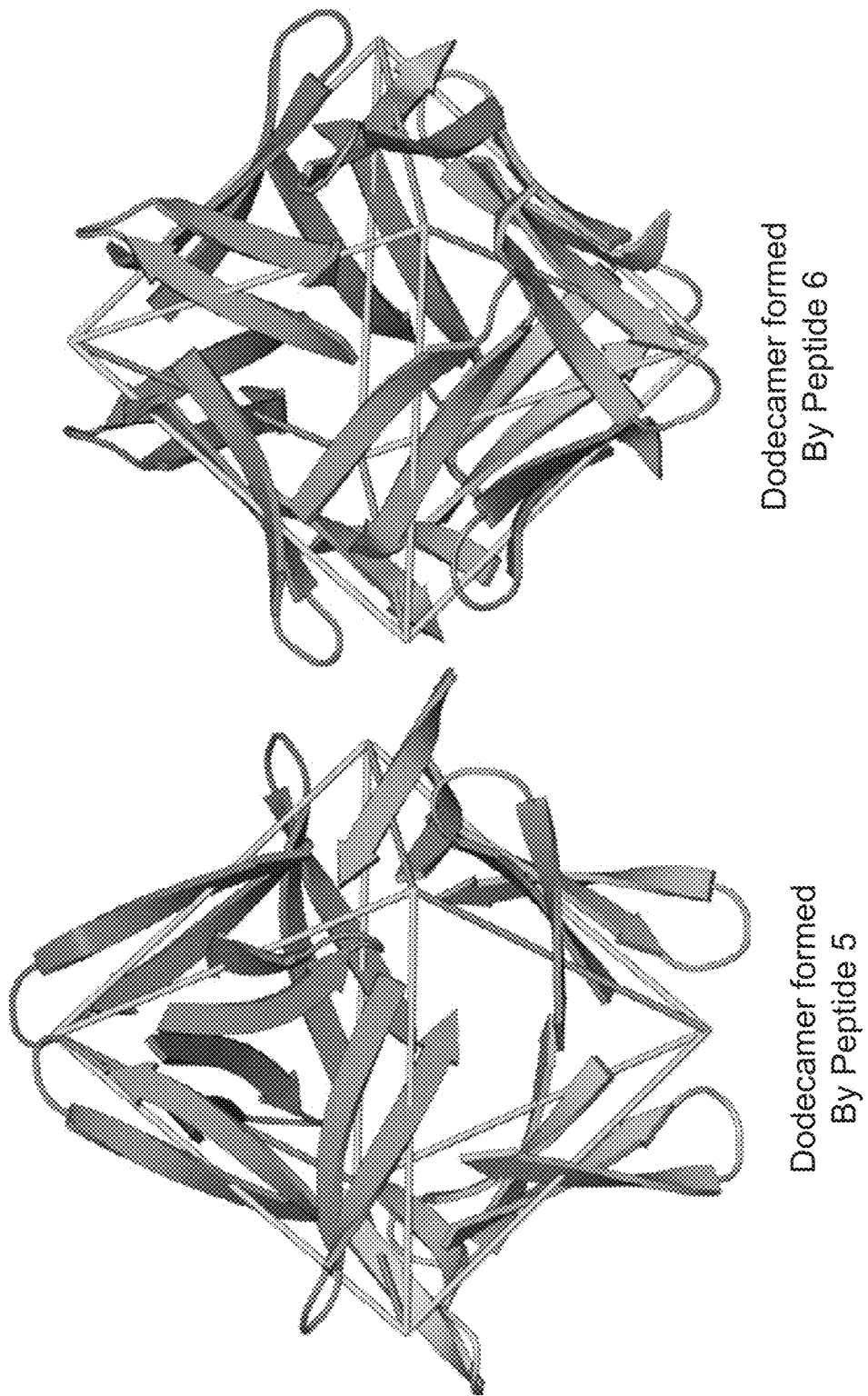
FIG. 34 provides X-ray crystallographic schematics detailing the chemical structure of dodecamers formed by peptides 5 and 6, generated in accordance with various embodiments of the invention.

The dodecamers formed by peptides 5 and 6 share similar themes in self-assembly, as both are composed of triangular trimer subunits. Mapping the triangular subunits of each dodecamer onto an octahedron highlights these similarities, as well as key differences (FIG. 34). In the dodecamer formed by peptide 5, the four trimers occupy four of the eight triangular faces of the octahedron. The interfaces between the trimers define the remaining four triangular faces. In the dodecamer formed by peptide 6, each monomer occupies one edge of the octahedron, and each trimer defines one of the eight triangular faces of the octahedron. At each of the six vertices of the octahedron, four monomers of peptide 6 form an eight-stranded β-barrel-like opening. An analogous opening is absent in the dodecamer formed by peptide 5. The hydrogen-bonding network that helps stabilize both dodecamers is more extensive in the dodecamer formed by peptide 6, which contains 36 additional intermolecular hydrogen bonds beyond those that compose the hydrogen-bonding network in the dodecamer formed by peptide 5. The dodecamer formed by peptide 6 is more densely packed than the dodecamer formed by peptide 5. Assembly of peptide 6 into a dodecamer buries ca. 10,800 Å$^2$ of surface area, whereas assembly of peptide 5 into a dodecamer buries only ca. 8,100 Å$^2$. It is not obvious from their sequences or structures why peptide 6 forms a more compact dodecamer that differs from that of peptide 5.

Figure 36:
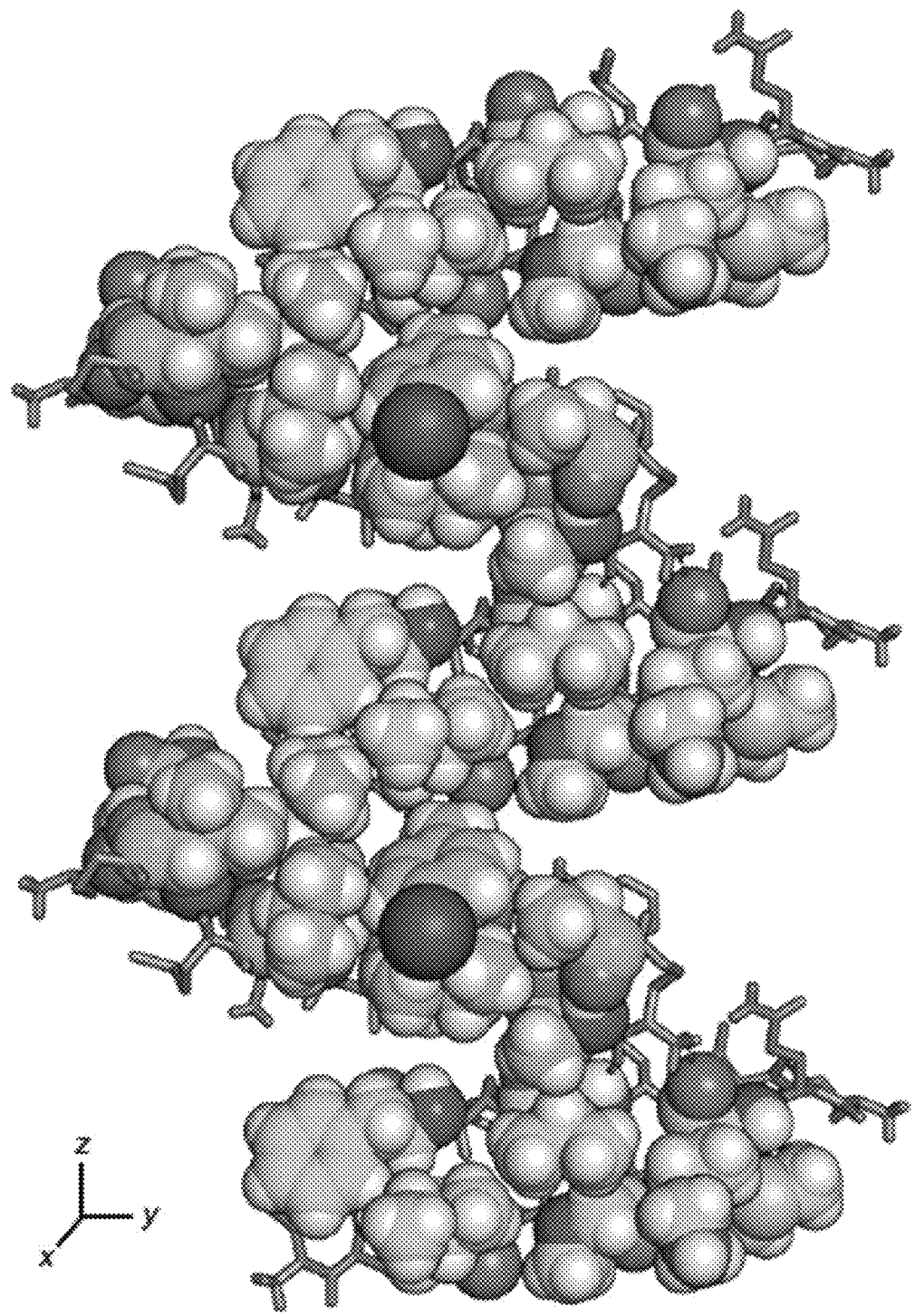

In contrast to the discrete oligomers formed by peptides 5 and 6, peptide 7 forms a fibril-like assembly (FIG. 35). Each monomer of peptide 7 hydrogen bonds with the two neighboring monomers along the fibril axis. The interface between monomers constitutes a parallel β-sheet with three intermolecular hydrogen bonds in which Leu$_{17}$, Val$_{18}$, and Phe$^{I}_{19}$ pair with □Orn$_2$, Alan, and Ile$_{31}$. The N-methyl group on Gly$_{33}$ blocks formation of a fully hydrogen-bonded interface, prying apart the β-sheets and requiring a water molecule to bridge a hydrogen bond between the NH group of Phe$_{20}$ and the carbonyl group of Ile$_{31}$. Each monomer is flipped upside down with respect to the neighboring monomers in the fibril such that the surfaces of the monomers are displayed in an alternating pattern along the surface of the fibril: one monomer displays its top surface, the next monomer displays its bottom surface, and so on down the fibril (FIG. 36).

The fibril-like assemblies formed by peptide 7 are not flat; instead they zig-zag in the x-z plane as depicted in FIG. 35. The fibrils stack along the x-axis, creating densely packed layers in the x-z plane. The layers run in opposite directions to one another. Within each layer, all of the N-methyl groups point in the same direction. In the green layers in FIG. 35, the N-methyl groups point in the negative z direction, while in the cyan layers, the N-methyl groups point in the positive z direction (FIG. 36). The lay layers pack tightly through hydrophobic interactions, with the top surface of a monomer in one layer packing against the bottom surface of its neighbor in the adjacent layer. This heterofacial packing of residues contrasts the exclusively homofacial packing of residues in the dodecamers formed by peptides 5 and 6. It is not obvious why peptide 7 forms fibril-like assemblies in the crystal lattice, instead of the trimers and dodecamers formed by peptides 5 and 6.

The different assemblies of peptides 5-7 reflect the rich and diverse modes of β-hairpin self-assembly and illustrate their propensity to form both fibril-like and oligomeric assemblies. The assembly of β-hairpins into dodecamers comprising triangular trimer subunits offers an alluring high-resolution model for the enigmatic oligomers reported for full-length Aβ. Townsend et al. reported that Aβ trimers inhibit long-term potentiation (M. Townsend, et al., *J. Physiol.* 2006, 572, 477-492, the disclosure of which is incorporated herein by reference). Lesne et al. reported that putative dodecamers of Aβ, termed Aβ*56, cause memory deficits in a mouse model of Alzheimer's disease (S. Lesne, et al., *Nature* 2006, 440, 352-357, the disclosure of which is incorporated herein by reference). The putative Aβ*56 dodecamers appear to be composed of trimer subunits. The trimers and dodecamers formed by peptides 5 and 6 provide two models of how Aβ may oligomerize in Alzheimer's disease. The formation of trimeric oligomers is also a common theme of full-length peptides and proteins associated with other amyloid diseases (B. Winner, et al, *Proc. Natl. Acad. Sci. U.S.A.* 2011, 108, 4194-4199, the disclosure of which is incorporated herein by reference).

Offsetting the residue pairings of the two β-strands within a β-hairpin may dramatically alter the self-assembly. The approach of systematically varying the residue pairings in constrained macrocyclic β-hairpins has revealed a compact ball-shaped dodecamer containing fused trimers and stabilized by an extensive network of hydrogen bonds. The importance of residues 15-36 in the aggregation of full-length Aβ makes peptides 5-7 relevant models for the assembly of full-length Aβ. It is possible that full-length Aβ may be able to fold and assemble in a similar fashion. The relationship between the sequence of a β-hairpin and its mode of assembly is still unknown.

Further Characterization of Peptide Oligomerization

Figure 37:
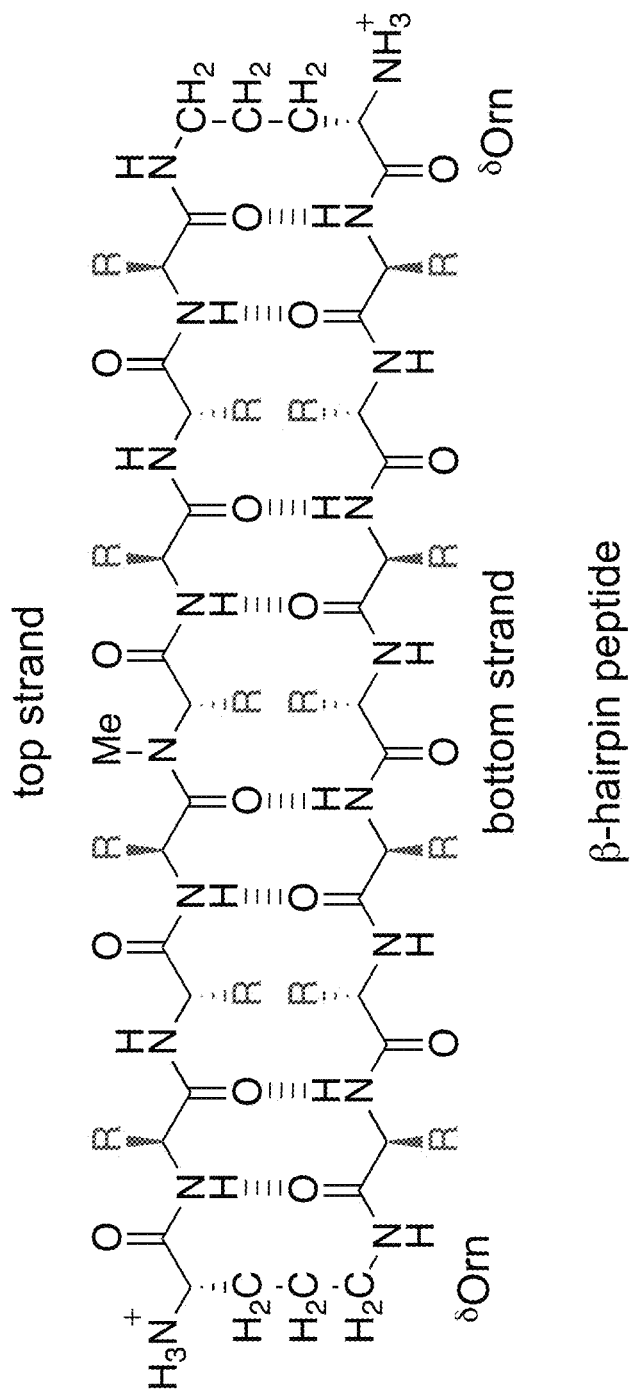
FIG. 37 provides a generic molecular structure diagram detailing the chemical structure and peptide sequence of a β-hairpin peptide.

In the examples in the preceding sections, X-ray crystallographic structures of oligomers formed by macrocyclic β-sheet peptides designed to mimic β-hairpins from amyloidogenic peptides and proteins were described. In some of these examples, β-hairpin peptides contain two heptapeptide β-strand fragments locked in an antiparallel β-sheet by two δ-linked ornithine ($^\delta$Orn) turn mimics, and also contain an N-methyl group that blocks uncontrolled aggregation. These design features permit crystallization of the β-hairpin peptides and structural elucidation of the higher-order oligomers they can form. The β-hairpin peptides have two surfaces: a major surface that displays eight of the fourteen side chains, and a minor surface that displays the remaining six side chains. FIG. 37 shows a generic structure of these β-hairpin peptides and highlights the major and minor surfaces in red and blue.

The elucidated the X-ray crystallographic structures of oligomers formed by β-hairpin peptides derived from Aβ revealed the propensity for β-hairpin peptides to form oligomers in the crystal state, including dimers, trimers, hexamers, octamers, nonamers, and dodecamers. The different oligomers identified in these examples demonstrate the diversity and polymorphism of the structures that different amyloid-derived β-hairpin peptides can form.

Figure 38:
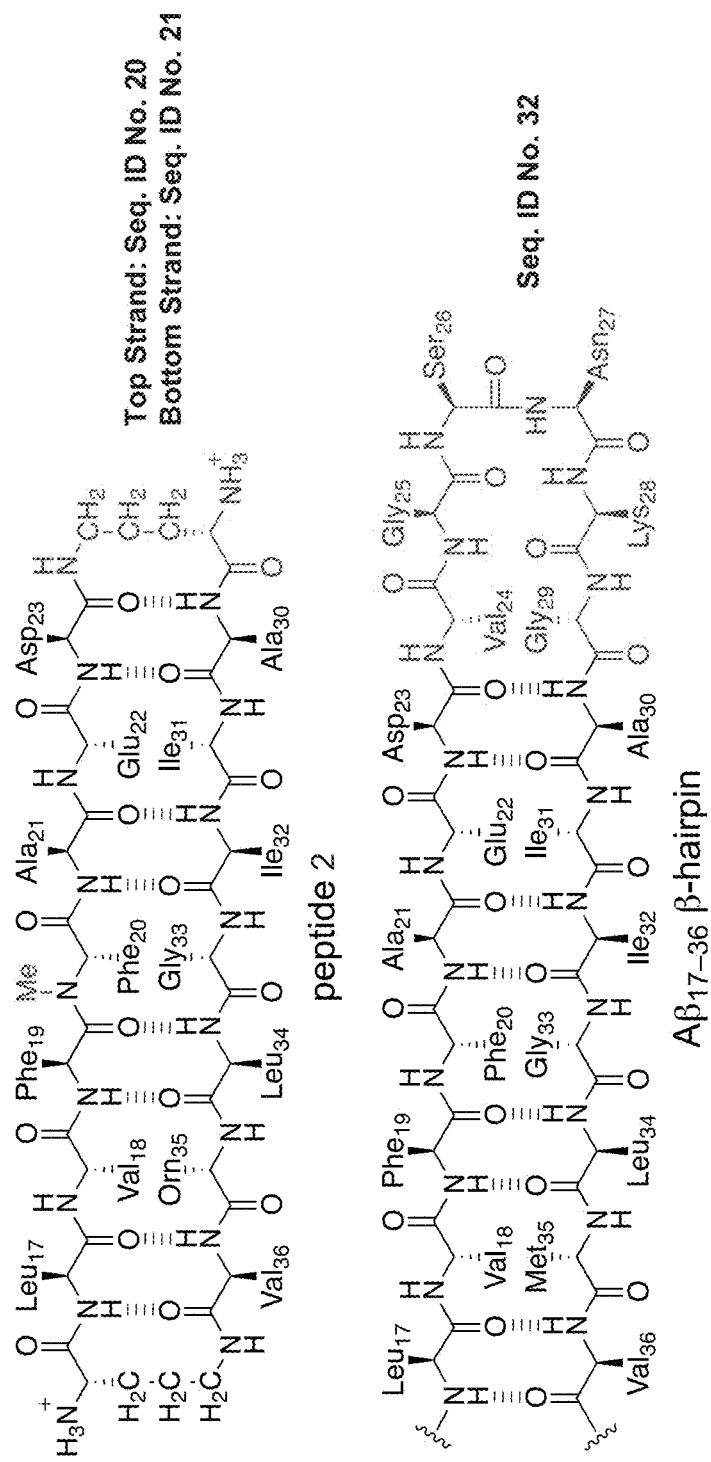
FIG. 38 provides molecular structure diagrams detailing the chemical structure and peptide sequence of $A\beta_{17-36}$ hairpin and peptide 2 in accordance with various embodiments of the invention.
Figure 39:
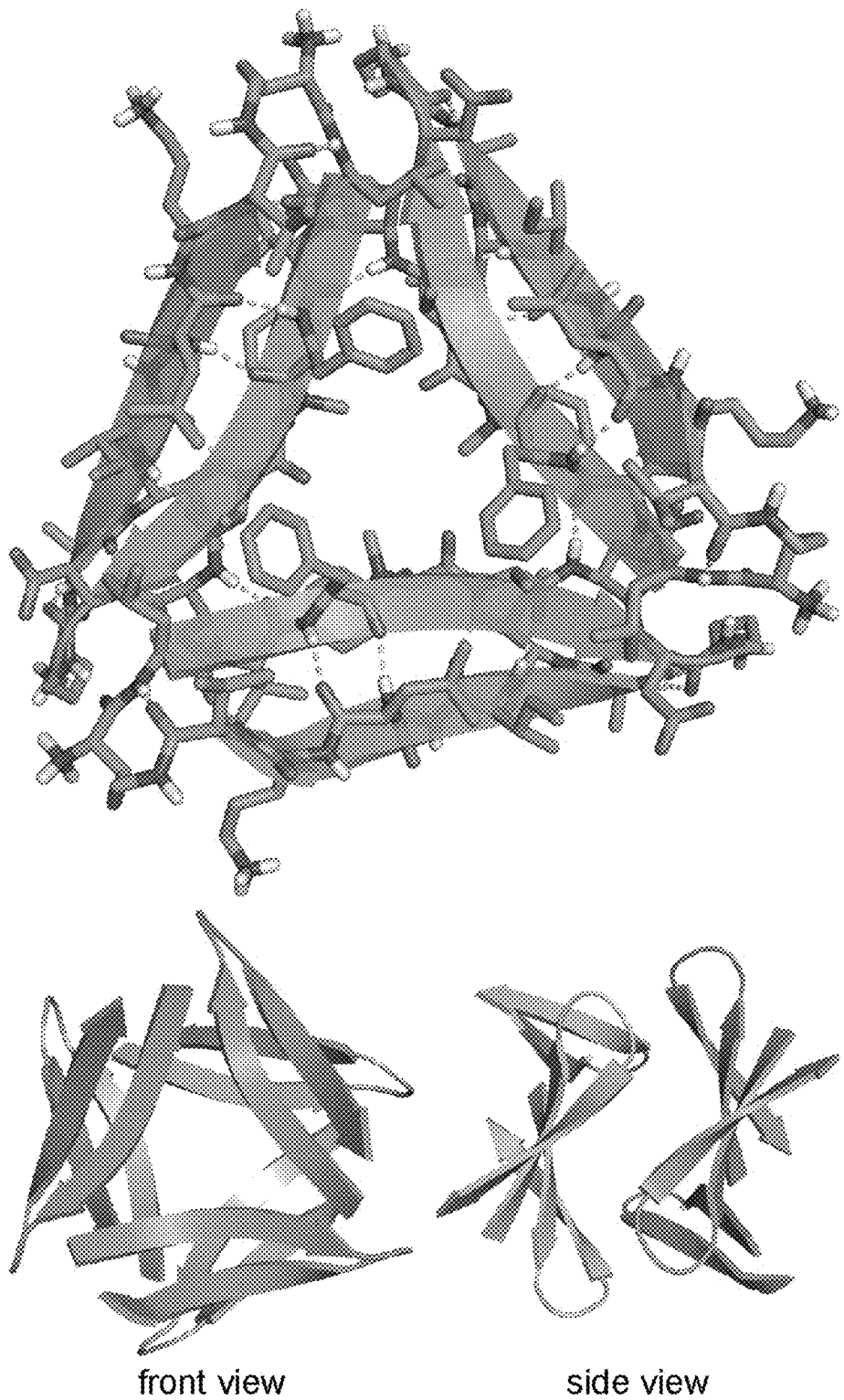
FIG. 39 provides an X-ray crystallographic schematic detailing the chemical structure of a trimer formed by peptide 2, generated in accordance with various embodiments of the invention.

The X-ray crystallographic structures of oligomers formed by β-hairpin peptide 2, which is derived from an Aβ$_{17-36}$ β-hairpin (FIG. 38; Seq. ID Nos. 20, 21, and 32). Peptide 2 contains Aβ$_{17-23}$ and Aβ$_{30-36}$ β-strands linked by two $^\delta$Orn turn units; the $^\delta$Orn turn that links Asp$_{23}$ and Alan replaces the Aβ$_{24-29}$ loop of the Aβ$_{17-36}$ β-hairpin. Peptide 2 also contains an N-methyl group on Phe$_{20}$ and α-linked ornithine at position 35 as a hydrophilic isostere of methionine. The X-ray crystallographic structure reveals that peptide 2 assembles hierarchically to form a triangular trimer that further assembles with a second triangular trimer to form a sandwich-like hexamer (FIG. 39).

In the example, it was set out to explore how shifting registration by one amino acid toward the N-terminus affects the structural and biological properties of a β-hairpin peptide. Offsetting β-hairpin registration is significant, because it changes both the pairings of the residues within the β-hairpin and the surfaces upon which the side chains are displayed. In the Aβ$_{17-36}$ β-hairpin, from which peptide 2 is derived, Ile$_{31}$ pairs with Glu$_{22}$; in the shifted Aβ$_{16-36}$ β-hairpin, Ile$_{31}$ pairs with Ala$_{21}$. In the Aβ$_{17-36}$ β-hairpin, the side chain of Glu$_{22}$ shares the same surface as the side chain of Ile$_{31}$; in the Aβ$_{16-36}$ β-hairpin, the side chain of Glu$_{22}$ is on the opposite surface. We find that the resulting shifted β-hairpin peptide not only assembles in the crystal state to form oligomers, but also exhibits both solution-phase assembly and toxicity reminiscent of amyloid oligomers.

Figure 40:
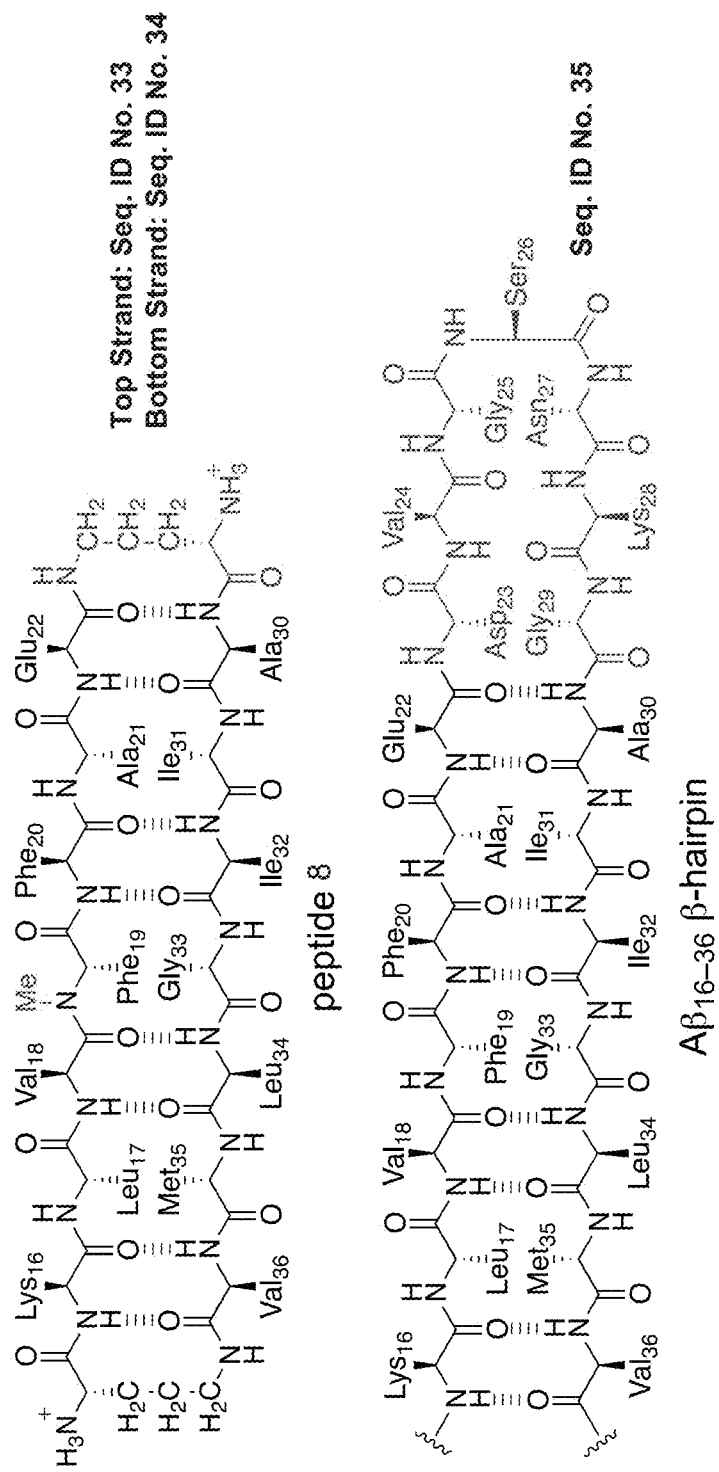
FIG. 40 provides molecular structure diagrams detailing the chemical structure and peptide sequence of $A\beta_{16-36}$ hairpin and peptide 8 in accordance with various embodiments of the invention.

The X-ray crystallographic, solution-phase, and biological studies of peptide 8, which is designed to mimic the A$_{116-36}$ β-hairpin (FIG. 40; Seq. ID Nos. 33-35), is described. Peptide 8 contains Aβ$_{16-22}$ and Aβ$_{30-36}$ β-strands linked by two $^\delta$Orn turn units, an N-methyl group on Phe$_{19}$, and the native methionine residue at position 35. Peptide 8 runs as a hexamer in SDS-PAGE and appears to form dimers and trimers in size exclusion chromatography (SEC). The oligomers formed by peptide 8 are toxic toward the human neuroblastoma cell line SH-SY5Y. X-ray crystallography reveals that peptide 8 also assembles to form a hexamer in the crystal state. The hexamer may be thought of as being composed of either dimers or trimers. The hexamer formed by peptide 2 is significant because it shares key characteristics with the oligomers formed by full-length amyloidogenic peptides and proteins and provides a structural model for an oligomer of Aβ.

Oligomerization of Peptide 8

Figure 41A:
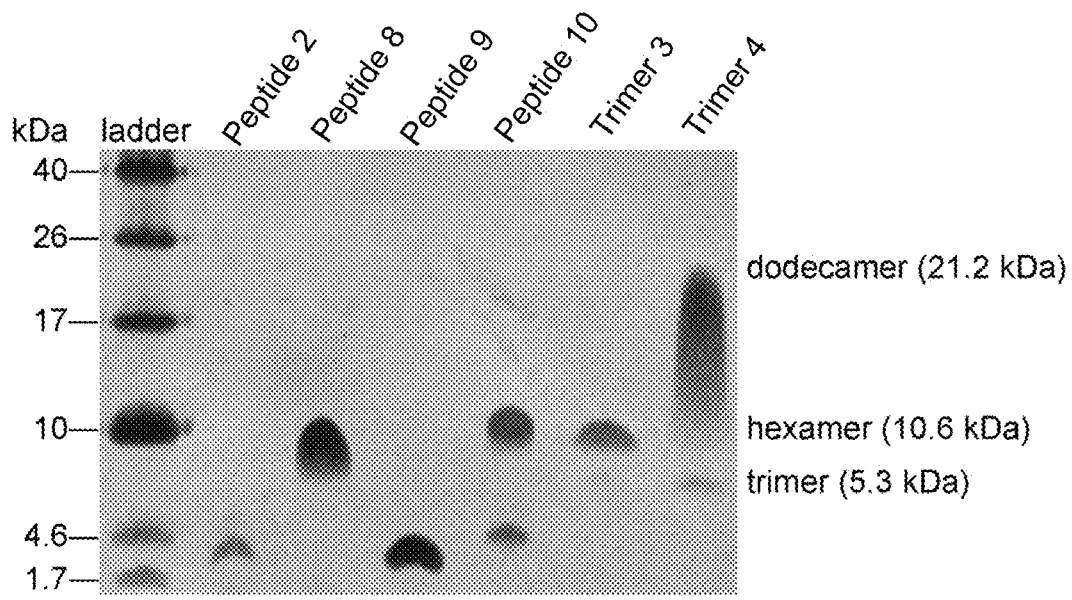
FIG. 41A provides a silver stain of an SDS-PAGE gel of peptides 2 and 8-10 and trimers 3 and 4 that were ran through an electrophoresis apparatus, generated in accordance with various embodiments of the invention.

Peptide 8 assembles to form a hexamer in SDS-PAGE. Tricine SDS-PAGE followed by silver staining shows that the 1.8 kDa peptide 8 migrates just above the 10 kDa band of the ladder (FIG. 41A). The band from peptide 8 is comet-shaped and streaks downward, suggesting that the hexamer is in equilibrium with lower molecular weight species. To further confirm the oligomerization state of peptide 1, it was compared to covalent trimers 3 and 4 (FIGS. 19A and 19B), which was previously determined to migrate respectively as 10.6 kDa hexamers and 21.2 kDa dodecamers in equilibrium with the 5.3 kDa trimers. Peptide 8 migrates at the same molecular weight as the hexamer band of trimer 3, providing further evidence that peptide 8 assembles to form a hexamer in SDS-PAGE. In contrast, peptide 2 does not assemble to form a hexamer in SDS-PAGE. Peptide 2 migrates well below the trimer band of trimer 4, and slightly below the 4.6 kDa band of the ladder, suggesting that peptide 2 migrates as a monomer or dimer.

Figure 41B:
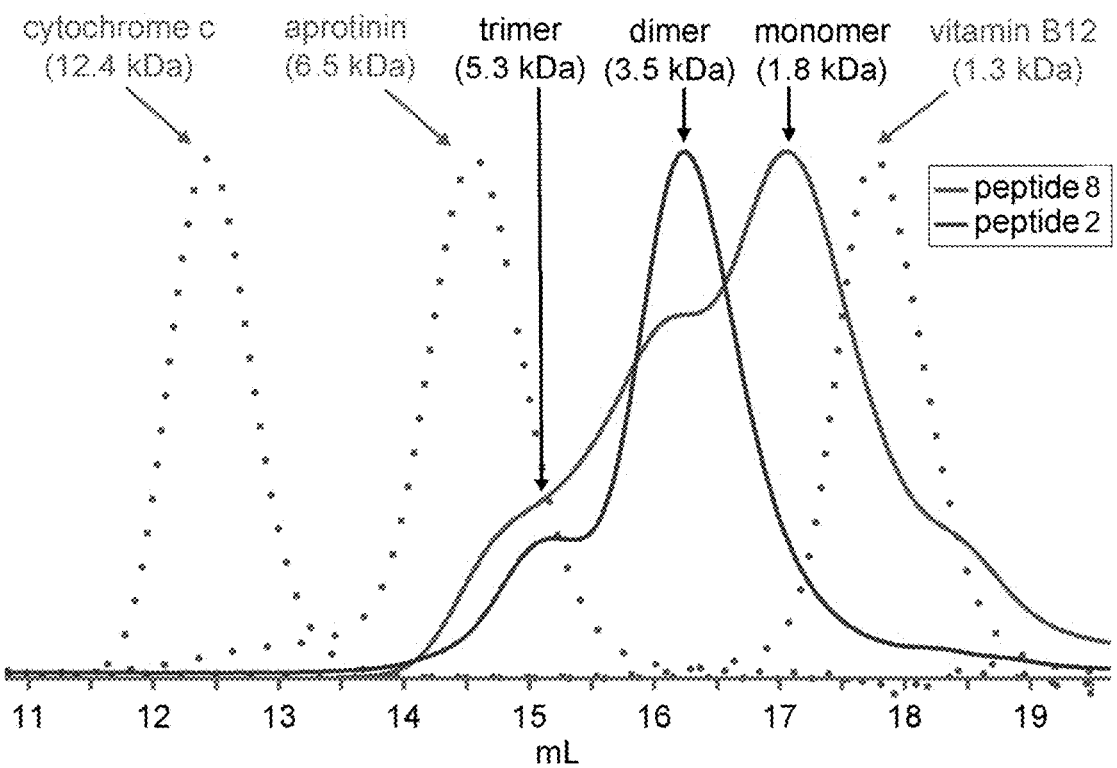
FIG. 41B provides a data graph of size exclusion chromatography of peptides 2 and 8 and other reference proteins, generated in accordance with embodiments of the invention.

Size exclusion chromatography reveals that peptide 8 also assembles to form oligomers in the absence of SDS. The elution profile of peptide 8 was compared to the size standards vitamin B12, aprotinin, and cytochrome c, as well as peptide 2. Peptide 8 elutes as a broad peak with three distinct humps (FIG. 41B). The elution volumes of the humps are consistent with the molecular weights of a monomer, dimer, and trimer, respectively. The broadness of the humps suggests moderately slow exchange between the trimer, dimer, and monomer. Peptide 2 elutes as two distinct peaks: a larger peak with an elution volume consistent with the molecular weight of a dimer, and a smaller peak with an elution volume consistent with the molecular weight of a trimer (FIG. 41B). Table 2 summarizes the SEC data for peptides 2 and 8.

TABLE 2

Size exclusion chromatography data for peptides 2, 8, 9 and 10.

| compound | molecular weight | elution volume (mL) | oligomer size |
| --- | --- | --- | --- |
| peptide 2 | 1.74 kDa | 16.2, 15.1 | dimer, trimer |
| peptide 8 | 1.77 kDa | 17.0, 16.1, 14.8 | monomer, dimer, trimer |

TABLE 2-continued

Size exclusion chromatography data for peptides 2, 8, 9 and 10.

| compound | molecular weight | elution volume (mL) | oligomer size |
| --- | --- | --- | --- |
| peptide 9 | 1.79 kDa | 17.6 | monomer |
| peptide 10 | 1.72 kDa | 17.0 | monomer |
| vitamin B12 | 1.3 kDa | 17.8 | |
| aprotinin | 6.5 kDa | 14.6 | |
| cytochrome c | 12.4 kDa | 12.4 | |

These solution-phase studies show that peptide 8 assembles to form oligomers in solution. In SDS-PAGE, peptide 8 assembles to form a hexamer. In SEC in Tris buffer, peptide 8 assembles to form dimers and trimers. These results suggest the intriguing hypothesis that the hexamer in SDS-PAGE may be composed of dimers or trimers that further assemble to form a hexamer in the lipophilic environment of SDS micelles. X-ray crystallography was performed to gain insights into the structures of these oligomers, and thus further explore this hypothesis.

X-Ray Crystallographic Structure of Peptide 8

Peptide 8 afforded crystals suitable for X-ray diffraction from aqueous HEPES buffer with sodium citrate and isopropanol. To determine the X-ray crystallographic phases of peptide 8, a crystal of the peptide was soaked in potassium iodide to incorporate iodide ions into the crystal lattice and performed conventional single-wavelength anomalous diffraction (SAD) phasing (A. G. Kruetzer, et al., *Am. Chem. Soc.* 2016 138, 4634-4642; Z. Dauter, M Dauter, and K. R. Rajaashankar Acta. *Crystallogr. D Biol. Crystallogr.* 2000 56, 232-237; and R. K. Spencer and J. S. Nowick 2015, cited supra; the disclosures of which are incorporated herein by reference). The X-ray crystallographic structure of the KI-soaked peptide 8 (PDB 5W4I) was then used as a search model for molecular replacement to determine the X-ray crystallographic phases of a higher resolution data set of unsoaked peptide 8, which was collected using a synchrotron radiation source (PDB 5W4H).

Figure 42:
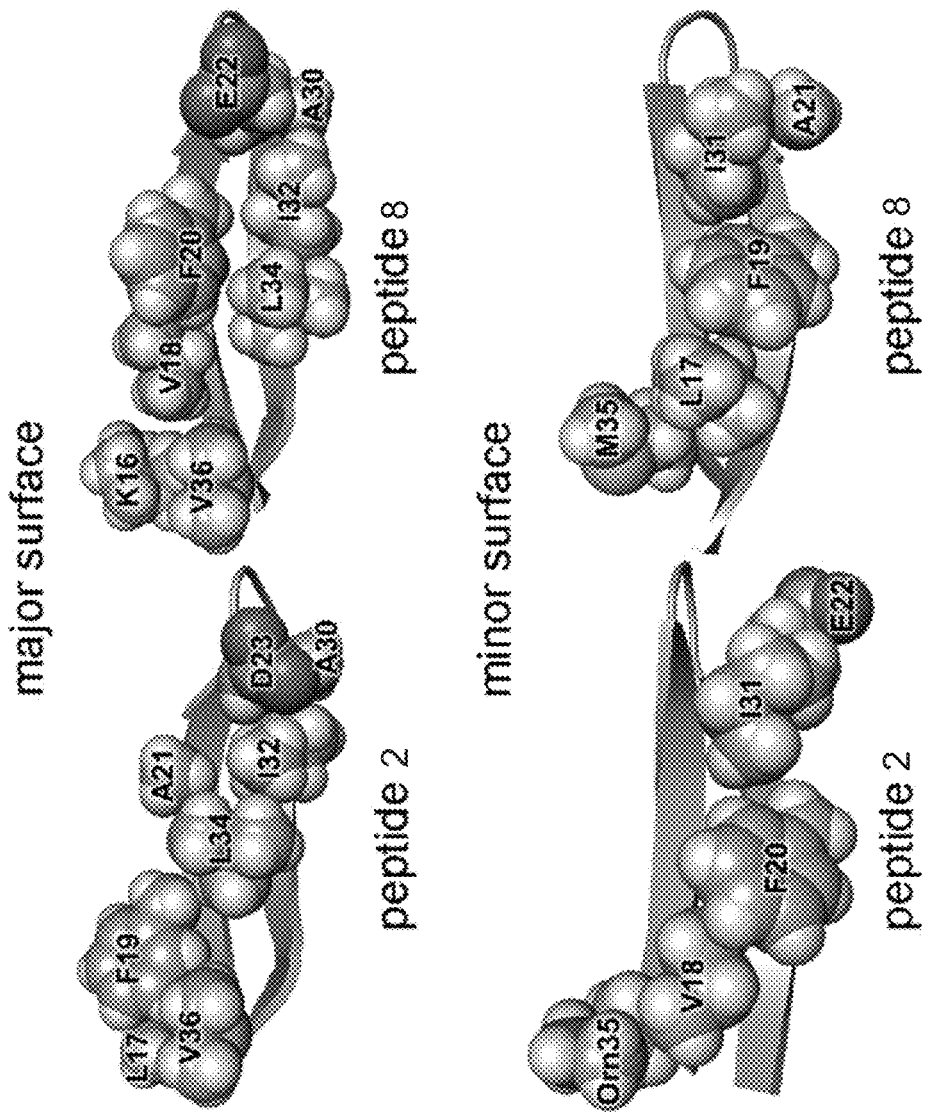
FIG. 42 provides X-ray crystallographic schematics detailing the chemical structures of the major and minor surfaces of peptides 2 and 8 in accordance with various embodiments of the invention.

The X-ray crystallographic structure of peptide 8 reveals that the peptide folds to form a twisted β-hairpin. The side chains displayed on the major and minor surfaces of peptide 8 differ from those displayed on the major and minor surfaces of peptide 2. The major surface of the peptide 8 β-hairpin displays the side chains of $Lys_{16}$, $Val_{18}$, $Phe_{20}$, $Glu_{22}$, $Alan$, $Ile_{32}$, $Leu_{34}$, and $Val_{36}$, while the major surface of the peptide 2 β-hairpin displays the side chains of $Leu_{17}$, $Phe_{19}$, $Ala_{21}$, $Asp_{23}$, $Alan$, $Ile_{32}$, $Leu_{34}$, and $Val_{36}$ (FIG. 42). The minor surface of the peptide 8 β-hairpin displays the side chains of $Leu_{17}$, $Phe_{19}$, $Ala_{21}$, $Ile_{31}$, $Gly_{33}$, and $Met_{35}$, while the minor surface of the peptide 2 β-hairpin displays the side chains of $Val_{18}$, $Phe_{20}$, $Glu_{22}$, $Ile_{31}$, $Gly_{33}$, and $Orn_{35}$ (FIG. 42). Thus, the minor surface of peptide 8 is wholly hydrophobic, while the minor surface of peptide 2 is not.

Figure 43:
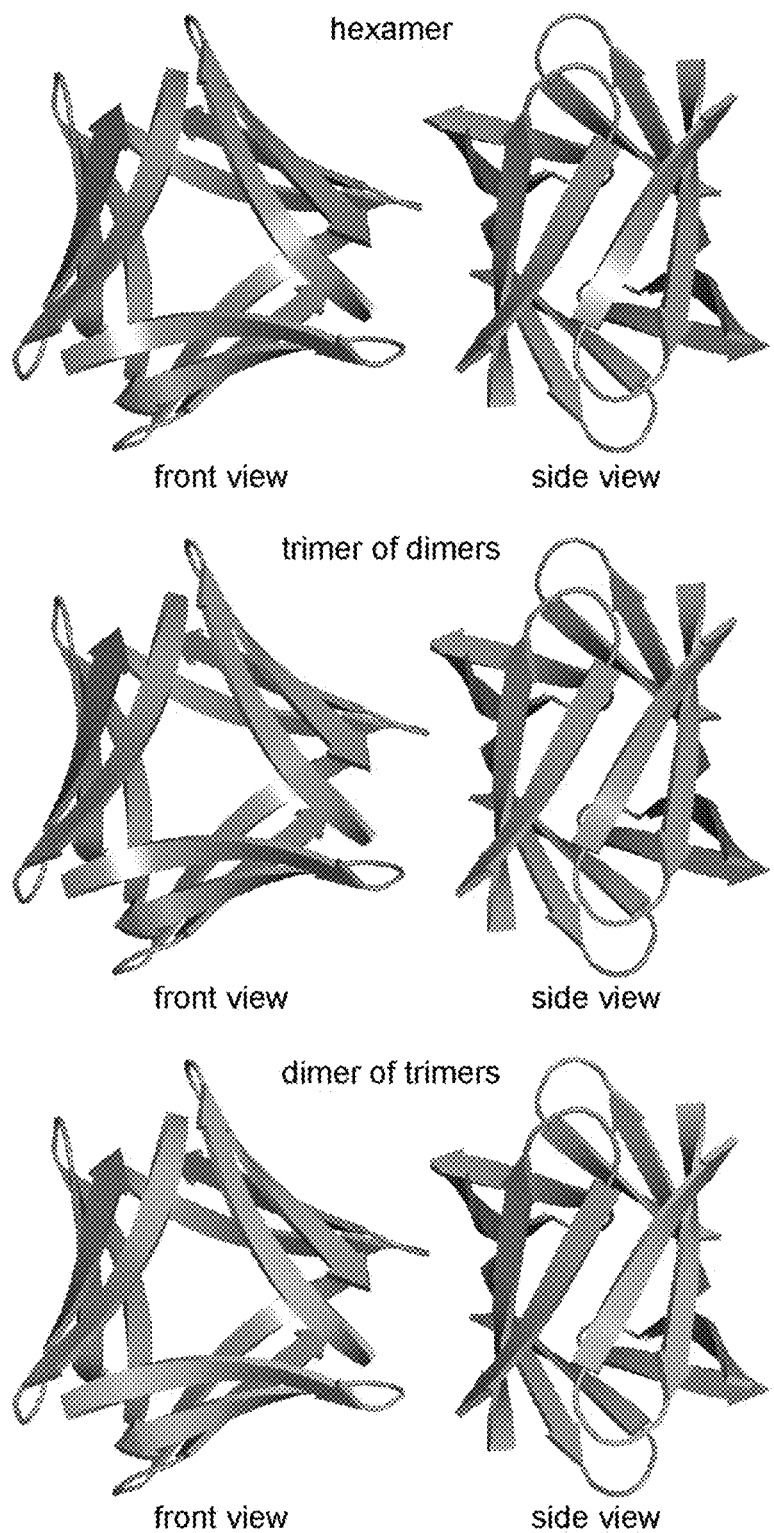
FIG. 43 provides X-ray crystallographic schematics detailing the chemical structures of hexamers formed by peptide 8, generated in accordance with various embodiments of the invention.

In the X-ray crystallographic structure of peptide 8, six β-hairpin monomers assemble to form a hexamer. The hexamer is composed of smaller oligomers and can be interpreted either as a trimer of dimers or as a dimer of trimers. FIG. 43 shows the structure of the hexamer and illustrates these two interpretations. In FIG. 43, one dimer subunit is colored green and one trimer subunit is colored cyan. The following subsections detail the structure of the hexamer as well as the structures of the component dimers or trimers.

Hexamer.

Figure 44:
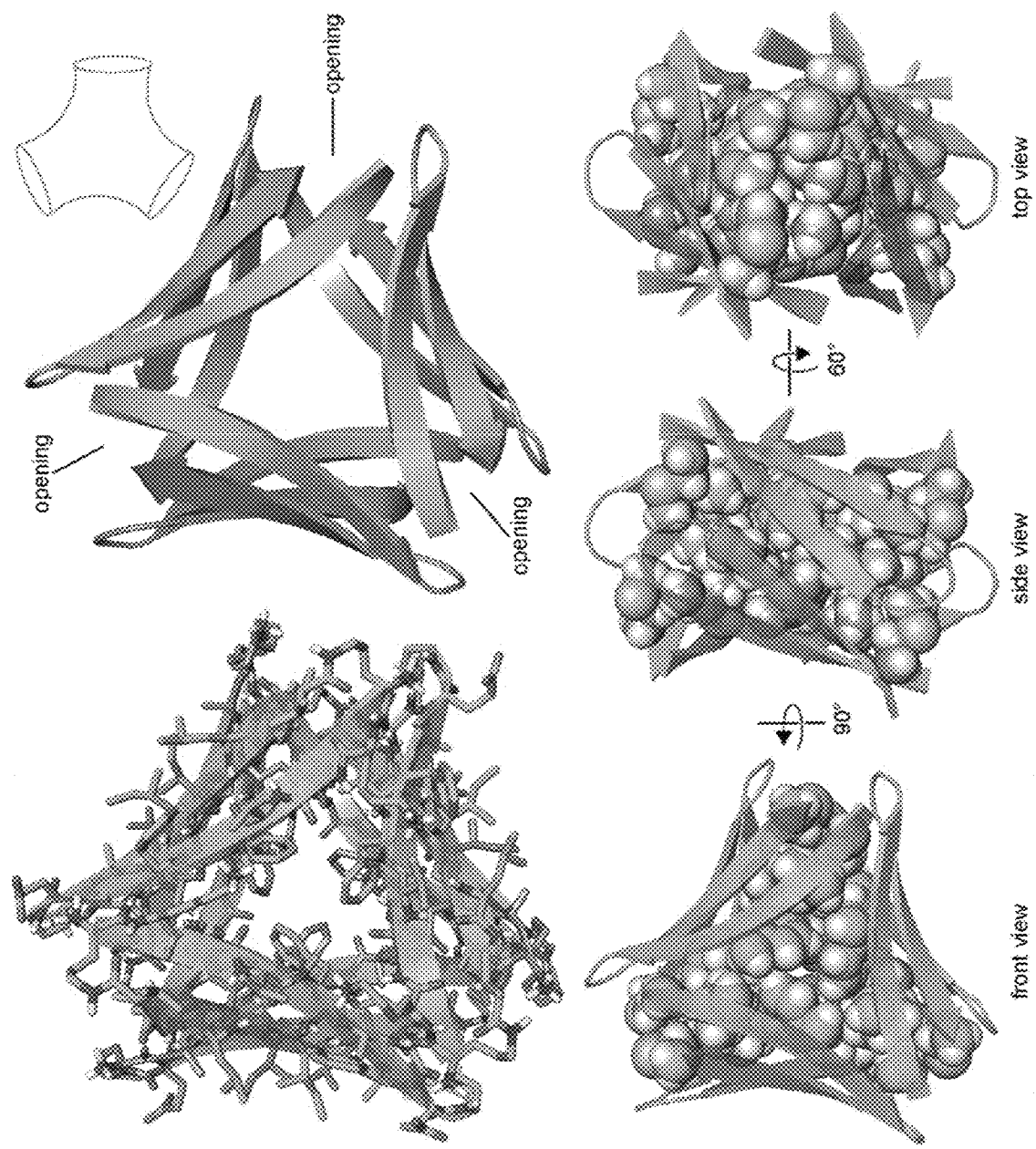
FIG. 44 provides X-ray crystallographic schematics detailing the chemical structures of hexamers formed by peptide 8, generated in accordance with various embodiments of the invention.

The hexamer formed by peptide 8 resembles a barrel with three openings (FIG. 44). The interior of the barrel is filled with the side chains of residues on the minor surface of peptide 8—$Leu_{17}$, $Phe_{19}$, $Ala_{21}$, $Ile_{31}$, $Gly_{33}$, and $Met_{35}$—creating a packed hydrophobic core that stabilizes the hexamer (FIG. 44). A network of hydrogen bonds between the main chains of the monomer subunits further stabilizes the hexamer. The outer surface of the hexamer displays the side chains of residues on the major surface of peptide 8—$Lys_{16}$, $Val_{18}$, $Phe_{20}$, $Glu_{22}$, $Ala_{30}$, $Ile_{32}$, $Leu_{34}$, and $Val_{36}$.

Figure 45:
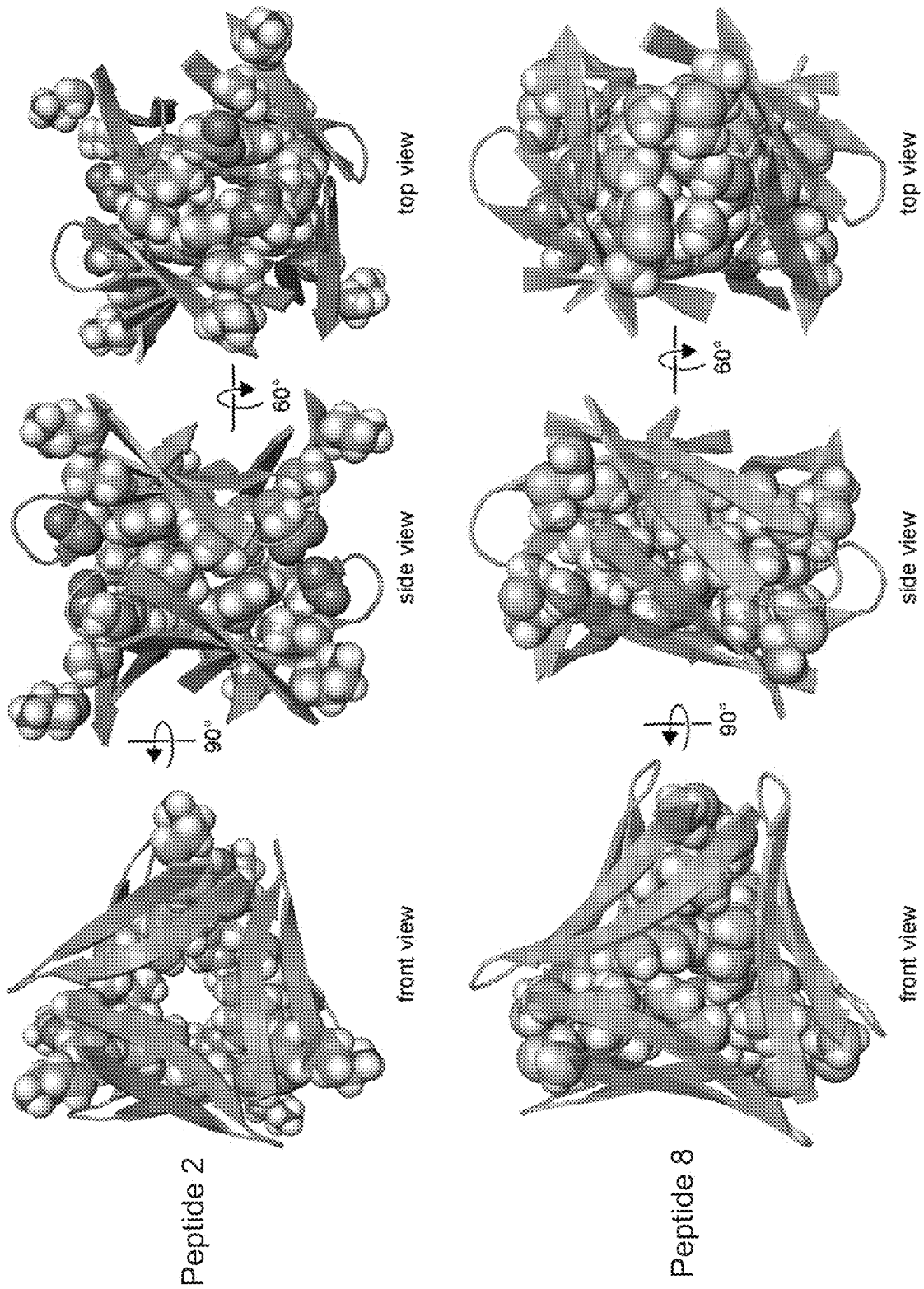
FIG. 45 provides X-ray crystallographic schematics detailing the chemical structures of hexamers formed by peptides 2 and 8, generated in accordance with various embodiments of the invention.

The hexamer formed by peptide 8 is more hydrogen bonded and better packed than the hexamer formed by peptide 2 (FIG. 45). The hexamer formed by peptide 8 forms a continuous hydrogen-bonding network containing 30 intermolecular hydrogen bonds, whereas the hexamer formed by peptide 2 does not form a continuous hydrogen-bonding network and contains only 18 intermolecular hydrogen bonds. In the hexamer formed by peptide 2, each β-hairpin monomer is only hydrogen bonded to the two adjacent β-hairpin monomers within the triangular trimer; in the hexamer formed by peptide 8, each β-hairpin monomer is hydrogen bonded not only to the two adjacent monomers within the triangular trimer, but also to the adjacent monomer within the β-sheet dimer. For these reasons, the hexamer formed by peptide 8 can either be interpreted as a trimer of β-sheet dimers or as a dimer of triangular trimers, whereas the hexamer formed by peptide 2 is unambiguously a dimer of triangular trimers.

Six sets of side chains from $Leu_{17}$, $Phe_{19}$, $Ala_{21}$, $Ile_{31}$, and $Met_{35}$ pack together to form a hydrophobic core that stabilizes the hexamer formed by peptide 8. While the minor surface of peptide 8 displays five hydrophobic side chains, which of peptide 2 displays only three—$Val_{18}$, $Phe_{20}$, and $Ile_{31}$. The hexamer formed by peptide 2 lacks the massive hydrophobic core and is only loosely packed at the interface between trimers. The buried surface area of the hexamer formed by peptide 8 is 5102 $Å^2$, whereas the buried surface area of the hexamer formed by peptide 2 is only 3514 $Å^2$.

Dimer.

Two peptide 8 β-hairpin monomers assemble edge-to-edge to form a hydrogen-bonded dimer, creating a four-stranded antiparallel β-sheet (FIG. 46A). Three such dimers make up the hexamer. The β-hairpin monomers are shifted out of registration by two residues toward the N-termini, such that Alan on one monomer is across from $Leu_{34}$ on the adjacent monomer (FIG. 46B). Four intermolecular hydrogen bonds between $Ile_{31}$ and $Gly_{33}$ of one monomer and $Gly_{33}$ and $Ile_{31}$ of the adjacent monomer help stabilize the dimer.

Figure 47:
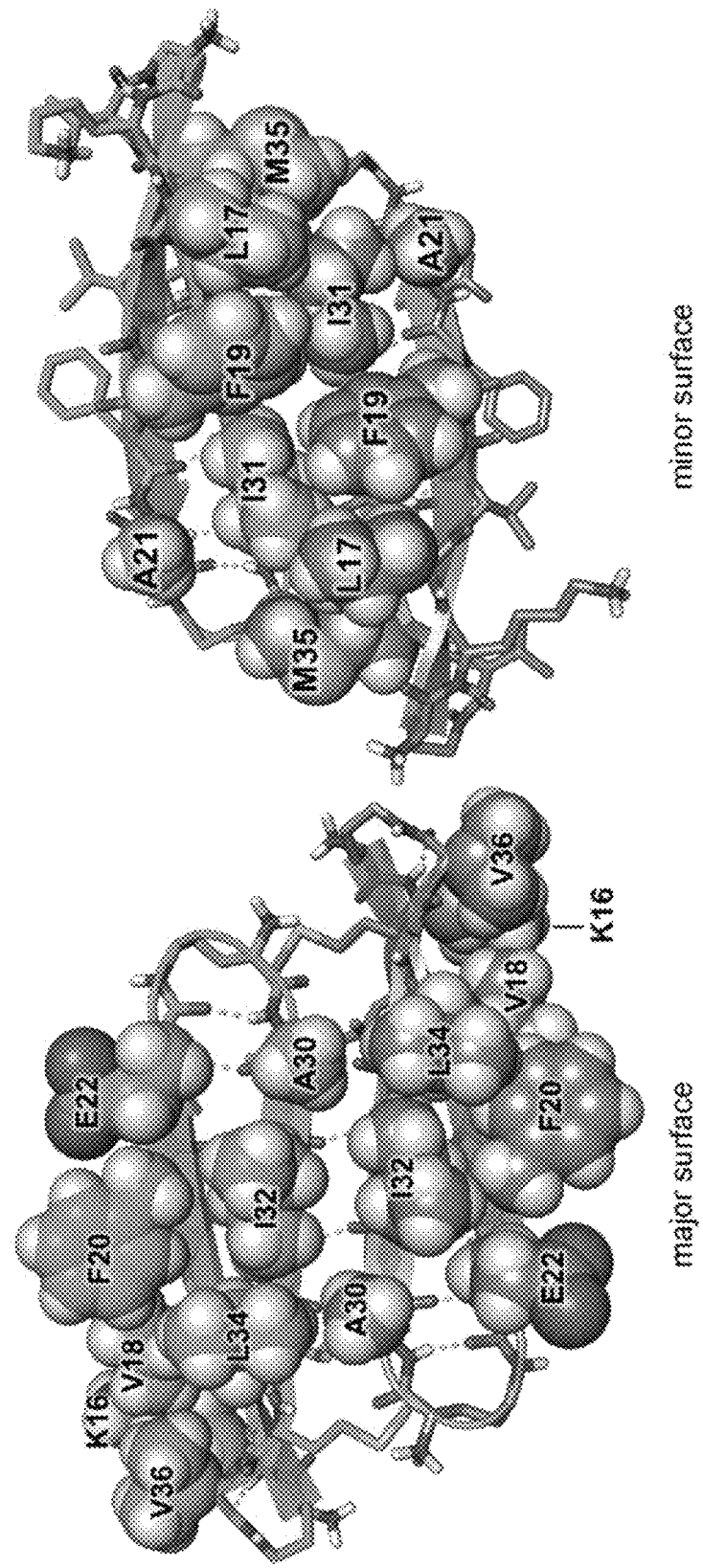
FIG. 47 provides X-ray crystallographic schematics detailing the chemical structures of the major and minor surfaces of a dimer formed by peptide 8, generated in accordance with various embodiments of the invention.

The β-sheet dimer has two surfaces: one surface displays the side chains of residues on the major surface of peptide 8; the other surface displays the side chains of residues on the minor surface of peptide 8 (FIG. 47). Hydrophobic packing between the side chains of residues on the minor surface further stabilizes the dimer: $Leu_{17}$, $Phe_{19}$, and $Ile_{31}$ on one monomer pack against $Ile_{31}$, $Phe_{19}$, and $Leu_{17}$ on the adjacent monomer. There are no substantial intermolecular contacts between the side chains of residues on the major surface of the dimer.

Trimer.

Figure 48B:
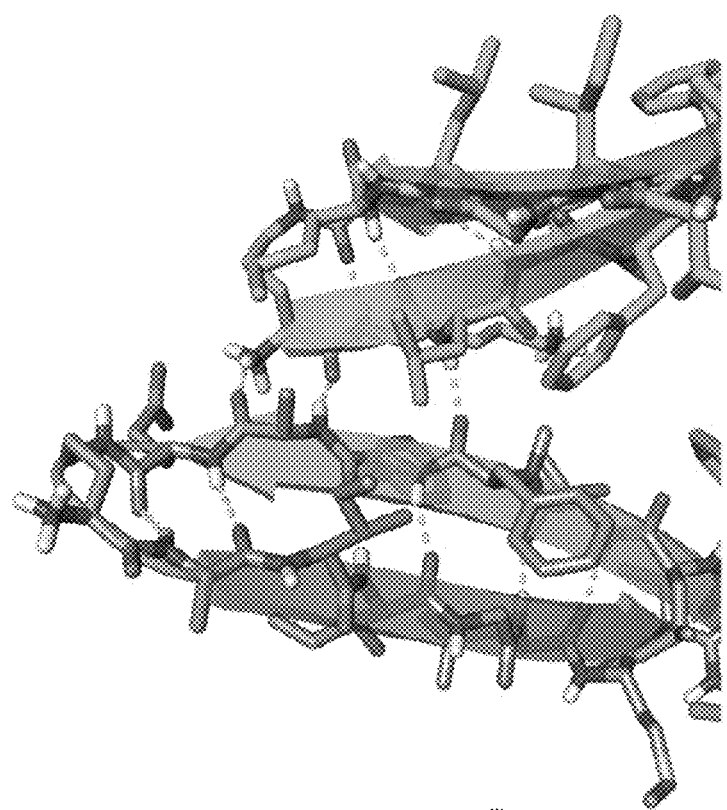
FIG. 48B provides an X-ray crystallographic schematic detailing the chemical structure of a corner of a trimer formed by peptide 8, generated in accordance with various embodiments of the invention.
Figure 48A:
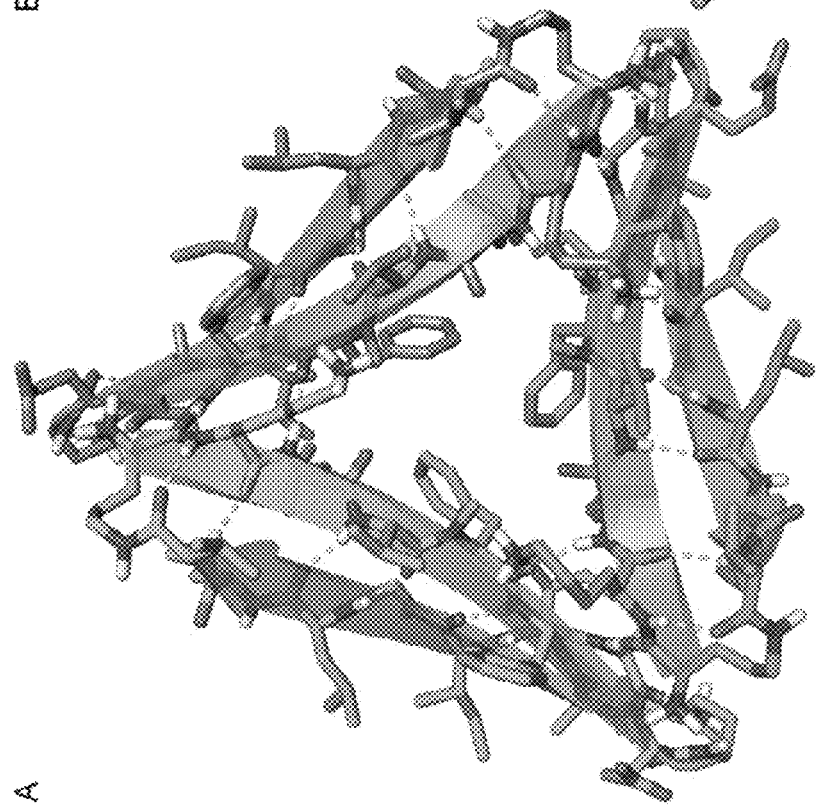
FIG. 48A provides an X-ray crystallographic schematic detailing the chemical structure of a trimer formed by peptide 8, generated in accordance with various embodiments of the invention.

Three peptide 8 β-hairpin monomers assemble to form a triangular trimer (FIG. 48A). Two such trimers make up the hexamer. The trimer is stabilized by intermolecular edge-to-edge hydrogen bonds between monomers, which create four-stranded β-sheets at each corner of the trimer. At each corner, the main chain of $^δOrn$ of one monomer hydrogen bonds with the main chain of $Ala_{21}$ of the adjacent monomer, and the carbonyl of $Phe_{19}9$ of one monomer hydrogen bonds with the NH of $Leu_{17}$ of the adjacent monomer (FIG. 48B).

Figure 49:
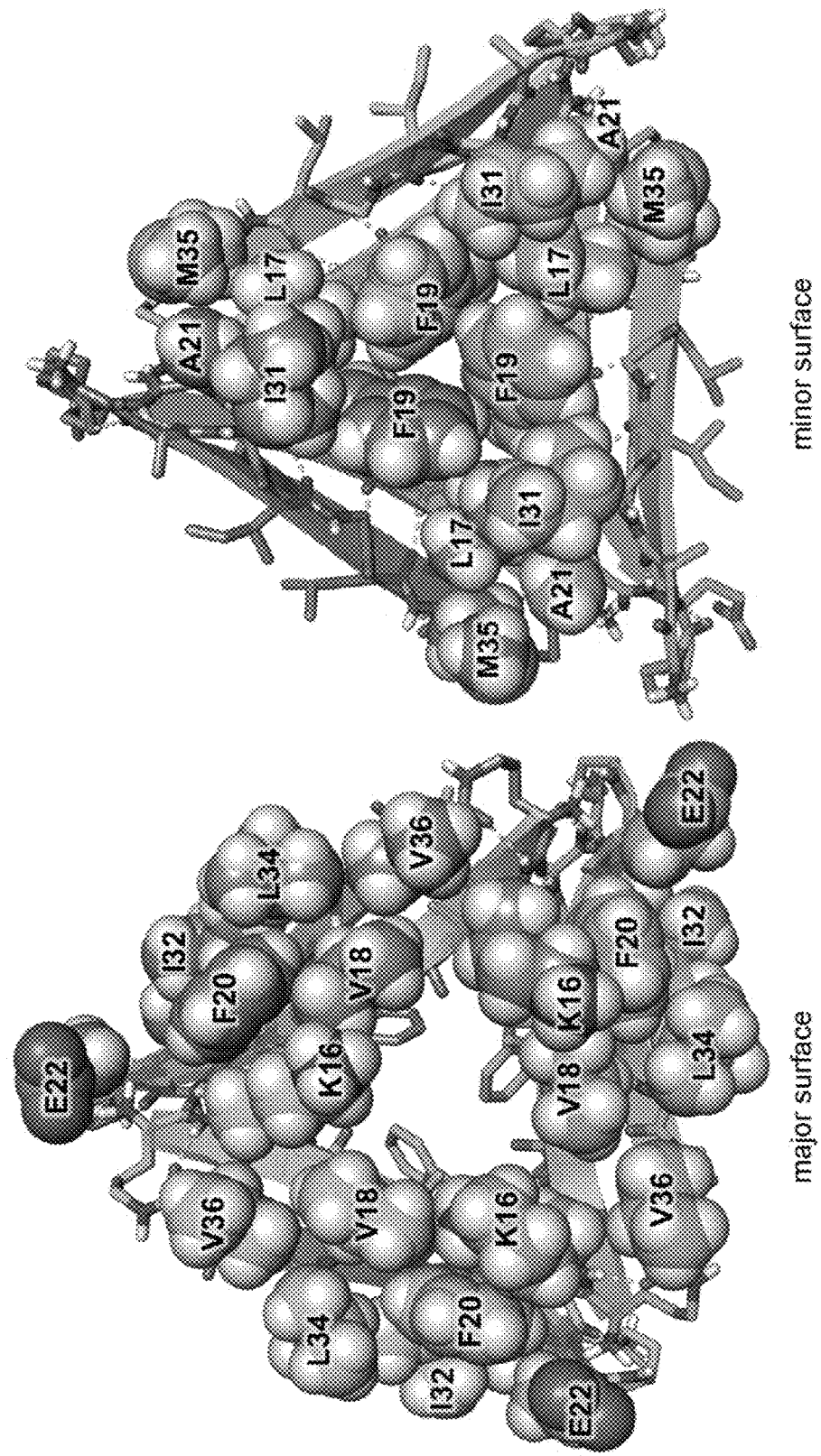
FIG. 49 provides X-ray crystallographic schematics detailing the chemical structures of the major and minor surfaces of a trimer formed by peptide 8, generated in accordance with various embodiments of the invention.

The triangular trimer has two surfaces that display the amino acid side chains of the major surfaces and the minor surfaces of the component β-hairpin monomers (FIG. 49). Hydrophobic packing between the side chains of residues on the minor surface further stabilizes the trimer: $Met_{35}$, $Leu_{17}$, and $Phe_{19}9$ on one monomer pack against $Ala_{21}$, $Ile_{31}$, and $Phe_{19}9$ on the adjacent monomer. There are no substantial intermolecular contacts between side chains of residues on the major surface of the trimer.

The hexamer, trimer, and dimer observed in the X-ray crystallographic structure of peptide 8 recapitulate the oligomers observed in SDS-PAGE and SEC. The assembly of the hexamer from either dimers or trimers may explain how the peptide 8 dimers and trimers observed in SEC come together to form the hexamer in SDS-PAGE. The structure of the hexamer shows key stabilizing contacts, such as edge-to-edge hydrogen bonding and hydrophobic packing. To better understand the importance of these contacts in the solution-phase oligomerization of peptide 8, peptides 9 and 10 were designed. The following sections describe studies of these peptides and also provide insights into why $Aβ_{16-36}$-derived peptide 8 forms a hexamer in SDS-PAGE, but $Aβ_{17-36}$-derived peptide 2 does not.

N-Methylation of Peptide 8 Disrupts Oligomerization

To test whether the hexamer observed in SDS-PAGE is similar in structure to the hexamer observed crystallographically, a homologue containing an additional N-methyl group designed to disrupt hexamer formation was prepared. Peptide 9 is a homologue of peptide 8 bearing an additional N-methyl group on $Gly_{33}$ (FIG. 5A; Seq. ID Nos. 36 and 37). In the X-ray crystallographic structure of the hexamer formed by peptide 8, the backbone of $Gly_{33}$ on one monomer hydrogen bonds with the backbone of $Ile_{31}$ on an adjacent monomer (FIG. 46B). Introduction of an N-methyl group on $Gly_{33}$ should prevent hydrogen bonding and thus disrupt the hexamer. In SDS-PAGE, peptide 9 does not migrate as a hexamer (FIG. 41A). Instead, peptide 9 migrates similarly to peptide 2, and thus appears to run as a monomer or dimer. This result supports a model in which the hexamer formed by peptide 8 in SDS-PAGE is similar in structure to the hexamer observed crystallographically. In SEC, peptide 9 elutes at a volume consistent with the molecular weight of a monomer (Table 2), further demonstrating that N-methylation on $Gly_{33}$ disrupts oligomer formation.

Mutation of Peptide 2 Induces Oligomerization

Figure 51:
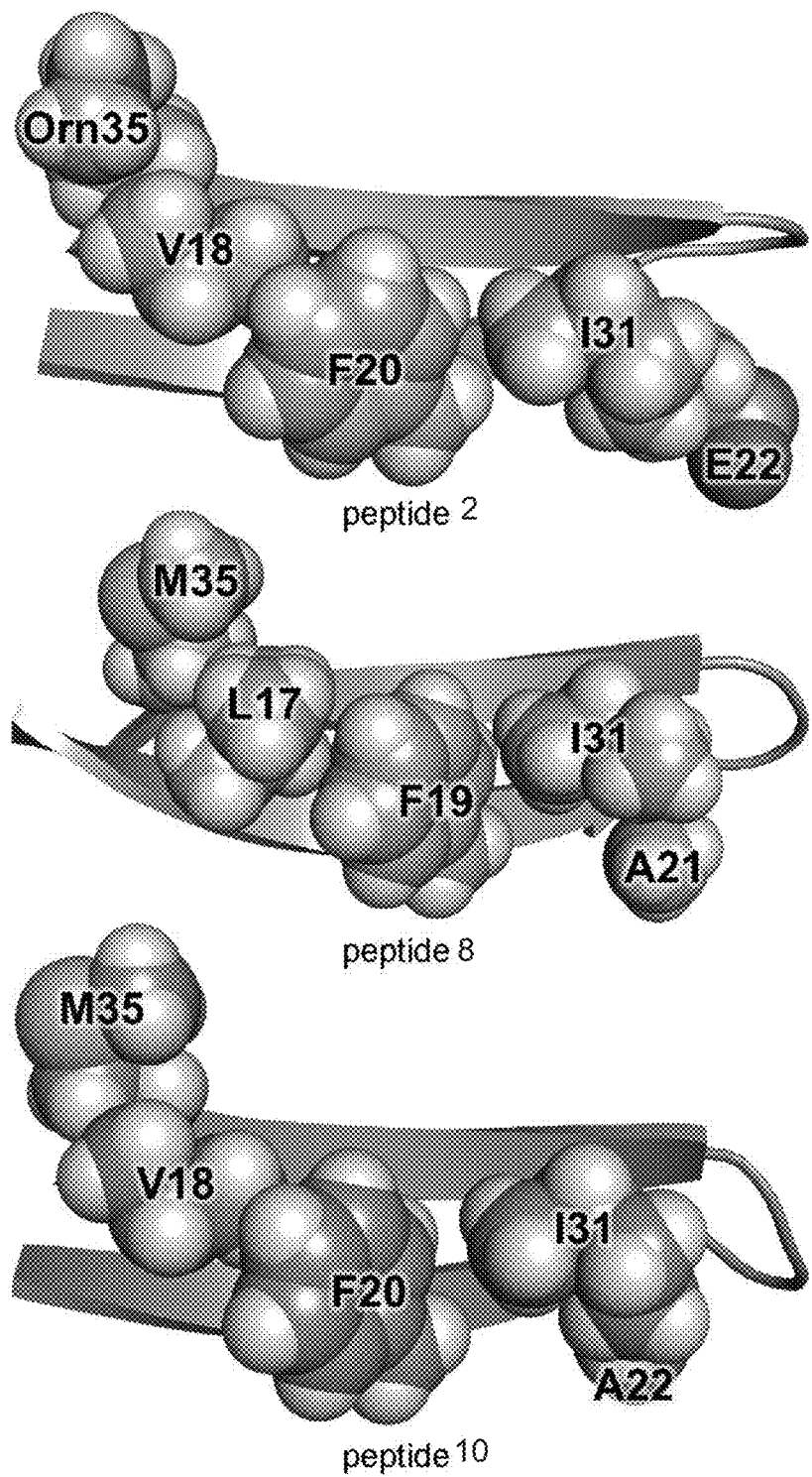
FIG. 51 provides X-ray crystallographic schematics detailing the chemical structures of the minor surfaces of peptides 2, 8, and 10 in accordance with various embodiments of the invention.

The SDS-PAGE and X-ray crystallographic studies of peptides 2 and 9 demonstrate that shifting the registration of a β-hairpin peptide affects its oligomerization. In the X-ray crystallographic structures, the hexamer formed by peptide 8 is better packed and has more hydrogen bonds than the hexamer formed by peptide 2. In SDS-PAGE, peptide 8 assembles to form a hexamer, whereas peptide 2 does not. The difference in the hydrophobicity and charge of the minor surfaces of peptides 2 and 9 may explain this difference in oligomerization. The minor surface of peptide 2 displays two charged hydrophilic side chains and three hydrophobic side chains, whereas the minor surface of peptide 8 displays five hydrophobic side chains (FIG. 51).

To explore the importance of charge and hydrophobicity in oligomerization, peptide 10 was prepared (FIG. 50B). Peptide 10 is a triple mutant of peptide 2, with $L_{17}K$, $E_{22}A$, and $Orn_{35}M$ mutations. Peptide 10 may be thought of as a chimera in which three residues of peptide 8 are grafted onto peptide 2 to eliminate charge on the minor surface. In peptide 10, $Ala_{22}$ and $Met_{35}$ occupy the same sites on the minor surface as $Ala_{21}$ and $Met_{35}$ in peptide 8. The $Lys_{17}$ residue in peptide 10 sits on the major surface, occupying the same site as $Lys_{16}$ in peptide 8 and providing charge to enhance solubility. The remaining 11 residues of peptide 10 are identical to those of peptide 2.

SDS-PAGE reveals that peptide 10 assembles to form an oligomer that migrates at a slightly higher molecular weight than the hexamer formed by peptide 8 (FIG. 41A). Replacement of the charged residues with hydrophobic residues on the minor surface of peptide 2 converts a peptide that does not form oligomers in aqueous SDS to a peptide that oligomerizes. This experiment confirms the importance of an uncharged, hydrophobic surface in the oligomerization of β-hairpin peptides. In SEC, peptide 10 elutes at a volume consistent with the molecular weight of a monomer (Table 2), suggesting that SDS promotes oligomerization of peptide 10 in the SDS-PAGE experiment.

The slightly higher position of the peptide 10 oligomer band in SDS-PAGE suggests that the oligomer formed by peptide 10 may differ in structure from the hexamer formed by peptide 8. To gain insights into the structure of the oligomer formed by peptide 10, X-ray crystallography was performed. Peptide 10 afforded crystals suitable for X-ray diffraction in aqueous HEPES buffer with potassium chloride and pentaerythritol propoxylate. The X-ray crystallographic phases of peptide 10 was determined by sulfur single-wavelength anomalous diffraction (S-SAD) using the anomalous signal from the sulfur in methionine (Q. Liu, et al., Science 2012 336, 1033-1037; and G. N. Sarma, et al., *Acta. Crystallogr. D Biol. Crystallogr.* 2006 62, 707-716; the disclosures of which are incorporated herein by reference).

Figure 52A:
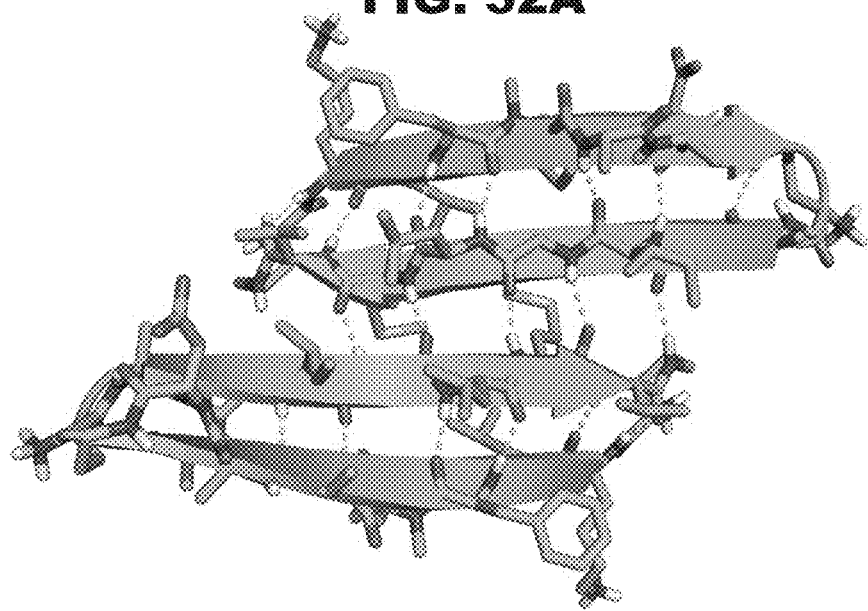
FIG. 52A provides an X-ray crystallographic schematic detailing the chemical structure of the antiparallel β-sheet formed by peptide 10 in accordance with various embodiments of the invention.
Figure 52B:
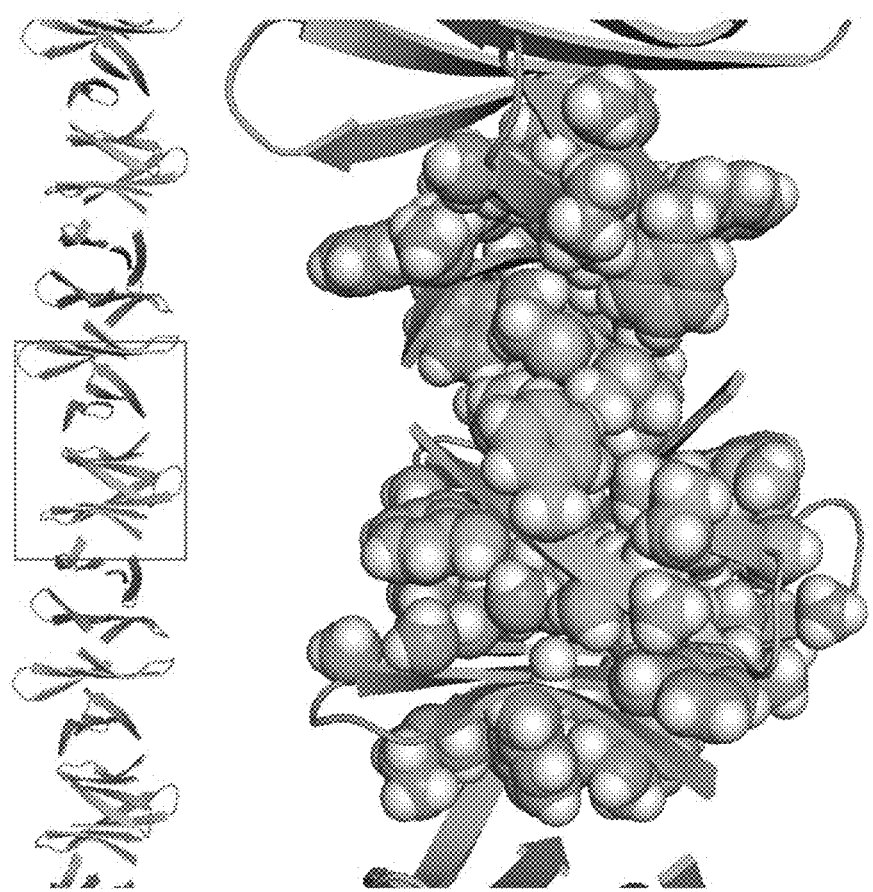
FIG. 52B provides an X-ray crystallographic schematic detailing the chemical structure of a column of laminated antiparallel β-sheet dimers formed by peptide 10, generated in accordance with various embodiments of the invention.

X-ray crystallography reveals that peptide 10 folds to form β-hairpins similar to those formed by peptides 2 and 9 (FIG. 51). The minor surface of peptide 10 is nearly identical to that of peptide 8, except that $Val_{18}$ takes the place of $Leu_{17}$. Peptide 10 assembles differently than peptides 2 and 9, forming packed columns in the crystal lattice rather than discrete oligomers (FIG. 52B). The columns are composed of antiparallel β-sheet dimers that are laminated on both faces through hydrophobic interactions. Each dimer consists of an antiparallel β-sheet formed by two peptide 10 β-hairpins (FIG. 52A). The dimer is shifted out of registration by two residues toward the C-termini, such that $Met_{35}$ pairs with $Gly_{33}$. The oligomer formed by peptide 10 in SDS-PAGE might be composed of three or four of these dimers packing through hydrophobic interactions.

Biological Studies of Peptides 2, 8, 9 and 10

Many oligomers formed by full-length Aβ are toxic toward cells (I. Benilove, E. Karan, and B. De Strooper, *Nat. Neurosci.* 2012 15, 349-357; and M. E. Larson and S. E. Lesne *J. Neurochem.* 2012 120, 125-139; the disclosures of which are incorporated herein by reference). To test whether the oligomers formed by peptide 8 are also toxic, the toxicity of peptide 8 toward neuronally derived SH-SY5Y cells were evaluated using a lactate dehydrogenase (LDH) release assay. Peptide 8 and 10 were compared to investigate how the hexamer-forming $Aβ_{16-36}$-derived peptide compares to a non-oligomerizing homologue. The toxicity of peptides 2 and 11 were also evaluated to better understand the relationship between oligomerization and toxicity.

Peptide 8 shows an increase in LDH release at concentrations as low as 50 μM, indicating toxicity toward SH-SY5Y cells (FIG. 53). Peptide 9, the non-oligomerizing homologue of peptide 8, is not toxic toward SH-SH5Y cells at concentrations as high as 200 μM, suggesting that oligomerization of peptide 8 to form a hexamer is important for toxicity. No dose dependence is observed in the LDH release induced by peptide 8 at concentrations of 50,100, and 200 µM, suggesting that oligomerization is cooperative and toxicity occurs above a critical concentration. Peptide 2 is toxic toward SH-SY5Y cells at concentrations as low as 100 µM, and peptide 10 is toxic toward SH-SY5Y cells at concentrations as low as 50 µM.

The onset of toxicity of peptides 2, 8, and 10 between 25 µM and 100 µM reflects the propensity of the hydrophobic peptides to form oligomers in the presence of the lipophilic cell membranes. In this model, none of the peptides are oligomeric in cell membranes at 25 µM. As the concentration is increased, oligomerization occurs, the oligomers disrupt the integrity of the cell membranes, and cell damage or death occurs.

Crystallographically Based Model of an $A\beta_{12-40}$ Hexamer

Figure 54:
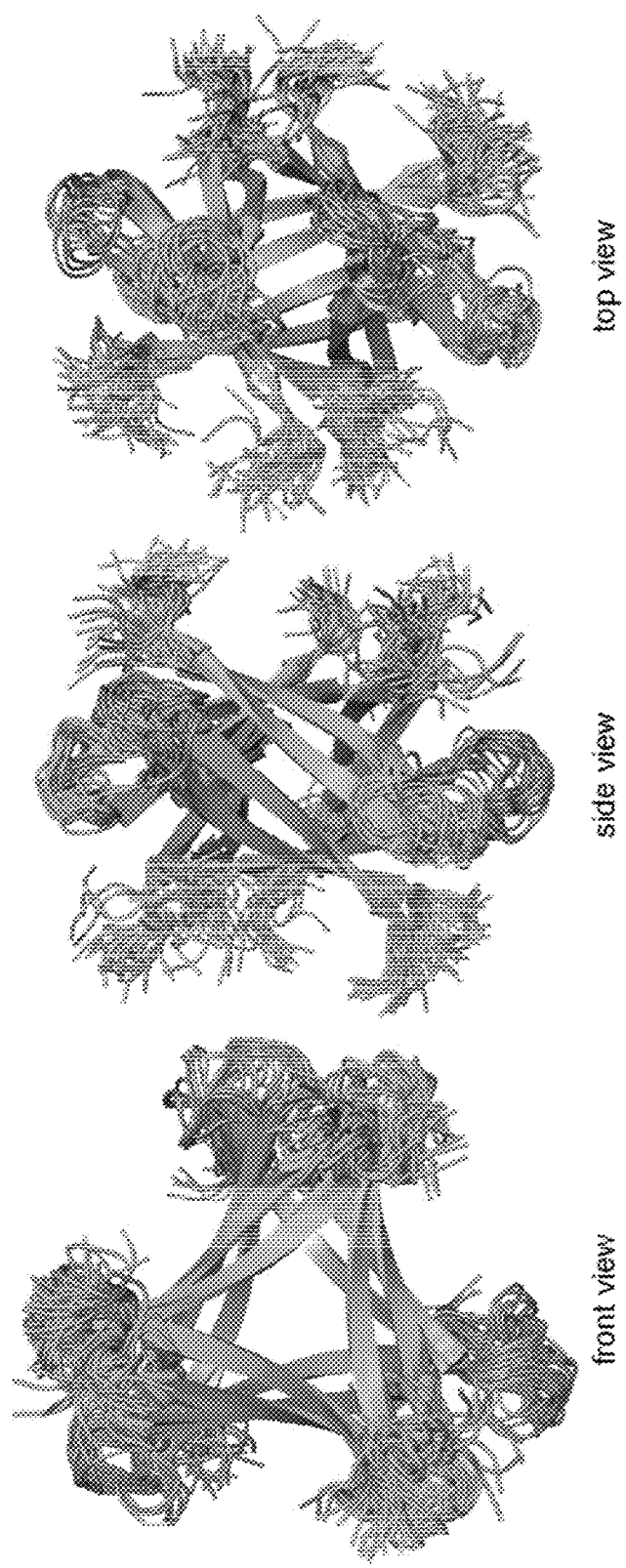
FIG. 54 provides a crystallographically based model of an $A\beta_{12\text{-}40}$ barrel-like hexamer, generated in accordance with various embodiments of the invention.

It is hypothesized that the full-length Aβ peptide can assemble in the same fashion as peptide 8 to form a barrel-like hexamer composed of β-sheet dimers or triangular trimers. To better understand what a hexamer containing the $A\beta_{23-29}$ loop and additional N- and C-terminal residues might look like, $A\beta_{12-40}$ was modeled into the crystallographic coordinates of the hexamer. Residues 23-29 (DVG-SNKG), 12-15 (VHHQ), and 37-40 (GGW) were built into the crystallographic coordinates of the six peptide 8 monomers that comprise the hexamer, and replica-exchange molecular dynamics (REMD) was performed to generate realistic conformations of the loops and the N- and C-terminal regions of the β-hairpins (FIG. 54) (Y. Sugita and Y Okamoto, Chem. Phys. Lett. 1999 314, 141-151; and J. C. Phillips, et al., J. Comput. Chem. 2005 26, 1781-1802; the disclosures of which are incorporated herein by reference).

The REMD simulation shows that full-length Aβ could form a barrel-like hexamer. The hexamer can accommodate the $A\beta_{23-29}$ loop and the remaining N- and C-terminal residues without steric clashes. In a hexamer formed by full-length Aβ, the loops from two monomers and the N- and C-termini from another two monomers would extend past the barrel-like openings. The loops might fold over the barrel-like openings and shield the hydrophobic core of the hexamer, which would otherwise be exposed to solvent.

Antibody Generation and Characterization

In this example, antibodies are generated that have high affinity for oligomeric species of Aβ but not monomers or fibrils. Furthermore, the generated antibodies are highly reactive in brain tissue of AD patients and transgenic AD mice, but not of healthy brain tissue. These data suggest that these generated antibodies are specific for soluble oligomers of Aβ, but do not react with Aβ monomers or insoluble fibrils.

Polyclonal antibodies were generated using trimer 4 (FIG. 19B; Seq. ID Nos, 24 and 25) chemically conjugated to the carrier protein hemocyanin. Conjugation of was performed using standard EDC coupling chemistry, as understood in the art. Next, the trimer 4-hemocyanin conjugate was used to immunize rabbits in either complete Freund's adjuvant or incomplete Freund's adjuvant. After about 30 days, ~50 ml of blood was drawn from the immunized rabbit, and either plasma or serum, containing the polyclonal antibodies, was prepared for further purification. The polyclonal antibodies were purified from the plasma or serum via specific affinity chromatography using timer 4 as a ligand. Antibodies were then separated from the ligand and subsequently resuspended in appropriate storage buffer. The purified antibodies were subsequently characterized for their affinity and specificity.

Figure 55:
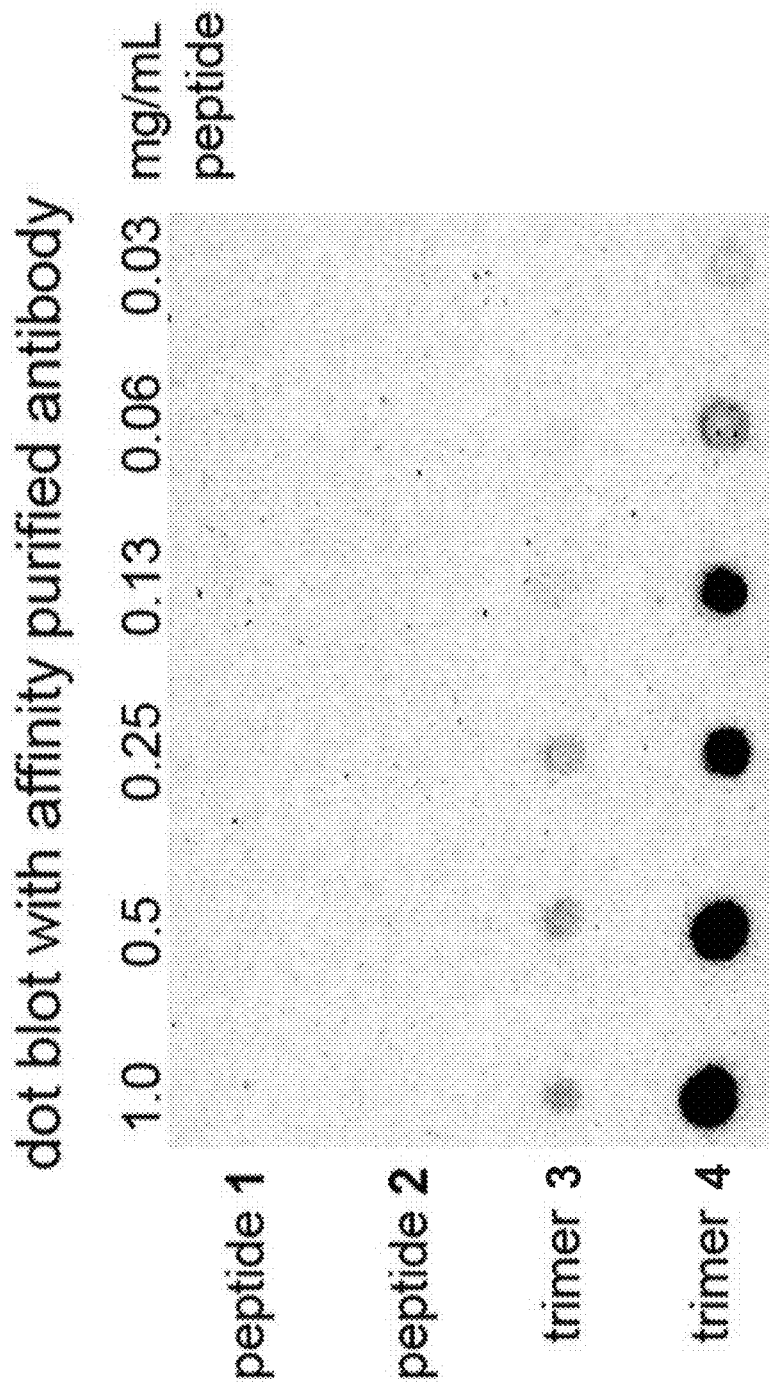
FIG. 55 provides a dot blot detailing affinity purified antibodies have high affinity for trimers 3 and 4, but not peptides 1 and 2, generated in accordance with embodiments of the invention.

Shown in FIG. 55 is a dot plot of the trimer affinity-purified antibodies bound to various concentrations of peptides and trimers. The affinity-purified antibodies do not appreciably appear to bind to peptides 1 and 3, even at concentrations of 1.0 mg/mL. The affinity-purified antibodies, however, has a strong affinity for trimers 3 and 4, as can be seen in at 0.25 and 0.06 mg/mL concentrations respectively.

Figure 56:
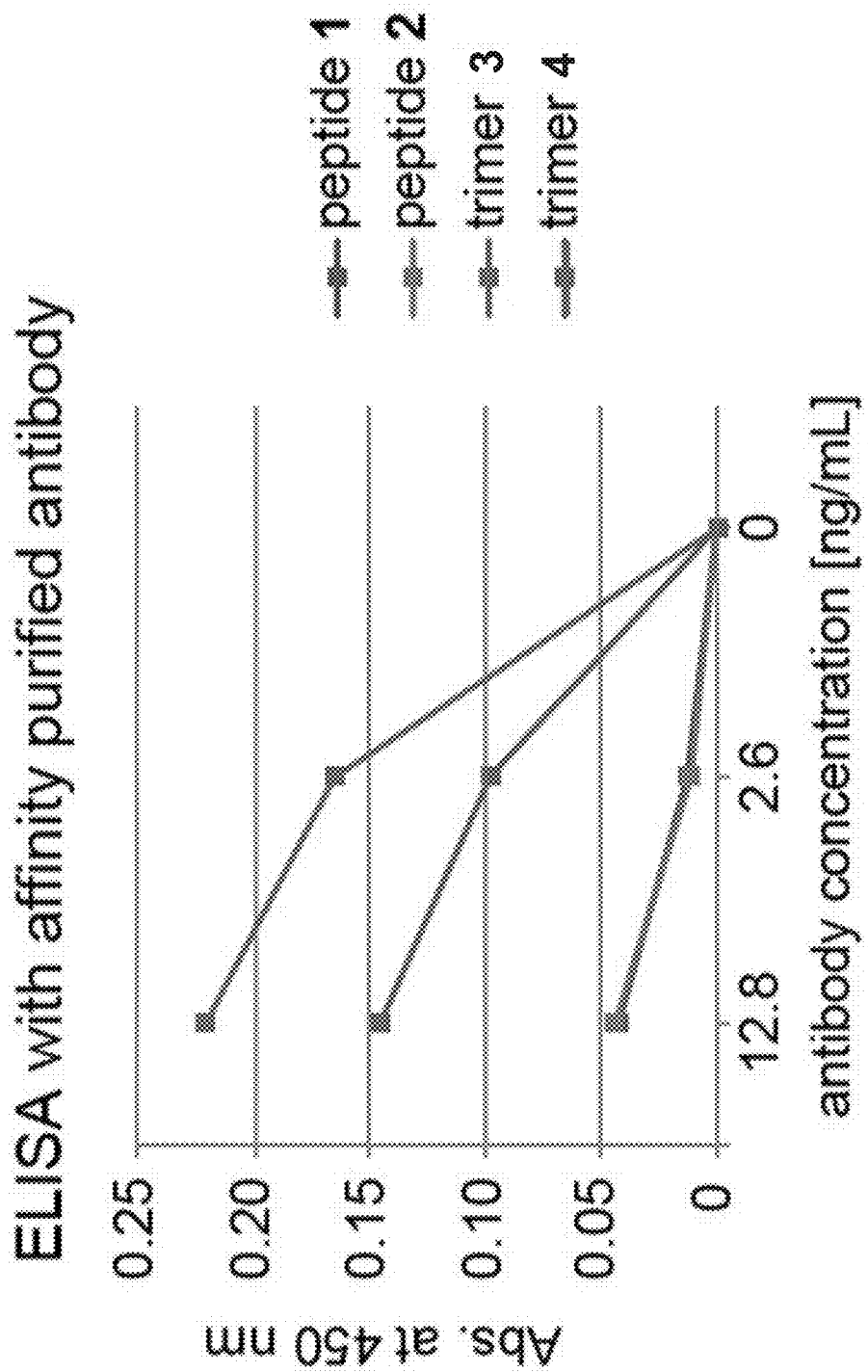
FIG. 56 provides a data graph of an ELISA experiment detailing affinity purified antibodies have high affinity for trimers 3 and 4, but not peptides 1 and 2, generated in accordance with various embodiments of the invention.

The trimer affinity-purified antibodies were also tested in an enzyme-linked immunosorbant assay (ELISA) (FIG. 56). In this assay, peptides 1 and 2 and trimers 3 and 4 were fixed to a 96-well plate at a fixed concentration. Affinity-purified antibodies, conjugated with a fluorophore, were incubated with the fixed peptides and trimers, and then washed to remove excess antibodies. Absorbance of the fluorophore is shown in FIG. 56. As shown in the chart, the affinity-purified antibodies have very high affinity for both trimers, but not the peptides, at 2.6 and 12.8 ng/mL of antibody. These results confirm that the trimer affinity-purified antibodies are specific for trimeric Aβ oligomers, but not the monomeric peptides.

Figure 57:
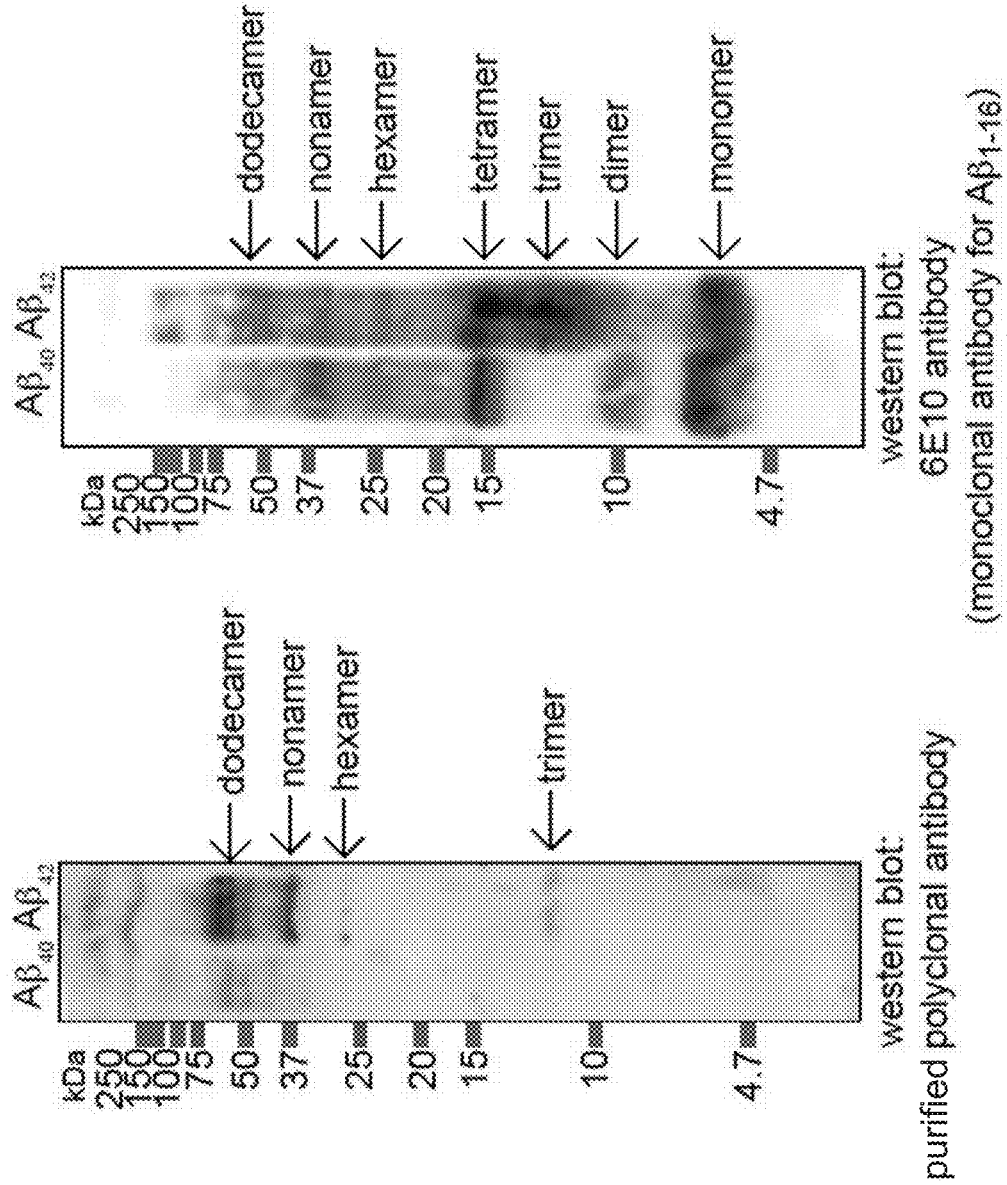
FIG. 57 provides an image of a Western blot detailing affinity purified antibodies recognizing oligomers of $A\beta_{1\text{-}40}$ and $A\beta_{1\text{-}42}$ of brain extracts from Alzheimer's disease and healthy individuals, generated in accordance with embodiments of the invention.

The trimer affinity-purified antibodies were compared to a popular Aβ antibody known as the "6E10" antibody, which is available from many commercial retailers. The antibody is monoclonal and specifically recognizes the first sixteen amino acids of Aβ (i.e., $A\beta_{1-16}$). FIG. 57 displays compares the ability of the affinity-purified antibodies and the 6E10 antibody to recognize recombinant $A\beta_{1-40}$ and $A\beta_{1-42}$. In this experiment, cell extracts were created from human cultured cells that expressed $A\beta_{1-40}$ and $A\beta_{1-42}$. The cell lysates were prepared and run in an SDS-PAGE gel using an electrophoresis apparatus, and then transferred onto a membrane for Western blot analysis. As shown in FIG. 57, the 6E10 antibody has a high affinity for the monomers, dimers, and tetramers of $A\beta_{1-40}$ and $A\beta_{1-42}$. Furthermore, the 6E10 antibody does not clearly identify the soluble trimers, hexamers, nonamers, and dodecamers. The affinity-purified antibodies, on the other hand, clearly identify and distinguish the soluble trimers, hexamers, nonamers, and dodecamers without any signal for the monomers, dimers, or tetramers. These results clearly show that the trimer affinity-purified antibodies outperform commercially available antibodies on affinity and specificity of soluble trimer and higher order oligomers.

Figure 58:
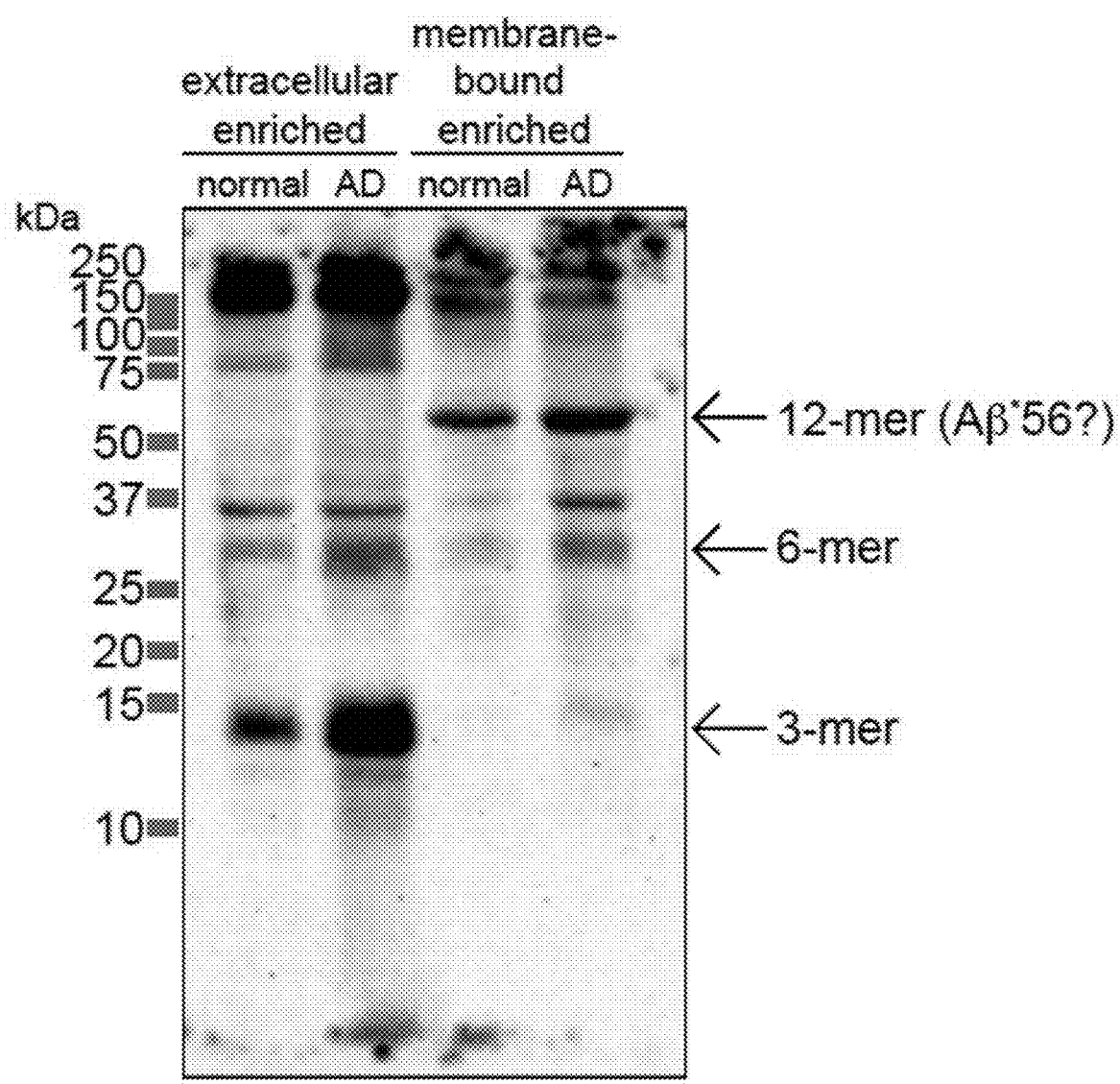
FIG. 58 provides an image of a Western blot detailing affinity purified antibodies, but not the 6E10 antibody, preferentially recognize oligomers of $A\beta_{1\text{-}40}$ and $A\beta_{1\text{-}42}$, generated in accordance with embodiments of the invention.

The trimer affinity-purified antibodies were also tested using human brain extracts and fixed tissue slices. In these experiments, extracts and tissue slices of an AD patients and healthy control were prepared according to standard protocols known in the art. The extracts were run in an SDS-PAGE gel using an electrophoresis apparatus. The extracts were transferred to a membrane for Western blot analysis, depicted in FIG. 58. As the figure shows, the antibodies recognized soluble Aβ trimers and hexamers in an extracellular fraction. The antibodies also recognized trimers, hexamers and dodecamers in the membrane-enriched fraction. As expected, the AD patient exhibited a higher level of soluble Aβ oligomers than the healthy control.

FIG. 59 depicts fluorescent images of human brain tissue slices taken from the superior temporal gyrus. The trimer affinity-purified antibodies (in yellow) displayed discreet, specific staining in the extranuclear and extracellular regions of the tissue, suggesting a secretory pathway. Provided as reference, DAPI staining (blue) depicts nuclei and a GFAP antibody (red) depicts astrocytes. The AD patient displays much greater amount of soluble oligomers than the patient, which would be expected. The human brain extract and tissue slice data show that the trimer affinity-purified antibodies can detect and distinguish AD-related levels of soluble Aβ oligomers.

Figure 60:
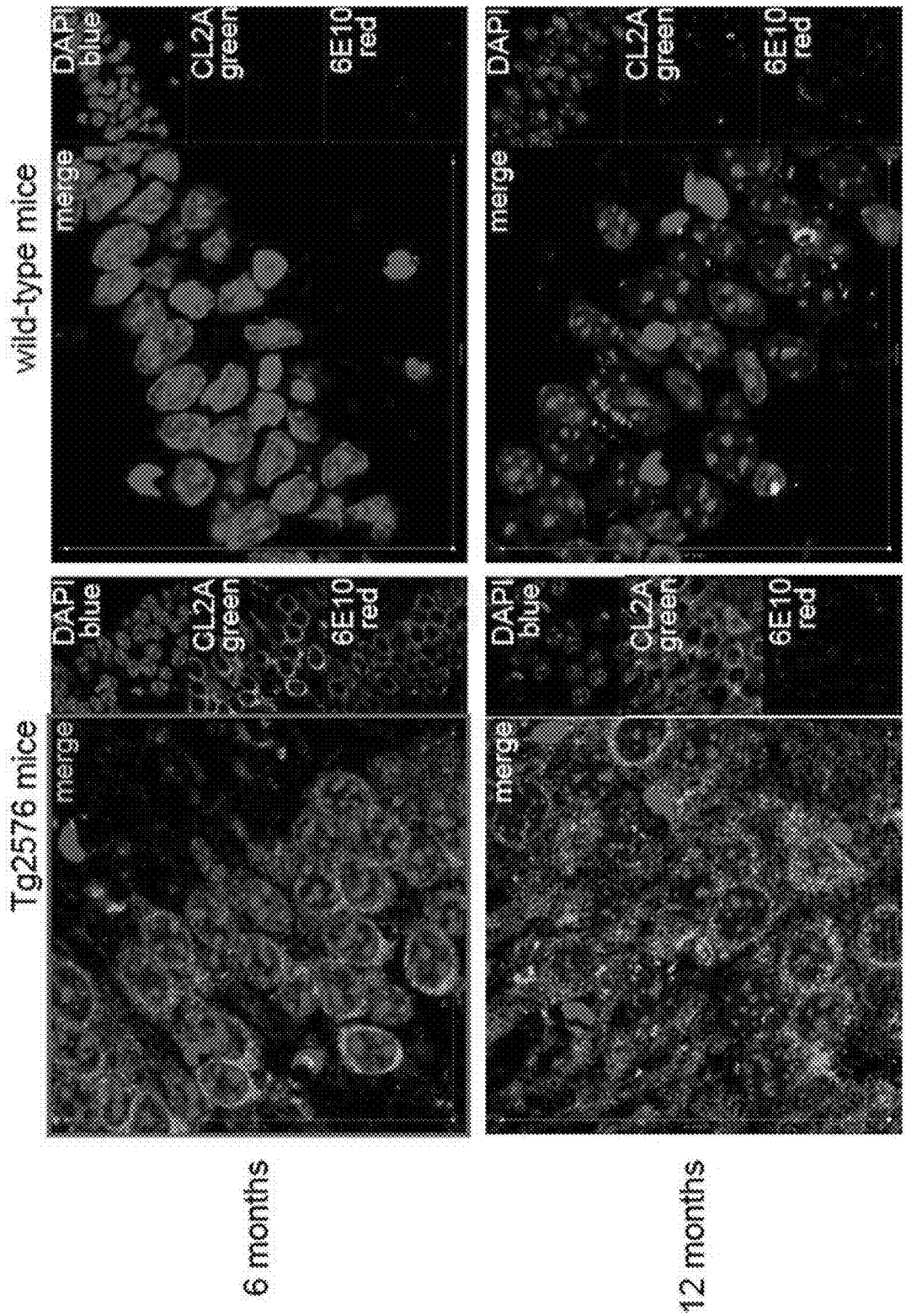
FIG. 60 provides fluorescent microscopic images of Tg2576 and wild-type mice brain tissue slices using affinity purified antibodies, generated in accordance with embodiments of the invention.

Trimer affinity-purified antibodies were also tested in hippocampal slices of Tg2576 AD transgenic mice. In Tg2576 mice, Aβ peptides are highly expressed which leads to prolonged oligomer accumulation. FIG. 60 depicts hippocampal slices of Tg2576 and wild-type mice at 6 months and 12 months. Each slice was immunostained using the 6E10 antibodies (red) and the trimer affinity-purified antibodies (CL2A green). At 6 months, the Tg2576 mice display a high level of 6E10 signal and moderate level of oligomer signal, suggesting a high accumulation of Aβ monomers and moderate accumulation of Aβ oligomers. At 12 months, however, the trimer affinity-purified antibodies exhibit much greater signal, which is consistent with the continuous accumulation of oligomers as the mice age. Of note, the wild-type mice showed little to no signal for either antibody, as expected. These results suggest that the trimer affinity-purified antibodies can detect the progression of AD in patients and mice.

Triphenylmethane Dyes Bind Crosslinked Aβ Trimers

In this example, crystal violet, a triphenylmethane dye, is used specifically detect trimeric Aβ (FIG. D1). The dye is sized and positioned to effectively bind within an Aβ trimer. While the precise mechanism of dye binding isn't precisely known, it is likely that the three phenyl groups on crystal violet dye interact with the three $F_{20}$ side chains through hydrophobic interactions. Additional proposed hydrophobic contacts include contacts between the methyl groups on crystal violet and the three 131 side chains. Once the dye is bound, a change in absorbance is observe, possibly due to changes in polarity surrounding the dye upon binding the trimer. Similarly, binding of the dye molecule increases fluorescence, likely due to the trimer/dye complex limiting vibrational modes of relaxation of the dye, favoring emission of photons. Accordingly, crystal violet can be used to measure the relative concentration of Aβ trimer in solution using absorption or fluorescence spectra (See FIGS. 62A-63B).

Figure 62A:
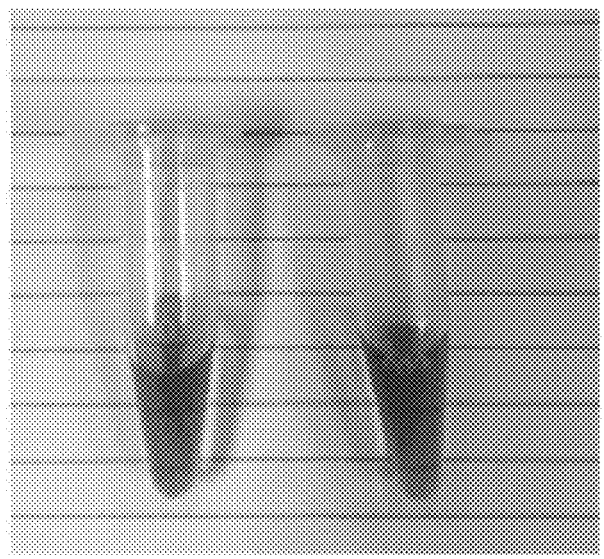
FIG. 62A provides an image showing the difference in absorbance of crystal violet dye with and without crosslinked trimer 4, generated in accordance with various embodiments of the invention.
Figure 62B:
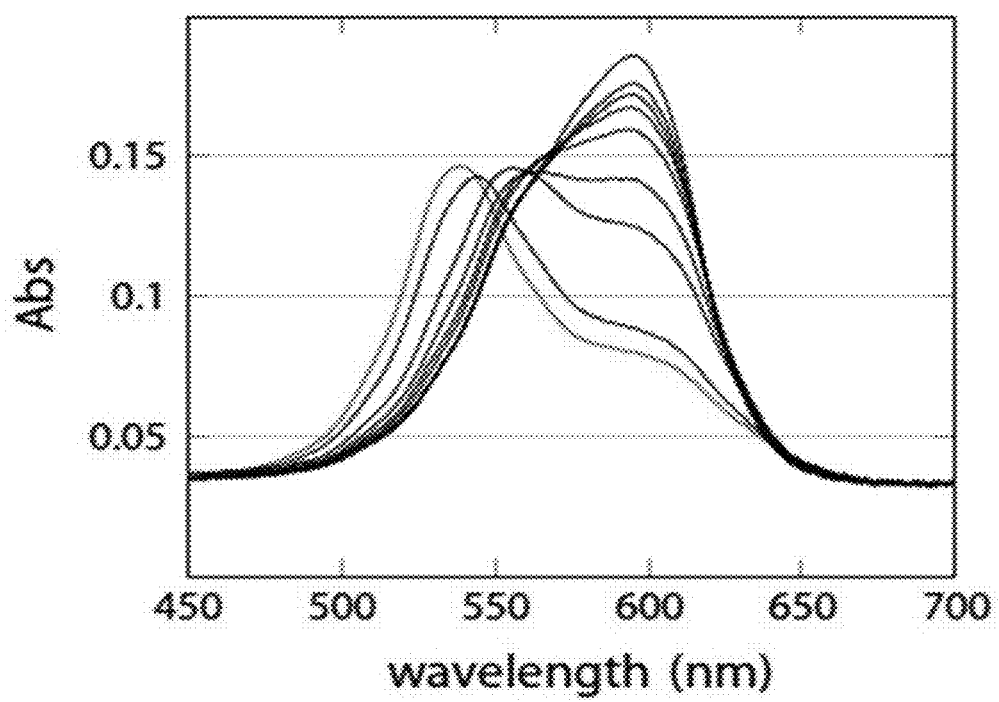
FIG. 62B provides a data graph detailing the absorbance spectra of crystal violet dye with various concentrations of crosslinked trimer 4, generated in accordance with various embodiments of the invention.

In FIGS. 62A and 62B, absorbance of crystal violet with various concentrations of Aβ trimer is presented. As shown in FIG. 62A, crystal violet in aqueous solution has a light violet color. As Aβ trimer is added, the crystal violet molecules bind within the Aβ trimer, changing its absorbance from light violet to a blue. FIG. 62B depicts this absorbance change in a visible spectra chart. Crystal violet in solution has a peak absorbance around 540 nm. The peak absorbance of crystal violet changes to around 600 nm when bound within an Aβ trimer. Accordingly, as the concentration of Aβ trimer is added to the crystal violet solution, the absorbance at 600 nm increases (FIG. 62A).

Figure 63A:
FIG. 63A provides an image showing the fluorescence of crystal violet dye with crosslinked trimer 4, generated in accordance with various embodiments of the invention.
Figure 63B:
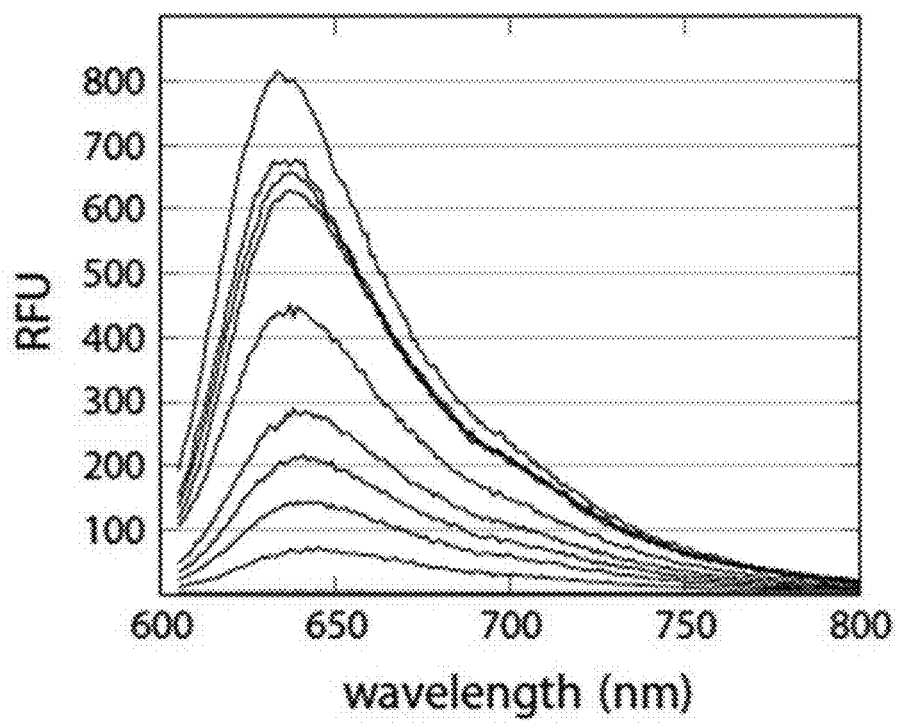
FIG. 63B provides a data graph detailing the fluorescence spectra of crystal violet dye with various concentrations of crosslinked trimer 4, generated in accordance with various embodiments of the invention.

FIGS. 63A and 63B provide fluorescence of crystal violet in solution with Aβ trimers. When crystal violet is bound to an Aβ trimer, it can emit light around 640 nm when stimulated (See pink band in FIG. 63A). Accordingly, as depicted in FIG. 63B, increases of Aβ trimer concentration can be measured using crystal violet. As concentration of Aβ trimer increases, the amount of light emitted at 640 nm increases.

Synthesis of Synthetic Aβ Peptides

Described in the subsequent paragraphs are methods of synthesis of synthetic Aβ peptides. These methods are merely exemplary of how to synthesize Aβ peptides. It should be understood that equivalent methods can be performed to achieve Aβ peptides with similar desirable properties.

Synthesis of Peptides

Loading of the resin. 2-Chlorotrityl chloride resin (300 mg, 1.2 mmol/g) was added to a Bio-Rad Poly-Prep chromatography column (10 mL). The resin was suspended in dry $CH_2Cl_2$ (10 mL) and allowed to swell for 30 min. The solution was drained from the resin and a solution of Boc-Orn(Fmoc)-OH (0.50 equiv, 82 mg, 0.18 mmol) in 6% (v/v) 2,4,6-collidine in dry $CH_2Cl_2$ (8 mL) was added immediately and the suspension was gently agitated for 12 h. The solution was then drained and a mixture of $CH_2Cl_2$/MeOH/N,N-diisopropylethylamine (DIPEA) (17:2:1, 10 mL) was added immediately. The mixture was gently agitated for 1 h to cap the unreacted 2-chlorotrityl chloride resin sites. The resin was then washed with dry $CH_2Cl_2$ (2×) and dried by passing nitrogen through the vessel. This procedure typically yields 0.12-0.15 mmol of loaded resin (0.4-0.5 mmol/g loading).

Peptide Coupling.

The Boc-Orn(Fmoc)-2-chlorotrityl resin generated from the previous step was transferred to a microwave-assisted solid-phase peptide synthesizer reaction vessel and submitted to cycles of automated peptide coupling with Fmoc-protected amino acid building blocks using a CEM Liberty 1 Automated Microwave Peptide Synthesizer. The linear peptide was synthesized from the C-terminus to the N-terminus. Each coupling cycle comprised of Fmoc-deprotection with 20% (v/v) piperidine in DMF for 2 min. at 50° C. (2×), washing with DMF (3×), coupling of the amino acid (0.75 mmol, 5 equiv) in the presence of HCTU (0.675 mmol, 4.5 equiv) and 20% (v/v) N-methylmorpholine (NMM) in DMF for 10 min. at 50° C., and washing with DMF (3×). Special coupling conditions were used for the phenylalanine that followed the N-methylphenylalanine: The phenylalanine was double coupled (0.75 mmol, 5 equiv.) and allowed to react at ambient temperature for 1 h per coupling with HATU (5 equiv) and HOAt (5 equiv) in 20% (v/v) NMM in DMF. After coupling of the last amino acid, the terminal Fmoc group was removed with 20% (v/v) piperidine in DMF (10 min. 50° C.). The resin was transferred from the reaction vessel of the peptide synthesizer to a Bio-Rad Poly-Prep chromatography column.

Cleavage of the Peptide from the Resin.

The linear peptide was cleaved from the resin by agitating the resin for 1 h with a solution of 1,1,1,3,3,3-hexafluoroisopropanol (HFIP) in $CH_2Cl_2$. (1:4, 7 mL). The suspension was filtered and the filtrate was collected in a 250 mL round-bottomed flask. The resin was washed with additional HFIP in $CH_2Cl_2$ (1:4, 7 mL) and then with $CH_2Cl_2$ (2×10 mL). The combined filtrates were concentrated by rotary evaporation to give a white solid. The white solid was further dried by vacuum pump to afford the crude protected linear peptide, which was macrolactamized without further purification.

Macrolactamization of the Linear Peptide.

The crude protected linear peptide was dissolved in dry DMF (150 mL). HOBt (114 mg, 0.75 mmol, 5 equiv) and HBTU (317 mg, 0.75 mmol, 5 equiv) were added to the solution. DIPEA (0.33 mL, 1.8 mmol, 12 equiv) was added to the solution and the mixture was stirred under nitrogen for 24 h. The mixture was concentrated under reduced pressure to afford the crude protected cyclic peptide.

Global Deprotection of the Cyclic Peptide.

The protected cyclic peptide was dissolved in TFA/triisopropylsilane (TIPS)/$H_2O$ (18:1:1, 20 mL) in a 250 mL round-bottomed flask equipped with a nitrogen-inlet adaptor. The solution was stirred for 1.5 h. The reaction mixture was then concentrated by rotary evaporation under reduced pressure to afford the crude cyclic peptide as a thin yellow film on the side of the round-bottomed flask. The crude cyclic peptide was immediately subjected to purification by reverse-phase HPLC (RP-HPLC), as described below.

Reverse-Phase HPLC Purification.

The peptide was dissolved in H$_2$O and acetonitrile (7:3, 10 mL), and the solution was filtered through a 0.2 μm syringe filter and purified by RP-HPLC (gradient elution with 20-50% CH$_3$CN over 50 min). Pure fractions were concentrated by rotary evaporation and lyophilized. Typical syntheses yielded ~55 mg of either peptide as the TFA salt.

Synthesis of Crosslinked Trimers

Trimers were synthesized by oxidizing peptides in 20% aqueous DMSO. A 6 mM solution of either lyophilized peptide was prepared gravimetrically by dissolving the peptide in an appropriate amount of 20% (v/v) aqueous DMSO prepared with deionized water. The reaction was carried out in a capped 25-mL glass scintillation vial with rocking at room temperature for 48-72 h. Next, the reaction mixture was diluted to a concentration of 300 μM peptide and transferred to a 500-mL round-bottomed flask. The solution was stirred with a magnetic stir bar for an additional 48 h. After 48 h, the reaction mixture was concentrated to ≤5 mL by rotary evaporation and immediately subjected to RP-HPLC purification (gradient elution with 20-50% CH$_3$CN over 60 min). Pure fractions were concentrated by rotary evaporation and lyophilized. Typical syntheses yielded ~10 mg trimer 3 and ~15 mg of trimer 4 from a 0.1 mmol scale synthesis of peptides 3 and 4.

Experimental Methods

Crystallization Procedure for Trimer 3

Trimer 3 afforded crystals in the same conditions that afforded crystals of peptides 1 and 3-0.1 M HEPES buffer, and Jeffamine M-600. These conditions were further optimized accordingly to yield crystals of trimer 4 suitable for X-ray crystallography. The optimized conditions consist of 0.1 M HEPES at pH 7.3 with 34% Jeffamine M-600.

Crystallization Procedure for Trimer 4.

Initial crystallization conditions for trimer 4 were determined using the hanging-drop vapor-diffusion method. Crystallization conditions were screened using three crystallization kits in a 96-well plate format (Hampton Index, PEG/Ion, and Crystal Screen). Three 150 nL hanging drops that differed in the ratio of peptide to well solution were made per condition in each 96-well plate for a total of 864 experiments. Hanging drops were made by combining an appropriate volume of trimer 4 (10 mg/mL in deionized water) with an appropriate volume of well solution to create three 150 nL hanging drops with 1:1, 1:2, and 2:1 peptide:well solution. The hanging drops were made using a TTP LabTech Mosquito nanodisperse instrument. Crystals of trimer 4 grew in ~48 h in a solution of 0.1 M Tris buffer at pH 7.0 with 0.2 M MgCl$_2$ and 3.5 M 1,6-hexanediol.

Crystallization conditions for trimer 4 were optimized using a 4×6 matrix Hampton VDX 24-well plate. The Tris buffer pH was varied in each row in increments of 0.5 pH units (6.5, 7.0, 7.5, and 8.0) and the 1,6-hexanediol concentration in each column in increments of 0.2 M (3.0 M, 3.2 M, 3.4 M, 3.6 M, 3.8 M, 4.0 M). The first well in the 4×6 matrix was prepared by combined 100 μL of 1 M Tris buffer at pH 6.5, 100 μL of 2 M MgCl$_2$, 600 μL of 5 M 1,6-hexanediol, and 200 μL of deionized water. The other wells were prepared in analogous fashion, by combining 100 μL of Tris buffer of varying pH, 100 μL of 2 M MgCl$_2$, 5 M 1,6-hexanediol in varying amounts, and deionized water for a total volume of 1 mL in each well.

Three hanging-drops were prepared per borosilicate glass slide by combining a solution of trimer 4 (10 mg/mL) and the well solution in the following amounts: 1 μL:1 μL, 2 μL:1 μL, and 1 μL:2 μL. Slides were inverted and pressed firmly against the silicone grease surrounding each well. Crystals of trimer 4 suitable for X-ray diffraction grew in ~5 days. Crystallization conditions were further optimized using smaller variations in Tris buffer pH (in increments of 0.25 pH units) and 1,6-hexanediol concentrations (in increments of 0.1 M). Crystals were harvested with a nylon loop attached to a copper or steel pin and flash frozen in liquid nitrogen prior to data collection.

X-Ray Crystallographic Data Collection, Data Processing, and Structure Determination for Trimers 3 and 4.

Diffraction data for trimers 3 and 4 were collected on a Rigaku Micromax-007HF X-ray diffractometer with a rotating copper anode at 1.54 Å wavelength with 0.5° oscillation. Diffraction data were collected using CrystalClear. Diffraction data were scaled and merged using XDS. Coordinates for the anomalous signals were determined by HySS in the Phenix software suite 1.10.1. Electron density maps were generated using anomalous coordinates determined by HySS as initial positions in Autosol. Molecular manipulation of the model was performed with Coot. Coordinates were refined with phenix.refine.

Diffraction data for frillier 3 were also collected at the Advanced Light Source at Lawrence Berkeley National Laboratory with a synchrotron source at 1.00-Å wavelength to achieve higher resolution. Data for trimer 3 suitable for refinement at 2.03 Å were obtained from the diffractometer; data for trimer 3 suitable for refinement at 1.90 Å were obtained from the synchrotron. Diffraction data were scaled and merged using XDS. The electron density map was generated by molecular replacement using the coordinates from the structure of trimer 3 generated by soaking in KI using the Phaser in software suite Phenix 1.10.1. Molecular manipulation of the model was performed with Coot. Coordinates were refined with phenix.refine.

Diffraction data for trimer 4 were also collected at the Stanford Synchrotron Radiation Lightsource (SSRL) with a synchrotron source at 0.97-Å wavelength. Diffraction data were scaled and merged using XDS. The electron density map was generated by molecular replacement using the coordinates from the structure of trimer 4 generated by S-SAD using the Phaser in software suite Phenix 1.10.1. Molecular manipulation of the model was performed with Coot. Coordinates were refined with phenix.refine.

LDH Release and Caspase-3 Activation Assays.

The toxicities of peptides 1 and 3, and trimers 3 and 4 toward SH-SY5Y cells were assessed by LDH release and caspase-3 activation assays. Cells were incubated in the presence or absence of equivalent concentrations of peptides 1 or 3, or trimers 3 and 4 for 72 h in 96-well plates. The LDH release assay was performed using the Pierce LDH Cytotoxicity Assay Kit from Thermo Scientific. The caspase-3 assay was performed using the Roche APO-One Homogeneous Caspase-3/7 Assay. Experiments were performed in replicates of five and an additional 10 wells were used for controls. Cells were cultured in the inner 60 wells (rows B-G, columns 2-11) of the 96-well plate. DMEM:F12 media (100 μL) was added to the outer wells (rows A and H, columns 1 and 12), in order to ensure the greatest reproducibility of data generated in the inner wells.

Preparation of Stock Solutions of Peptides 1 and 3, and Trimers 3 and 4.

A 10 mg/mL stock solution of peptides 1 or 3, or trimers 3 and 4 was prepared gravimetrically by dissolving 1 mg of each compound in 100 μL of deionized water that was either filtered through a 0.2 μm syringe filter or autoclaved. The stock solution was used to create 180 μM working solutions of peptides 1 or 3, or 60 μM working solutions of trimers 3 and 4 (these solutions contain equivalent concentrations of peptide). The 180 μM working solutions of peptides 1 and 2 were serially diluted with deionized water to create 90 μM working solutions of peptides 1 and 2. The 60 μM working solutions of trimers 3 and 4 were serially diluted with deionized water to create 30 μM, 15 μM, and 7.5 μM working solutions of trimers 3 and 4.

Preparation of SH-SY5Y Cells for LDH Release and Caspase-3 Assays.

SH-SY5Y cells were plated in a 96-well plate at 30,000 cells per well. Cells were incubated in 100 μL of a 1:1 mixture of DMEM:F12 media supplemented with 10% fetal bovine serum, 100 U/mL penicillin, and 100 μg/mL streptomycin at 37° C. in a 5% $CO_2$ atmosphere and allowed to adhere to the bottom of the plate for 24 hours.

Treatment of SH-SY5Y Cells with Peptides 1 and 2, and Trimers 3 and 4.

After 24 hours, the culture media was removed and replaced with 90 μL of serum-free DMEM:F12 media. A 10 μL aliquot of the working solutions of peptides 1 or 2, or trimers 3 and 4 was added to each well, for a well-concentration of 18 μM and 9 μM for peptides 1 and 2, 6 μM and 3 μM for trimer 3 or 6 μM, 3 μM, 1.5 μM, and 0.75 μM for trimer 4. Experiments were run in replicates of five. Five wells were used as controls and received a 10 μL aliquot of deionized water (vehicle). Another five wells were left untreated, to be subsequently used as controls with lysis buffer for the LDH release assay, or staurosporine for the caspase-3 activation assay. Cells were incubated at 37° C. in a 5% $CO_2$ atmosphere for 72 hours.

LDH Release Assay.

After 72 hours, 10 μL of 10× lysis buffer—included with the assay kit—was added to the five untreated wells, and the cells were incubated for an additional 45 minutes. After 45 min, a 50-μL aliquot of the supernatant media from each well was transferred to a new 96-well plate and 50 μL of LDH substrate solution, prepared according to manufacturer's protocol, was added to each well. The treated plates were stored in the dark for 30 min, then 100 μL of stop solution was added to each well. The absorbance of each well was measured at 490 and 680 nm ($A_{400}$ and $A_{680}$). Data were processed by calculating the differential absorbance for each well ($A_{400}-A_{680}$) and comparing those values to those of the lysis buffer controls and the untreated controls: % cell death=$[(A_{490}-A_{680})_{compound}-(A_{490}-A_{680})_{vehicle}]/[(A_{490}-A_{680})_{lysis}(A_{490}-A_{680})_{vehicle}]$ Caspase-3 Activation Assay.

After 67 hours, 10 μL of 10× staurosporine was added to the control wells, and the cells were incubated for an additional 5 h. Next, the compound-containing media was removed and replaced with 25 μL of fresh serum-free DMEM/F12 media. A 25-μL aliquot of caspase-3 substrate, prepared according to manufacturer's protocol, was then added to each well. The plate was sealed with a clear adhesive plate sealer and fluorescence was monitored over 18 h while shaking at 250 rpm using a Gemini XPS fluorescence plate reader (excitation at 499 nm, emission at 521 nm). Data from the 18 h time point were processed by subtracting the relative fluorescence units (RFU) of the vehicle control wells from the RFU of the peptides 1 and 2 or trimers 3 and 4-treated wells.

Dot Blot Analysis of Peptides 1 and 2 and Trimers 3 and 4.

A 10 mg/mL stock solution of peptides 1 or 2, or trimers 3 or 4 was prepared gravimetrically by dissolving 1 mg of each compound in 100 μL of deionized water that was either filtered through a 0.2 μm syringe filter. An aliquot of each stock solution was diluted with deionized water to make 3 mg/mL solutions. The 3 mg/mL solutions were then serially diluted with deionized water to create 1.5 mg/mL, 0.75 mg/mL, and 0.37 mg/mL solutions. A 5 μL aliquot of each solution from the serial dilution was combined with 5 μL of a 2× solution of phosphate buffered saline (PBS) at pH 7.4 to generate 1.5 mg/mL, 0.75 mg/mL, and 0.37 mg/mL, and 0.18 mg/mL buffered solutions of peptides 1 or 2 or trimers 3 or 4. A 1-μL aliquot of each buffered solution was spotted onto a nitrocellulose membrane and allowed to aft dry (~5 min). Non-reactive sites were blocked with 10% (w/v) non-fat powdered milk in low-Tween Tris-buffered saline (TBS-IT: 20 mM Tris, 137 mM NaCl; 0.01% Tween 20, pH 7.6) for 1 h at room temperature with rocking. The membrane was then incubated while rocking overnight at 4° C. in primary A11 antibody (200 μg/mL) in 5% non-fat powdered milk in TBS-IT. The next day, the membrane was washed with TBS-IT for 5 min (3×). The membrane was then incubated while rocking with horseradish peroxidase conjugated goat anti-rabbit antibody (100 μg/mL) (Jackson ImmunoResearch catalog #111-035-003) in 5% non-fat powdered milk in TBS-IT for 1 h at room temperature. The membrane was then washed with TBS-IT for 5 min (3×). A 10 mL portion of chemiluminescence substrate (Thermo Scientific SuperSignal West Femto Maximum Sensitivity Substrate, product #34095) was prepared according to manufacturer's protocol and poured onto the membrane. The membrane was allowed to incubate in the chemiluminescence substrate for ~10 min before imaging. The blot was imaged using a standard digital SLR camera.

Size Exclusion Chromatography.

The oligomerization of peptides 1 and 2 and trimers 3 and 4 was studied by size-exclusion chromatography (SEC) at 4 CC in 50 mM sodium acetate/50 mM acetic acid buffer (sodium acetate buffer) at pH 4.5 as follows: Each peptide or trimer was dissolved in deionized water to a concentration of 10 mg/mL. The peptide or trimer solutions were then diluted to 1 mg/mL by adding 80 μL of the 10 mg/mL solutions to 720 μL of sodium acetate buffer. The peptide or trimer solutions were loaded onto a GE Superdex 75 10/300 GL column at 0.5 mL/min over 1 min. After loading, the samples were run with sodium acetate buffer at 1 mL/min, Chromatograms were recorded at 214 nm and normalized to the highest absorbance value. Standards (cytochrome C, aprotinin, and vitamin B12) were run in the same fashion.

SDS-PAGE and Silver Staining.

The oligomerization of peptides 1 and 2 and trimers 3 and 4 was studied by Tricine SDS-PAGE.

Sample Preparation.

Each peptide or trimer was dissolved in deionized water to a concentration of 10 mg/mL. An aliquot of the 10 mg/mL solutions was diluted with deionized water to create 2 mg/mL solutions of peptides 1 and 2, or 0.12 mg/mL solutions of trimers 3 and 4. The 1 mg/mL solutions of peptides 1 and 2, as well as the 0.12 mg/mL solutions of trimers 3 and 4 were further diluted with 2×SDS-PAGE loading buffer (100 mM Tris buffer at pH 6.8, 20% (v/v) glycerol, and 4% SDS) to create 1 mg/mL working solutions of peptides 1 and 2, and 0.06 mg/mL working solutions of trimers 3 and 4. A 5 μL aliquot of each working solution was run on a 16% polyacrylamide gel with a 4% stacking polyacrylamide gel. The gels were run at a constant 60 volts at 4° C.

Staining with silver nitrate was used to visualize peptides 1 and 2 and trimers 3 and 4 in the SDS-PAGE gel. Briefly, the gel was removed from the casting glass and rocked in fixing solution (50% (v/v) methanol and 5% (v/v) acetic acid in deionized water) for 20 min. Next, the fixing solution was discarded and the gel was rocked in 50% (v/v) methanol for 10 min. Next, the 50% methanol was discarded and the gel was rocked in deionized water for 10 min. Next, the water was discarded and the gel was rocked in 0.02% (w/v) sodium thiosulfate in deionized water for 1 min. The sodium thiosulfate was discarded and the gel was rinsed with deionized water (2×). After the last rinse, the gel was submerged in chilled 0.1% (w/v) silver nitrate in deionized water and rocked at 4° C. for 20 min. Next, the silver nitrate solution was discarded and the gel was rinsed with deionized water (2×). To develop the gel, the gel was incubated in developing solution (2% w/v sodium carbonate, 0.04% formaldehyde until the desired intensity of staining was reached (~1-3 min). When the desired intensity of staining was reached, the development was topped by discarding the developing solution and submerging the gel in 5% acetic acid.

Circular Dichroism Spectroscopy.

A 0.30 mg/mL solution of either trimer 3 or peptide 1 was prepared by adding 15 µL of 10 mg/mL stock solutions in deionized water to 385 µL of 10 mM potassium phosphate buffer at pH 7.4. Each solution was transferred to a 1 mm quartz cuvette for data acquisition. CD spectra were acquired on a Masco J-810 circular dichroism spectropolarimeter at room temperature. Data were collected using 0.2 nm intervals from 260 nm to 190 nm and averaged over five accumulations with smoothing.

TABLE 3

Sequencing Listing of Peptides

| Seq. ID No. | Name | Sequence | Modifications |
|---|---|---|---|
| 1 | $A\beta_{1-40}$ | DAEFRHDSGY EVHHQLKVFF AEDVGSNKGA IIGLMVGGVV | |
| 2 | $A\beta_{1-42}$ | DAEFRHDSGY EVHHQLKVFF AEDVGSNKGA IIGLMVGGVV IA | |
| 3 | FIG. 3A | XCVFFCXXVG SNKGAIIGLX VX | $X_1 = A\beta_{1-16}$, deleted; $X_7 = E, Q, K$; $X_8 = D, N$; $X_{20} = M$, Orn, MetO; $X_{22} = A\beta_{37-40}$, $A\beta_{37-42}$, deleted; Optional N-substitution on $F_5$ and $G_{18}$ (Me, alkyl, aryl, etc.) |
| 4 | FIG. 3B | XLVFFAXXVG SNKGCIIGCX VX | $X_1 = A\beta_{1-16}$, deleted; $X_7 = E, Q, K$; $X_8 = D, N$; $X_{20} = M$, Orn, MetO; $X_{22} = A\beta_{37-40}$, $A\beta_{37-42}$, deleted; Optional N-substitution on $F_5$ and $G_{18}$ (Me, alkyl, aryl, etc.) |
| 5 | FIG. 4A Top | XCVFFCXX | $X_1 = $ Orn; $X_7 = E, Q, K$; $X_8 = D, N$; Option N-substitution of $F_5$ (Me, alkyl, aryl, etc.) |
| 6 | FIG. 4A Bottom | XAIIGLXV | $X_1 = $ Orn; $X_7 = M$, Orn, MetO; Option N-substitution of $G_5$ (Me, alkyl, aryl, etc.) |
| 7 | FIG. 4B Top | XLVFFAXX | $X_1 = $ Orn; $X_7 = E, Q, K$; $X_8 = D, N$; Option N-substitution of $F_5$ (Me, alkyl, aryl, etc.) |
| 8 | FIG. 4B Bottom | XCIIGCXV | $X_1 = $ Orn; $X_7 = M$, Orn, MetO; Option N-substitution of $G_5$ (Me, alkyl, aryl, etc.) |
| 9 | $A\beta_{1-16}$ | DAEFRHDSGY EVHHQK | |
| 10 | $A\beta_{37-40}$ | GGVV | |
| 11 | $A\beta_{37-42}$ | GGVVIA | |
| 12 | FIG. 12 Top | XLVFFAXX | $X_1 = $ Orn; $X_7 = E, Q, K$; $X_8 = D, N$; Option N-substitution of $F_5$ (Me, alkyl, aryl, etc.) |
| 13 | FIG. 12 Bottom | XAIGGLXV | $X_1 = $ Orn; $X_7 = M$, Orn, MetO; Option N-substitution of $G_5$ (Me, alkyl, aryl, etc.) |
| 14 | FIG. 12 full | XLVFFAXXVG SNKGAIIGLX VX | $X_1 = A\beta_{1-16}$, deleted; $X_7 = E, Q, K$; $X_8 = D, N$; $X_{20} = M$, Orn, MetO; $X_{22} = A\beta_{37-40}$, $A\beta_{37-42}$, deleted; Optional N-substitution on $F_5$ and $G_{18}$ (Me, alkyl, aryl, etc.) |
| 15 | FIG. 13 Top | XKLVFFAX | $X_1 = $ Orn; $X_7 = E, Q, K$; $X_8 = D, N$; Option N-substitution of $F_5$ (Me, alkyl, aryl, etc.) |
| 16 | FIG. 13 Bottom | XAIIGLXV | $X_1 = $ Orn; $X_7 = M$, Orn, MetO; Option N-substitution of $G_5$ (Me, alkyl, aryl, etc.) |
| 17 | FIG. 13 full | XKLVFFAXXV GSNKGAIIGL XVX | $X_1 = A\beta_{1-16}$, deleted; $X_8 = E, Q, K$; $X_9 = D, N$; $X_{21} = M$, Orn, MetO; $X_{23} = A\beta_{37-40}$, $A\beta_{37-42}$, deleted; Optional N-substitution on $F_5$ and $G_{19}$ (Me, alkyl, aryl, etc.) |

TABLE 3-continued

Sequencing Listing of Peptides

| Seq. ID No. | Name | Sequence | Modifications |
|---|---|---|---|
| 18 | Peptide 1 Top | XLVFFAED | $X_1$ = Orn |
| 19 | Peptide 1 Bottom | XAIIGLXV | $X_1$ = Orn; $X_7$ = Orn; N-methylation on $G_5$ |
| 20 | Peptide 2 Top | XLVFFAED | $X_1$ = Orn; N-methylation of $F_5$ |
| 21 | Peptide 2 Bottom | XAIIGLXV | $X_1$ = Orn; $X_7$ = Orn |
| 22 | Peptide 3 Top | XCVFFCED | $X_1$ = Orn |
| 23 | Peptide 3 Bottom | XAIIGLXV | $X_1$ = Orn; $X_7$ = Orn; N-methylation on $G_5$ |
| 24 | Peptide 4 Top | XCVFFCED | $X_1$ = Orn; N-methylation of $F_5$ |
| 25 | Peptide 4 Bottom | XAIIGLXV | $X_1$ = Orn; $X_7$ = Orn |
| 26 | Peptide 5 Top | XLVFFAED | $X_1$ = Orn; $F_4$ = para-iodophenylalanine |
| 27 | Peptide 5 Bottom | XAIIGLMV | $X_1$ = Orn; N-methylation of $G_5$ |
| 28 | Peptide 6 Top | XKLVFFAE | $X_1$ = Orn; $F_5$ = para-iodophenylalanine |
| 29 | Peptide 6 Bottom | XAIIGLMV | $X_1$ = Orn; N-methylation of $G_5$ |
| 30 | Peptide 7 Top | XQKLVFFA | $X_1$ = Orn; $F_6$ = para-iodophenylalanine |
| 31 | Peptide 7 Bottom | XAIIGLMV | $X_1$ = Orn; N-methylation of $G_5$ |
| 32 | $A\beta_{17-36}$ | LVFFAEDVGS NKGAIIGLMV | |
| 33 | peptide 8 top | XKLVFFAE | $X_1$ = Orn; N-methylation of $F_5$ |
| 34 | peptide 8 bottom | XAIIGLMV | $X_1$ = Orn |
| 35 | $A\beta 616_{-36}$ | KVLFFAEDVG SNKGAIIGLM V | |
| 36 | peptide 9 top | XKLVFFAE | $X_1$ = Orn; N-methylation of $F_5$ |
| 37 | peptide 9 bottom | XAIIGLMV | $X_1$ = Orn; N-methylation of $G_5$ |
| 38 | peptide 10 top | XKVFFAAD | $X_1$ = Orn; N-methylation of $F_5$ |
| 39 | peptide 10 bottom | XAIIGLMV | $X_1$ = Orn |

DOCTRINE OF EQUIVALENTS

Those skilled in the art will appreciate that the foregoing examples and descriptions of various preferred embodiments of the present invention are merely illustrative of the invention as a whole, and that variations in the steps and various components of the present invention may be made within the spirit and scope of the invention. Accordingly, the present invention is not limited to the specific embodiments described herein but, rather, is defined by the scope of the appended claims.

What is claimed is:

1. A method of producing antibodies having affinity for soluble beta-amyloid oligomers comprising:

administering to an immunocompetent animal with an immunogenic cocktail comprising a synthetic beta-amyloid trimer;

wherein the beta-amyloid trimer is a trimer selected from the group consisting of:

a trimer having a first, a second, and a third synthetic beta-amyloid peptide, each peptide comprises Seq. ID No. 3 or a substantially similar sequence;

wherein the cysteine in amino acid position two of the first peptide forms a disulfide linkage with the cysteine in amino acid position six of the second peptide;

wherein the cysteine in amino acid position two of the second peptide forms a disulfide linkage with the cysteine in amino acid position six of the third peptide;

wherein the cysteine in amino acid position two of the third peptide forms a disulfide linkage with the cysteine in amino acid position six of the first peptide; and wherein the substantially similar sequence consists of an addition, a removal, or a substitution of up to three amino acids yet maintains each cysteine amino acid of the peptide in its identified position;

a trimer having a first, a second, and a third synthetic beta-amyloid peptide, each peptide comprises Seq. ID No. 4 or a substantially similar sequence;

wherein the cysteine in amino acid position fifteen of the first peptide forms a disulfide linkage with the cysteine in amino acid position nineteen of the second peptide;

wherein the cysteine in amino acid position fifteen of the second peptide forms a disulfide linkage with the cysteine in amino acid position nineteen of the third peptide;

wherein the cysteine in amino acid position fifteen of the third peptide forms a disulfide linkage with the cysteine in amino acid position nineteen of the first peptide; and wherein the substantially similar sequence consists of an addition, a removal, or a substitution of up to three amino acids yet maintains each cysteine amino acid of the peptide in its identified position;

a trimer having a first, a second, and a third synthetic beta-amyloid peptide, each peptide consists of a first and a second strand, the first strand comprises Seq. ID No. 5 or a substantially similar sequence, and the second strand comprises Seq. ID No. 6 or a substantially similar sequence;

wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand;

wherein the cysteine in amino acid position two of the first strand of the first peptide forms a disulfide linkage with the cysteine in amino acid position six of the first strand of the second peptide;

wherein the cysteine in amino acid position two of the first strand of the second peptide forms a disulfide linkage with the cysteine in amino acid position six of the first strand of the third peptide;

wherein the cysteine in amino acid position two of the first strand of the third peptide forms a disulfide linkage with the cysteine in amino acid position six of the first strand of the first peptide; and wherein any of the substantially similar sequences is a sequence that allows consists of an addition, a removal, or a substitution of up to three amino acids yet maintains each cysteine amino acid of the peptide its identified position; and a trimer having a first, a second, and a third synthetic beta-amyloid peptide, each peptide consists of a first and a second strand, the first strand comprises Seq. ID No. 7 or a substantially similar sequence, and the second strand comprises Seq. ID No. 8 or a substantially similar sequence;

wherein the first and second strand are covalently linked by the delta-amino group of the side chain of the N-terminal ornithine of the first strand to the C-terminus of the second strand, and wherein the first and second strand are also covalently linked by the delta-amino group of the side chain of the N-terminal ornithine of the second strand to the C-terminus of the first strand;

wherein the cysteine in amino acid position two of the second strand of the first peptide forms a disulfide linkage with the cysteine in amino acid position six of the second strand of the second peptide;

wherein the cysteine in amino acid position two of the second strand of the second peptide forms a disulfide linkage with the cysteine in amino acid position six of the second strand of the third peptide;

wherein the cysteine in amino acid position two of the second strand of the third peptide forms a disulfide linkage with the cysteine in amino acid position six of the second strand of the first peptide; and wherein any of the substantially similar sequences is a sequence that allows consists of an addition, a removal, or a substitution of up to three amino acids yet maintains each cysteine amino acid of the peptide in its identified position.

2. The method of claim 1, wherein at least one synthetic beta-amyloid peptide incorporates an ornithine in the amino acid position that corresponds to methionine35 of a naturally occurring beta-amyloid peptide.

3. The method of claim 1, wherein at least one central amino acid is N-methylated.

4. The method of claim 1, wherein the synthetic beta-amyloid peptide has at least one amino acid mutation that corresponds to familial Alzheimer's disease.

5. The method of claim 1, wherein any of the substantially similar sequences is a sequence that allows consists of an addition, a removal, or a substitution of up to two amino acids but still maintains each cysteine amino acid of the peptide in its identified position.

6. The method of claim 1, wherein any of the substantially similar sequences is a sequence that allows consists of an addition, a removal, or a substitution of one amino acids but still maintains each cysteine amino acid of the peptide in its identified position.

7. The method of claim 1, wherein any of the substantially similar sequences is an identical sequence that does not have an addition, a removal, or a substitution of an amino acid.

8. The method of claim 1 further comprising: harvesting antibodies from the immunocompetent animal.

9. The method of producing antibodies of claim 1 further comprising repeating administration of beta-amyloid trimers to the immunocompetent animal.

10. The method of claim 1, wherein the immunocompetent animal is selected from the group consisting of human, rabbit, goat, mouse, rat, chicken, and guinea pig.

11. The method of claim 1, wherein the immunogenic cocktail further comprises an adjuvant.

12. The method of claim 1, wherein the adjuvant is Freund's adjuvant.

13. The method of claim 1, wherein the at least one beta-amyloid trimer is conjugated with hemocyanin.

14. The method of claim 1, wherein the immunocompetent animal is a human individual for the purpose of vaccination.

* * * * *

SEQUENCE LISTING

<160> NUMBER OF SEQ ID NOS: 39

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 22
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Abeta1-16 (DAEFRHDSGYEVHHQK), Orn, or deleted
<220> FEATURE:
<221> NAME/KEY: optional_N-substitution
<222> LOCATION: (5)..(5)
<223> OTHER INFORMATION: optional N-methylation, alkylation, arylation,
    or similar bulky group
<220> FEATURE:
<221> NAME/KEY: Xaa
<222> LOCATION: (7)..(7)
<223> OTHER INFORMATION: Glu, Gln, Lys
<220> FEATURE:
<221> NAME/KEY: Xaa
<222> LOCATION: (8)..(8)
<223> OTHER INFORMATION: Asp, Asn
<220> FEATURE:
<221> NAME/KEY: optional_N-substitution
<222> LOCATION: (18)..(18)
<223> OTHER INFORMATION: optional N-methylation, alkylation, arylation,
    or similar bulky group
<220> FEATURE:
<221> NAME/KEY: Xaa
<222> LOCATION: (20)..(20)
<223> OTHER INFORMATION: Met, Orn, methionine sulfoxide, methionine
    sulfone
<220> FEATURE:
<221> NAME/KEY: Xaa
<222> LOCATION: (22)..(22)
<223> OTHER INFORMATION: Abeta37-40 (GGVV), Abeta37-42 (GGVVIA), deleted

<400> SEQUENCE: 3

Xaa Cys Val Phe Phe Cys Xaa Xaa Val Gly Ser Asn Lys Gly Ala Ile
1               5                   10                  15

```
Ile Gly Leu Xaa Val Xaa
            20

<210> SEQ ID NO 4
<211> LENGTH: 22
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Abeta1-16 (DAEFRHDSGYEVHHQK), Orn, or deleted
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (7)..(7)
<223> OTHER INFORMATION: Glu, Gln, Lys
<220> FEATURE:
<221> NAME/KEY: Xaa
<222> LOCATION: (8)..(8)
<223> OTHER INFORMATION: Asp, Asn
<220> FEATURE:
<221> NAME/KEY: optional_N-substitution
<222> LOCATION: (18)..(18)
<223> OTHER INFORMATION: optional N-methylation, alkylation, arylation,
      or similar bulky group
<220> FEATURE:
<221> NAME/KEY: Xaa
<222> LOCATION: (20)..(20)
<223> OTHER INFORMATION: Met, Orn, methionine sulfoxide, methionine
      sulfone
<220> FEATURE:
<221> NAME/KEY: Xaa
<222> LOCATION: (22)..(22)
<223> OTHER INFORMATION: Abeta37-40 (GGVV), Abeta37-42 (GGVVIA), deleted

<400> SEQUENCE: 4

Xaa Leu Val Phe Phe Ala Xaa Xaa Val Gly Ser Asn Lys Gly Cys Ile
1               5                   10                  15

Ile Gly Cys Xaa Val Xaa
            20

<210> SEQ ID NO 5
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (7)..(7)
<223> OTHER INFORMATION: Glu, Gln, Lys
<220> FEATURE:
<221> NAME/KEY: Xaa
<222> LOCATION: (8)..(8)
<223> OTHER INFORMATION: Asp, Asn

<400> SEQUENCE: 5

Xaa Cys Val Phe Phe Cys Xaa Xaa
```

```
<210> SEQ ID NO 6
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (7)..(7)
<223> OTHER INFORMATION: Met, Orn, methionine sulfoxide, methionine
      sulfone

<400> SEQUENCE: 6

Xaa Ala Ile Ile Gly Leu Xaa Val
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (7)..(7)
<223> OTHER INFORMATION: Glu, Gln, Lys
<220> FEATURE:
<221> NAME/KEY: Xaa
<222> LOCATION: (8)..(8)
<223> OTHER INFORMATION: Asp, Asn

<400> SEQUENCE: 7

Xaa Leu Val Phe Phe Ala Xaa Xaa
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (7)..(7)
<223> OTHER INFORMATION: Met, Orn, methionine sulfoxide, methionine
```

-continued

```
        sulfone

<400> SEQUENCE: 8

Xaa Cys Ile Ile Gly Cys Xaa Val
1               5

<210> SEQ ID NO 9
<211> LENGTH: 16
<212> TYPE: PRT
<213> ORGANISM: Homo sapiens

<400> SEQUENCE: 9

Asp Ala Glu Phe Arg His Asp Ser Gly Tyr Glu Val His His Gln Lys
1               5                   10                  15

<210> SEQ ID NO 10
<211> LENGTH: 4
<212> TYPE: PRT
<213> ORGANISM: Homo sapiens

<400> SEQUENCE: 10

Gly Gly Val Val
1

<210> SEQ ID NO 11
<211> LENGTH: 6
<212> TYPE: PRT
<213> ORGANISM: Homo sapiens

<400> SEQUENCE: 11

Gly Gly Val Val Ile Ala
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (7)..(7)
<223> OTHER INFORMATION: Glu, Gln, Lys
<220> FEATURE:
<221> NAME/KEY: Xaa
<222> LOCATION: (8)..(8)
<223> OTHER INFORMATION: Asp, Asn

<400> SEQUENCE: 12

Xaa Leu Val Phe Phe Ala Xaa Xaa
1               5

<210> SEQ ID NO 13
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
```

```
<222> LOCATION: (1)..(1)
<223> OTHER INFORMATION: Orn
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (7)..(7)
<223> OTHER INFORMATION: Met, Orn, methionine sulfoxide, methionine
      sulfone

<400> SEQUENCE: 13

Xaa Ala Ile Ile Gly Leu Xaa Val
1               5

<210> SEQ ID NO 14
<211> LENGTH: 22
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Abeta1-16 (DAEFRHDSGYEVHHQK), Orn, or deleted
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (7)..(7)
<223> OTHER INFORMATION: Glu, Gln, Lys
<220> FEATURE:
<221> NAME/KEY: Xaa
<222> LOCATION: (8)..(8)
<223> OTHER INFORMATION: Asp, Asn
<220> FEATURE:
<221> NAME/KEY: optional_N-substitution
<222> LOCATION: (18)..(18)
<223> OTHER INFORMATION: optional N-methylation, alkylation, arylation,
      or similar bulky group
<220> FEATURE:
<221> NAME/KEY: Xaa
<222> LOCATION: (20)..(20)
<223> OTHER INFORMATION: Met, Orn, methionine sulfoxide, methionine
      sulfone
<220> FEATURE:
<221> NAME/KEY: Xaa
<222> LOCATION: (22)..(22)
<223> OTHER INFORMATION: Abeta37-40 (GGVV), Abeta37-42 (GGVVIA), deleted

<400> SEQUENCE: 14

Xaa Leu Val Phe Phe Ala Xaa Xaa Val Gly Ser Asn Lys Gly Ala Ile
1               5                   10                  15

Ile Gly Leu Xaa Val Xaa
            20

<210> SEQ ID NO 15
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: optional_N-substitution
<222> LOCATION: (5)..(5)
```

```
<223> OTHER INFORMATION: optional N-methylation, alkylation, arylation,
      or similar bulky group
<220> FEATURE:
<221> NAME/KEY: Xaa
<222> LOCATION: (8)..(8)
<223> OTHER INFORMATION: Glu, Gln, Lys

<400> SEQUENCE: 15

Xaa Lys Leu Val Phe Phe Ala Xaa
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (7)..(7)
<223> OTHER INFORMATION: Met, Orn, methionine sulfoxide, methionine
      sulfone

<400> SEQUENCE: 16

Xaa Ala Ile Ile Gly Leu Xaa Val
1               5

<210> SEQ ID NO 17
<211> LENGTH: 23
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Abeta1-16 (DAEFRHDSGYEVHHQK), Orn, or deleted
<220> FEATURE:
<221> NAME/KEY: optional_N-substitution
<222> LOCATION: (5)..(5)
<223> OTHER INFORMATION: optional N-methylation, alkylation, arylation,
      or similar bulky group
<220> FEATURE:
<221> NAME/KEY: Xaa
<222> LOCATION: (8)..(8)
<223> OTHER INFORMATION: Glu, Gln, Lys
<220> FEATURE:
<221> NAME/KEY: Xaa
<222> LOCATION: (9)..(9)
<223> OTHER INFORMATION: Asp, Asn
<220> FEATURE:
<221> NAME/KEY: optional_N-substitution
<222> LOCATION: (19)..(19)
<223> OTHER INFORMATION: optional N-methylation, alkylation, arylation,
      or similar bulky group
<220> FEATURE:
<221> NAME/KEY: Xaa
<222> LOCATION: (21)..(21)
<223> OTHER INFORMATION: Met, Orn, methionine sulfoxide, methionine
      sulfone
<220> FEATURE:
<221> NAME/KEY: Xaa
<222> LOCATION: (23)..(23)
<223> OTHER INFORMATION: Abeta37-40 (GGVV), Abeta37-42 (GGVVIA), deleted

<400> SEQUENCE: 17
```

```
Xaa Lys Leu Val Phe Phe Ala Xaa Xaa Val Gly Ser Asn Lys Gly Ala
1               5                   10                  15

Ile Ile Gly Leu Xaa Val Xaa
                20
```

<210> SEQ ID NO 18
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn

<400> SEQUENCE: 18

```
Xaa Leu Val Phe Phe Ala Glu Asp
1               5
```

<210> SEQ ID NO 19
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Gly
<220> FEATURE:
<221> NAME/KEY: Xaa
<222> LOCATION: (7)..(7)
<223> OTHER INFORMATION: Orn

<400> SEQUENCE: 19

```
Xaa Ala Ile Ile Gly Leu Xaa Val
1               5
```

<210> SEQ ID NO 20
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Phe

<400> SEQUENCE: 20

```
Xaa Leu Val Phe Phe Ala Glu Asp
1               5
```

<210> SEQ ID NO 21
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa

```
<222> LOCATION: (1)..(1)
<223> OTHER INFORMATION: Orn
<220> FEATURE:
<221> NAME/KEY: Xaa
<222> LOCATION: (7)..(7)
<223> OTHER INFORMATION: Orn

<400> SEQUENCE: 21

Xaa Ala Ile Ile Gly Leu Xaa Val
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn

<400> SEQUENCE: 22

Xaa Cys Val Phe Phe Cys Glu Asp
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Gly
<220> FEATURE:
<221> NAME/KEY: Xaa
<222> LOCATION: (7)..(7)
<223> OTHER INFORMATION: Orn

<400> SEQUENCE: 23

Xaa Ala Ile Ile Gly Leu Xaa Val
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Phe

<400> SEQUENCE: 24

Xaa Cys Val Phe Phe Cys Glu Asp
1               5

<210> SEQ ID NO 25
<211> LENGTH: 8
<212> TYPE: PRT
```

```
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: Xaa
<222> LOCATION: (7)..(7)
<223> OTHER INFORMATION: Orn

<400> SEQUENCE: 25

Xaa Ala Ile Ile Gly Leu Xaa Val
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: Modification
<222> LOCATION: (4)..(4)
<223> OTHER INFORMATION: para-iodophenylalanine

<400> SEQUENCE: 26

Xaa Leu Val Phe Phe Ala Glu Asp
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Gly

<400> SEQUENCE: 27

Xaa Ala Ile Ile Gly Leu Met Val
1               5

<210> SEQ ID NO 28
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: Modification
<222> LOCATION: (5)..(5)
<223> OTHER INFORMATION: para-iodophenylalanine

<400> SEQUENCE: 28

Xaa Lys Leu Val Phe Phe Ala Glu
1               5
```

```
<210> SEQ ID NO 29
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Gly

<400> SEQUENCE: 29

Xaa Ala Ile Ile Gly Leu Met Val
1               5

<210> SEQ ID NO 30
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: Modification
<222> LOCATION: (6)..(6)
<223> OTHER INFORMATION: para-iodophenylalanine

<400> SEQUENCE: 30

Xaa Gln Lys Leu Val Phe Phe Ala
1               5

<210> SEQ ID NO 31
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Gly

<400> SEQUENCE: 31

Xaa Ala Ile Ile Gly Leu Met Val
1               5

<210> SEQ ID NO 32
<211> LENGTH: 20
<212> TYPE: PRT
<213> ORGANISM: Homo sapiens

<400> SEQUENCE: 32

Leu Val Phe Phe Ala Glu Asp Val Gly Ser Asn Lys Gly Ala Ile Ile
1               5                   10                  15

Gly Leu Met Val
            20
```

-continued

```
<210> SEQ ID NO 33
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Phe

<400> SEQUENCE: 33

Xaa Lys Leu Val Phe Phe Ala Glu
1               5

<210> SEQ ID NO 34
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn

<400> SEQUENCE: 34

Xaa Ala Ile Ile Gly Leu Met Val
1               5

<210> SEQ ID NO 35
<211> LENGTH: 21
<212> TYPE: PRT
<213> ORGANISM: Homo sapiens

<400> SEQUENCE: 35

Lys Leu Val Phe Phe Ala Glu Asp Val Gly Ser Asn Lys Gly Ala Ile
1               5                   10                  15

Ile Gly Leu Met Val
            20

<210> SEQ ID NO 36
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylatoin
<222> LOCATION: (5)..(5)
<223> OTHER INFORMATION: N-methylation on Phe

<400> SEQUENCE: 36

Xaa Lys Leu Val Phe Phe Ala Glu
1               5

<210> SEQ ID NO 37
<211> LENGTH: 8
<212> TYPE: PRT
<213> ORGANISM: Artificial Sequence
<220> FEATURE:
<223> OTHER INFORMATION: synthetic peptide derived from beta-amyloid
```

```
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Gly

<400> SEQUENCE: 37

Xaa Ala Ile Ile Gly Leu Met Val
1               5

<210> SEQ ID NO 38
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn
<220> FEATURE:
<221> NAME/KEY: N-methylation
<222> LOCATION: (5)..(5)
<223> OTHER INFORMATION: N-methylation on Phe

<400> SEQUENCE: 38

Xaa Lys Val Phe Phe Ala Ala Asp
1               5

<210> SEQ ID NO 39
<211> LENGTH: 8
<212> TYPE: PRT
<213> ORGANISM: Artificial Sequence
<220> FEATURE:
<223> OTHER INFORMATION: synthetic peptide derived from beta-amyloid
<220> FEATURE:
<221> NAME/KEY: Xaa
<222> LOCATION: (1)..(1)
<223> OTHER INFORMATION: Orn

<400> SEQUENCE: 39

Xaa Ala Ile Ile Gly Leu Met Val
1               5
```